US012697362B2

(12) United States Patent
Herlands et al.

(10) Patent No.: US 12,697,362 B2
(45) Date of Patent: Aug. 4, 2026

(54) NON-HALLUCINOGENIC PSYCHEDELIC FUNGI

(71) Applicant: Luminous Mind Inc., Woods Hole, MA (US)

(72) Inventors: Louis Herlands, Woods Hole, MA (US); David Thaler, Zurich (CH); John Myles Axton, Campbell Hall, NY (US)

(73) Assignee: Luminous Mind Inc., Woods Hole, MA (US)

( * ) Notice: Subject to any disclaimer, the term of this patent is extended or adjusted under 35 U.S.C. 154(b) by 0 days.

(21) Appl. No.: 18/848,641

(22) PCT Filed: Aug. 11, 2023

(86) PCT No.: PCT/US2023/030116
§ 371 (c)(1),
(2) Date: Sep. 19, 2024

(87) PCT Pub. No.: WO2024/035954
PCT Pub. Date: Feb. 15, 2024

(65) Prior Publication Data
US 2025/0255913 A1 Aug. 14, 2025

Related U.S. Application Data

(60) Provisional application No. 63/371,121, filed on Aug. 11, 2022.

(51) Int. Cl.
*A61K 36/07* (2006.01)
*C12N 15/113* (2010.01)

(52) U.S. Cl.
CPC ........ *A61K 36/078* (2024.05); *C12N 15/1137* (2013.01); *C12N 2310/14* (2013.01)

(58) Field of Classification Search
None
See application file for complete search history.

(56) References Cited

U.S. PATENT DOCUMENTS

2010/0099191 A1* 4/2010 Biekle .................. C12Q 1/6897
435/320.1
2015/0240253 A1 8/2015 McGonigle et al.

FOREIGN PATENT DOCUMENTS

WO 2021067626 A2 4/2021
WO WO 2021/067626 * 11/2024

OTHER PUBLICATIONS

International Search Report (Form PCT/ISA/210), PCT/US2023/030116, mailed May 7, 2024.
(Continued)

*Primary Examiner* — Erin M. Bowers
(74) *Attorney, Agent, or Firm* — CALYX LAW; Graham Pechenik

(57) ABSTRACT

The present invention provides genetically modified fungi, such as non-hallucinogenic psychedelic fungi, in which a biochemical pathway to produce a bioactive alkaloid is disrupted. In some aspects, the psilocybin biosynthesis pathway is disrupted, resulting in non-hallucinogenic psychedelic fungi which do not produce or contain psilocybin, or which produce or contain a substantially reduced amount of psilocybin relative to wild-type fungi. Also provided are methods of making genetically modified fungi, for example by disrupting or rebalancing a biochemical pathway therein, such as the psilocybin biosynthesis pathway, such as by using gene editing techniques, including gene inactivation by small interfering RNAs (siRNAs), microRNAs (miRNAs), and CRISPR/Cas9. Also provided are compositions of genetically modified fungi, such as compositions of non-hallucinogenic psychedelic fungi, and methods of their
(Continued)

use, including as functional foods, nootropics, legal micro-doses, nutraceuticals, and therapeutics.

12 Claims, 17 Drawing Sheets

Specification includes a Sequence Listing.

(56) References Cited

OTHER PUBLICATIONS

Search Strategy/Search History, PCT/US2023/030116, date of search Dec. 20, 2023.
Written Opinion of the USPTO as ISA (Form PCT/ISA/237), PCT/US2023/030116, mailed May 7, 2024.

* cited by examiner

```
P.Cubensis        1 ATGCAGGTGATACCCGCGTGCAACTCGGCAGCAATAAGATCACTATGTCC          50
                    ||||||||..|.||||||||||.|.||..|.||..|.|.|.||.|.||.||
P.Cyanescens      1 ATGCAGGTACTGCCCGCGTGCCAATCTTCCGCGCTTAAAACATTGTGCCC          50

P.Cubensis       51 TACTCCCGAGTCTTTTAGAAACATGGGATGGCTCTCTGTCAGCGATGCGG         100
                    ..|.|||||||.|.|||.||||..|.||.||||||.||...|||||.|.||
P.Cyanescens     51 ATCCCCCGAGGCCTTTCGAAAGCTCGGTTGGCTCCCTACTAGCGACGAGG         100

P.Cubensis      101 TCTACAGCGAGTTCATAGGAGAGTTGGCTACCCGCGCTTCCAATCGAAAT         150
                    |.||||.|||.|||||.|...||.|||.|....|||.|.|.|||||..|||.
P.Cyanescens    101 TTTACAACGAATTCATCGATGACTTGACCGGTCGCACGTGCAATGAAAAG         150

P.Cubensis      151 TACTCCAACGAGTTCGGCCTCATGCAACCTATCCAGGAATTCAAGGCTTT         200
                    ||||||||.|.||.|....||..||.|.|||||||||.||.||||||.|.||
P.Cyanescens    151 TACTCCAGCCAGGTTACACTTTTGAAGCCTATCCAAGATTTCAAGACATT         200

P.Cubensis      201 CATTGAAAGCGACCCGGTGGTGCACCAAGAATTTATTGACATGTTCGAGG         250
                    |||.||.|..||..|.||.|.||||||||||||||||....||||||.||.|
P.Cyanescens    201 CATCGAGAATGATCCCATAGTGTATCAAGAATTTATCTCTATGTTTGAAG         250

P.Cubensis      251 GCATTCAGGACTCTCCAAGGAATTATCAGGAACTATGTAATATGTTCAAC         300
                    |.||..||.|.|.||||||.|...||.||.||.|||.||||||||||||||
P.Cyanescens    251 GAATCGAGCAGTCTCCCACCAACTACCACGAGCTATGTAACATGTTCAAC         300

P.Cubensis      301 GATATCTTTCGCAAAGCTCCCGTCTACGGAGACCTTGGCCCTCCCGTTTA         350
                    ||.|||||||||||||.||..|||||||.||.|.|||||.|||||.||||||
P.Cyanescens    301 GACATCTTTCGCAAAGCCCCACTCTACGGCGATCTTGGTCCTCCGGTTTA         350

P.Cubensis      351 TATGATTATGGCCAAATTAATGAACACCCGAGCGGGCTTCTCTGCATTCA         400
                    .||||||.|||||||.|.|||||||||.||.|.|...|||||.|||||||.||||
P.Cyanescens    351 CATGATCATGGCCAGAATAATGAATACGCAGGCGGGTTTCTCTGCGTTCA         400

P.Cubensis      401 CGAGACAAAGGTTGAACCTTCACTTCAAAAAACTTTTCGATACCTGGGGA         450
                    |.|.|.|.||.|||||||.|.||.|||||||||.||.|||||.|||||||||.
P.Cyanescens    401 CAAAAGAGAGCTTGAACTTCCATTTCAAAAAGCTCTTCGACACCTGGGGG         450

P.Cubensis      451 TTGTTCCTGTCTTCGAAAGATTCTCGAAATGTTCTTGTGGCCGACCAGTT         500
                    .|.|||||.||.|||||||.|.|||||||||.||.|||||.||.||||||||
P.Cyanescens    451 CTATTCCTTTCCTCGAAAAACTCTCGAAACGTGCTTGTTGCAGACCAGTT         500

P.Cubensis      501 CGACGACAGACATTGCGGCTGGTTGAACGAGCGGGCCTTGTCTGCTATGG         550
                    .|||||.|.|.||||.|||.|||||.|||||.|.|||||||.|||...|.||||.
P.Cyanescens    501 TGACGATAAGCATTACGGGTGGTTCAGCGAGCGAGCCAAGACTGCCATGA         550

P.Cubensis      551 TTAAACATTACAATGGACGCGCATTTGATGAAGTCTTCCTCTGCGATAAA         600
                    |.|....||||....||.||.||..||||.||...|||||||||.||||||..|.
P.Cyanescens    551 TGATTAATTATCCAGGGCGTACATTCGAGAAAGTCTTCATCTGCGACGAG         600

P.Cubensis      601 AATGCCCCATACTACGGCTTCAACTCTTACGACGACTTCTTTAATCGCAG         650
                    .|.|..|||||||.|.|||||||..||.||.|||||.|||||.||||||||
P.Cyanescens    601 CACGTTCCATACCATGGCTTCACTTCCTATGACGATTTCTTCAATCGCAG         650

P.Cubensis      651 ATTTCGAAACCGAGATATCGACCGACCTGTAGTCGGTGGAGTTAACAACA         700
                    .||..|..||...|||||.||.||.||.||.||||||||||||||.|||||...|||
P.Cyanescens    651 GTTCAGGGACAAGGATACAGATCGGCCCGTAGTCGGTGGGGGTTACTGACA         700

P.Cubensis      701 CCACCCTCATTTCTGCTGCTTGCGAATCACTTTCCTACAACGTCTCTTAT         750
                    ||||..|.|.||....|||||.||.||.|||||..|.||.||.||.||||||||||.|.
P.Cyanescens    701 CCACTTTAATCGGGGCTGCCTGTGAATCGTTGTCATATAACGTCTCTCAC         750
```

FIG. 1

```
P.Cubensis     751 GACGTCCAGTCTCTCGACACTTTAGTTTTCAAAGGAGAGACTTATTCGCT      800
                   .||||||||||||.|||||..|||||..||||.||||||.|.||||||.||
P.Cyanescens   751 AACGTCCAGTCTCTTGACACGCTAGTCATCAAGGGAGAGGCCTATTCACT      800

P.Cubensis     801 TAAGCATTTGCTGAATAATGACCCTTTCACCCCACAATTCGAGCATGGGA      850
                   |||.|||.|.||..|||||.|||||.|||||.||.|||||||||.|||||||
P.Cyanescens   801 TAAACATCTACTTCATAACGACCCCTTCACACCGCAATTCGAACATGGGA      850

P.Cubensis     851 GTATTCTACAAGGATTCTTGAACGTCACCGCTTACCACCGATGGCACGCA      900
                   |.||..|.||||||||||.|.||.||||||||||||||||||.||||||.|.
P.Cyanescens   851 GCATCATTCAAGGATTCCTAAATGTCACCGCTTACCACCGCTGGCACTCC      900

P.Cubensis     901 CCCGTCAATGGGACAATCGTCAAAATCATCAACGTTCCAGGTACCTACTT      950
                   ||||||||||||.||.||.||.||.|||.||||||||||||||||||||||
P.Cyanescens   901 CCCGTCAATGGGACGATTGTGAAGATCGTCAACGTTCCAGGTACCTACTT      950

P.Cubensis     951 TGCGCAAGCCCCGAGCACGATTGGCGACCCTATCCCGGATAACGATTACG     1000
                   .||.|||||.||....||.|||||....|||||||||.||||||||...||
P.Cyanescens   951 CGCTCAAGCTCCATATACAATTGGATCTCCTATCCCCGATAACGACCGCG     1000

P.Cubensis    1001 ACCCACCTCCTTACCTTAAGTCTCTTGTCTACTTCTCTAATATTGCCGCA     1050
                   ||||.||||||||||||||.|||||.||.||.|||||||||.||.||.||.|||
P.Cyanescens  1001 ACCCGCCTCCTTACCTCAAGTCACTCGTATACTTCTCCAACATCGCTGCA     1050

P.Cubensis    1051 AGGCAAATTATGTTTATTGAAGCCGACAACAAGGAAATTGGCCTCATTTT     1100
                   .|||||||||||||.||.||.||||||||||.||.||.||||||||||||
P.Cyanescens  1051 CGGCAAATTATGTTCATCGAGGCCGACAACAAAGACATCGGCCTCATTTT     1100

P.Cubensis    1101 CCTTGTGTTCATCGGCATGACCGAAATCTCGACATGTGAAGCCACGGTGT     1150
                   |.|.||.||||||.||.||||||.||.|||||||||.||.||.||.|||||||
P.Cyanescens  1101 CTTGGTCTTCATTGGAATGACTGAGATCTCGACTTGCGAGGCGACGGTGT     1150

P.Cubensis    1151 CCGAAGGTCAACACGTCAATCGTGGCGATGACTTGGGAATGTTCCATTTC     1200
                   .||||||||||.||.|||||.||.||.||.||.||.|||||.||||||||||||
P.Cyanescens  1151 GCGAAGGTCAGCATGTCAACCGCGGTGACGATTTGGGCATGTTCCATTTC     1200

P.Cubensis    1201 GGTGGTTCTTCGTTCGCGCTTGGTCTGAGGAAGGATTGCAGGGCAGAGAT     1250
                   |||||||||.||.||.||.||.|||||..||.|||||||.|...|.|||..||||
P.Cyanescens  1201 GGTGGTTCATCTTTTGCCCTTGGCTTGCGGAAGGACTCGAAGGCGAAGAT     1250

P.Cubensis    1251 CGTTGAAAAGTTCACCGAACCCGGAACAGTGATCAGAATCAACGAAGTCG     1300
                   ..|.||||||||||.|..|||||.||.||.||.||.||.||.||||||||..|.|
P.Cyanescens  1251 TTTGGAAAAGTTCGCGAAACCGGGGACCGTTATTAGGATCAACGAGCTAG     1300

P.Cubensis    1301 TCGCTGCTCTAAAGGCTTAG      1320
                   |.||..||.|||.|.....|||
P.Cyanescens  1301 TTGCATCTGTAAGGAAGTAG      1320
```

```
P.CUBENSIS       1 ATGGCGTTCGATCTCAAGACTGAAGACGGCCTCATCACATATCTCACTAA      50
                   |||.|.||||||||||||||||||||||.|||||..||.|||||.|||||.||
P.CYANESCENS     1 ATGACTTTCGATCTCAAGACTGAAGAAGGCCTGCTCTCATACCTCACAAA      50

P.CUBENSIS      51 ACATCTTTCTTTGGACGTCGACACGAGCGGAGTGAAGCGCCTTAGCGGAG     100
                   .||.||.||..|||||||.|....|.|.|||.|||||.||.|||||.||||
P.CYANESCENS    51 GCACCTATCGCTGGACGTTGCTCCCAACGGGGTGAAACGTCTTAGTGGAG     100

P.CUBENSIS     101 GCTTTGTCAATGTAACCTGGCGCATTAAGCTCAATGCTCCTTATCAAGGT     150
                   ||||.|||||.||.||||||||..|...|||||||||.|||||||.|||
P.CYANESCENS   101 GCTTCGTCAACGTTACCTGGCGGGTCGGGCTCAATGCCCCTTATCATGGT     150

P.CUBENSIS     151 CATACGAGCATCATCCTGAAGCATGCTCAGCCGCACATGTCTACGGATGA     200
                   ||.|||||||||.||.||||||||||||||.||||||.||||||.|.||...
P.CYANESCENS   151 CACACGAGCATTATTCTGAAGCATGCTCAACCGCACCTGTCTTCAGACAT     200

P.CUBENSIS     201 GGATTTTAAGATAGGTGTAGAACGTTCGGTTTACGAATACCAGGCTATCA     250
                   .||||||.||||||||||.|||||.||||..|||||.||.||.||..|||
P.CYANESCENS   201 AGATTTCAAGATAGGTGTTGAACGATCGGCGTACGAGTATCAAGCGCTCA     250

P.CUBENSIS     251 AGCTCATGATGGCCAATCGGGAG----GTTCT-GGGAG--GCGTGGATGG     293
                   |..||.||...||||||     ||     .||||  ||.||   |||
P.CYANESCENS   251 AAATCGTGTCAGCCAAT----AGCTCCCTTCTAGGCAGCAGCG-------     289

P.CUBENSIS     294 CATA-----GTTTCTGTGCCAGAAGGCCTGAACTACGACTTAGAGAATAA     338
                   |||        ||.|||||.|||||||||.||..|||||||||.|.|..|||||
P.CYANESCENS   290 -ATATTCGGGTCTCTGTACCAGAAGGTCTTCACTACGACGTCGTTAATAA     338

P.CUBENSIS     339 TGCATTGATCATGCAAGATGTCGGGAAGATGAAGACCCTTTTAGATTATG     388
                   .||||||||||||||||||||||||||..||||||||||||.||.||.||||
P.CYANESCENS   339 CGCATTGATCATGCAAGATGTCGGGACAATGAAGACCCTGTTGGACTATG     388

P.CUBENSIS     389 TCACCGCCAAACCGCCACTTGCGACGGATATAGCCCGCCTTGTTGGGACA     438
                   ||||.||||||||.|||.||.|.|...|.||.||.|||.|.||.||.|| ||
P.CYANESCENS   389 TCACTGCCAAACCACCAATTTCTGCAGAGATCGCCAGTCTCGTAGG--CA     436

P.CUBENSIS     439 G--AAATTGGGGGGTTCGTTGCCAGACTCCATAACATAGGCCGCGAGAGG     486
                   |    ||||||||.|..||..|.||.||.||.||.||.|||.|.||||||||||..
P.CYANESCENS   437 GTCAAATTGGTGCATTTATCGCTAGGCTGCACAACCTCGGCCGCGAGAAT     486

P.CUBENSIS     487 CGAGACGATCCTGAGTTCAAATTCTTCTCTGGAAATATTGTCGGAAGGAC     536
                   ..||||.|.....||.||||||.||||||||||||||||.||.|||||.||.||
P.CYANESCENS   487 AAAGACAAGGACGACTTCAAGTTCTTCTCTGGAAACATCGTCGGGAGAAC     536

P.CUBENSIS     537 GACTTCAGACCAGCTGTATCAAACCATCATACCCAACGCAGCGAAATATG     586
                   .||..||||||||.||||||||||||||||||||.||.||.||.||||||.|
P.CYANESCENS   537 AACCGCAGACCAGTTGTATCAAACCATCATACCTAATGCCGCTAAATACG     586

P.CUBENSIS     587 GCGTCGATGACCCCTTGCTGCCTACTGTGGTTAAGGACCTTGTGGACGAT     636
                   |...||||.||.||..|.||.||.|.|||||||.|||||..|.||||||.||.
P.CYANESCENS   587 GTATCGACGATCCAATTCTCCCAATTGTGGTAAAGGAGTTGGTGGAGGAG     636

P.CUBENSIS     637 GTCATGCACAGCGAAGAGACCCTTGTCATGGCGGACCTGTGGAGTGGAAA     686
                   ||||||.|.||.|||||.||.|||.||.|||||||||||||...|.||||||||.||
P.CYANESCENS   637 GTCATGAATAGTGAAGAAACGCTTATCATGGCGGATTTATGGAGTGGCAA     686

P.CUBENSIS     687 TATTCTTCTCCAGTTGGAGGAGGGAAACCCATCGAAGCTGCAGAAGATAT     736
                   |||||||||||||||.||.||     ||||.|..||.|..||..||.|||||
P.CYANESCENS   687 TATTCTTCTCCAGTTTGATGA---AAACTCGACGGAATTGACGAGGATAT     733
```

FIG. 2

```
P.CUBENSIS      737 ATATCCTGGATTGGGAACTTTGCAAGTACGGCCCAGCGTCGTTGGACCTG    786
                    ...|..|.|| .||||||..|.|||||.||.||.|||.||||.||||||.||
P.CYANESCENS    734 GGCTGGTAGACTGGGAGTTGTGCAAATATGGTCCACCGTCTTTGGACATG    783

P.CUBENSIS      787 GGCTATTTCTTGGGTGACTGCTATTTGATATCCCGCTTTCAAGACGAGCA    836
                    ||.||.|||||.||.|||||.|...||.|..|.||.||||||||||..|||.
P.CYANESCENS    784 GGGTACTTCTTAGGCGACTGTTTCCTGGTCGCTCGATTTCAAGATCAGCT    833

P.CUBENSIS      837 GGTCGGTACGACGATGCGGCAAGCCTACTTGCAAAGCTATGCGC------    880
                    .||.||.||..|.|||||.||.||||||||||.|.||||| |||
P.CYANESCENS    834 CGTAGGGACATCAATGCGACAGGCCTACTTGAAGAGCTA--CGCAAGGAA    881

P.CUBENSIS      881 -GTACGAGCAAGCATTCGATCAACTACGCCAAAGTCACTGCAGGTATTGC    929
                    ||        ||||.|..|.|||||.||.||.||||.|||.||||||.||.|.
P.CYANESCENS    882 TGT-----CAAGGAGCCAATCAATTATGCAAAAGCCACCGCAGGCATCGG    926

P.CUBENSIS      930 TGCTCATATTGTGATGTGGACCGACTTTATGCAGTGGGGGAGCGAGGAAG    979
                    .||.|||.|.|.||.|||||||||.||.||.|||.||||||||||.|||.||||
P.CYANESCENS    927 CGCGCATCTCGTCATGTGGACTGATTTCATGAAGTGGGGGAACGATGAAG    976

P.CUBENSIS      980 AAAGGATAAATTTTGTGAAAAAGGGGGTAGCTGCCTTTCACGACGCCAGG   1029
                    |.|||..|.|.|||||.||.||.||.||.||.|...|||||.||.||.||
P.CYANESCENS    977 AGAGGGAAGAGTTTGTTAAGAAAGGCGTGGAAGCCTTCCATGAAGC----   1022

P.CUBENSIS     1030 GGCAACAACGACAAT------GGGGAAATTACGTCTACCTTAC---TGAA   1070
                    .||..|.||||||        |||||.|||||||||||    ||| ||||
P.CYANESCENS   1023 --AAATGAGGACAATAGAAACGGGGAGATTACGTCTA---TACTTGTGAA   1067

P.CUBENSIS     1071 GGAATCATC---CACTGCGTAA    1089
                    ||||.||||   ||||..|
P.CYANESCENS   1068 GGAAGCATCGCGCACTTAG---    1086
```

```
P.CUBENSIS       1 ATGCATATCAGAAATCCTTACCGTACACCAA-----TTGACTATCAAGCA   45
                   ||||||||||||.||.||.||||||     |.|    |||||||.||||||
P.CYANESCENS     1 ATGCATATCAGGAACCCATACCG-----CGATGGTGTTGACTACCAAGCA   45

P.CUBENSIS      46 CTTTCAGAGGCCTTCCCTCCCCTCAAGCCATTTGTGTCTGTCAATGCAGA   95
                   ||..|.||.||.||.||.||..|.|||||.|||..|||..|.||.|||.||||
P.CYANESCENS    46 CTCGCTGAAGCATTTCCGGCTCTCAAACCACATGTCACAGTAAATTCAGA   95

P.CUBENSIS      96 TGGTACCAGTTCTGTTGACCTCACTATCCCAGAAGCCCAGAGGGCGTTCA   145
                   ...|||.|..||..|.|||.|..||.|.|||||||||||.||...||..|
P.CYANESCENS    96 CAATACGACCTCCATCGACTTTGCTGTGCCAGAAGCCCAAAGACTGTATA   145

P.CUBENSIS     146 CGGCCGCTCTTCTTCATCGTGACTTCGGGCTCACCATGACCATACCAGAA   195
                   |.||.||.|||||.||.||.||.|||||.||.||.||.||.||..|.||.|||
P.CYANESCENS   146 CAGCTGCCCTTCTACACCGGGATTTCGGTCTTACGATCACACTCCCGGAA   195

P.CUBENSIS     196 GACCGTCTGTGCCCAACAGTCCCCAATAGGTTGAACTACGTTCTGTGGAT   245
                   |||||||.||.||.||||||.||.|||.||.|.|||||.||.||.||||.|
P.CYANESCENS   196 GACCGTCTTTGTCCGACAGTGCCTAATCGGCTCAACTATGTCCTTTGGGT   245

P.CUBENSIS     246 TGAAGATAT-TTTCAACTACAC----GAACAAAACCCTCGGCCTGTCGGA   290
                   ||||||||| .||.||.| |||     |    |..|.|||||.||..||||
P.CYANESCENS   246 TGAAGATATCCTTAAAGT-CACTTCTG----ATGCTCTCGGTCTTCCGGA   290

P.CUBENSIS     291 TGACCGTCCTATTAAAGGCGTTGATATTGGTACAGGAGCCTCCGCAATTT   340
                   |.|.||||...||||.||..|.|||||.||.||.||.||.||.||.||.|
P.CYANESCENS   291 TAATCGTCAAGTTAAGGGGATCGATATCGGAACTGGCGCATCAGCGATAT   340

P.CUBENSIS     341 ATCCTATGCTTGCCTGTGCTCGGTTCAAGGCATGGTCTATGGTTGGAACA   390
                   |||.|||||.||.||.||..||||.||.|||.||||||||.||||||.||||
P.CYANESCENS   341 ATCCCATGCTCGCATGCTCTCGTTTTAAGACATGGTCCATGGTTGCAACA   390

P.CUBENSIS     391 GAGGTCGAGAGGAAGTGCATTGACACGGCCCGCCTCAATGTCGTCGCGAA   440
                   |||||.||...||||||.|||||||||.||.||.|||||.|||.|.||.||
P.CYANESCENS   391 GAGGTAGACCAGAAGTGTATTGACACTGCTCGTCTCAACGTCATTGCCAA   440

P.CUBENSIS     441 CAATCTCCAAGACCGTCTCTCGATATTAGAGACATCCATTGATGGTCCTA   490
                   |||.||||||||.|||||||.|||||||.|.||..|||..||.|||.|.||||||||||
P.CYANESCENS   441 CAACCTCCAAGAACGTCTCGCAATTATAGCCACCTCCGTCGATGGTCCTA   490

P.CUBENSIS     491 TTCTCGTCCCCATTTTCGAGGCGACTGAAGAATACGAATACGAGTTTACT   540
                   |.||.||||||.|.|.||..|||||||.|....||.|...||.|||||.|||||.
P.CYANESCENS   491 TACTTGTCCCCCTCTTGCAGGCGAATTCTGATTTTGAGTACGATTTTACG   540

P.CUBENSIS     541 ATGTGTAACCCTCCATTCTACGACGGTGCTGCCGATATGCAGACTTCGGA   590
                   |||||||||.||.||.||||||||||.||.||.||||||||.||||||||.|||||
P.CYANESCENS   541 ATGTGTAATCCGCCCTTCTACGATGGGGCATCCGACATGCAGACATCGGA   590

P.CUBENSIS     591 TGCTGCCAAAGGATTTGGATTTGGCGTGGGCGCTCCCCATTCTGGAACAG   640
                   ||||||.||.||.||||||||||.||.|||..||||||.|||.|.||.||.|
P.CYANESCENS   591 TGCTGCGAAGGGGTTTGGATTCGGTGTGAACGCTCCGCATACCGGCACGG   640

P.CUBENSIS     641 TCATCGAAATGTCGACTGAGGGAGGTGAATCGGCTTTCGTCGCTCAGATG   690
                   |...||||.|||.|.|.||.|||||||||||||||||||.||||||.||.||.||.|||
P.CYANESCENS   641 TGCTCGAGATGGCCACCGAGGGAGGTGAATCGGCCTTCGTAGCCCAAATG   690

P.CUBENSIS     691 GTCCGTGAGAGCTTGAAGCTTCGAACACGATGCAGATGGTACACGAGTAA   740
                   |||||.||.||.|||||.|||||.|||||||||||||.||||.|||||||||||
P.CYANESCENS   691 GTCCGCGAAAGTTTGAATCTTCAAACACGATGCAGGTGGTTCACGAGTAA   740
```

FIG. 3

```
P.CUBENSIS      741 CTTGGGAAAGCTGAAATCCTTGAAAGAAATAGTGGGGCTGCTGAAAGAAC      790
                    .|||||.||..||||.||||||.|.|||||.||||||||||||..|||||
P.CYANESCENS    741 TTTGGGGAAATTGAAGTCCTTGTACGAAATTGTGGGGCTGCTGCGAGAAC      790

P.CUBENSIS      791 TTGAGATAAGCAACTATGCCATTAACGAATACGTTCAGGGGTCCACACGT      840
                    .|.|||||||||.|||||.||.||.|||||||||||.||.||..|||||.|||
P.CYANESCENS    791 ATCAGATAAGTAACTACGCAATCAACGAATACGTCCAAGGAGCCACTCGT      840

P.CUBENSIS      841 CGTTATGCCGTTGCGTGGTCTTTCACTGATATTCAACTGCCTGAGGAGCT      890
                    ||.|||||..||||.|||||.||||..|||.|||.||||||||||..|..|
P.CYANESCENS    841 CGATATGCGATTGCATGGTCGTTCATCGATGTTCGACTGCCTGATCATTT      890

P.CUBENSIS      891 TTCTCGTCCCTCTAACCCCGAGCTCAGCTCTCTTTTCTAG      930
                    .||.|||||.|||||||||||.||.||||||||||||||||
P.CYANESCENS    891 GTCCCGTCCATCTAACCCCGACCTAAGCTCTCTTTTCTAG      930
```

```
P.CUBENSIS       1 ATGATCGCTGTACTAT---TCTCCTTCGTCATTGCAGGATGCATATACTA    47
                   |||||   |||.||||    ||||..|||||.||||||||||||||||||||
P.CYANESCENS     1 ATGAT---TGTTCTATTGGTCTCGCTCGTCCTTGCAGGATGCATATACTA    47

P.CUBENSIS      48 ---CATCGTTTCTCGTAGAGTGAGGCGGTCGCGCTTGCCACCAGGGCCGC    94
                      ||.||   |||||||||||.|||||.|||||||||.|||||.||.||||
P.CYANESCENS    48 CGCCAACG---CTCGTAGAGTAAGGCGCTCGCGCTTACCACCGGGCCCGC    94

P.CUBENSIS      95 CTGGCATTCCTATTCCCTTCATTGGGAACATGTTTGATATGCCTGAAGAA   144
                   |||||||.||..|.||||||||||||||||.||||||||||||||..|||.
P.CYANESCENS    95 CTGGCATACCACTGCCCTTCATTGGGAATATGTTTGATATGCCTTCAGAG   144

P.CUBENSIS     145 TCTCCATGGTTAACATTTCTACAATGGGGACGGGATTACAGTCTGTC---   191
                   ||.||.|||||||.|||||||.||||||.||||||||||||.||..||..|||
P.CYANESCENS   145 TCACCGTGGTTAAGATTTCTTCAATGGGGACGGGACTATCGTACGTCAAA   194

P.CUBENSIS     192 --TTGCCGCGTTGACTTCTAATATATGAACAGCTAAT--ATATTGTC-AG   236
                     |||        ||.|   ||.||..||..|||| |||  |.||  ||
P.CYANESCENS   195 CATTG----------TTTT--GATTTGCGCATTTAATTGATA-TCTCTAG   231

P.CUBENSIS     237 ACACCGATATTCTCTACGTGGATGCTGGAGGGACAGAAATGGTTATTCTT   286
                   ||||.|||||.||.|||.||.||||||||.||.||.|||||...||||||.
P.CYANESCENS   232 ACACTGATATCCTTTACTTGAATGCTGGCGGAACGGAAATAATTATTCTG   281

P.CUBENSIS     287 AACACGTTGGAGACCATTACCGATCTATTAGAAAAGCGAGGGTCCATTTA   336
                   |||||..|||||..|.||.|||||..|.||.|||||||||||||||.||.||
P.CYANESCENS   282 AACACACTGGATGCTATAACCGACTTGTTGGAAAAGCGAGGGTCGATGTA   331

P.CUBENSIS     337 TTCTGGCCGGTGAGCTGATGTTGAGTTTTTT--------GCAATT---GA   375
                   |||.||.|||||.||.||.||.||.|..||.|||       |..|||   ||
P.CYANESCENS   332 TTCGGGTCGGTAAGTTGTTGCTATGTCTTTTATGGATAAGATATTAAAGA   381

P.CUBENSIS     376 ATTTGTGGTCACACGTTTCCAGACTTGAGAGTACAATGGTCAACGAACTT   425
                   |..||        |||    ||||||.||||||.||.||||||.|||||||.
P.CYANESCENS   382 AGATG--------CGT---CAGACTCGAGAGCACCATGGTGAACGAACTC   420

P.CUBENSIS     426 ATGGGGTGGGAGTTTGACTTAGGGTTCATCACATACGGCGACAGGTGGCG   475
                   ||||||||||||||.|||||.||.||.|||||.||.||.||.||.||.|||||
P.CYANESCENS   421 ATGGGGTGGGAGTTCGACTTGGGATTCATAACCTATGGTGAAAGATGGCG   470

P.CUBENSIS     476 CGAAGAAAGGCGCATGTTCGCCAAGGAGTTCAGTGAGAAGGGCATCAAGC   525
                   ||||||||||.|||||||||||||||||||||||||||.||.||...||||.||
P.CYANESCENS   471 CGAAGAAAGACGCATGTTCGCCAAGGAGTTCAGCGAAAAAAACATCAGGC   520

P.CUBENSIS     526 AATTTCGCCATGCTCAAGTGAAAGCTGCCCATCAGCTTGTCCAACAGCTT   575
                   ||||.||||||.||.|||.|.|||||||||.||||||||||.|...|||||.
P.CYANESCENS   521 AATTCCGCCACGCCCAAATTAAAGCTGCCAATCAGCTTGTTCGGCAGCTG   570

P.CUBENSIS     576 ACCAAAACGCCAGACCGCTGGGCACAACATATTCGCCAGTAAGTACTACT   625
                   |.||||||||||||.||.|||.|.||.||.||.||.||.||.||||||||..||
P.CYANESCENS   571 ATCAAAACGCCAGATCGTTGGTCGCAGCACATCCGGCAGTAAGTTGTA--   618

P.CUBENSIS     626 TGAGGAAAATAGCGTAC--GCTTC---------GCTGACC----------GG   656
                   ||||||..| ||  ||.|| |||||||        ||
P.CYANESCENS   619 -----AAAATATAG-ACAAGCATCGAGTCGAGGCTGACCATTAATTATGG   662

P.CUBENSIS     657 TCCGTACATCAAAGTCAGATAGCGGCAATGTCACTGGATATTGGTTATGG   706
                   |          |.||||||||||||.||.|||||.||.||.||||||||||||
P.CYANESCENS   663 T---------ACAGTCAGATAGCAGCCATGTCTCTAGACATTGGTTATGG   703
```

FIG. 4

```
P.CUBENSIS      707 AATTGATCTTGCAGAAGACGACCCTTGGCTGGAAGCGACCCATTTGGCTA   756
                    | | | | | | | | | .| | | | | .| | .| | | | | .| | | .| .| .| | | .| | | | | ..| .| | | |
P.CYANESCENS    704 AATTGATCTCGCAGAGGATGACCCCTGGATTGCAGCAACCCAGCTAGCTA   753

P.CUBENSIS      757 ATGAAGGCCTCGCCATAGCATCAGTGCCGGGCAAATTTTGGGTCGATTCG   806
                    | .| | | | | .| | | | | ..| | | .| | | | | .| | | | | | ..| | .| | | | | | | | .| | .
P.CYANESCENS    754 ACGAAGGGCTCGCCGAAGCTTCAGTACCGGGCAGTTTCTGGGTCGACTCA   803

P.CUBENSIS      807 TTCCCTTCTCGTGAG---CATCCTTCTTCTATGTAGGAAGGGA--AGGAG   851
                    | | | | | ..| .| | | | | |     ..| .| | | | .| | .| | | |     | |   | ..| |
P.CYANESCENS    804 TTCCCCGCCCGTGAGTGCTTTTCTTCCTCCAT-TA------GACTACTAG   846

P.CUBENSIS      852 TC---TAACAAGTG--------TTAGTAAAATACCTTCCTGCTTGGTTCC   890
                    | |     .| .| | ..| |         | .| | | .| | | | | | | | | | | | .| .| | | .| .|
P.CYANESCENS    847 TCACGAATCATTTGATTTCTACTCAGTCAAATACCTTCCTTCATGGCTTC   896

P.CUBENSIS      891 CAGGTGCTGTCTTCAAGCGCAAAGCGAAGGTCTGGCGAGAAGCCGCCGAC   940
                    | .| | | | | .| .. .| | | | | | | | | | | | | | .| | | | | .| | | ...| | | | ..| | .| | |
P.CYANESCENS    897 CTGGTGCAGGATTCAAGCGCAAAGCAAAGGTATGGAAGGAAGGTGCTGAC   946

P.CUBENSIS      941 CATATGGTTGACATGCCTTATGAAACTATGAGGAAATTAGCAGTTAGTCA   990
                    | | | | | | | | ..| | | | | | | .| | | | | | | | .| | | | ..| | | | | ..| .| | |
P.CYANESCENS    947 CATATGGTGAACATGCCGTATGAAACGATGAAAAAATTGACTGT------   990

P.CUBENSIS      991 AATGCGTTCTCCC---------CGTATTTTTTC----AAT---ACT----   1020
                    | | | ...| | | .| |         | | | |         |     | | |     | | |
P.CYANESCENS    991 -ATGTTATCTTCCGTGATGGCTCGTA------CGGAGAATTGCACTGATT   1033

P.CUBENSIS     1021 -CTA-ACTTCAGCTCACAGCCTCAAGGATTGACTCGTCCGTCGTATGCTT   1068
                    | | |   | | |         | | | | ..| | | | | | .| | | .| .| | .| | .| | .| | | | | | .|
P.CYANESCENS   1034 GCTACACT-------ACAGGTTCAAGGCTTGGCCCGACCTTCATATGCCT   1076

P.CUBENSIS     1069 CAGCTCGTCTGCAAGCCATGGATCTCAACGGTGACCTTGAGCATCAAGAA   1118
                    | | | | | | | | | | | | | .| | | | | | | | .| .| .| .| | .| | .| | .| | | | | | | | | | .| | |
P.CYANESCENS   1077 CAGCTCGTCTGCAGGCCATGGACCCCGATGGCGATCTCGAGCATCAGGAA   1126

P.CUBENSIS     1119 CACGTAATCAAGAACACAGCCGCAGAGGTTAATGTCGGTAAGTCA-----   1163
                    | | | | | .| | | | ..| | | | | | | | ..| .| | | | | .| | | | | | | | | | | | | .|
P.CYANESCENS   1127 CACGTGATCAGAAACACAGCGACTGAGGTCAATGTCGGTAAGTTACTAGT   1176

P.CUBENSIS     1164 AAAGCGTCCGTCGGCAATTCAA-AATTCAGGCGCTAAAGTGGGTCTTC--   1210
                    | | .| | .| | .| | | | | .| | | .| | | | | .| | | |   | | | | | | | |   | .| .| .| .|
P.CYANESCENS   1177 AATGCCT-CTTCGGCTATTAAAGAATT-GGGCGCTAA--TTGATTTGCAT   1222

P.CUBENSIS     1211 TCACCAAGGTGGAGGCGATACTGTAAGGATTTCTCAATC-GTTA------   1253
                    | .| | | .| | | .| | | | | .| | | | | .| | | | ..| | ..| | |     | | .| |
P.CYANESCENS   1223 TGACCTAGGCGGAGGTGATACGGTAAATATACCTC---CTGCTACTACCC   1269

P.CUBENSIS     1254 GAGTATAAGTGTTCTAATGCAGTACATACTCCAC------CAACCAGACT   1297
                    | | .| ..|     .| | | | |         | | | | | .| | ..| |         | | ..| | | | | |
P.CYANESCENS   1270 GACTGCA--CGTTCT-------TACATGCTTTACATTTAACATTCAGACT   1310

P.CUBENSIS     1298 GTCTCTGCTATGTCTGCGTTCATCTTGGCCATGGTGAAGTACCCTGAGGT   1347
                    | | .| | | | | | .| | | | .| | .| | .| | .| | | | | | | | | | | | | | .| | .| | .| | .| | .| |
P.CYANESCENS   1311 GTTTCTGCTGTGTCAGCCTTTATTTTGGCCATGGTCAAATATCCAGAAGT   1360
```

```
P.CUBENSIS      1348 CCAGCGAAAGGTTCAAGCGGAGCTTGATGCTCTGACCAATAACGG-----  1392
                     .||.||..|.||.|||||.||.||.|||||.||.||||..||.||
P.CYANESCENS    1361 TCAACGCCAAGTCCAAGCAGAACTGGATGCACTCACCAGCAAAGGAGTTG  1410

P.CUBENSIS      1393 --CCAAATTCCTGACTATGACGAAGAAGATGACTCCTTGCCATACCTCAC  1440
                       ||||     ||||||||||||||||.||||||||||||||||.||
P.CYANESCENS    1411 TCCCAA-------ACTATGACGAAGAAGACGACTCCTTGCCATACCTTAC  1453

P.CUBENSIS      1441 CGCATGTATCAAGGAGCTTTTCCGGTGGAATCAAATCGCACCCCTCGCTA  1490
                     .||.||..|||||||..|.||.||.|||||.|||||.|||||||.||||
P.CYANESCENS    1454 GGCTTGCGTCAAGGAAATCTTTCGATGGAACCAAATAGCACCCCTTGCTA  1503

P.CUBENSIS      1491 TACCGCACAAAT----TAATGAAGGACGACGTGTACCGCGGGTATCTGAT  1536
                     |.||.|    ||   |.||.||.|||||.||.||.||.||||||||.||
P.CYANESCENS    1504 TCCCTC----ATCGGCTGATCAAAGACGATGTTTATCGTGGGTATCTCAT  1549

P.CUBENSIS      1537 TCCCAAGAACACTCTAGTCTTCGCAAACACCTGGTGAGG----CTGTCCA  1582
                     .||.|||||..||.|.||||.|||.|||.|.||||..||    |||| |
P.CYANESCENS    1550 ACCAAAGAATGCTTTGGTCTACGCCAACTCATGGTATGGCGTTCTGT--A  1597

P.CUBENSIS      1583 TTC-----ATTCCTAGTACATCCGTTGCCCCACTAATAGCATCTTGATAA  1627
                     |||     ||||.| |.|||||||     |.||          |||.|.|
P.CYANESCENS    1598 TTCCCTATATTCAT-GCACATCCG----CTCA-----------TTGTTTA  1631

P.CUBENSIS      1628 C----AGGGCAGTATTAAACGATCCAGAAGTCTATCCAGATCCCTCTGTG  1673
                     |     |||||.||.||.||.||.||||||.|...||.|||.|||||||.|
P.CYANESCENS    1632 CTCGTAGGGCTGTGTTGAATGACCCAGAGGAGTACCCAAATCCCTCTGAG  1681

P.CUBENSIS      1674 TTCCGCCCAGAAAGATATCTTG-GTCCTGACGGGAAGCCTGATAACACTG  1722
                     |||||.||||||.||||| |||| |...||||||||.|||||.||....||.|
P.CYANESCENS    1682 TTCCGACCAGAACGATAT-TTGAGCTCTGACGGAAAGCCCGACCCAACGG  1730

P.CUBENSIS      1723 TACGCGACCCACGTAAAGCGGCATTTGGCTATGGACGACGAAATTGGTAA  1772
                     |.||.||.||.||.||||||.|||||||||||||.|||||.||.|||||||
P.CYANESCENS    1731 TCCGTGATCCCCGCAAAGCAGCATTTGGCTATGGTCGACGCAACTGGTAA  1780

P.CUBENSIS      1773 GTGCGCT------TTCAGAACCCCCCCTTCCGTTGACTAGTGCCATGCGC  1816
                        |||     ||||.|.|          |||||   |...||.|| |
P.CYANESCENS    1781 ----GCTTTTCAATTCATATC------------TGACT--TCACAAGC-C  1811

P.CUBENSIS      1817 GCATACAATATCGCTATTGATCTGATATAACTTCCCTGCGGCATTTATTT  1866
                     ||                .||||||||| ..|||..|||||||||||
P.CYANESCENS    1812 GC--------------CGATCTGAT-GCACTAACCTGCGGCAT------  1839

P.CUBENSIS      1867 TGGCATTCCTTTAGTCCCGGAATTCATCTAGCGCAGTCGACGGTTTGGAT  1916
                        ||.||.|||||||||||||||.||.||.||.||.|||||||||.|||||
P.CYANESCENS    1840 -----TTTCTGTAGTCCCGGAATCCACCTGGCACAATCGACGGTATGGAT  1884

P.CUBENSIS      1917 TGCAGGGGCAACCCTCTTATCAGCGTTCAATATCGAGCGACCTGTCGATC  1966
                     |||.||.||.||.||.||..|.||.|...|||||||||||.||.|||||.|||.
P.CYANESCENS    1885 TGCTGGAGCCACTCTTCTCTCGGTATTCAATATCGAACGTCCTGTTGATG  1934

P.CUBENSIS      1967 AGAATGGGAAGCCCATTGACATACCGGCTGA-TTTTACTACAGGATTCTT  2015
                     .||||||.||.||||||.|||||.|||||| || .||.||||||.||||||||
P.CYANESCENS    1935 GGAATGGAAAACCCATCGACATCCCGGC-GACGTTCACTACCGGATTCTT  1983
```

```
P.CUBENSIS      2016 CAGGTAGCTAATTTCCGTCTT---------------TGTGTGCATAATA   2049
                     ||||||...||||....||||                ||..|||||
P.CYANESCENS    1984 CAGGTATTCAATTAAGCTCTTGCCCTAGGGCATGGAGTGATTGCAT----   2029

P.CUBENSIS      2050 CCCC--TAACGA---CGCACGTTTACCTTTTTGTAAAGACACCCAGTGCC   2094
                     |.|   ||||||   .|.|| |||||            |||||.||.|.|||
P.CYANESCENS    2030 -CTCATTAACGATATGGAAC-TTTAC---------AGACATCCCGAGCC    2067

P.CUBENSIS      2095 TTTCCAGTGCAGGTTTGTTCCTCGAACAGAGCA-AGTCTCACAGTCGGTA   2143
                     ||||||||||||.|||||.|||||.||..||.| |.||| |.|.||.||.
P.CYANESCENS    2068 TTTCCAGTGCAGATTTGTCCCTCGCACTCAGGAGATTCT-AAAATCCGTT   2116

P.CUBENSIS      2144 TCCGGACCCTGA    2155
                     |||||.
P.CYANESCENS    2117 TCCGGT------    2122
```

```
P.CUBENSIS        1  MQVIPACNSAAIRSLCPTPESFRNMGWLSVSDAVYSEFIGELATRASNRN     50
                     |||:|||.|:|:::|||:|||:||.:|||..||.||:|||.:|..|..|..
P.CYANESCENS      1  MQVLPACQSSALKTLCPSPEAFRKLGWLPTSDEVYNEFIDDLTGRTCNEK     50

P.CUBENSIS       51  YSNEFGLMQPIQEFKAFIESDPVVHQEFIDMFEGIQDSPRNYQELCNMFN    100
                     ||::..|::||||:||.|||:||:|:||||.|||||:.||.||.||||||||
P.CYANESCENS     51  YSSQVTLLKPIQDFKTFIENDPIVYQEFISMFEGIEQSPTNYHELCNMFN    100

P.CUBENSIS      101  DIFRKAPVYGDLGPPVYMIMAKLMNTRAGFSAFTRQRLNLHFKKLFDTWG    150
                     ||||||||:|||||||||||||::|||:|||||||::.||.|||||||||
P.CYANESCENS    101  DIFRKAPLYGDLGPPVYMIMARIMNTQAGFSAFTKESLNFHFKKLFDTWG     150

P.CUBENSIS      151  LFLSSKDSRNVLVADQFDDRHCGWLNERALSAMVKHYNGRAFDEVFLCDK    200
                     ||||||:|||||||||||||:|.||.:|||.:||.:::|.||.|::||:||:
P.CYANESCEN     151  LFLSSKNSRNVLVADQFDDKHYGWFSERAKTAMMINYPGRTFEKVFICDE    200

P.CUBENSIS      201  NAPYYGFNSYDDFFNRRFRNRDIDRPVVGGVNNTTLISAACESLSYNVSY    250
                     :.||:||.||||||||||||::|.||||||||.:||||.|||||||||||:
P.CYANESCENS    201  HVPYHGFTSYDDFFNRRFRDKDTDRPVVGGVTDTTLIGAACESLSYNVSH    250

P.CUBENSIS      251  DVQSLDTLVFKGETYSLKHLLNNDPFTPQFEHGSILQGFLNVTAYHRWHA    300
                     :||||||||.|||.|||||||||:||||||||||||||:|||||||||||:
P.CYANESCENS    251  NVQSLDTLVIKGEAYSLKHLLHNDPFTPQFEHGSIIQGFLNVTAYHRWHS    300

P.CUBENSIS      301  PVNGTIVKIINVPGTYFAQAPSTIGDPIPDNDYDPPPYLKSLVYFSNIAA    350
                     ||||||||||:||||||||||.|||.||||||.||||||||||||||||||
P.CYANESCENS    301  PVNGTIVKIVNVPGTYFAQAPYTIGSPIPDNDRDPPPYLKSLVYFSNIAA    350

P.CUBENSIS      351  RQIMFIEADNKEIGLIFLVFIGMTEISTCEATVSEGQHVNRGDDLGMFHF    400
                     ||||||||||:||||||||||||||||||||||.||||||||||||||||
P.CYANESCENS    351  RQIMFIEADNKDIGLIFLVFIGMTEISTCEATVCEGQHVNRGDDLGMFHF    400

P.CUBENSIS      401  GGSSFALGLRKDCRAEIVEKFTEPGTVIRINEVVAALKA        439
                     |||||||||||.:|:|:|||.:||||||||||:||:::.
P.CYANESCENS    401  GGSSFALGLRKDSKAKILEKFAKPGTVIRINELVASVRK        439
```

FIG. 5

```
P.CUBENSIS       1 MAFDLKTEDGLITYLTKHLSLDVDTSGVKRLSGGFVNVTWRIKLNAPYQG        50
                   |.||||||:||::|||||||||||..:|||||||||||||||:.|||||.|
P.CYANESCENS     1 MTFDLKTEEGLLSYLTKHLSLDVAPNGVKRLSGGFVNVTWRVGLNAPYHG        50

P.CUBENSIS      51 HTSIILKHAQPHMSTDEDFKIGVERSVYEYQAIKLMMANREVLGGVDGIV       100
                   ||||||||||||:|:|.||||||||||.|||||:|::.||..:||..|..|
P.CYANESCENS    51 HTSIILKHAQPHLSSDIDFKIGVERSAYEYQALKIVSANSSLLGSSDIRV       100

P.CUBENSIS     101 SVPEGLNYDLENNALIMQDVGKMKTLLDYVTAKPPLATDIARLVGTEIGG       150
                   ||||||:||:.||||||||||.|||||||||||||::.:||.|||::||.
P.CYANESCENS   101 SVPEGLHYDVVNNALIMQDVGTMKTLLDYVTAKPPISAEIASLVGSQIGA       150

P.CUBENSIS     151 FVARLHNIGRERRDDPEFKFFSGNIVGRTTSDQLYQTIIPNAAKYGVDDP       200
                   |:||||:|||.:|..:||||||||||||||DQLYQTIIPNAAKY|:|||
P.CYANESCENS   151 FIARLHNLGRENKDKDDFKFFSGNIVGRTTADQLYQTIIPNAAKYGIDDP       200

P.CUBENSIS     201 LLPTVVKDLVDDVMHSEETLVMADLWSGNILLQLEEGNPSKLQKIYILDW       250
                   :||.|||:||::||:|||||:|||||WSGNILL|.:| |.::|.:|:::||
P.CYANESCENS   201 ILPIVVKELVEEVMNSEETLIMADLWSGNILLQFDE-NSTELTRIWLVDW       249

P.CUBENSIS     251 ELCKYGPASLDLGYFLGDCYLISRFQDEQVGTTMRQAYLQSYARTSKHSI       300
                   ||||||||.|||:|||||||:|::||||:.|||:|||||||:|||..|..|
P.CYANESCENS   250 ELCKYGPPSLDMGYFLGDCFLVARFQDQLVGTSMRQAYLKSYARNVKEPI       299

P.CUBENSIS     301 NYAKVTAGIAAHIVMWTDFMQWGSEEERINFVKKGVAAFHDARGNNDNGE       350
                   ||||.|||||.||:|||||||:||::|||..||||||.|||:|..:|.|||
P.CYANESCENS   300 NYAKATAGIGAHLVMWTDFMKWGNDEEREEFVKKGVEAFHEANEDNRNGE       349

P.CUBENSIS     351 ITSTLLKESSTA*       363
                   |||.|:||:|..
P.CYANESCENS   350 ITSILVKEASRT*       362
```

FIG. 6

```
P.CUBENSIS       1 MHIRNPYRTPIDYQALSEAFPPLKPFVSVNADGTSSVDLTIPEAQRAFTA    50
                   |||||||||..:|||||:||||.|||.|:||:|.|:|:|..:||||.:||
P.CYANESCENS     1 MHIRNPYRDGVDYQALAEAFPALKPHVTVNSDNTTSIDFAVPEAQRLYTA    50

P.CUBENSIS      51 ALLHRDFGLTMTIPEDRLCPTVPNRLNYVLWIEDIFNYTNKTLGLSDDRP   100
                   |||||||||||:|:|||||||||||||||||||:|||...|:..|||.|:|.
P.CYANESCENS    51 ALLHRDFGLTITLPEDRLCPTVPNRLNYVLWVEDILKVTSDALGLPDNRQ   100

P.CUBENSIS     101 IKGVDIGTGASAIYPMLACARFKAWSMVGTEVERKCIDTARLNVVANNLQ   150
                   :||:|||||||||||||||:|||.||||.|||::|||||||||:|||||
P.CYANESCENS   101 VKGIDIGTGASAIYPMLACSRFKTWSMVATEVDQKCIDTARLNVIANNLQ   150

P.CUBENSIS     151 DRLSILETSIDGPILVPIFEATEEYEYEFTMCNPPFYDGAADMQTSDAAK   200
                   :||:|:.||:|||||||:..:|..::||:|||||||||||||:||||||||
P.CYANESCENS   151 ERLAIIATSVDGPILVPLLQANSDFEYDFTMCNPPFYDGASDMQTSDAAK   200

P.CUBENSIS     201 GFGFGVGAPHSGTVIEMSTEGGESAFVAQMVRESLKLRTRCRWYTSNLGK   250
                   ||||||.|||:|||:||:|:|||||||||||||||||.|:|||||:|||||
P.CYANESCENS   201 GFGFGVNAPHTGTVLEMATEGGESAFVAQMVRESLNLQTRCRWFTSNLGK   250

P.CUBENSIS     251 LKSLKEIVGLLKELEISNYAINEYVQGSTRRYAVAWSFTDIQLPEELSRP   300
                   ||||.||||||:|.:||||||||||||:|||||:|||||.|::||:.||||
P.CYANESCENS   251 LKSLYEIVGLLREHQISNYAINEYVQGATRRYAIAWSFIDVRLPDHLSRP   300

P.CUBENSIS     301 SNPELSSLF*      310
                   |||:||||||
P.CYANESCENS   301 SNPDLSSLF*      310
```

FIG. 7

```
P.CUBENSIS       1 MIAVLFSFVIAGCIYYIVSRRVRRSRLPPGPPGIPIPFIGNMFDMPEESP    50
                   ||.:|.|.|:||||||||..:|||||||||||||||||:|||||||||.|||
P.CYANESCENS     1 MIVLLVSLVLAGCIYYANARRVRRSRLPPGPPGIPLPFIGNMFDMPSESP    50

P.CUBENSIS      51 WLTFLQWGRDYSLS-----CRVDF*YM------------NS*YIVRHRYS    83
                   ||.|||||||||..|     |..:  |:            .. ....|...
P.CYANESCENS    51 WLRFLQWGRDYRTSNIVLICAFN-*YL*TLISFT*MLAERK*LF*THWML    99

P.CUBENSIS      84 LRGCWRDRNGYS*HVGDHYRSIR--KARVHLFWPVS*C*VFCN*I-----   126
                   ...||:...        |.||   |..:.|.|              |
P.CYANESCENS   100 *PTCWKSEG----------RCIRVGKLLLCLLW-----------IRY*RR   128

P.CUBENSIS     127 C---GHTFPDLRVQWSTNLWGGSLT*GSSHT------ATGGAKKGACSPR   167
                   |    ..|..:.:.|..:|  |.:|.|....      |...::|.....|
P.CYANESCENS   129 CVRLESTMVNELMGWEFDL--GFITYGERWREERRMFAKEFSEKNIRQFR   176

P.CUBENSIS     168 SSVRRASSNFAMLK*KLP-----------ISLSNSLPKRQTAGHNIFASK   206
                   .:..:|::.....|.|            :.:..|:..|
P.CYANESCENS   177 HAQIKAANQLVRQLIKTPDRWSQHIRQ*VVKI*TSIESR-----------   215

P.CUBENSIS     207 YYLRKIAYASLTGPYIKVR*RQCHWILVMELILQKTTLGWKRPIWLMKAS   256
                                 ||..|..|| :.|...|||||||.|:.|.|..::|.|.|
P.CYANESCENS   216 ----------LTINYGTVR*QPCL*TLVMELISQRMTPGLQQPS*LTKGS   255

P.CUBENSIS     257 P*HQCRANFGSIRSLLVSILL--LCRKGRSL-TSVSKIPSCLVPRCCLQA   303
                   |..|.||..||..|..||..|  |....|.: ..:|:|||.:...|.:||
P.CYANESCENS   256 PKLQYRAVSGSTHSPPVSAFLPPLDY*SRII*FLLSQIPSFMASWCRIQA   305

P.CUBENSIS     304 QSEGLARSRRPYG*HAL*NYEEIS----------------S*SNAFSPY   336
                   ||:|:.....|||.||: |.|:|.                :..:..|.
P.CYANESCENS   306 QSKGMEGRC*PYGEHAV*NDEKIDCMLSSVMARTENCTDCYTTGSRLGPT   355

P.CUBENSIS     337 FFNTLTSA-HSLKD*LVRRMLQLVCKPWISTVTLSIKNT*SRTQPQRLMS   385
                   |....:|| |..:            |.|.. |.|:.|:...
P.CYANESCENS   356 FICLSSSAGHGPR-------------WRSRA--------SGTRDQKHSD   383

P.CUBENSIS     386 ------VSQKRPSAIQNSGAKVGLLTKVEAIL*GFLNR*SISVLMQYILH   429
                         |:....|||:..||....||..|.|.        .|:|.
P.CYANESCENS   384 *GQCR*VTSNASSAIKELGAN*FALT*AEVIR*-----------IYLLL   421

P.CUBENSIS     430 QPDCLCYVCVHLGHGEVP*GPAKGSSGA*CSDQ*RPNS*L*RRR*LLAIP   479
                   .|||.....:||..                            |..||..|
P.CYANESCENS   422 LPDCTFLHALHLTF---------------------------RLFLLCQP   443

P.CUBENSIS     480 ----------------HRMYQGAFPVESNRTPRYTAQINEGRRVP----   508
                                   :..|:..|..:....|.:.|         |
P.CYANESCENS   444 LFWPWSNIQKFNAKSKQNWMHSPAKELSQTMTKKTT---------PCHTL   484

P.CUBENSIS     509 RVSDSQEHSSLRKH------------LVRLSIHS*YIRCPTNSILITGQ   545
                   |::..:.....:.|            :|.:|........||:.:...
P.CYANESCENS   485 RLASRKSFDGTK*HPLLSLIG*SKTMFIVGISYQRMLWSTPTHGMAFCIP   534

P.CUBENSIS     546 Y----------------*TIQKSIQIPLC--------------SAQKD   563
                   |                ..:.||:.:|..              |.|..
P.CYANESCENS   535 YIHAHPLIVYS*GCVE*PRGVPKSL*VPTRTIFEL*RKARPNGP*SPQSS   584

P.CUBENSIS     564 ILVLTGSLITLYATHVKRHLAMDDEIGKCAFRTPPSVD*CHARIQYRY*S   613
                   |.:.:..|::.::..|...|            .||.   |
P.CYANESCENS   585 IWLWSTQLVS-FSIHI*LH-------------KPPI--*C----------   608
```

FIG. 8

```
P.CUBENSIS      614 DITSLRHLF--------------WHSFSPGIHLAQSTVWIAGATLLSAFN    649
                    |:|||..              |...|.||....|..|         .:.
P.CYANESCENS    609 --TNLRHFL*SRNPPGTIDGMDCWSHSSLGIQYRTSC*W--------EWK    648

P.CUBENSIS      650 IER-PVDQNGKPIDIPADFTTGFFR*LISVFVCIIPLTTH-VYLFVKTPS    697
                    ..| |.|.:.:.:.:        |. .::::...:|  .:| .|..::|..
P.CYANESCENS    649 THRHPGDVHYRILQV--------FN*ALALGHGVI--ASH*RYGTLQTSR    688

P.CUBENSIS      698 AFPVQVCSSNRASLTVGIRTLX    719
                    |||||:|.|:.......:..|.
P.CYANESCENS    689 AFPVQICPSHSGDSKIRFRX--    708
```

| | | |
|---|---|---|
| Psilocybin | $R = N\text{-}(CH_3)_2$ | |
| Baeocystin | $R = NH\text{-}CH_3$ | |
| Norbaeocystin | $R = NH_2$ | |
| Aeruginascin | $R = N^+\text{-}(CH_3)_3$ | |

| | | |
|---|---|---|
| Psilocin | $R^1 = OH$ | $R^2 = N\text{-}(CH_3)_2$ |
| Tryptamine | $R^1 = H$ | $R^2 = NH_2$ |
| 4-Hydroxytryptamine | $R^1 = OH$ | $R^2 = NH_2$ |
| *N,N*-Dimethyltryptamine | $R^1 = H$ | $R^2 = N\text{-}(CH_3)_2$ |

| | |
|---|---|
| L-Tryptophan | $R = H$ |
| 4-Hydroxy-L-tryptophan | $R = OH$ |

SEQUENCE LISTING

```
Sequence total quantity: 133
SEQ ID NO: 1              moltype = AA  length = 439
FEATURE                   Location/Qualifiers
source                    1..439
                          mol_type = protein
                          organism = Psilocybe cubensis
SEQUENCE: 1
MQVIPACNSA AIRSLCPTPE SFRNMGWLSV SDAVYSEFIG ELATRASNRN YSNEFGLMQP  60
IQEFKAFIES DPVVHQEFID MFEGIQDSPR NYQELCNMFN DIFRKAPVYG DLGPPVYMIM  120
AKLMNTRAGF SAFTRQRLNL HFKKLFDTWG LFLSSKDSRN VLVADQFDDR HCGWLNERAL  180
SAMVKHYNGR AFDEVFLCDK NAPYYGFNSY DDFFNRRFRN RDIDRPVVGG VNNTTLISAA  240
CESLSYNVSY DVQSLDTLVF KGETYSLKHL LNNDPFTPQF EHGSILQGFL NVTAYHRWHA  300
PVNGTIVKII NVPGTYFAQA PSTIGDPIPD NDYDPPPYLK SLVYFSNIAA RQIMFIEADN  360
KEIGLIFLVF IGMTEISTCE ATVSEGQHVN RGDDLGMFHF GGSSFALGLR KDCRAEIVEK  420
FTEPGTVIRI NEVVAALKA                                              439

SEQ ID NO: 2              moltype = DNA  length = 1320
FEATURE                   Location/Qualifiers
source                    1..1320
                          mol_type = other DNA
                          organism = Psilocybe cubensis
SEQUENCE: 2
atgcaggtga tacccgcgtg caactcggca gcaataagat cactatgtcc tactcccgag  60
tcttttagaa acatgggatg gctctctgtc agcgatgcgg tctacagcga gttcatagga  120
gagttggcta cccgcgcttc caatcgaaat tactccaacg agttcggcct catgcaacct  180
atccaggaat tcaaggcttt cattgaaagc gacccggtgg tgcaccaaga atttattgac  240
```

-continued

```
atgttcgagg gcattcagga ctctccaagg aattatcagg aactatgtaa tatgttcaac    300
gatatctttc gcaaagctcc cgtctacgga gaccttggcc ctcccgttta tatgattatg    360
gccaaattaa tgaacacccg agcgggcttc tctgcattca cgagacaaag gttgaacctt    420
cacttcaaaa aacttttcga tacctgggga ttgttcctgt cttcgaaaga ttctcgaaat    480
gttcttgtgg ccgaccagtt cgacgacaga cattgcggct ggttgaacga gcgggccttg    540
tctgctatgg ttaaacatta caatggacgc gcatttgatg aagtcttcct ctgcgataaa    600
aatgccccat actacggctt caactcttac gacgacttct ttaatcgcag atttcgaaac    660
cgagatatcg accgacctgt agtcggtgga gttaacaaca ccaccctcat ttctgctgct    720
tgcgaatcac tttcctacaa cgtctcttat gacgtccagt ctctcgacac tttagttttc    780
aaaggagaga cttattcgct taagcatttg ctgaataatg accctttcac cccacaattc    840
gagcatggga gtattctaca aggattcttg aacgtcaccg cttaccaccg atggcacgca    900
cccgtcaatg ggacaatcgt caaaatcatc aacgttccag gtacctactt tgcgcaagcc    960
ccgagcacga ttggcgaccc tatcccggat aacgattacg acccacctcc ttaccttaag   1020
tctcttgtct acttctctaa tattgccgca aggcaaatta tgtttattga agccgacaac   1080
aaggaaattg gcctcatttt ccttgtgttc atcggcatga ccgaaatctc gacatgtgaa   1140
gccacggtgt ccgaaggtca acacgtcaat cgtggcgatg acttgggaat gttccatttc   1200
ggtggttctt cgttcgcgct tggtctgagg aaggattgca gggcagagat cgttgaaaag   1260
ttcaccgaac ccgaacagt gatcagaatc aacgaagtcg tcgctgctct aaaggcttag   1320
```

SEQ ID NO: 3          moltype = AA   length = 362
FEATURE               Location/Qualifiers
source                1..362
                      mol_type = protein
                      organism = Psilocybe cubensis
SEQUENCE: 3
```
MAFDLKTEDG LITYLTKHLS LDVDTSGVKR LSGGFVNVTW RIKLNAPYQG HTSIILKHAQ    60
PHMSTDEDFK IGVERSVYEY QAIKLMMANR EVLGGVDGIV SVPEGLNYDL ENNALIMQDV   120
GKMKTLLDYV TAKPPLATDI ARLVGTEIGG FVARLHNIGR ERRDDPEFKF FSGNIVGRTT   180
SDQLYQTIIP NAAKYGVDDP LLPTVVKDLV DDVMHSEETL VMADLWSGNI LLQLEEGNPS   240
KLQKIYILDW ELCKYGPASL DLGYFLGDCY LISRFQDEQV GTTMRQAYLQ SYARTSKHSI   300
NYAKVTAGIA AHIVMWTDFM QWGSEEERIN FVKKGVAAFH DARGNNDNGE ITSTLLKESS   360
TA                                                                  362
```

SEQ ID NO: 4          moltype = DNA   length = 1089
FEATURE               Location/Qualifiers
source                1..1089
                      mol_type = other DNA
                      organism = Psilocybe cubensis
SEQUENCE: 4
```
atggcgttcg atctcaagac tgaagacggc ctcatcacat atctcactaa acatctttct    60
ttggacgtcg acacgagcgg agtgaagcgc cttagcggag gctttgtcaa tgtaacctgg   120
cgcattaagc tcaatgctcc ttatcaaggt catacgagca tcatcctgaa gcatgctcag   180
ccgcacatgt ctacggatga ggattttaag ataggtgtag aacgttcggt ttacgaatac   240
caggctatca agctcatgat ggccaatcgg gaggttctgg gaggcgtgga tggcatagtt   300
tctgtgccag aaggcctgaa ctacgactta gagaataatg cattgatcat gcaagatgtc   360
gggaagatga agaccctttt agattatgtc accgccaaac cgccacttgc gacggatata   420
gcccgccttg ttgggacaga aattggggg ttcgttcgca gactccataa cataggccgc   480
gagaggcgag acgatcctga gttcaaattc ttctctggaa atattgtcgg aaggacgact   540
tcagaccagc tgtatcaaac catcataccc aacgcagcga aatatggcgt cgatgacccc   600
ttgctgccta ctgtggttaa ggaccttgtg gacgatgtca tgcacagcga agagacctt    660
gtcatggcga acctgtggag tggaaatatt tttctccagt tggaggaggg aaacccatg    720
aagctgcaga agatatatat cctgggattgg gaactttgca agtacggccc agcgtcgttg   780
gacctgggct atttcttggg tgactgctat ttgatatccc gctttcaaga cgagcaggtc   840
ggtacgacga tgcggcaagc ctacttgcaa agctatgcgc gtacgagcaa gcattcgatc   900
aactacgcca aagtcactgc aggtattgct gctcatattg tgatgtggac cgactttatg   960
cagtgggga gcgaggaaga aaggataaat tttgtgaaaa aggggggtagc tgcctttcac   1020
gacgccaggg gcaacaacga caatggggaa attacgtcta cctactgaa ggaatcatcc   1080
actgcgtaa                                                          1089
```

SEQ ID NO: 5          moltype = AA   length = 508
FEATURE               Location/Qualifiers
source                1..508
                      mol_type = protein
                      organism = Psilocybe cubensis
SEQUENCE: 5
```
MIAVLFSFVI AGCIYYIVSR RVRRSRLPPG PPGIPIPFIG NMFDMPEESP WLTFLQWGRD    60
YNTDILYVDA GGTEMVILNT LETITDLLEK RGSIYSGRLE STMVNELMGW EFDLGFITYG   120
DRWREERRMF AKEFSEKGIK QFRHAQVKAA HQLVQQLTKT PDRWAQHIRH QIAAMSLDIG   180
YGIDLAEDDP WLEATHLANE GLAIASVPGK FWVDSFPSLK YLPAWFPGAV FKRKAKVWRE   240
AADHMVDMPY ETMRKLAPQG LTRPSYASAR LQAMDLNGDL EHQEHVIKNT AAEVNVGGGD   300
TTVSAMSAFI LAMVKYPEVQ RKVQAELDAL TNNGQIPDYD EEDDSLPYLT ACIKELFRWN   360
QIAPLAIPHK LMKDDVYRGY LIPKNTLVFA NTWAVLNDPE VYPDPSVFRP ERYLGPDGKP   420
DNTVRDPRKA AFGYGRRNCP GIHLAQSTVW IAGATLLSAF NIERPVDQNG KPIDIPADFT   480
TGFFRHPVPF QCRFVPRTEQ VSQSVSGP                                      508
```

SEQ ID NO: 6          moltype = DNA   length = 2155
FEATURE               Location/Qualifiers
source                1..2155
                      mol_type = other DNA -continued

```
                        organism = Psilocybe cubensis
SEQUENCE: 6
atgatcgctg tactattctc cttcgtcatt gcaggatgca tatactacat cgtttctcgt   60
agagtgaggc ggtcgcgctt gccaccaggg ccgcctggca ttcctattcc cttcattggg  120
aacatgtttg atatgcctga agaatctcca tggttaacat ttctacaatg gggacgggat  180
tacagtctgt cttgccgcgt tgacttctaa tatatgaaca gctaatatat tgtcagacac  240
cgatattctc tacgtggatg ctggagggac agaaatggtt attcttaaca cgttggagac  300
cattaccgat ctattagaaa agcgagggtc catttattct ggccggtgag ctgatgttga  360
gtttttgca attgaatttg tggtcacacg tttccagact tgagagtaca atggtcaacg  420
aacttatggg gtgggagttt gacttagggt tcatcacata cggcgacagg tggcgcgaag  480
aaaggcgcat gttcgccaag gagttcagtg agaagggcat caagcaattt cgccatgctc  540
aagtgaaagc tgcccatcag cttgtccaac agcttaccaa aacgccagac cgctgggcac  600
aacatattcg ccagtaagta ctacttgagg aaaatagcgt acgcttcgct gaccggtccg  660
tacatcaaag tcagatagcg gcaatgtcac tggatattgg ttatggaatt gatcttgcag  720
aagacgaccc ttggctggaa gcgacccatt tggctaatga aggcctcgcc atagcatcag  780
tgccgggcaa attttgggtc gattcgttcc cttctcgtga gcatccttct tctatgtagg  840
aagggaagga gtctaacaag tgttagtaaa ataccttcct gcttggttcc caggtgctgt  900
cttcaagcgc aaagcgaagg tctggcgaga agccgccgaa catatggttg acatgcctta  960
tgaaactatg aggaaattag cagttagtca aatgcgttct ccccgtattt tttcaatact 1020
ctaacttcag ctcacagcct caaggattga ctcgtccgtc gtatgcttca gctcgtctgc 1080
aagccatgga tctcaacggt gaccttgagc atcaagaaca cgtaatcaag aacacagccg 1140
cagaggttaa tgtcggtaag tcaaaagcgt ccgtcgggca ttcaaaattc aggcgctaaa 1200
gtgggtcttc tcaccaaggt gggaggcgata ctgtaaggat ttctcaatcg ttagagtata 1260
agtgttctaa tgcagtacat actccaccaa ccagactgtc tctgctatgt ctgcgttcat 1320
cttggccatg gtgaagtacc ctgaggtcca gcgaaaggtt caagcggagc ttgatgctct 1380
gaccaataac ggccaaattc ctgactatga cgaagaagat gactccttgc catacctcac 1440
cgcatgtatc aaggagcttt tccggtggaa tcaaatcgca cccctcgcta taccgcacaa 1500
attaatgaag gacgacgtgt accgcgggta tctgattccc aagaacactc tagtcttcgc 1560
aaacacctgg tgaggctgtc cattcattcc tagtacatcc gttgccccac taatagcatc 1620
ttgataacag ggcagtatta aacgatccag aagtctatcc agatccctct gtgttccgcc 1680
cagaaagata tcttggtcct gacgggaagc ctgataacac tgtacgcgac ccacgtaaag 1740
cggcatttgg ctatggacga cgaaattggt aagtgcgctt tcagaacccc cccttccgtt 1800
gactagtgcc atgcgcgcat acaatatcgc tattgatctg atataacttc cctgcggcat 1860
ttattttggc attcctttag tcccggaatt catctagcgc agtcgacggt ttggattgca 1920
ggggcaaccc tcttatcagc gttcaatatc gagcgacctg tcgatcagaa tggggaagccc 1980
attgacatac cggctgattt tactacagga ttcttcaggt agctaatttc cgtctttgtg 2040
tgcataaatac ccctaacgac gcacgtttac cttttttgtaa agacacccag tgcctttcca 2100
gtgcaggttt gttcctcgaa cagagcaagt ctcacagtcg gtatccggac cctga        2155

SEQ ID NO: 7          moltype = AA  length = 309
FEATURE               Location/Qualifiers
source                1..309
                      mol_type = protein
                      organism = Psilocybe cubensis
SEQUENCE: 7
MHIRNPYRTP IDYQALSEAF PPLKPFVSVN ADGTSSVDLT IPEAQRAFTA ALLHRDFGLT   60
MTIPEDRLCP TVPNRLNYVL WIEDIFNYTN KTLGLSDDRP IKGVDIGTGA SAIYPMLACA  120
RFKAWSMVGT EVERKCIDTA RLNVVANNLQ DRLSILETSI DGPILVPIFE ATEEYEYEFT  180
MCNPPFYDGA ADMQTSDAAK GFGFGVGAPH SGTVIEMSTE GGESAFVAQM VRESLKLRTR  240
CRWYTSNLGK LKSLKEIVGL LKELEISNYA INEYVQGSTR RYAVAWSFTD IQLPEELSRP  300
SNPELSSLF                                                          309

SEQ ID NO: 8          moltype = DNA  length = 930
FEATURE               Location/Qualifiers
source                1..930
                      mol_type = other DNA
                      organism = Psilocybe cubensis
SEQUENCE: 8
atgcatatca gaaatcctta ccgtacacca attgactatc aagcactttc agaggccttc   60
cctcccctca agccatttgt gtctgtcaat gcagatggta ccagttctgt tgacctcact  120
atcccagaag cccagagggc gttcacggcc gctcttcttc atcgtgactt cgggctcacc  180
atgaccatac cagaagaccg tctgtgccca acagtcccca ataggttgaa ctacgttctg  240
tggattgaag atattttcaa ctacacgaac aaaaccctcg gcctgtcgga tgaccgtcct  300
attaaaggcg ttgatattgg tacaggagcc tccgcaattt atcctatgct tgcctgtgct  360
cggttcaagg catggtctat ggttggaaca gaggtcgaga ggaagtgcat tgacacggcc  420
cgcctcaatg tcgtcgcgaa caatctccaa gaccgtctct cgatattaga gacatccatt  480
gatggtccta ttctcgtccc catttttcgag gcgactgaag aatacgaata cgagtttact  540
atgtgtaacc ctccattcta cgacggtgct gccgatatgc agactcggga tgctgccaaa  600
ggatttggat ttggcgtggg cgctccccat tctggaacag tcatcgaaat gtcgactgag  660
ggaggtgaat cggctttcgt cgctcagatg gtccgtgaga gcttgaagct tcgaacacga  720
tgcagatggt acacgagtaa cttgggaaag ctgaaatcct tgaaagaaat agtggggctg  780
ctgaaagaac ttgagataag caactatgcc attaacgaat acgttcaggg gtccacacgt  840
cgttatgccg ttgcgtggtc tttcactgat attcaactgc ctgaggagct ttctcgtccc  900
tctaaccccg agctcagctc tctttttctag                                   930

SEQ ID NO: 9          moltype = DNA  length = 1320
FEATURE               Location/Qualifiers
source                1..1320
                      mol_type = other DNA
```

```
                         organism = Psilocybe cubensis
SEQUENCE: 9
atgcaggtga tacccgcgtg caactcggca gcaataagat cactatgtcc tactcccgag  60
tcttttagaa acatgggatg gctctctgtc agcgatgcgg tctacagcga gttcatagga  120
gagttggcta cccgcgcttc caatcgaaat tactccaacg agttcggcct catgcaacct  180
atccaggaat tcaaggcttt cattgaaagc gacccggtgg tgcaccaaga atttattgac  240
atgttcgagg gcattcagga ctctccaagg aattatcagg aactatgtaa tatgttcaac  300
gatatctttc gcaaagctcc cgtctacgga gaccttggcc ctcccgttta tatgattatg  360
gccaaattaa tgaacacccg agcgggcttc tctgcattca cgagacaaag gttgaacctt  420
cacttcaaaa aacttttcga tacctgggga ttgttcctgt cttcgaaaga ttctcgaaat  480
gttcttgtgg ccgaccagtt cgacgacaga cattgcggct ggttgaacga gcgggccttg  540
tctgctatgg ttaaacatta caatggacgc gcatttgatg aagtcttcct ctgcgataaa  600
aatgccccat actacggctt caactcttac gacgacttct ttaatcgcag atttcgaaac  660
cgagatatcg accgacctgt agtcggtgga gttaacaaca ccaccctcat ttctgctgct  720
tgcgaatcac tttcctacaa cgtctcttat gacgtccagt ctctcgacac tttagttttc  780
aaaggagaga cttattcgct taagcatttg ctgaataatg accctttcac cccacaattc  840
gagcatggga gtattctaca aggattcttg aacgtcaccg cttaccaccg atggcacgca  900
cccgtcaatg ggacaatcgt caaaatcatc aacgttccag gtacctactt tgcgcaagcc  960
ccgagcacga ttggcgaccc tatcccggat aacgattacg acccacctcc ttaccttaag  1020
tctcttgtct acttctctaa tattgccgca aggcaaatta tgtttattga agccgacaac  1080
aaggaaattg gcctcatttt ccttgtgttc atcggcatga ccgaaatctc gacatgtgaa  1140
gccacggtgt ccgaaggtca acacgtcaat cgtggcgatg acttgggaat gttccatttc  1200
ggtggttctt cgttcgcgct tggtctgagg aaggattgca gggcagagat cgttgaaaag  1260
ttcaccgaac ccggaacagt gatcagaatc aacgaagtcg tcgctgctct aaaggcttag  1320

SEQ ID NO: 10          moltype = DNA  length = 1089
FEATURE                Location/Qualifiers
source                 1..1089
                       mol_type = other DNA
                       organism = Psilocybe cubensis
SEQUENCE: 10
atggcgttcg atctcaagac tgaagacggc ctcatcacat atctcactaa acatctttct  60
ttggacgtcg acacgagcgg agtgaagcgc cttagcggag gctttgtcaa tgtaacctgg  120
cgcattaagc tcaatgctcc ttatcaaggt catacgagca tcatcctgga gcatgctcag  180
ccgcacatgt ctacggatga ggattttaag ataggtgtag aacgttcggt ttacgaatac  240
caggctatca agctcatgat ggccaatcgg gaggttctgg gaggcgtgga tggcatagtt  300
tctgtgccag aaggcctgaa ctacgactta gagaataatg cattgatcat gcaagatgtc  360
gggaagatga agaccctttt agattatgtc accgccaaac cgccacttgc gacggatata  420
gcccgccttg ttgggacaga aattgggggg ttcgttgcca gactccataa cataggccgc  480
gagaggcgag acgatcctga gttcaaattc ttctctggaa atattgtcgg aaggacgact  540
tcagaccagc tgtatcaaac catcataccc aacgcagcga aatatggcgt cgatgacccc  600
ttgctgccta ctgtggttaa ggaccttgtg dacgatgtca tgcacagcga agagaccctt  660
gtcatggcag acctgtggag tggaaatatt cttctccagt tggaggaggg aaacccatcg  720
aagctgcaga agatatatat cctggattgg gaactttgca agtacggccc agcgtcgttg  780
gacctgggct atttcttggg tgactgctat ttgatatccc gctttcaaga cgagcaggtc  840
ggtacgacga tgcggcaagc ctacttgcaa agctatgcgc gtacgagcaa gcattcgatc  900
aactacgcca aagtcactgc aggtattgct gctcatattg tgatgtggac cgactttatg  960
cagtggggga gcgaggaaga aaggataaat tttgtgaaaa aggggtagc tgcctttcac  1020
gacgccaggg gcaacaacga caatgggaa attacgtcta ccttactgaa ggaatcatcc  1080
actgcgtaa                                                          1089

SEQ ID NO: 11          moltype = DNA  length = 930
FEATURE                Location/Qualifiers
source                 1..930
                       mol_type = other DNA
                       organism = Psilocybe cubensis
SEQUENCE: 11
atgcatatca gaaatcctta ccgtacacca attgactatc aagcactttc agaggccttc  60
cctcccctca agccatttgt gtctgtcaat gcagatggta ccagttctgt tgaccccact  120
atcccagaag cccagagggc gttcacggcc gctcttcttc atcgtgactt cgggctcacc  180
atgaccatac cagaagaccg tctgtgccca acagtcccca ataggttgaa ctacgttctg  240
tggattgaag atattttcaa ctacacgaac aaaaccctcg gcctgtcgga tgaccgtcct  300
attaaaggcg ttgatattgg tacaggagcc tccgcaattt atcctatgct tgcctgtgct  360
cggttcaagg catggtctat ggttggaaca gaggtcgaga gaagtgcat tgacacgcgc  420
cgcctcaatg tcgtcgcgaa caatctccaa gaccgtctct cgatattaga gacatccatt  480
gatggtccta ttctcgtccc cattttcgag gcgactgaag aatacgaata cgagtttact  540
atgtgtaacc ctccattcta cgacggtgct gccgatatgc agacttcgga tgctgccaaa  600
ggatttggat ttggcgtggg cgctccccat tctggaacag tcatcgaaat gtcgactgag  660
ggaggtgaat cggctttcgt cgctcagatg gtccgtgaga gcttgaagct tcgaacacga  720
tgcagatggt acacgagtaa cttgggaaag ctgaaatcct tgaaagaaat agtggggctg  780
ctgaaagaac ttgagataag caactatgcc attaacgaat acgttcaggg gtccacacgt  840
cgttatgccg ttgcgtggtc tttcactgat attcaactgc ctgaggagct ttctcgtccc  900
tctaacccc agctcagctc tcttttctag                                     930

SEQ ID NO: 12          moltype = DNA  length = 2155
FEATURE                Location/Qualifiers
source                 1..2155
                       mol_type = other DNA
                       organism = Psilocybe cubensis
```

```
SEQUENCE: 12
atgatcgctg tactattctc cttcgtcatt gcaggatgca tatactacat cgtttctcgt   60
agagtgaggc ggtcgcgctt gccaccaggg ccgcctggca ttcctattcc cttcattggg   120
aacatgtttg atatgcctga agaatctcca tggttaacat ttctacaatg gggacgggat   180
tacagtctgt cttgccgcgt tgacttctaa tatatgaaca gctaatatat tgtcagacac   240
cgatattctc tacgtggatg ctggagggac agaaatggtt attcttaaca cgttggagac   300
cattaccgat ctattagaaa agcgagggtc catttattct ggccggtgag ctgatgttga   360
gtttttttgca attgaatttg tggtcacacg tttccagact tgagagtaca atggtcaacg   420
aacttatggg gtgggagttt gacttagggt tcatcacata cggcgacagg tggcgcgaag   480
aaaggcgcat gttcgccaag gagttcagtg agaagggcat caagcaattt cgccatgctc   540
aagtgaaagc tgcccatcag cttgtccaac agcttaccaa aacgccagac cgctgggcac   600
aacatattcg ccagtaagta ctacttgagg aaaatagcgt acgcttcgct gaccggtccg   660
tacatcaaag tcagatagcg gcaatgtcac tggatattgg ttatggaatt gatcttgcag   720
aagacgaccc ttggctggaa gcgacccatt tggctaatga aggcctcggc atagcatcag   780
tgccgggcaa attttgggtc gattcgttcc cttctcgtga gcatccttct tctatgtagg   840
aagggaagga gtctaacaag tgttagtaaa ataccttcct gcttggttcc caggtgctgt   900
cttcaagcgc aaagcgaagg tctggcgaga agccgccgac catatggttg acatgcctta   960
tgaaactatg aggaaattag cagttagtca aatgcgttct ccccgtattt tttcaatact  1020
ctaacttcag ctcacagcct caaggattga ctcgtccgtc gtatgcttca gctcgtctgc  1080
aagccatgga tctcaacggt gaccttgagc atcaagaaca cgtaatcaag aacacagccg  1140
cagaggttaa tgtcggtaag tcaaaagcgt ccgtcggcaa ttcaaaattc aggcgctaaa  1200
gtgggtcttc tcaccaaggt ggaggcgata ctgtaaggat ttctcaatcg ttagagtata  1260
agtgttctaa tgcagtacat actccaccaa ccagactgtc tctgctatgt ctgcgttcat  1320
cttggccatg gtgaagtacc ctgaggtcca gcgaaaggtt caagcggagc ttgatgctct  1380
gaccaataac ggccaaattc ctgactatga cgaagaagat gactccttgc catacctcac  1440
cgcatgtatc aaggagcttt tccggtggaa tcaaatcgca cccctcgcta taccgcacaa  1500
attaatgaag gacgacgtgt accgcgggta tctgattccc aagaacactc tagtcttcgc  1560
aaacacctgg tgaggctgtc cattcattcc tagtacatcc gttgcccac taatagcatc  1620
ttgataacag ggcagtatta aacgatccag aagtctatcc agatccctct gtgttccgcc  1680
cagaaagata tcttggtcct gacgggaagc ctgataacac tgtacgcgac ccacgtaaag  1740
cggcatttgg ctatggacga cgaaattggt aagtgcgctt tcagaaccc cccttccgtt  1800
gactagtgcc atgcgcgcat acaatatcgc tattgatctg atataacttc cctgcggcat  1860
ttattttggc attcctttag tcccggaatt catctagcgc agtcgacggt ttggattgca  1920
ggggcaaccc tcttatcagc gttcaatatc gagcgacctg tcgatcagaa tgggaagccc  1980
attgacatac cggctgattt tactacagga ttcttcaggt agctaatttc cgtctttgca  2040
tgcataatac ccctaacgac gcacgtttac cttttttgtaa agacacccag tgcctttcca  2100
gtgcaggttt gttcctcgaa cagagcaagt ctcacagtcg gtatccggac cctga        2155

SEQ ID NO: 13          moltype = DNA   length = 23
FEATURE                Location/Qualifiers
misc_feature          1..23
                       note = CRISPR oligonucleotide
source                 1..23
                       mol_type = other DNA
                       organism = synthetic construct
SEQUENCE: 13
ggtgataccc gcgtgcaact cgg                                             23

SEQ ID NO: 14          moltype = DNA   length = 24
FEATURE                Location/Qualifiers
misc_feature          1..24
                       note = CRISPR oligonucleotide
source                 1..24
                       mol_type = other DNA
                       organism = synthetic construct
SEQUENCE: 14
gatggctctc tgtcagcgat gcgg                                            24

SEQ ID NO: 15          moltype = DNA   length = 21
FEATURE                Location/Qualifiers
misc_feature          1..21
                       note = CRISPR oligonucleotide
source                 1..21
                       mol_type = other DNA
                       organism = synthetic construct
SEQUENCE: 15
gcgagttcat aggagagttg g                                               21

SEQ ID NO: 16          moltype = DNA   length = 22
FEATURE                Location/Qualifiers
misc_feature          1..22
                       note = CRISPR oligonucleotide
source                 1..22
                       mol_type = other DNA
                       organism = synthetic construct
SEQUENCE: 16
gaaattactc caacgagttc gg                                              22

SEQ ID NO: 17          moltype = DNA   length = 23
```

-continued

```
FEATURE               Location/Qualifiers
misc_feature          1..23
                      note = CRISPR oligonucleotide
source                1..23
                      mol_type = other DNA
                      organism = synthetic construct
SEQUENCE: 17
gcaacctatc caggaattca agg                                              23

SEQ ID NO: 18         moltype = DNA   length = 24
FEATURE               Location/Qualifiers
misc_feature          1..24
                      note = CRISPR oligonucleotide
source                1..24
                      mol_type = other DNA
                      organism = synthetic construct
SEQUENCE: 18
gttcgatctc aagactgaag acgg                                             24

SEQ ID NO: 19         moltype = DNA   length = 23
FEATURE               Location/Qualifiers
misc_feature          1..23
                      note = CRISPR oligonucleotide
source                1..23
                      mol_type = other DNA
                      organism = synthetic construct
SEQUENCE: 19
tctttggacg tcgacacgag cgg                                              23

SEQ ID NO: 20         moltype = DNA   length = 23
FEATURE               Location/Qualifiers
misc_feature          1..23
                      note = CRISPR oligonucleotide
source                1..23
                      mol_type = other DNA
                      organism = synthetic construct
SEQUENCE: 20
gaggctttgt caatgtaacc tgg                                              23

SEQ ID NO: 21         moltype = DNA   length = 26
FEATURE               Location/Qualifiers
misc_feature          1..26
                      note = CRISPR oligonucleotide
source                1..26
                      mol_type = other DNA
                      organism = synthetic construct
SEQUENCE: 21
gcatgctcag ccgcacatgt ctacgg                                           26

SEQ ID NO: 22         moltype = DNA   length = 23
FEATURE               Location/Qualifiers
misc_feature          1..23
                      note = CRISPR oligonucleotide
source                1..23
                      mol_type = other DNA
                      organism = synthetic construct
SEQUENCE: 22
tttgtgtctg tcaatgcaga tgg                                              23

SEQ ID NO: 23         moltype = DNA   length = 23
FEATURE               Location/Qualifiers
misc_feature          1..23
                      note = CRISPR oligonucleotide
source                1..23
                      mol_type = other DNA
                      organism = synthetic construct
SEQUENCE: 23
tttgtgtctg tcaatgcaga tgg                                              23

SEQ ID NO: 24         moltype = DNA   length = 23
FEATURE               Location/Qualifiers
misc_feature          1..23
                      note = CRISPR oligonucleotide
source                1..23
                      mol_type = other DNA
                      organism = synthetic construct
SEQUENCE: 24
cactatccca gaagcccaga ggg                                              23
```

-continued

```
SEQ ID NO: 25          moltype = DNA   length = 24
FEATURE                Location/Qualifiers
misc_feature           1..24
                       note = CRISPR oligonucleotide
source                 1..24
                       mol_type = other DNA
                       organism = synthetic construct
SEQUENCE: 25
gctcttcttc atcgtgactt cggg                                          24

SEQ ID NO: 26          moltype = DNA   length = 26
FEATURE                Location/Qualifiers
misc_feature           1..26
                       note = CRISPR oligonucleotide
source                 1..26
                       mol_type = other DNA
                       organism = synthetic construct
SEQUENCE: 26
gtctgtgccc aacagtcccc aatagg                                        26

SEQ ID NO: 27          moltype = DNA   length = 26
FEATURE                Location/Qualifiers
misc_feature           1..26
                       note = CRISPR oligonucleotide
source                 1..26
                       mol_type = other DNA
                       organism = synthetic construct
SEQUENCE: 27
gtactattct ccttcgtcat tgcagg                                        26

SEQ ID NO: 28          moltype = DNA   length = 24
FEATURE                Location/Qualifiers
misc_feature           1..24
                       note = CRISPR oligonucleotide
source                 1..24
                       mol_type = other DNA
                       organism = synthetic construct
SEQUENCE: 28
gcgcttgcca ccagggccgc ctgg                                          24

SEQ ID NO: 29          moltype = DNA   length = 24
FEATURE                Location/Qualifiers
misc_feature           1..24
                       note = CRISPR oligonucleotide
source                 1..24
                       mol_type = other DNA
                       organism = synthetic construct
SEQUENCE: 29
gatatgcctg aagaatctcc atgg                                          24

SEQ ID NO: 30          moltype = DNA   length = 23
FEATURE                Location/Qualifiers
misc_feature           1..23
                       note = CRISPR oligonucleotide
source                 1..23
                       mol_type = other DNA
                       organism = synthetic construct
SEQUENCE: 30
ggatgctgga gggacagaaa tgg                                           23

SEQ ID NO: 31          moltype = DNA   length = 23
FEATURE                Location/Qualifiers
misc_feature           1..23
                       note = CRISPR oligonucleotide
source                 1..23
                       mol_type = other DNA
                       organism = synthetic construct
SEQUENCE: 31
ccgatctatt agaaaagcga ggg                                           23

SEQ ID NO: 32          moltype = DNA   length = 57
FEATURE                Location/Qualifiers
misc_feature           1..57
                       note = siRNA oligonucleotide
source                 1..57
                       mol_type = other DNA
                       organism = synthetic construct
misc_difference        52..57
                       note = This region may encompass 4 or 6 nucleotides or may
```

-continued

```
                          be absent
SEQUENCE: 32
aataagatca ctatgtccta cgctggtgga gtaggacata gtgatcttat ttttttt     57

SEQ ID NO: 33            moltype = DNA  length = 57
FEATURE                  Location/Qualifiers
misc_feature             1..57
                         note = siRNA oligonucleotide
source                   1..57
                         mol_type = other DNA
                         organism = synthetic construct
misc_difference          52..57
                         note = This region may encompass 4 or 6 nucleotides or may
                          be absent
SEQUENCE: 33
aatttattga catgttcgag ggctggtgga cctcgaacat gtcaataaat ttttttt     57

SEQ ID NO: 34            moltype = DNA  length = 57
FEATURE                  Location/Qualifiers
misc_feature             1..57
                         note = siRNA oligonucleotide
source                   1..57
                         mol_type = other DNA
                         organism = synthetic construct
misc_difference          52..57
                         note = This region may encompass 4 or 6 nucleotides or may
                          be absent
SEQUENCE: 34
ggagagttgg ctacccgcgc tgctggtgga agcgcgggta gccaactctc ctttttt     57

SEQ ID NO: 35            moltype = DNA  length = 57
FEATURE                  Location/Qualifiers
misc_feature             1..57
                         note = siRNA oligonucleotide
source                   1..57
                         mol_type = other DNA
                         organism = synthetic construct
misc_difference          52..57
                         note = This region may encompass 4 or 6 nucleotides or may
                          be absent
SEQUENCE: 35
aagctcccgt ctacggagac cgctggtgga ggtctccgta gacgggacgt ttttttt     57

SEQ ID NO: 36            moltype = DNA  length = 57
FEATURE                  Location/Qualifiers
misc_feature             1..57
                         note = siRNA oligonucleotide
source                   1..57
                         mol_type = other DNA
                         organism = synthetic construct
misc_difference          52..57
                         note = This region may encompass 4 or 6 nucleotides or may
                          be absent
SEQUENCE: 36
gggcttctct gcattcacga ggctggtgga ctcgtgaatg cagagaagcc ctttttt     57

SEQ ID NO: 37            moltype = DNA  length = 57
FEATURE                  Location/Qualifiers
misc_feature             1..57
                         note = siRNA oligonucleotide
source                   1..57
                         mol_type = other DNA
                         organism = synthetic construct
misc_difference          52..57
                         note = This region may encompass 4 or 6 nucleotides or may
                          be absent
SEQUENCE: 37
aacgttcggt ttacgaatac cgctggtgga ggtattcgta aaccgaacgt ttttttt     57

SEQ ID NO: 38            moltype = DNA  length = 57
FEATURE                  Location/Qualifiers
misc_feature             1..57
                         note = siRNA oligonucleotide
source                   1..57
                         mol_type = other DNA
                         organism = synthetic construct
misc_difference          52..57
                         note = This region may encompass 4 or 6 nucleotides or may
                          be absent
```

```
SEQUENCE: 38
aaggcctgaa ctacgactta ggctggtgga ctaagtcgta gttcaggcct ttttttt       57

SEQ ID NO: 39            moltype = DNA   length = 59
FEATURE                  Location/Qualifiers
misc_feature             1..59
                         note = siRNA oligonucleotide
source                   1..59
                         mol_type = other DNA
                         organism = synthetic construct
misc_difference          54..59
                         note = This region may encompass 4 or 6 nucleotides or may
                          be absent
SEQUENCE: 39
aacataggcc gcgagaggcg aggctggtgg actcgcctct cgcggcctat gtttttttt   59

SEQ ID NO: 40            moltype = DNA   length = 57
FEATURE                  Location/Qualifiers
misc_feature             1..57
                         note = siRNA oligonucleotide
source                   1..57
                         mol_type = other DNA
                         organism = synthetic construct
misc_difference          52..57
                         note = This region may encompass 4 or 6 nucleotides or may
                          be absent
SEQUENCE: 40
ggctggttga acgagcgggc cgctggtgga ggcccgctcg ttcaaccagc ctttttt       57

SEQ ID NO: 41            moltype = DNA   length = 57
FEATURE                  Location/Qualifiers
misc_feature             1..57
                         note = siRNA oligonucleotide
source                   1..57
                         mol_type = other DNA
                         organism = synthetic construct
misc_difference          52..57
                         note = This region may encompass 4 or 6 nucleotides or may
                          be absent
SEQUENCE: 41
ggcggacctg tggagtggaa agctggtgga tttccactcc acaggtccgc ctttttt       57

SEQ ID NO: 42            moltype = DNA   length = 57
FEATURE                  Location/Qualifiers
misc_feature             1..57
                         note = siRNA oligonucleotide
source                   1..57
                         mol_type = other DNA
                         organism = synthetic construct
misc_difference          52..57
                         note = This region may encompass 4 or 6 nucleotides or may
                          be absent
SEQUENCE: 42
aatgtcgtcg cgaacaatct cgctggtgga gagattgttc gcgacgacat ttttttt       57

SEQ ID NO: 43            moltype = DNA   length = 57
FEATURE                  Location/Qualifiers
misc_feature             1..57
                         note = siRNA oligonucleotide
source                   1..57
                         mol_type = other DNA
                         organism = synthetic construct
misc_difference          52..57
                         note = This region may encompass 4 or 6 nucleotides or may
                          be absent
SEQUENCE: 43
aaccctccat tctacgacgg tgctggtgga accgtcgtag aatggagggt ttttttt       57

SEQ ID NO: 44            moltype = DNA   length = 57
FEATURE                  Location/Qualifiers
misc_feature             1..57
                         note = siRNA oligonucleotide
source                   1..57
                         mol_type = other DNA
                         organism = synthetic construct
misc_difference          52..57
                         note = This region may encompass 4 or 6 nucleotides or may
                          be absent
SEQUENCE: 44
```

```
aacagtcatc gaaatgtcga cgctggtgga gtcgacattt cgatgactgt ttttttt        57

SEQ ID NO: 45          moltype = DNA   length = 57
FEATURE                Location/Qualifiers
misc_feature           1..57
                       note = siRNA oligonucleotide
source                 1..57
                       mol_type = other DNA
                       organism = synthetic construct
misc_difference        52..57
                       note = This region may encompass 4 or 6 nucleotides or may
                        be absent
SEQUENCE: 45
ggatgctgcc aaaggatttg ggctggtgga ccaaatcctt tggcagcatc ctttttt        57

SEQ ID NO: 46          moltype = DNA   length = 57
FEATURE                Location/Qualifiers
misc_feature           1..57
                       note = siRNA oligonucleotide
source                 1..57
                       mol_type = other DNA
                       organism = synthetic construct
misc_difference        52..57
                       note = This region may encompass 4 or 6 nucleotides or may
                        be absent
SEQUENCE: 46
ggtacacgag taacttggga agctggtgga ttcccaagtt actcgtgtac ctttttt        57

SEQ ID NO: 47          moltype = DNA   length = 57
FEATURE                Location/Qualifiers
misc_feature           1..57
                       note = siRNA oligonucleotide
source                 1..57
                       mol_type = other DNA
                       organism = synthetic construct
misc_difference        52..57
                       note = This region may encompass 4 or 6 nucleotides or may
                        be absent
SEQUENCE: 47
aatggggacg ggattacagt cgctggtgga gactgtaatc ccgtccccat ttttttt        57

SEQ ID NO: 48          moltype = DNA   length = 57
FEATURE                Location/Qualifiers
misc_feature           1..57
                       note = siRNA oligonucleotide
source                 1..57
                       mol_type = other DNA
                       organism = synthetic construct
misc_difference        52..57
                       note = This region may encompass 4 or 6 nucleotides or may
                        be absent
SEQUENCE: 48
aatatattgt cagacaccga tgctggtgga atcggtgtct gacaatatat ttttttt        57

SEQ ID NO: 49          moltype = DNA   length = 57
FEATURE                Location/Qualifiers
misc_feature           1..57
                       note = siRNA oligonucleotide
source                 1..57
                       mol_type = other DNA
                       organism = synthetic construct
misc_difference        52..57
                       note = This region may encompass 4 or 6 nucleotides or may
                        be absent
SEQUENCE: 49
aatggtcaac gaacttatgg ggctggtgga cccataagtt cgttgaccat ttttttt        57

SEQ ID NO: 50          moltype = DNA   length = 57
FEATURE                Location/Qualifiers
misc_feature           1..57
                       note = siRNA oligonucleotide
source                 1..57
                       mol_type = other DNA
                       organism = synthetic construct
misc_difference        52..57
                       note = This region may encompass 4 or 6 nucleotides or may
                        be absent
SEQUENCE: 50
ggagttcagt gagaagggca tgctggtgga atgcccttct cactgaactc ctttttt        57
```

```
SEQ ID NO: 51            moltype = DNA  length = 57
FEATURE                  Location/Qualifiers
misc_feature             1..57
                         note = siRNA oligonucleotide
source                   1..57
                         mol_type = other DNA
                         organism = synthetic construct
misc_difference          52..57
                         note = This region may encompass 4 or 6 nucleotides or may
                          be absent
SEQUENCE: 51
ggcaatgtca ctggatattg ggctggtgga ccaatatcca gtgacattgc ctttttt     57

SEQ ID NO: 52            moltype = RNA  length = 57
FEATURE                  Location/Qualifiers
misc_feature             1..57
                         note = siRNA oligonucleotide
source                   1..57
                         mol_type = other RNA
                         organism = synthetic construct
misc_difference          52..57
                         note = This region may encompass 4 or 6 nucleotides or may
                          be absent
SEQUENCE: 52
aataagatca ctatgtccta cgctggtgga gtaggacata gtgatcttat ttttttt     57

SEQ ID NO: 53            moltype = RNA  length = 57
FEATURE                  Location/Qualifiers
misc_feature             1..57
                         note = siRNA oligonucleotide
source                   1..57
                         mol_type = other RNA
                         organism = synthetic construct
misc_difference          52..57
                         note = This region may encompass 4 or 6 nucleotides or may
                          be absent
SEQUENCE: 53
aatttattga catgttcgag ggctggtgga cctcgaacat gtcaataaat ttttttt     57

SEQ ID NO: 54            moltype = RNA  length = 57
FEATURE                  Location/Qualifiers
misc_feature             1..57
                         note = siRNA oligonucleotide
source                   1..57
                         mol_type = other RNA
                         organism = synthetic construct
misc_difference          52..57
                         note = This region may encompass 4 or 6 nucleotides or may
                          be absent
SEQUENCE: 54
ggagagttgg ctacccgcgc tgctggtgga agcgcgggta gccaactctc ctttttt     57

SEQ ID NO: 55            moltype = RNA  length = 57
FEATURE                  Location/Qualifiers
misc_feature             1..57
                         note = siRNA oligonucleotide
source                   1..57
                         mol_type = other RNA
                         organism = synthetic construct
misc_difference          52..57
                         note = This region may encompass 4 or 6 nucleotides or may
                          be absent
SEQUENCE: 55
aagctcccgt ctacggagac cgctggtgga ggtctccgta gacgggacgt ttttttt     57

SEQ ID NO: 56            moltype = RNA  length = 57
FEATURE                  Location/Qualifiers
misc_feature             1..57
                         note = siRNA oligonucleotide
source                   1..57
                         mol_type = other RNA
                         organism = synthetic construct
misc_difference          52..57
                         note = This region may encompass 4 or 6 nucleotides or may
                          be absent
SEQUENCE: 56
gggcttctct gcattcacga ggctggtgga ctcgtgaatg cagagaagcc ctttttt     57
```

-continued

```
SEQ ID NO: 57            moltype = RNA   length = 57
FEATURE                  Location/Qualifiers
misc_feature             1..57
                         note = siRNA oligonucleotide
source                   1..57
                         mol_type = other RNA
                         organism = synthetic construct
misc_difference          52..57
                         note = This region may encompass 4 or 6 nucleotides or may
                          be absent
SEQUENCE: 57
aacgttcggt ttacgaatac cgctggtgga ggtattcgta aaccgaacgt tttttttt      57

SEQ ID NO: 58            moltype = RNA   length = 57
FEATURE                  Location/Qualifiers
misc_feature             1..57
                         note = siRNA oligonucleotide
source                   1..57
                         mol_type = other RNA
                         organism = synthetic construct
misc_difference          52..57
                         note = This region may encompass 4 or 6 nucleotides or may
                          be absent
SEQUENCE: 58
aaggcctgaa ctacgactta ggctggtgga ctaagtcgta gttcaggcct tttttttt      57

SEQ ID NO: 59            moltype = RNA   length = 59
FEATURE                  Location/Qualifiers
misc_feature             1..59
                         note = siRNA oligonucleotide
source                   1..59
                         mol_type = other RNA
                         organism = synthetic construct
misc_difference          54..59
                         note = This region may encompass 4 or 6 nucleotides or may
                          be absent
SEQUENCE: 59
aacataggcc gcgagaggcg aggctggtgg actcgcctct cgcggcctat gttttttttt     59

SEQ ID NO: 60            moltype = RNA   length = 57
FEATURE                  Location/Qualifiers
misc_feature             1..57
                         note = siRNA oligonucleotide
source                   1..57
                         mol_type = other RNA
                         organism = synthetic construct
misc_difference          52..57
                         note = This region may encompass 4 or 6 nucleotides or may
                          be absent
SEQUENCE: 60
ggctggttga acgagcgggc cgctggtgga ggcccgctcg ttcaaccagc cttttttt      57

SEQ ID NO: 61            moltype = RNA   length = 57
FEATURE                  Location/Qualifiers
misc_feature             1..57
                         note = siRNA oligonucleotide
source                   1..57
                         mol_type = other RNA
                         organism = synthetic construct
misc_difference          52..57
                         note = This region may encompass 4 or 6 nucleotides or may
                          be absent
SEQUENCE: 61
ggcggacctg tggagtggaa agctggtgga tttccactcc acaggtccgc cttttttt      57

SEQ ID NO: 62            moltype = RNA   length = 57
FEATURE                  Location/Qualifiers
misc_feature             1..57
                         note = siRNA oligonucleotide
source                   1..57
                         mol_type = other RNA
                         organism = synthetic construct
misc_difference          52..57
                         note = This region may encompass 4 or 6 nucleotides or may
                          be absent
SEQUENCE: 62
aatgtcgtcg cgaacaatct cgctggtgga gagattgttc gcgacgacat tttttttt      57

SEQ ID NO: 63            moltype = RNA   length = 57
```

```
FEATURE                    Location/Qualifiers
misc_feature               1..57
                           note = siRNA oligonucleotide
source                     1..57
                           mol_type = other RNA
                           organism = synthetic construct
misc_difference            52..57
                           note = This region may encompass 4 or 6 nucleotides or may
                            be absent
SEQUENCE: 63
aaccctccat tctacgacgg tgctggtgga accgtcgtag aatggagggt ttttttt      57

SEQ ID NO: 64              moltype = RNA   length = 57
FEATURE                    Location/Qualifiers
misc_feature               1..57
                           note = siRNA oligonucleotide
source                     1..57
                           mol_type = other RNA
                           organism = synthetic construct
misc_difference            52..57
                           note = This region may encompass 4 or 6 nucleotides or may
                            be absent
SEQUENCE: 64
aacagtcatc gaaatgtcga cgctggtgga gtcgacattt cgatgactgt ttttttt      57

SEQ ID NO: 65              moltype = RNA   length = 57
FEATURE                    Location/Qualifiers
misc_feature               1..57
                           note = siRNA oligonucleotide
source                     1..57
                           mol_type = other RNA
                           organism = synthetic construct
misc_difference            52..57
                           note = This region may encompass 4 or 6 nucleotides or may
                            be absent
SEQUENCE: 65
ggatgctgcc aaaggatttg ggctggtgga ccaaatcctt tggcagcatc ctttttt      57

SEQ ID NO: 66              moltype = RNA   length = 57
FEATURE                    Location/Qualifiers
misc_feature               1..57
                           note = siRNA oligonucleotide
source                     1..57
                           mol_type = other RNA
                           organism = synthetic construct
misc_difference            52..57
                           note = This region may encompass 4 or 6 nucleotides or may
                            be absent
SEQUENCE: 66
ggtacacgag taacttggga agctggtgga ttcccaagtt actcgtgtac ctttttt      57

SEQ ID NO: 67              moltype = RNA   length = 57
FEATURE                    Location/Qualifiers
misc_feature               1..57
                           note = siRNA oligonucleotide
source                     1..57
                           mol_type = other RNA
                           organism = synthetic construct
misc_difference            52..57
                           note = This region may encompass 4 or 6 nucleotides or may
                            be absent
SEQUENCE: 67
aatggggacg ggattacagt cgctggtgga gactgtaatc ccgtccccat ttttttt      57

SEQ ID NO: 68              moltype = RNA   length = 57
FEATURE                    Location/Qualifiers
misc_feature               1..57
                           note = siRNA oligonucleotide
source                     1..57
                           mol_type = other RNA
                           organism = synthetic construct
misc_difference            52..57
                           note = This region may encompass 4 or 6 nucleotides or may
                            be absent
SEQUENCE: 68
aatatattgt cagacaccga tgctggtgga atcggtgtct gacaatatat ttttttt      57

SEQ ID NO: 69              moltype = RNA   length = 57
FEATURE                    Location/Qualifiers
```

```
misc_feature            1..57
                        note = siRNA oligonucleotide
source                  1..57
                        mol_type = other RNA
                        organism = synthetic construct
misc_difference         52..57
                        note = This region may encompass 4 or 6 nucleotides or may
                         be absent
SEQUENCE: 69
aatggtcaac gaacttatgg ggctggtgga cccataagtt cgttgaccat tttttt      57

SEQ ID NO: 70           moltype = RNA   length = 57
FEATURE                 Location/Qualifiers
misc_feature            1..57
                        note = siRNA oligonucleotide
source                  1..57
                        mol_type = other RNA
                        organism = synthetic construct
misc_difference         52..57
                        note = This region may encompass 4 or 6 nucleotides or may
                         be absent
SEQUENCE: 70
ggagttcagt gagaagggca tgctggtgga atgcccttct cactgaactc cttttt       57

SEQ ID NO: 71           moltype = RNA   length = 57
FEATURE                 Location/Qualifiers
misc_feature            1..57
                        note = siRNA oligonucleotide
source                  1..57
                        mol_type = other RNA
                        organism = synthetic construct
misc_difference         52..57
                        note = This region may encompass 4 or 6 nucleotides or may
                         be absent
SEQUENCE: 71
ggcaatgtca ctggatattg ggctggtgga ccaatatcca gtgacattgc ctttttt      57

SEQ ID NO: 72           moltype = DNA   length = 1320
FEATURE                 Location/Qualifiers
source                  1..1320
                        mol_type = other DNA
                        organism = Psilocybe cyanescens
SEQUENCE: 72
atgcaggtac tgcccgcgtg ccaatcttcc gcgcttaaaa cattgtgccc atccccgag    60
gcctttcgaa agctcggttg gctccctact agcgacgagg tttacaacga attcatcgat  120
gacttgaccg gtcgcacgtg caatgaaaag tactccagcc aggttacact tttgaagcct  180
atccaagatt tcaagacatt catcgagaat gatcccatag tgtatcaaga atttatctct  240
atgtttgaag gaatcgagca gtctcccacc aactaccacg agctatgtaa catgttcaac  300
gacatctttc gcaaagcccc actctacggc gatcttggtc ctccggttta catgatcatg  360
gccagaataa tgaatacgca ggcgggtttc tctgcgttca caaaagagag cttgaacttc  420
catttcaaaa agctcttcga cacctggggg ctattccttt cctcgaaaaa ctctcgaaac  480
gtgcttgttg cagaccagtt tgacgataag cattacgggg ggttcagcga gcgagccaag  540
actgccatga tgattaatta tccagggcgt acattcgaga aagtcttcat ctgcgacgag  600
cacgttccat accatggctt cacttcctat gacgatttct tcaatcgcag gttcagggac  660
aaggatacag atcggcccgt agtcggtggg gttactgaca ccactttaat cggggctgcc  720
tgtgaatcgt tgtcatataa cgtctctcac aacgtccagt ctcttgacac gctagtcatc  780
aagggagagg cctattcact taaacatcta cttcataacg accccttcac accgcaattc  840
gaacatggga gcatcattca aggattccta aatgtcaccg cttaccaccg ctggcactcc  900
ccgtcaatg gcacgattgt gaagatcgtc aacgttccag gtacctactt cgctcaagct  960
ccatatacaa ttggatctcc tatccccgat aacgaccgcg acccgcctcc ttacctcaag  1020
tcactcgtat acttctccaa catcgctgca cggcaaatta tgttcatcga ggccgacaac  1080
aaagacatcg gcctcatttt cttggtcttc attggaatga ctgagatctc gacttgcgag  1140
gcgacggtgt gcgaaggtca gcatgtcaac cgcggtgacg atttgggcat gttccatttc  1200
ggtggttcat cttttgccct tggcttgcgg aaggactcga aggcgaagat tttggaaaag  1260
ttcgcgaaac cggggaccgt tattaggatc aacgagctag ttgcatctgt aaggaagtag  1320

SEQ ID NO: 73           moltype = DNA   length = 930
FEATURE                 Location/Qualifiers
source                  1..930
                        mol_type = other DNA
                        organism = Psilocybe cyanescens
SEQUENCE: 73
atgcatatca ggaacccata ccgcgatggt gttgactacc aagcactcgc tgaagcattt   60
ccggctctca aaccacatgt cacagtaaat tcagacaata cgacctccat cgactttgct  120
gtgccagaag cccaaagact gtatacagct gcccttctac accgggattt cggtcttacg  180
atcacactcc cggaagaccg tctttgtccg acagtgccta atcggctcaa ctatgtcctt  240
tgggttgaag atatccttaa agtcacttct gatgctctcg gtcttccgga taatcgtcaa  300
gttaagggga tcgatatcgg aactggcgca tcagcgatat atcccatgct cgcatgctct  360
cgttttaaga catggtccat ggttgcaaca gaggtagacc agaagtgtat tgacactgct  420
```

-continued

```
cgtctcaacg tcattgccaa caacctccaa gaacgtctcg caattatagc cacctccgtc  480
gatggtccta tacttgtccc cctcttgcag gcgaattctg attttgagta cgattttacg  540
atgtgtaatc cgcccttcta cgatggggca tccgacatgc agacatcgga tgctgcgaag  600
gggtttggat tcggtgtgaa cgctccgcat accggcacgg tgctcgagat ggccaccgag  660
ggaggtgaat cggccttcgt agcccaaatg gtccgcgaaa gtttgaatct tcaaacacga  720
tgcaggtggt tcacgagtaa tttgggaaa ttgaagtcct tgtacgaaat tgtggggctg  780
ctgcgagaac atcagataag taactacgca atcaacgaat acgtccaagg agccactcgt  840
cgatatgcga ttgcatggtc gttcatcgat gttcgactgc ctgatcattt gtcccgtcca  900
tctaaccccg acctaagctc tcttttctag                                    930

SEQ ID NO: 74            moltype = DNA  length = 1086
FEATURE                  Location/Qualifiers
source                   1..1086
                         mol_type = other DNA
                         organism = Psilocybe cyanescens
SEQUENCE: 74
atgactttcg atctcaagac tgaagaaggc ctgctctcat acctcacaaa gcacctatcg  60
ctggacgttg ctcccaacgg ggtgaaacgt cttagtggag gcttcgtcaa cgttacctgg  120
cgggtcgggc tcaatgcccc ttatcatggt cacacgagca ttattctgaa gcatgctcaa  180
ccgcacctgt cttcagacat agatttcaag ataggtgttg aacgatcggc gtacgagtat  240
caagcgctca aaatcgtgtc agccaatagc tcccttctag gcagcagcga tattcgggtc  300
tctgtaccag aaggtcttca ctacgacgtc gttaataacg cattgatcat gcaagatgtc  360
gggacaatga agaccctgtt ggactatgtc actgccaaac caccaatttc tgcagagatc  420
gccagtctcg taggcagtca aattggtgca tttatcgcta ggctgcacaa cctcggccgc  480
gagaataaag acaaggacga cttcaagttc ttctctggaa acatcgtcgg gagaacaacc  540
gcagaccagt tgtatcaaac catcatacct aatgccgcta aatacggtat cgacgatcca  600
attctcccaa ttgtggtaaa ggagttggtg gaggaggtca tgaatagtga agaaacgctt  660
atcatggcgg atttatggag tggcaatatt cttctccagt ttgatgaaaa ctcgacggaa  720
ttgacgagga tatggctggt agactgggag ttgtgcaaat atggtccacc gtctttggac  780
atggggtact tcttaggcga ctgtttcctg gtcgctcgat ttcaagatca gctcgtaggg  840
acatcaatgc gacaggccta cttgaagagc tacgcaagga atgtcaagga gccaatcaat  900
tatgcaaaag ccaccgcagg catcggcgcg catctcgtca tgtggactga tttcatgaag  960
tgggggaacg atgaagagag ggaagagttt gttaagaaag gcgtggaagc cttccatgaa  1020
gcaaatgagg acaatagaaa cggggagatt acgtctatac ttgtgaagga agcatcgcgc  1080
acttag                                                              1086

SEQ ID NO: 75            moltype = DNA  length = 2122
FEATURE                  Location/Qualifiers
source                   1..2122
                         mol_type = other DNA
                         organism = Psilocybe cyanescens
SEQUENCE: 75
atgattgttc tattggtctc gctcgtcctt gcaggatgca tatactacgc caacgctcgt  60
agagtaaggc gctcgcgctt accaccgggc ccgcctggca taccactgcc cttcattggg  120
aatatgtttg atatgccttc agagtcaccg tggttaagat ttcttcaatg gggacgggac  180
tatcgtacgt caaacattgt tttgatttgc gcatttaatt gatatctcta gacactgata  240
tcctttactt gaatgctggc ggaacggaaa taattattct gaacacactg gatgctataa  300
ccgacttgtt ggaaaagcga gggtcgatgt attcgggtcg gtaagttgtt gctatgtctt  360
ttatggataa gatattaaag aagatgcgtc agactcgaga gcaccatggt gaacgaactc  420
atggggtggg agttcgactt gggattcata acctatggtg aaagatggcg cgaagaaaga  480
cgcatgttcg ccaaggagtt cagcgaaaaa aacatcgagt aattccgcca cgcccaaatt  540
aaagctgcca atcagcttgt tcggcagctg atcaaaacgc cagatcgttg gtcgcagcac  600
atccggcagt aagttgtaaa aatatagaca agcatcgagt cgaggctgac cattaattat  660
ggtacagtca gatagcagcc atgtctctag acattggtta tggaattgat ctcgcagagg  720
atgacccctg gattgcagca acccagctag ctaacgaagg gctcgccgaa gcttcagtac  780
cgggcagttt ctgggtcgac tcattccccg cccgtgagtg cttttcttcc tccattagac  840
tactagtcac gaatcatttg atttctactc agtcaaatac cttccttcat ggcttcctgg  900
tgcaggattc aagcgcaaag caaaggtatg gaaggaaggt gctgaccata tggtgaacat  960
gccgtatgaa acgatgaaaa aattgactgt atgttatctt ccgtgatggc tcgtacggag  1020
aattgcactg attgctacac tacaggttca aggcttggcc cgaccttcat atgcctcagc  1080
tcgtctgcag gccatggacc ccgatggcga tctcgagcat caggaacacg tgatcagaaa  1140
cacagcgact gaggtcaatg tcggtaagtt actagtaatg cctcttcggc tattaaagaa  1200
ttgggcgcta attgatttgc attgacctag gcggaggtga tacggtaaat atacctcctg  1260
ctactacccg actgcacgtt cttacatgct ttacatttaa cattcagact gtttctgctg  1320
tgtcagcctt tattttggcc atggtcaaat atccagaagt tcaacgccaa gtccaagcag  1380
aactggatgc actcaccagc aaaggagttg tcccaaacta tgacgaagaa gacgactcct  1440
tgccatacct tacggcttgc gtcaaggaaa tctttcgatg gaaccaaata gcacccttg  1500
ctatccctca tcggctgatc aaagacgatg tttatcgtgg gtatctcata ccaaagaatg  1560
ctttggtcta cgccaactca tggtatggcg ttctgtattc cctatattca tgcacatccg  1620
ctcattgttt actcgtaggg ctgtgttgaa tgacccagag gagtacccaa atccctctga  1680
gttccgacca gaacgatatt tgagctctga cggaaagccc gacccaacgg tccgtgatcc  1740
ccgcaaagca gcatttggct atggtcgacg caactggtaa gcttttcaat tcatatctga  1800
cttcacaagc cgccgatctg atgcactaac ctgcggcatt ttctgtagtc ccggaatcca  1860
cctggcacaa tcgacggtat ggattgctgg agccactctt ctctcggtat tcaatatcga  1920
acgtcctgtt gatgggaatg gaaaaaccat cgacatcccg gcgacgttca ctaccggatt  1980
cttcaggtat tcaattaagc tcttgcccta gggcatggag tgattgcatc tcattaacga  2040
tatgaaactt tacagacatc ccgagccttt ccagtgcaga tttgtccctc gcactcagga  2100
gattctaaaa tccgtttccg gt                                             2122
```

```
SEQ ID NO: 76            moltype = AA   length = 439
FEATURE                  Location/Qualifiers
source                   1..439
                         mol_type = protein
                         organism = Psilocybe cyanescens
SEQUENCE: 76
MQVLPACQSS ALKTLCPSPE AFRKLGWLPT SDEVYNEFID DLTGRTCNEK YSSQVTLLKP    60
IQDFKTFIEN DPIVYQEFIS MFEGIEQSPT NYHELCNMFN DIFRKAPLYG DLGPPVYMIM   120
ARIMNTQAGF SAFTKESLNF HFKKLFDTWG LFLSSKNSRN VLVADQFDDK HYGWFSERAK   180
TAMMINYPGR TFEKVFICDE HVPYHGFTSY DDFFNRRFRD KDTDRPVVGG VTDTTLIGAA   240
CESLSYNVSH NVQSLDTLVI KGEAYSLKHL LHNDPFTPQF EHGSIIQGFL NVTAYHRWHS   300
PVNGTIVKIV NVPGTYFAQA PYTIGSPIPD NDRDPPPYLK SLVYFSNIAA RQIMFIEADN   360
KDIGLIFLVF IGMTEISTCE ATVCEGQHVN RGDDLGMFHF GGSSFALGLR KDSKAKILEK   420
FAKPGTVIRI NELVASVRK                                              439

SEQ ID NO: 77            moltype = AA   length = 309
FEATURE                  Location/Qualifiers
source                   1..309
                         mol_type = protein
                         organism = Psilocybe cyanescens
SEQUENCE: 77
MHIRNPYRDG VDYQALAEAF PALKPHVTVN SDNTTSIDFA VPEAQRLYTA ALLHRDFGLT    60
ITLPEDRLCP TVPNRLNYVL WVEDILKVTS DALGLPDNRQ VKGIDIGTGA SAIYPMLACS   120
RPKTWSMVAT EVDQKCIDTA RLNVIANNLQ ERLAIIATSV DGPILVPLLQ ANSDFEYDFT   180
MCNPPFYDGA SDMQTSDAAK GFGFGVNAPH TGTVLEMATE GGESAFVAQM VRESLNLQTR   240
CRWFTSNLGK LKSLYEIVGL LREHQISNYA INEYVQGATR RYAIAWSFID VRLPDHLSRP   300
SNPDLSSLF                                                         309

SEQ ID NO: 78            moltype = AA   length = 361
FEATURE                  Location/Qualifiers
source                   1..361
                         mol_type = protein
                         organism = Psilocybe cyanescens
SEQUENCE: 78
MTFDLKTEEG LLSYLTKHLS LDVAPNGVKR LSGGFVNVTW RVGLNAPYHG HTSIILKHAQ    60
PHLSSDIDFK IGVERSAYEY QALKIVSANS SLLGSSDIRV SVPEGLHYDV VNNALIMQDV   120
GTMKTLLDYV TAKPPISAEI ASLVGSQIGA FIARLHNLGR ENKDKDDFKF FSGNIVGRTT   180
ADQLYQTIIP NAAKYGIDDP ILPIVVKELV EEVMNSEETL IMADLWSGNI LLQFDENSTE   240
LTRIWLVDWE LCKYGPPSLD MGYFLGDCFL VARFQDQLVG TSMRQAYLKS YARNVKEPIN   300
YAKATAGIGA HLVMWTDFMK WGNDEEREEF VKKGVEAFHE ANEDNRNGEI TSILVKEASR   360
T                                                                361

SEQ ID NO: 79            moltype = AA   length = 507
FEATURE                  Location/Qualifiers
source                   1..507
                         mol_type = protein
                         organism = Psilocybe cyanescens
SEQUENCE: 79
MIVLLVSLVL AGCIYYANAR RVRRSRLPPG PPGIPLPFIG NMFDMPSESP WLRFLQWGRD    60
YHTDILYLNA GGTEIIILNT LDAITDLLEK RGSMYSGRLE STMVNELMGW EFDLGFITYG   120
ERWREERRMF AKEFSEKNIR QFRHAQIKAA NQLVRQLIKT PDRWSQHIRH QIAAMSLDIG   180
YGIDLAEDDP WIAATQLANE GLAEASVPGS FWVDSFPALK YLPSWLPGAG FKRKAKVWKE   240
GADHMVNMPY ETMKKLTVQG LARPSYASAR LQAMDPDGDL EHQEHVIRNT ATEVNVGGGD   300
TTVSAVSAFI LAMVKYPEVQ RQVQAELDAL TSKGVVPNYD EEDDSLPYLT ACVKEIFRWN   360
QIAPLAIPHR LIKDDVYRGY LIPKNALVYA NSWAVLNDPE EYPNPSEFRP ERYLSSDGKP   420
DPTVRDPRKA AFGYGRRNCP GIHLAQSTVW IAGATLLSVF NIERPVDGNG KPIDIPATFT   480
TGFFRHPEPF QCRFVPRTQE ILKSVSG                                     507

SEQ ID NO: 80            moltype = DNA   length = 20
FEATURE                  Location/Qualifiers
misc_feature             1..20
                         note = Conserved sequences for PsiK gene
source                   1..20
                         mol_type = other DNA
                         organism = synthetic construct
SEQUENCE: 80
ttcgatctca agactgaaga                                              20

SEQ ID NO: 81            moltype = DNA   length = 14
FEATURE                  Location/Qualifiers
misc_feature             1..14
                         note = Conserved sequences for PsiK gene
source                   1..14
                         mol_type = other DNA
                         organism = synthetic construct
SEQUENCE: 81
ctgaagcatg ctca                                                    14

SEQ ID NO: 82            moltype = DNA   length = 11
```

-continued

```
FEATURE              Location/Qualifiers
misc_feature         1..11
                     note = Conserved sequences for PsiK gene
source               1..11
                     mol_type = other DNA
                     organism = synthetic construct
SEQUENCE: 82
aagataggtg t                                                        11

SEQ ID NO: 83        moltype = DNA  length = 25
FEATURE              Location/Qualifiers
misc_feature         1..25
                     note = Conserved sequences for PsiK gene
source               1..25
                     mol_type = other DNA
                     organism = synthetic construct
SEQUENCE: 83
gcattgatca tgcaagatgt cggga                                         25

SEQ ID NO: 84        moltype = DNA  length = 11
FEATURE              Location/Qualifiers
misc_feature         1..11
                     note = Conserved sequences for PsiK gene
source               1..11
                     mol_type = other DNA
                     organism = synthetic construct
SEQUENCE: 84
atgaagaccc t                                                        11

SEQ ID NO: 85        moltype = DNA  length = 14
FEATURE              Location/Qualifiers
misc_feature         1..14
                     note = Conserved sequences for PsiK gene
source               1..14
                     mol_type = other DNA
                     organism = synthetic construct
SEQUENCE: 85
ttcttctctg gaaa                                                     14

SEQ ID NO: 86        moltype = DNA  length = 19
FEATURE              Location/Qualifiers
misc_feature         1..19
                     note = Conserved sequences for PsiK gene
source               1..19
                     mol_type = other DNA
                     organism = synthetic construct
SEQUENCE: 86
tgtatcaaac catcatacc                                               19

SEQ ID NO: 87        moltype = DNA  length = 15
FEATURE              Location/Qualifiers
misc_feature         1..15
                     note = Conserved sequences for PsiK gene
source               1..15
                     mol_type = other DNA
                     organism = synthetic construct
SEQUENCE: 87
tattcttctc cagtt                                                    15

SEQ ID NO: 88        moltype = DNA  length = 11
FEATURE              Location/Qualifiers
misc_feature         1..11
                     note = Conserved sequences for PsiM gene
source               1..11
                     mol_type = other DNA
                     organism = synthetic construct
SEQUENCE: 88
ccagaagccc a                                                        11

SEQ ID NO: 89        moltype = DNA  length = 11
FEATURE              Location/Qualifiers
misc_feature         1..11
                     note = Conserved sequences for PsiM gene
source               1..11
                     mol_type = other DNA
                     organism = synthetic construct
SEQUENCE: 89
gaagaccgtc t                                                        11
```

-continued

```
SEQ ID NO: 90          moltype = DNA   length = 17
FEATURE                Location/Qualifiers
misc_feature           1..17
                       note = Conserved sequences for PsiM gene
source                 1..17
                       mol_type = other DNA
                       organism = synthetic construct
SEQUENCE: 90
gagggaggtg aatcggc                                              17

SEQ ID NO: 91          moltype = DNA   length = 12
FEATURE                Location/Qualifiers
misc_feature           1..12
                       note = Conserved sequences for PsiM gene
source                 1..12
                       mol_type = other DNA
                       organism = synthetic construct
SEQUENCE: 91
aacacgatgc ag                                                   12

SEQ ID NO: 92          moltype = DNA   length = 12
FEATURE                Location/Qualifiers
misc_feature           1..12
                       note = Conserved sequences for PsiM gene
source                 1..12
                       mol_type = other DNA
                       organism = synthetic construct
SEQUENCE: 92
gtggggctgc tg                                                   12

SEQ ID NO: 93          moltype = DNA   length = 11
FEATURE                Location/Qualifiers
misc_feature           1..11
                       note = Conserved sequences for PsiM gene
source                 1..11
                       mol_type = other DNA
                       organism = synthetic construct
SEQUENCE: 93
aacgaatacg t                                                    11

SEQ ID NO: 94          moltype = DNA   length = 11
FEATURE                Location/Qualifiers
misc_feature           1..11
                       note = Conserved sequences for PsiM gene
source                 1..11
                       mol_type = other DNA
                       organism = synthetic construct
SEQUENCE: 94
tctaacgccg a                                                    11

SEQ ID NO: 95          moltype = DNA   length = 15
FEATURE                Location/Qualifiers
misc_feature           1..15
                       note = Conserved sequences for PsiM gene
source                 1..15
                       mol_type = other DNA
                       organism = synthetic construct
SEQUENCE: 95
agctctcttt tctag                                                15

SEQ ID NO: 96          moltype = DNA   length = 19
FEATURE                Location/Qualifiers
misc_feature           1..19
                       note = Conserved sequences for PsiH gene
source                 1..19
                       mol_type = other DNA
                       organism = synthetic construct
SEQUENCE: 96
ttgcaggatg catatacta                                            19

SEQ ID NO: 97          moltype = DNA   length = 30
FEATURE                Location/Qualifiers
misc_feature           1..30
                       note = Conserved sequences for PsiH gene
source                 1..30
                       mol_type = other DNA
                       organism = synthetic construct
SEQUENCE: 97
cccttcattg ggaacatgtt tgatatgcct                                30
```

-continued

```
SEQ ID NO: 98          moltype = DNA  length = 14
FEATURE                Location/Qualifiers
misc_feature           1..14
                       note = Conserved sequences for PsiH gene
source                 1..14
                       mol_type = other DNA
                       organism = synthetic construct
SEQUENCE: 98
caatggggac ggga                                                     14

SEQ ID NO: 99          moltype = DNA  length = 14
FEATURE                Location/Qualifiers
misc_feature           1..14
                       note = Conserved sequences for PsiH gene
source                 1..14
                       mol_type = other DNA
                       organism = synthetic construct
SEQUENCE: 99
gaaaagcgag ggtc                                                     14

SEQ ID NO: 100         moltype = DNA  length = 14
FEATURE                Location/Qualifiers
misc_feature           1..14
                       note = Conserved sequences for PsiH gene
source                 1..14
                       mol_type = other DNA
                       organism = synthetic construct
SEQUENCE: 100
atggggtggg agtt                                                     14

SEQ ID NO: 101         moltype = DNA  length = 23
FEATURE                Location/Qualifiers
misc_feature           1..23
                       note = Conserved sequences for PsiH gene
source                 1..23
                       mol_type = other DNA
                       organism = synthetic construct
SEQUENCE: 101
cgcatgttcg ccaaggagtt cag                                           23

SEQ ID NO: 102         moltype = DNA  length = 12
FEATURE                Location/Qualifiers
misc_feature           1..12
                       note = Conserved sequences for PsiH gene
source                 1..12
                       mol_type = other DNA
                       organism = synthetic construct
SEQUENCE: 102
caaaacgcca ga                                                       12

SEQ ID NO: 103         moltype = DNA  length = 14
FEATURE                Location/Qualifiers
misc_feature           1..14
                       note = Conserved sequences for PsiH gene
source                 1..14
                       mol_type = other DNA
                       organism = synthetic construct
SEQUENCE: 103
ttcaagcgca aagc                                                     14

SEQ ID NO: 104         moltype = DNA  length = 13
FEATURE                Location/Qualifiers
misc_feature           1..13
                       note = Conserved sequences for PsiH gene
source                 1..13
                       mol_type = other DNA
                       organism = synthetic construct
SEQUENCE: 104
cagctcgtct gca                                                      13

SEQ ID NO: 105         moltype = DNA  length = 13
FEATURE                Location/Qualifiers
misc_feature           1..13
                       note = Conserved sequences for PsiH gene
source                 1..13
                       mol_type = other DNA
                       organism = synthetic construct
SEQUENCE: 105
```

-continued

```
aatgtcggta agt                                                         13

SEQ ID NO: 106          moltype = DNA   length = 34
FEATURE                 Location/Qualifiers
misc_feature            1..34
                        note = Conserved sequences for PsiH gene
source                  1..34
                        mol_type = other DNA
                        organism = synthetic construct
SEQUENCE: 106
actatgacga agaagatgac tccttgccat acct                                  34

SEQ ID NO: 107          moltype = DNA   length = 14
FEATURE                 Location/Qualifiers
misc_feature            1..14
                        note = Conserved sequences for PsiH gene
source                  1..14
                        mol_type = other DNA
                        organism = synthetic construct
SEQUENCE: 107
gcatttggct atgg                                                        14

SEQ ID NO: 108          moltype = DNA   length = 12
FEATURE                 Location/Qualifiers
misc_feature            1..12
                        note = Conserved sequences for PsiH gene
source                  1..12
                        mol_type = other DNA
                        organism = synthetic construct
SEQUENCE: 108
tttccagtgc ag                                                          12

SEQ ID NO: 109          moltype = DNA   length = 11
FEATURE                 Location/Qualifiers
misc_feature            1..11
                        note = Conserved sequences for PsiD gene
source                  1..11
                        mol_type = other DNA
                        organism = synthetic construct
SEQUENCE: 109
caagaattta t                                                           11

SEQ ID NO: 110          moltype = DNA   length = 18
FEATURE                 Location/Qualifiers
misc_feature            1..18
                        note = Conserved sequences for PsiD gene
source                  1..18
                        mol_type = other DNA
                        organism = synthetic construct
SEQUENCE: 110
ctatgtaata tgttcaac                                                    18

SEQ ID NO: 111          moltype = DNA   length = 14
FEATURE                 Location/Qualifiers
misc_feature            1..14
                        note = Conserved sequences for PsiD gene
source                  1..14
                        mol_type = other DNA
                        organism = synthetic construct
SEQUENCE: 111
atctttcgca aagc                                                        14

SEQ ID NO: 112          moltype = DNA   length = 11
FEATURE                 Location/Qualifiers
misc_feature            1..11
                        note = Conserved sequences for PsiD gene
source                  1..11
                        mol_type = other DNA
                        organism = synthetic construct
SEQUENCE: 112
gtagtcggtg g                                                           11

SEQ ID NO: 113          moltype = DNA   length = 13
FEATURE                 Location/Qualifiers
misc_feature            1..13
                        note = Conserved sequences for PsiD gene
source                  1..13
                        mol_type = other DNA
                        organism = synthetic construct
```

```
SEQUENCE: 113
acgtccagtc tct                                                              13

SEQ ID NO: 114      moltype = DNA  length = 17
FEATURE             Location/Qualifiers
misc_feature        1..17
                    note = Conserved sequences for PsiD gene
source              1..17
                    mol_type = other DNA
                    organism = synthetic construct
SEQUENCE: 114
gtcaccgctt accaccg                                                          17

SEQ ID NO: 115      moltype = DNA  length = 22
FEATURE             Location/Qualifiers
misc_feature        1..22
                    note = Conserved sequences for PsiD gene
source              1..22
                    mol_type = other DNA
                    organism = synthetic construct
SEQUENCE: 115
tcaacgttcc aggtacctac tt                                                    22

SEQ ID NO: 116      moltype = DNA  length = 11
FEATURE             Location/Qualifiers
misc_feature        1..11
                    note = Conserved sequences for PsiD gene
source              1..11
                    mol_type = other DNA
                    organism = synthetic construct
SEQUENCE: 116
gccgacaaca a                                                                11

SEQ ID NO: 117      moltype = DNA  length = 12
FEATURE             Location/Qualifiers
misc_feature        1..12
                    note = Conserved sequences for PsiD gene
source              1..12
                    mol_type = other DNA
                    organism = synthetic construct
SEQUENCE: 117
atgttccatt tc                                                               12

SEQ ID NO: 118      moltype = DNA  length = 1320
FEATURE             Location/Qualifiers
source              1..1320
                    mol_type = genomic DNA
                    organism = Psilocybe cubensis
SEQUENCE: 118
atgcaggtga tacccgcgtg caactcggca gcaataagat cactatgtcc tactcccgag   60
tcttttagaa acatgggatg gctctctgtc agcgatgcgg tctacagcga gttcatagga   120
gagttggcta cccgcgcttc caatcgaaat tactccaacg agttcggcct catgcaacct   180
atccaggaat tcaaggcttt cattgaaagc gacccggtgg tgcaccaaga atttattgac   240
atgttcgagg gcattcagga ctctccaagg aattatcagg aactatgtaa tatgttcaac   300
gatatctttc gcaaagctcc cgtctacgga gaccttggcc ctcccgttta tatgattatg   360
gccaaattaa tgaacacccg agcgggcttc tctgcattca cgagacaaag gttgaacctt   420
cacttcaaaa aacttttcga tacctgggga ttgttcctgt cttcgaaaga ttctcgaaat   480
gttcttgtgg ccgaccagtt cgacgacaga cattgcggct ggttgaacga gcgggccttg   540
tctgctatgg ttaaacatta caatggacgc gcatttgatg aagtcttcct ctgcgataaa   600
aatgccccat actacggctt caactcttac gacgacttct ttaatcgcag atttcgaaac   660
cgagatatcg accgacctgt agtcggtgga gttaacaaca ccaccctcat ttctgctgct   720
tgcgaatcac tttcctacaa cgtctcttat gacgtccagt ctctcgacac tttagttttc   780
aaaggagaga cttattcgct taagcatttg ctgaataatg accctttcac cccacaattc   840
gagcatggga gtattctaca aggattcttg aacgtcaccg cttaccaccg atggcacgca   900
cccgtcaatg ggacaatcgt caaaatcatc aacgttccag gtacctactt tgcgcaagcc   960
ccgagcacga ttggcgaccc tatcccggat aacgattacg acccacctcc ttaccttaag   1020
tctcttgtct acttctctaa tattgccgca aggcaaatta tgtttattga agccgacaac   1080
aaggaaattg gcctcatttt ccttgtgttc atcggcatga ccgaaatctc gacatgtgaa   1140
gccacggtgt ccgaaggtca acacgtcaat cgtggcgatg acttgggaat gttccatttc   1200
ggtggttctt cgttcgcgct tggtctgagg aaggattgca gggcagagat cgttgaaaag   1260
ttcaccgaac ccggaacagt gatcagaatc aacgaagtcg tcgctgctct aaaggcttag   1320

SEQ ID NO: 119      moltype = DNA  length = 1320
FEATURE             Location/Qualifiers
source              1..1320
                    mol_type = genomic DNA
                    organism = Psilocybe cyanescens
SEQUENCE: 119
atgcaggtac tgcccgcgtg ccaatcttcc gcgcttaaaa cattgtgccc atcccccgag   60
```

```
gcctttcgaa agctcggttg gctccctact agcgacgagg tttacaacga attcatcgat  120
gacttgaccg gtcgcacgtg caatgaaaag tactccagcc aggttacact tttgaagcct  180
atccaagatt tcaagacatt catcgagaat gatcccatag tgtatcaaga atttatctct  240
atgtttgaag gaatcgagca gtctcccacc aactaccacg agctatgtaa catgttcaac  300
gacatctttc gcaaagcccc actctacggc gatcttggtc ctccggttta catgatcatg  360
gccagaataa tgaatacgca ggcgggtttc tctgcgttca caaaagagag cttgaacttc  420
catttcaaaa agctcttcga cacctggggg ctattccttt cctcgaaaaa ctctcgaaac  480
gtgcttgttg cagaccagtt tgacgataag cattacgggt ggttcagcga gcgagccaag  540
actgccatga tgattaatta tccagggcgt acattcgaga aagtcttcat ctgcgacgag  600
cacgttccat accatggctt cacttcctat gacgatttct tcaatcgcag gttcagggac  660
aaggatacag atcggcccgt agtcggtggg gttactgaca ccactttaat cggggctgcc  720
tgtgaatcgt tgtcatataa cgtctctcac aacgtccagt ctcttgacac gctagtcatc  780
aagggagagg cctattcact taaacatcta cttcataacg accccttcac accgcaattc  840
gaacatggga gcatcattca aggattccta aatgtcaccg cttaccaccg ctggcactcc  900
cccgtcaatg gcacgattgt gaagatcgtc aacgttccag gtacctactt cgctcaagct  960
ccatatacaa ttggatctcc tatccccgat aacgaccgcg acccgcctcc ttacctcaag  1020
tcactcgtat acttctccaa catcgctgca cggcaaatta tgttcatcga ggccgacaac  1080
aaagacatcg gcctcatttt cttggtcttc attggaatga ctgagatctc gacttgcgag  1140
gcgacggtgt gcgaaggtca gcatgtcaac cgccggtgacg atttgggcat gttccatttc  1200
ggtggttcat cttttgccct tggcttgcgg aaggactcga aggcgaagat tttgaaaag  1260
ttcgcgaaac cggggaccgt tattaggatc aacgagctag ttgcatctgt aaggaagtag  1320
```

SEQ ID NO: 120          moltype = DNA  length = 1089
FEATURE                 Location/Qualifiers
source                  1..1089
                        mol_type = genomic DNA
                        organism = Psilocybe cubensis
SEQUENCE: 120
```
atggcgttcg atctcaagac tgaagacggc ctcatcacat atctcactaa acatctttct  60
ttggacgtcg acacgagcgg agtgaagcgc cttagcggag gctttgtcaa tgtaacctgg  120
cgcattaagc tcaatgctcc ttatcaaggt catacgagca tcatcctgaa gcatgctcag  180
ccgcacatgt ctacggatga ggattttaag ataggtgtag aacgttcggt ttacgaatac  240
caggctatca agctcatgat ggccaatcgg gaggttctgg gaggcgtgga tggcatagtt  300
tctgtgccag aaggcctgaa ctacgactta gagaataatg cattgatcat gcaagatgtc  360
gggaagatga agacccttt agattatgtc accgccaaac cgccacttgc gacggatata  420
gcccgccttg ttgggacaga aattggggg ttcgttgcca gactccataa cataggccgc  480
gagaggcgag acgatcctga gttcaaattc ttctctggaa atattgtcgg aaggacgact  540
tcagaccagc tgtatcaaac catcataccc aacgcagcga aatatggcgt cgatgacccc  600
ttgctgccta ctgtggttaa ggaccttgtg gacgatgtca tgcacagcga agagaccctt  660
gtcatggcgg acctgtggag tggaaatatt cttctccagt tggaggaggg aaacccatcg  720
aagctgcaga agatatatat cctggattgg gaactttgca gtacggccc agcgtcgttg  780
gacctgggct atttcttggg tgactgctat ttgatatccc gctttcaaga cgagcaggtc  840
ggtacgacga tgcggcaagc ctacttgcaa agctatgcgc gtacgagcaa gcattcgatc  900
aactacgcca aagtcactgc aggtattgct gctcatattg tgatgtggac cgactttatg  960
cagtgggga gcgaggaaga aaggatataaat tttgtgaaaa aggggtagc tgcctttcac  1020
gacgccaggg gcaacaacga caatgggaa attacgtcta ccttactgaa ggaatcatcc  1080
actgcgtaa                                                            1089
```

SEQ ID NO: 121          moltype = DNA  length = 1086
FEATURE                 Location/Qualifiers
source                  1..1086
                        mol_type = genomic DNA
                        organism = Psilocybe cyanescens
SEQUENCE: 121
```
atgactttcg atctcaagac tgaagaaggc ctgctctcat acctcacaaa gcacctatcg  60
ctggacgttg ctcccaacgg ggtgaaacgt cttagtggag gcttcgtcaa cgttacctgg  120
cgggtcgggc tcaatgcccc ttatcatggt cacacgagca ttattctgaa gcatgctcaa  180
ccgcacctgt cttcagacat agatttcaag ataggtgttg aacgatcggc gtacgagtat  240
caagcgctca aaatcgtgtc agccaatagc tcccttctag gcagcagcga tattcgggtc  300
tctgtaccag aaggtcttca ctacgacgtc gttaataacg cattgatcat gcaagatgtc  360
gggacaatga agaccctgtt ggactatgtc actgccaaac caccaatttc tgcagagatc  420
gccagtctcg taggcagtca aattggtgca tttatcgcta ggctgcacaa cctcggccgc  480
gagaataaag acaaggacga cttcaagttc ttctctggaa acatcgtcgg gagaacaacc  540
gcagaccagt tgtatcaaac catcatacct aatgccgcta aatacggtca cgacgatccc  600
attctcccaa ttgtggtaaa ggagttggtg gaggaggtca tgaatagtga agaaacgctt  660
atcatggcgg atttatggag tggcaatatt cttctccagt ttgatgaaaa ctcgacggaa  720
ttgacgagga tatggctggt agactgggag ttgtgcaaat atggtccacc gtctttggac  780
atggggtact tcttaggcga ctgtttcctg gtcgctcgat ttcaagatca gctccgtaggg  840
acatcaatgc gacaggccta cttgaagagc tacgcaagga atgtcaagga gccaatcaat  900
tatgcaaaag ccaccgcagg catcggccgcg catctcgtca tgtggactga tttcatgaag  960
tgggggaacg atgaagagag ggaagagttt gttaagaaag gcgtgaagc cttccatgaa  1020
gcaaatgagg acaatagaaa cggggagatt acgtctatac ttgtgaagga agcatcgcgc  1080
acttag                                                              1086
```

SEQ ID NO: 122          moltype = DNA  length = 930
FEATURE                 Location/Qualifiers
source                  1..930
                        mol_type = genomic DNA
                        organism = Psilocybe cubensis

```
SEQUENCE: 122
atgcatatca gaaatcctta ccgtacacca attgactatc aagcactttc agaggccttc   60
cctcccctca agccatttgt gtctgtcaat gcagatggta ccagttctgt tgacctcact  120
atcccagaag cccagagggc gttcacggcc gctcttcttc atcgtgactt cgggctcacc  180
atgaccatac cagaagaccg tctgtgccca acagtcccca ataggttgaa ctacgttctg  240
tggattgaag atattttcaa ctacacgaac aaaaccctcg gcctgtcgga tgaccgtcct  300
attaaaggcg ttgatattgg tacaggagcc tccgcaattt atcctatgct tgcctgtgct  360
cggttcaagg catggtctat ggttggaaca gaggtcgaga ggaagtgcat tgacacggcc  420
cgcctcaatg tcgtcgcgaa caatctccaa gaccgtctct cgatattaga gacatccatt  480
gatggtccta ttctcgtccc cattttcgag gcgactgaag aatacgaata cgagtttact  540
atgtgtaacc ctccattcta cgacggtgct gccgatatgc agacttcgga tgctgccaaa  600
ggatttggat ttggcgtggg cgctccccat tctggaacag tcatcgaaat gtcgactgag  660
ggaggtgaat cggctttcgt cgctcagatg gtccgtgaga gcttgaagct tcgaacacga  720
tgcagatggt acacgagtaa cttgggaaag ctgaaatcct tgaaagaaat agtggggctg  780
ctgaaagaac ttgagataag caactatgcc attaacgaat acgttcaggg gtccacacgt  840
cgttatgccg ttgcgtggtc tttcactgat attcaactgc ctgaggagct ttctcgtccc  900
tctaaccccg agctcagctc tcttttctag                                    930

SEQ ID NO: 123      moltype = DNA  length = 930
FEATURE             Location/Qualifiers
source              1..930
                    mol_type = genomic DNA
                    organism = Psilocybe cyanescens
SEQUENCE: 123
atgcatatca ggaacccata ccgcgatggt gttgactacc aagcactcgc tgaagcattt   60
ccggctctca aaccacatgt cacagtaaat tcagacaatt cgacctccat cgactttgct  120
gtgccagaag cccaaagact gtatacagct gcccttctac accgggattt cggtcttacg  180
atcacactcc cggaagaccg tctttgtccg acagtgccta atcggctcaa ctatgtcctt  240
tgggttgaag atatccttaa agtcacttct gatgctctcg gtcttccgga taatcgtcaa  300
gttaagggga tcgatatcgg aactggcgca tcagcgatat atcccatgct cgcatgctct  360
cgtttttaaga catggtccat ggttgcaaca gaggtagacc agaagtgtat tgacactgct  420
cgtctcaacg tcattgccaa caacctccaa gaacgtctcg caattatagc cacctccgtc  480
gatggtccta tacttgtccc cctcttgcag gcgaattctg attttgagta cgattttacg  540
atgtgtaatc cgcccttcta cgatgggca tccgacatgc agacatcgga tgctgcgaag  600
gggtttggat tcggtgtgaa cgctccgcat accggcacgg tgctcgagat ggccaccgag  660
ggaggtgaat cggccttcgt agcccaaatg gtccgcgaaa gtttgaatct tcaaacacga  720
tgcaggtggt tcacgagtaa tttggggaaa ttgaagtcct tgtacgaaat tgtggggctg  780
ctgcgagaac atcagataag taactacgca atcaacgaat acgtccaagg agccactcgt  840
cgatatgcga ttgcatggtc gttcatcgat gttcgactgc ctgatcattt gtcccgtcca  900
tctaaccccg acctaagctc tcttttctag                                    930

SEQ ID NO: 124      moltype = DNA  length = 2155
FEATURE             Location/Qualifiers
source              1..2155
                    mol_type = genomic DNA
                    organism = Psilocybe cubensis
SEQUENCE: 124
atgatcgctg tactattctc cttcgtcatt gcaggatgca tatactacat cgtttctcgt   60
agagtgaggc ggtcgcgctt gccaccaggg ccgcctggca ttcctattcc cttcattggg  120
aacatgtttg atatgcctga agaatctcca tggttaacat ttctacaatg gggacgggat  180
tacagtctgt cttgccgcgt tgacttctaa tatatgaaca gctaatatat tgtcagacac  240
cgatattctc tacgtggatg ctggagggac agaaatggtt attcttaaca cgttggagac  300
cattaccgat ctattagaaa agcgagggtc catttattct ggccggtgag ctgatgttga  360
gttttttgca attgaatttg tggtcacacg tttccagact tgagagtaca atggtcaacg  420
aacttatggg gtgggagttt gacttagggt tcatcacata cggcgacagg tggcgcgaag  480
aaaggcgcat gttcgccaag gagttcagtg agaagggcat caagcaattt cgccatgctc  540
aagtgaaagc tgcccatcag cttgtccaac agcttaccaa aacgcagac cgctgggcac  600
aacatattcg ccagtaagta ctacttgagg aaaatagcgt acgcttcgct gaccggtccg  660
tacatcaaag tcagatagcg gcaatgtcac tggatattgt ttatggaatt gatcttgcag  720
aagacgaccc ttggctggaa gcgacccatt tggctaatga aggcctcgcc atagcatcag  780
tgccgggcaa attttgggtc gattcgttcc cttctcgtga gcatcctct tctatgtagg  840
aagggaagga gtctaacaag tgttagtaaa atacttcct gcttggttcc caggtgctgt  900
cttcaagcgc aaagcgaagg tctggcgaga agccgccgac catatggttg acatgcctta  960
tgaaactatg aggaaattag cagttagtca aatgcgttct ccccgtattt tttcaatact 1020
ctaacttcag ctcacagcct caaggattga ctcgtccgtc gtatgcttca gctcgtctgc 1080
aagccatgga tctcaacggt gaccttgagc atcaagaaca cgtaatcaag aacacagccg 1140
cagaggttaa tgtcggtaag tcaaaagcgt ccgtcggcaa ttcaaaattc aggcgctaaa 1200
gtgggtcttc tcaccaaggt ggaggcgata ctgtaaggat ttctcaatcg ttagagtata 1260
agtgttctaa tgcagtacat actccaccaa ccagactgtc tctgctatgt ctgcgttcat 1320
cttggccatg gtgaagtacc ctgaggtcca gcgaaaggtt caagcggagc ttgatgctct 1380
gaccaataac ggccaaattc ctgactatga cgaagaagat gactccttgc catacctcac 1440
cgcatgtatc aaggagcttt tccggtggaa tcaaatcgca cccctcgcta taccgcacaa 1500
attaatgaag gacgacgtgt accgcgggta tctgattccc aagaacactc tagtcttcgc 1560
aaacacctgg tgaggctgtc cattcattcc tagtacatcc gttgccccac taatagcatc 1620
ttgataacag ggcagtatta aacgatccag aagtctatcc agatccctct gtgttccgcc 1680
cagaaagata tcttggtcct gacgggaagc ctgataacac tgtacgcgac ccacgtaaag 1740
cggcatttgg ctatggacga cgaaattggt aagtgcgctt tcagaacccc ccttccgtt 1800
gactagtgcc atgcgcgcat acaatatcgc tattgatctg atataacttc cctgcggcat 1860
ttattttggc attcctttag tcccggaatt catctagcgc agtcgacggt ttggattgca 1920
```

```
ggggcaaccc tcttatcagc gttcaatatc gagcgacctg tcgatcagaa tgggaagccc   1980
attgacatac cggctgattt tactacagga ttcttcaggt agctaatttc cgtctttgtg   2040
tgcataatac ccctaacgac gcacgtttac ctttttgtaa agacacccag tgcctttcca   2100
gtgcaggttt gttcctcgaa cagagcaagt ctcacagtcg gtatccggac cctga         2155
```

SEQ ID NO: 125            moltype = DNA   length = 2122
FEATURE                   Location/Qualifiers
source                    1..2122
                          mol_type = genomic DNA
                          organism = Psilocybe cyanescens
SEQUENCE: 125
```
atgattgttc tattggtctc gctcgtcctt gcaggatgca tatactacgc caacgctcgt   60
agagtaaggc gctcgcgctt accaccgggc ccgcctggca taccactgcc cttcattggg   120
aatatgtttg atatgccttc agagtcaccg tggttaagat ttcttcaatg gggacgggac   180
tatcgtacgt caaacattgt tttgatttgc gcatttaatt gatatctcta gacactgata   240
tcctttactt gaatgctggc ggaacggaaa taattattct gaacacactg gatgctataa   300
ccgacttgtt ggaaaagcga gggtcgatgt attcgggtcg gtaagttgtt gctatgtctt   360
ttatggataa gatattaaag aagatgcgtc agactcgaga gcaccatggt gaacgaactc   420
atggggtggg agttcgactt gggattcata acctatggtg aaagatggcg cgaagaaaga   480
cgcatgttcg ccaaggagtt cagcgaaaaa aacatcaggc aattccgcca cgcccaaatt   540
aaagctgcca atcagcttgt tcggcagctg atcaaaacgc cagatcgttg gtcgcagcac   600
atccggcagt aagttgtaaa aatatagaca agcatcgagt cggaggctgac cattaattat   660
ggtacagtca gatagcagcc atgtctctag acattggtta tggaattgat ctcgcagagg   720
atgacccctg gattgcagca acccagctag ctaacgaagg gctcgccgaa gcttcagtac   780
cgggcagttt ctgggtcgac tcattccccg cccgtgagtg ctttcttcc tccattagac    840
tactagtcac gaatcatttg atttctactc agtcaaatac cttccttcat ggcttcctgg   900
tgcaggattc aagcgcaaag caaaggtatg gaaggaaggt gctgaccata tggtgaacat   960
gccgtatgaa acgatgaaaa aattgactgt atgttatctt ccgtgatggc tcgtacggag   1020
aattgcactg attgctacac tacaggttca aggcttggcc cgaccttcat atgcctcagc   1080
tcgtctgcag gccatggacc ccgatggcga tctcgagcat caggaacacg tgatcagaaa   1140
cacagcgact gaggtcaatg tcggtaagtt actagtaatg cctcttcggc tattaaagaa   1200
ttgggcgcta attgatttgc attgacctag gcggaggtga tacggtaaat atacctcctg   1260
ctactacccg actgcacgtt cttacatgct ttacatttaa cattcagact gtttctgctg   1320
tgtcagcctt tattttggcc atggtcaaat atccagaagt tcaacgccaa gtccaagcag   1380
aactggatgc actcaccagc aaaggagttg tcccaaacta tgacgaagaa gacgactcct   1440
tgccatacct tacggcttgc gtcaaggaaa tctttcgatg gaaccaaata gcacccttg    1500
ctatccctca tcggctgatc aaagacgatg tttatcgtgg gtatctcata ccaaagaatg   1560
ctttggtcta cgccaactca tggtatggcg ttctgtattc cctatattca tgcacatccg   1620
ctcattgttt actcgtaggg ctgtgttgaa tgacccagag ggtgacccaa atccctctga   1680
gttccgacca gaacgatatt tgagctctga cggaaagccc gacccaacgg tccgtgatcc   1740
ccgcaaagca gcatttggct atggtcgacg caactggtaa gcttttcaat tcatatctga   1800
cttcacaagc cgccgatctg atgcactaac ctgcggcatt ttctgtagtc ccggaatcca   1860
cctggcacaa tcgacggtat ggattgctgg agccactctt ctctcggtat tcaatatcga   1920
acgtcctgtt gatgggaatg gaaaacccat cgacatcccg gcgacgttca ctaccggatt   1980
cttcaggtat tcaattaagc tcttgcccta gggcatggag tgattgcatc tcattaacga   2040
tatggaactt tacagacatc ccgagccttt ccagtgcaga tttgtccctc gcactcagga   2100
gattctaaaa tccgtttccg gt                                            2122
```

SEQ ID NO: 126            moltype = AA   length = 439
FEATURE                   Location/Qualifiers
source                    1..439
                          mol_type = protein
                          organism = Psilocybe cubensis
SEQUENCE: 126
```
MQVIPACNSA AIRSLCPTPE SFRNMGWLSV SDAVYSEFIG ELATRASNRN YSNEFGLMQP   60
IQEFKAFIES DPVVHQEFID MFEGIQDSPR NYQELCNMFN DIFRKAPVYG DLGPPVYMIM   120
AKLMNTRAGF SAFTRQRLNL HFKKLFDTWG LFLSSKDSRN VLVADQFDDR HCGWLNERAL   180
SAMVKHYNGR AFDEVFLCDK NAPYYGFNSY DDFFNRRFRN RDIDRPVVGG VNNTTLISAA   240
CESLSYNVSY DVQSLDTLVF KGETYSLKHL LNNDPFTPQF EHGSILQGFL NVTAYHRWHA   300
PVNGTIVKII NVPGTYFAQA PSTIGDPIPD NDYDPPPYLK SLVYFSNIAA RQIMFIEADN   360
KEIGLIFLVF IGMTEISTCE ATVSEGQHVN RGDDLGMFHF GGSSFALGLR KDCRAEIVEK   420
FTEPGTVIRI NEVVAALKA                                                439
```

SEQ ID NO: 127            moltype = AA   length = 439
FEATURE                   Location/Qualifiers
source                    1..439
                          mol_type = protein
                          organism = Psilocybe cyanescens
SEQUENCE: 127
```
MQVLPACQSS ALKTLCPSPE AFRKLGWLPT SDEVYNEFID DLTGRTCNEK YSSQVTLLKP   60
IQDFKTFIEN DPIVYQEFIS MFEGIEQSPT NYHELCNMFN DIFRKAPLYG DLGPPVYMIM   120
ARIMNTQAGF SAFTKESLNF HFKKLFDTWG LFLSSKNSRN VLVADQFDDK HYGWFSERAK   180
TAMMINYPGR TFEKVFICDE HVPYHGFTSY DDFFNRRFRD KDTDRPVVGG VTDTTLIGAA   240
CESLSYNVSH NVQSLDTLVI KGEAYSLKHL LHNDPFTPQF EHGSIIQGFL NVTAYHRWHS   300
PVNGTIVKIV NVPGTYFAQA PYTIGSPIPD NDRDPPPYLK SLVYFSNIAA RQIMFIEADN   360
KDIGLIFLVF IGMTEISTCE ATVCEGQHVN RGDDLGMFHF GGSSFALGLR KDSKAKILEK   420
FAKPGTVIRI NELVASVRK                                                439
```

SEQ ID NO: 128            moltype = AA   length = 362

-continued

```
FEATURE                  Location/Qualifiers
source                   1..362
                         mol_type = protein
                         organism = Psilocybe cubensis
SEQUENCE: 128
MAFDLKTEDG LITYLTKHLS LDVDTSGVKR LSGGFVNVTW RIKLNAPYQG HTSIILKHAQ    60
PHMSTDEDFK IGVERSVYEY QAIKLMMANR EVLGGVDGIV SVPEGLNYDL ENNALIMQDV   120
GKMKTLLDYV TAKPPLATDI ARLVGTEIGG FVARLHNIGR ERRDDPEFKF FSGNIVGRTT   180
SDQLYQTIIP NAAKYGVDDP LLPTVVKDLV DDVMHSEETL VMADLWSGNI LLQLEEGNPS   240
KLQKIYILDW ELCKYGPASL DLGYFLGDCY LISRFQDEQV GTTMRQAYLQ SYARTSKHSI   300
NYAKVTAGIA AHIVMWTDFM QWGSEEERIN FVKKGVAAFH DARGNNDNGE ITSTLLKESS   360
TA                                                                 362

SEQ ID NO: 129           moltype = AA  length = 361
FEATURE                  Location/Qualifiers
source                   1..361
                         mol_type = protein
                         organism = Psilocybe cyanescens
SEQUENCE: 129
MTFDLKTEEG LLSYLTKHLS LDVAPNGVKR LSGGFVNVTW RVGLNAPYHG HTSIILKHAQ    60
PHLSSDIDFK IGVERSAYEY QALKIVSANS SLLGSSDIRV SVPEGLHYDV VNNALIMQDV   120
GTMKTLLDYV TAKPPISAEI ASLVGSQIGA FIARLHLGR ENKDKDDPKF FSGNIVGRTT    180
ADQLYQTIIP NAAKYGIDDP ILPIVVKELV EEVMNSEETL IMADLWSGNI LLQFDENSTE   240
LTRIWLVDWE LCKYGPPSLD MGYFLGDCFL VARFQDQLVG TSMRQAYLKS YARNVKEPIN   300
YAKATAGIGA HLVMWTDFMK WGNDEEREEF VKKGVEAFHE ANEDNRNGEI TSILVKEASR   360
T                                                                  361

SEQ ID NO: 130           moltype = AA  length = 309
FEATURE                  Location/Qualifiers
source                   1..309
                         mol_type = protein
                         organism = Psilocybe cubensis
SEQUENCE: 130
MHIRNPYRTP IDYQALSEAF PPLKPFVSVN ADGTSSVDLT IPEAQRAFTA ALLHRDFGLT    60
MTIPEDRLCP TVPNRLNYVL WIEDIFNYTN KTLGLSDDRP IKGVDIGTGA SAIYPMLACA   120
RPFKAWSMVGT EVERKCIDTA RLNVVANNLQ DRLSILETSI DGPILVPIFE ATEEYEYEFT   180
MCNPPFYDGA ADMQTSDAAK GFGFGVGAPH SGTVIEMSTE GGESAFVAQM VRESLKLRTR   240
CRWYTSNLGK LKSLKEIVGL LKELEISNYA INEYVQGSTR RYAVAWSFTD IQLPEELSRP   300
SNPELSSLF                                                          309

SEQ ID NO: 131           moltype = AA  length = 309
FEATURE                  Location/Qualifiers
source                   1..309
                         mol_type = protein
                         organism = Psilocybe cyanescens
SEQUENCE: 131
MHIRNPYRDG VDYQALAEAF PALKPHVTVN SDNTTSIDFA VPEAQRLYTA ALLHRDFGLT    60
ITLPEDRLCP TVPNRLNYVL WVEDILKVTS DALGLPDNRQ VKGIDIGTGA SAIYPMLACS   120
RPFKTWSMVAT EVDQKCIDTA RLNVIANNLQ ERLAIIATSV DGPILVPLLQ ANSDFEYDFT   180
MCNPPFYDGA SDMQTSDAAK GFGFGVNAPH TGTVLEMATE GGESAFVAQM VRESLNLQTR   240
CRWFTSNLGK LKSLYEIVGL LREHQISNYA INEYVQGATR RYAIAWSFID VRLPDHLSRP   300
SNPDLSSLF                                                          309

SEQ ID NO: 132           moltype = AA  length = 691
FEATURE                  Location/Qualifiers
source                   1..691
                         mol_type = protein
                         organism = Psilocybe cubensis
VARIANT                  691
                         note = Any amino acid
SEQUENCE: 132
MIAVLFSFVI AGCIYYIVSR RVRRSRLPPG PPGIPIPFIG NMFDMPEESP WLTFLQWGRD    60
YSLSCRVDFY MNSYIVRHRY SLRGCWRDRN GYSHVGDHYR SIRKARVHLF WPVSCVFCNI   120
CGHTFPDLRV QWSTNLWGGS LTGSSHTATG GAKKGACSPR SSVRRASSNF AMLKKLPISL   180
SNSLPKRQTA GHNIFASKYY LRKIAYASLT GPYIKVRRQC HWILVMELIL QKTTLGWKRP   240
IWLMKASPHQ CRANFGSIRS LLVSILLLCR KGRSLTSVSK IPSCLVPRCC LQAQSEGLAR   300
SRRPYGHALN YEEISSSNAF SPYFNTLTS  AHSLKDLVRR MLQLVCKPWI STVTLSIKNT   360
SRTQPQRLMS VSQKRPSAIQ NSGAKVGLLT KVEAILGFLN RSISVLMQYI LHQPDCLCYV   420
CVHLGHGEVP GPAKGSSGAC SDQRPNSLRR RLLAIPHRMY QGAFPVESNR TPRYTAQINE   480
GRRVPRVSDS QEHSSLRKHL VRLSIHSYIR CPTNSILITG QYTIQKSIQI PLCSAQKDIL   540
VLTGSLITLY ATHVKRHLAM DDEIGKCAFR TPPSVDCHAR IQYRYSDITS LRHLFWHSFS   600
PGIHLAQSTV WIAGATLLSA FNIERPVDQN GKPIDIPADF TTGFFRLISV FVCIIPLTTH   660
VYLFVKTPSA FPVQVCSSNR ASLTVGIRTL X                                 691

SEQ ID NO: 133           moltype = AA  length = 674
FEATURE                  Location/Qualifiers
source                   1..674
                         mol_type = protein
                         organism = Psilocybe cyanescens
```

-continued

```
VARIANT          674
                 note = Any amino acid
SEQUENCE: 133
MIVLLVSLVL AGCIYYANAR RVRRSRLPPG PPGIPLPFIG NMFDMPSESP WLRFLQWGRD  60
YRTSNIVLIC AFNYLTLISF TMLAERKLFT HWMLPTCWKS EGRCIRVGKL LLCLLWIRYR  120
RCVRLESTMV NELMGWEFDL GFITYGERWR EERRMFAKEF SEKNIRQFRH AQIKAANQLV  180
RQLIKTPDRW SQHIRQVVKI TSIESRLTIN YGTVRQPCLT LVMELISQRM TPGLQQPSLT  240
KGSPKLQYRA VSGSTHSPPV SAFLPPLDYS RIIFLLSQIP SFMASWCRIQ AQSKGMEGRC  300
PYGEHAVNDE KIDCMLSSVM ARTENCTDCY TTGSRLGPTF ICLSSSAGHG PRWRSRASGT  360
RDQKHSDGQC RVTSNASSAI KELGANFALT AEVIRIYLLL LPDCTFLHAL HLTFRLFLLC  420
QPLFWPWSNI QKFNAKSKQN WMHSPAKELS QTMTKKTTPC HTLRLASRKS FDGTKHPLLS  480
LIGSKTMFIV GISYQRMLWS TPTHGMAFCI PYIHAHPLIV YSGCVEPRGV PKSLVPTRTI  540
FELRKARPNG PSPQSSIWLW STQLVSFSIH ILHKPPICTN LRHFLSRNPP GTIDGMDCWS  600
HSSLGIQYRT SCWEWKTHRH PGDVHYRILQ VFNALALGHG VIASHRYGTL QTSRAFPVQI  660
CPSHSGDSKI RFRX                                                    674
```

NON-HALLUCINOGENIC PSYCHEDELIC FUNGI

CROSS-REFERENCE

This application is a U.S. national stage entry under 35 U.S.C. § 371 of International Application No. PCT/US2023/030116, filed Aug. 11, 2023, which claims priority under PCT Article 8(1) and Rule 4.10 to U.S. Provisional Application No. 63/371,121, filed Aug. 11, 2022, and incorporated by reference for all purposes as if fully set forth herein.

SEQUENCE LISTING

This application includes an accompanying ST.26 Sequence Listing of 162.273 bytes submitted electronically in xml format, created on Aug. 4, 2022, named 122313-10103_sequence.xml; and an accompanying ST.26 Sequence Listing of 208.929 bytes submitted electronically in xml format, created on Nov. 1, 2023, named LMI-PCT-001_SL.xml: both of which are hereby incorporated by reference in their entirety for all purposes.

FIELD OF THE INVENTION

The invention relates generally to genetically modified fungi and their use. In some aspects, the invention relates to non-hallucinogenic psychedelic fungi, methods of producing the fungi, compositions of the fungi, and methods of using the fungi and compositions thereof.

BACKGROUND OF THE INVENTION

Psilocybin-producing fungi, commonly known as "magic mushrooms," are a polyphyletic group of fungi that enzymatically synthesize and thus contain psilocybin. Upon ingestion of a psilocybin-producing fungi, the psilocybin is rapidly converted to its metabolite psilocin, which is the compound responsible for the "hallucinogenic" or "psychedelic" effects of magic mushrooms. Genera containing psilocybin-producing fungi include, e.g., *Conocybe, Copelandia, Galerina, Gymnopilus, Inocybe, Mycena, Panaeolus, Pholiotina, Pluteus, and Psilocybe.*

Besides containing psilocybin, psilocybin-producing fungi are rich in numerous other bioactive metabolites which provide therapeutic and other benefits to human health. These include other alkaloids such as the "minor" tryptamines, including norbaeocystin, baeocystin, norpsilocin, and aeruginascin, as well as compounds such as phenolics, terpenoids, glucans, polysaccharides, and lectins, which can provide antioxidant and other beneficial effects.

The U.S. Drug Enforcement Administration places psilocybin among Schedule I drugs in the Controlled Substances Act, meaning it has no currently accepted medical use and a high potential for abuse. Hence, the beneficial effects of psilocybin-producing fungi cannot be obtained without violating federal law. Further, the hallucinogenic effects of psilocybin, which include profound alterations in consciousness, may be inappropriate for some individuals (such as with certain pre-existing mental health conditions), or for some individuals at certain times.

Accordingly, there is a need for fungi that can confer the many benefits of psilocybin-producing fungi, but with eliminated or reduced psilocybin content, and thus without the legal risks or other drawbacks associated with psilocybin. Such "non-hallucinogenic psychedelic fungi," and compositions made therefrom, are useful, in non-limiting examples, as functional foods, as nootropics, and as legal "microdoses" of otherwise psychedelic fungi.

To meet this need and others, provided herein are such non-hallucinogenic psychedelic fungi, methods of producing the fungi, compositions of the fungi, and methods of using the fungi and compositions thereof, each of which will be appreciated to have such advantages and improvements as will become readily apparent through the disclosure below.

INCORPORATION BY REFERENCE

Each cited patent, publication, and non-patent literature is incorporated by reference in its entirety as if incorporated by reference individually. Unless specifically stated otherwise, reference is not to be construed as an admission that a document or any underlying information therein is prior art in any jurisdiction, or forms part of the common general knowledge in the art.

BRIEF SUMMARY OF THE INVENTION

The following presents a simplified summary of some embodiments of the invention in order to provide a basic understanding thereof. This summary is not an extensive overview of the invention. It is not intended to identify key or critical elements of the invention or to delineate the scope of the invention. Its sole purpose is to present some embodiments of the invention in a simplified form as a prelude to the more detailed description that is presented later.

In some aspects are disclosed non-hallucinogenic psychedelic fungi having reduced production of a bioactive alkaloid, wherein such fungi have disrupted activity of one or more of a PsiD, PsiH, PsiK, or PsiM enzyme.

In some embodiments, the bioactive alkaloid is tryptamine, 4-hydroxytryptamine, norbaeocystin, baeocystin, or psilocybin. In some embodiments, the bioactive alkaloid is a hallucinogenic tryptamine. In some embodiments, the hallucinogenic tryptamine is psilocybin.

In some embodiments, the fungus is a Psilocybe spp. fungus. In some embodiments, the *Psilocybe* spp. fungus is a *Psilocybe cubensis* fungus or a *Psilocybe* cyanescens fungus.

In some embodiments, the non-hallucinogenic psychedelic fungus has disrupted activity of a PsiD enzyme. In some embodiments, the non-hallucinogenic psychedelic fungus has disrupted activity of a PsiH enzyme. In some embodiments, the non-hallucinogenic psychedelic fungus has disrupted activity of a PsiK enzyme. In some embodiments, the non-hallucinogenic psychedelic fungus has disrupted activity of a PsiM enzyme. In some embodiments, the disrupted activity is a result of disrupted expression of one or more of a PsiD, PsiH, PsiK, or PsiM gene.

In some embodiments, the non-hallucinogenic psychedelic fungus has disrupted expression of a PsiD gene. In some embodiments, the disrupted expression of a PsiD gene comprises down-regulation of the PsiD gene to a steady state transcript level reduced at least twofold, at least threefold, at least fivefold, or at least tenfold relative to the unmodified strain under comparable growth conditions, as determined by qRT-PCR. In some embodiments, the non-hallucinogenic psychedelic fungus comprises no detectable transcript of the PsiD gene, when measured by qRT-PCR. In some embodiments, the PsiD gene expression is disrupted using siRNA. In some embodiments, the siRNA has at least 75%, at least 80%, at least 85%, at least 90%, at least 95%, or at least 99% sequence identity to a sequence selected from the group consisting of SEQ ID NOS: 52, 53, 54, 55, or 56, or a reverse complement thereof.

In some embodiments, the non-hallucinogenic psychedelic fungus has disrupted expression of a PsiH gene. In some embodiments, the disrupted expression of a PsiH gene comprises down-regulation of the PsiH gene to a steady state transcript level reduced at least twofold, at least threefold, at least fivefold, or at least tenfold relative to the unmodified strain under comparable growth conditions, as determined by qRT-PCR. In some embodiments, the non-hallucinogenic psychedelic fungus comprises no detectable transcript of the PsiH gene, when measured by qRT-PCR. In some embodiments, the PsiH gene expression is disrupted using siRNA. In some embodiments, the siRNA has at least 75%, at least 80%, at least 85%, at least 90%, at least 95%, or at least 99% sequence identity to a sequence selected from the group consisting of SEQ ID NOS: 67, 68, 69, 70, or 71, or a reverse complement thereof.

In some embodiments, the non-hallucinogenic psychedelic fungus has disrupted expression of the PsiK gene. In some embodiments, the disrupted expression of a PsiK gene comprises down-regulation of the PsiK gene to a steady state transcript level reduced at least twofold, at least threefold, at least fivefold, or at least tenfold relative to the unmodified strain under comparable growth conditions, as determined by qRT-PCR. In some embodiments, the non-hallucinogenic psychedelic fungus comprises no detectable transcript of the PsiK gene, when measured by qRT-PCR. In some embodiments, the PsiK gene expression is disrupted using siRNA. In some embodiments, the siRNA has at least 75%, at least 80%, at least 85%, at least 90%, at least 95%, or at least 99% sequence identity to a sequence selected from the group consisting of SEQ ID NOS: 57, 58, 59, or 61, or a reverse complement thereof.

In some embodiments, the non-hallucinogenic psychedelic fungus has disrupted expression of the PsiM gene. In some embodiments, the disrupted expression of a PsiM gene comprises down-regulation of the PsiM gene to a steady state transcript level reduced at least twofold, at least threefold, at least fivefold, or at least tenfold relative to the unmodified strain under comparable growth conditions, as determined by qRT-PCR. In some embodiments, the non-hallucinogenic psychedelic fungus comprises no detectable transcript of the PsiM gene, when measured by qRT-PCR. In some embodiments, the PsiM gene expression is disrupted using siRNA. In some embodiments, the siRNA has at least 75%, at least 80%, at least 85%, at least 90%, at least 95%, or at least 99% sequence identity to a sequence selected from the group consisting of SEQ ID NOS: 62, 63, 64, 65, or 66, or a reverse complement thereof.

In some embodiments, the non-hallucinogenic psychedelic fungus comprises a deletion in one or more of the PsiD, PsiH, PsiK, and PsiM genes.

In some embodiments, the non-hallucinogenic psychedelic fungus comprises a deletion of the PsiD gene. In some embodiments, the PsiD gene is deleted using CRISPR/Cas9. In some embodiments, deleting the PsiD gene comprises using an sgRNA having at least 75%, at least 80%, at least 85%, at least 90%, at least 95%, or at least 99% % sequence identity to a sequence selected from the group consisting of SEQ ID NOS: 13, 14, 15, 16, or 17, or a reverse complement thereof.

In some embodiments, the non-hallucinogenic psychedelic fungus comprises a deletion of the PsiH gene. In some embodiments, the PsiH gene is deleted using CRISPR/Cas9. In some embodiments, deleting the PsiH gene comprises using an sgRNA having at least 75%, at least 80%, at least 85%, at least 90%, at least 95%, or at least 99% sequence identity to a sequence selected from the group consisting of SEQ ID NOS: 27, 28, 29, 30, or 31, or a reverse complement thereof.

In some embodiments, the non-hallucinogenic psychedelic fungus comprises a deletion of the PsiK gene. In some embodiments, the PsiK gene is deleted using CRISPR/Cas9. In some embodiments, deleting the PsiK gene comprises using an sgRNA having at least 75%, at least 80%, at least 85%, at least 90%, at least 95%, or at least 99% sequence identity to a sequence selected from the group consisting of SEQ ID NOS: 18, 19, 20, 21, or 22, or a reverse complement thereof.

In some embodiments, the non-hallucinogenic psychedelic fungus comprises a deletion of the PsiM gene. In some embodiments, the PsiM gene is deleted using CRISPR/Cas9. In some embodiments, deleting the PsiM gene comprises using an sgRNA having at least 75%, at least 80%, at least 85%, at least 90%, at least 95%, or at least 99% sequence identity to a sequence selected from the group consisting of SEQ ID NO: 22, 23, 24, 25, or 26, or a reverse complement thereof.

In some embodiments, the disrupted activity or disrupted expression results from a gene knockout of one or more of the PsiD, PsiH, PsiK, and PsiM genes. In some embodiments, the disrupted activity or disrupted expression results from a gene knockout of two or more of the PsiD, PsiH, PsiK, and PsiM genes. In some embodiments, the disrupted activity or disrupted expression results from a gene knockout of three or more of the PsiD, PsiH, PsiK, and PsiM genes. In some embodiments, the disrupted activity or disrupted expression results from a gene knockout of all four of the PsiD, PsiH, PsiK, and PsiM genes. In some embodiments, the gene knockout results at least in part from homologous recombination. In some embodiments, the gene knockout results at least in part from using a zinc finger nuclease. In some embodiments, the gene knockout results at least in part from using TALENs. In some embodiments, the gene knockout results at least in part from using CRISPR/Cas9. In some embodiments, the gene knockout results at least in part from using a small interfering RNA (siRNA). In some embodiments, the gene knockout results at least in part from using a microRNA (miRNA).

In some embodiments, the disrupted activity or disrupted expression does not result from the insertion of exogenous genetic material.

In some embodiments, the production of psilocybin is reduced by an amount of greater than 90%, greater than 91%, greater than 92%, greater than 93%, greater than 94%, greater than 95%, greater than 96%, greater than 97%, greater than 98%, greater than 99%, greater than 99.5%, greater than 99.9%, greater than 99.95%, or greater than 99.99%, relative to a comparable wild-type fungus. In some embodiments, the fungus, when dried, comprises a weight/weight percent of psilocybin of less than 0.15, less than 0.10, less than 0.05, less than 0.001, or less than 0.005. In some embodiments, the non-hallucinogenic psychedelic fungus comprises no detectable psilocybin.

In some embodiments, the non-hallucinogenic psychedelic fungus further comprises a bioactive alkaloid other than psilocybin. In some embodiments, the bioactive alkaloid other than psilocybin is tryptamine, 4-hydroxytryptamine, norbaeocystin, or baeocystin. In some embodiments, the bioactive alkaloid other than psilocybin has a therapeutic or beneficial property. In some embodiments, the therapeutic or beneficial property is any of an antibacterial, antibiotic, antifungal, anticancer, immunosuppressant, immune-boosting, anti-inflammatory, hypoglycemic, antioxidant, antiviral, anti-neurodegenerative, anti-epileptic, neuroprotective, anti-angiogenic, antidiabetic, or hypocholesterolemic property. In some embodiments, the non-hallucinogenic psychedelic fungus comprises an increased amount of the bioactive alkaloid other than psilocybin, relative to a comparable wild-type fungus. In some embodiments, the increased amount is an increase of at least 5%, at least 10%, at least 15%, at least 20%, at least 25%, at least 30%, at least 40%, at least 50%, at least 75%, at least 100%, at least 200%, at least 300%, or at least 500%, relative to a comparable wild-type fungus.

In some aspects are disclosed methods of producing a non-hallucinogenic psychedelic fungus having reduced production of a bioactive alkaloid, comprising disrupting the activity of one or more of a PsiD, PsiH, PsiK, or PsiM enzyme.

In some embodiments, the bioactive alkaloid is tryptamine, 4-hydroxytryptamine, norbaeocystin, baeocystin, or psilocybin. In some embodiments, the bioactive alkaloid is a hallucinogenic tryptamine. In some embodiments, the hallucinogenic tryptamine is psilocybin.

In some embodiments, the fungus is a *Psilocybe* spp. fungus. In some embodiments, the *Psilocybe* spp. fungus is a *Psilocybe cubensis* fungus or a *Psilocybe* cyanescens fungus.

In some embodiments, the method comprises disrupting the activity of a PsiD enzyme. In some embodiments, the method comprises disrupting the activity of a PsiH enzyme. In some embodiments, the method comprises disrupting the activity of a PsiK enzyme. In some embodiments, the method comprises disrupting the activity of a PsiM enzyme.

In some embodiments, the method comprises disrupting the expression of one or more of a PsiD, PsiH, PsiK, or PsiM gene.

In some embodiments, the method comprises disrupting the expression of a PsiD gene. In some embodiments, the PsiD gene expression is disrupted using siRNA. In some embodiments, the siRNA has at least 75%, at least 80%, at least 85%, at least 90%, at least 95%, or at least 99% sequence identity to a sequence selected from the group consisting of SEQ ID NOS: 52, 53, 54, 55, or 56, or a reverse complement thereof.

In some embodiments, the method comprises disrupting the expression of a PsiH gene. In some embodiments, the PsiH gene expression is disrupted using siRNA. In some embodiments, the siRNA has at least 75%, at least 80%, at least 85%, at least 90%, at least 95%, or at least 99% sequence identity to a sequence selected from the group consisting of SEQ ID NOS: 67, 68, 69, 70, or 71, or a reverse complement thereof.

In some embodiments, the method comprises disrupting the expression of the PsiK gene. In some embodiments, the PsiK gene expression is disrupted using siRNA. In some embodiments, the siRNA has at least 75%, at least 80%, at least 85%, at least 90%, at least 95%, or at least 99% sequence identity to a sequence selected from the group consisting of SEQ ID NOS: 57, 58, 59, or 61, or a reverse complement thereof.

In some embodiments, the method comprises disrupting the expression of the PsiM gene. In some embodiments, the PsiM gene expression is disrupted using siRNA. In some embodiments, the siRNA has at least 75%, at least 80%, at least 85%, at least 90%, at least 95%, or at least 99% sequence identity to a sequence selected from the group consisting of SEQ ID NOS: 62, 63, 64, 65, or 66, or a reverse complement thereof.

In some embodiments, the method comprises deleting one or more of the PsiD, PsiH, PsiK, and PsiM genes.

In some embodiments, the method comprises deleting the PsiD gene. In some embodiments, the PsiD gene is deleted using CRISPR/Cas9. In some embodiments, deleting the PsiD gene comprises using an sgRNA having at least 75%, at least 80%, at least 85%, at least 90%, at least 95%, or at least 99% % sequence identity to a sequence selected from the group consisting of SEQ ID NOS: 13, 14, 15, 16, or 17, or a reverse complement thereof.

In some embodiments, the method comprises deletion of the PsiH gene. In some embodiments, the PsiH gene is deleted using CRISPR/Cas9. In some embodiments, deleting the PsiH gene comprises using an sgRNA having at least 75%, at least 80%, at least 85%, at least 90%, at least 95%, or at least 99% sequence identity to a sequence selected from the group consisting of SEQ ID NOS: 27, 28, 29, 30, or 31, or a reverse complement thereof.

In some embodiments, the method comprises deletion of the PsiK gene. In some embodiments, the PsiK gene is deleted using CRISPR/Cas9. In some embodiments, deleting the PsiK gene comprises using an sgRNA having at least 75%, at least 80%, at least 85%, at least 90%, at least 95%, or at least 99% sequence identity to a sequence selected from the group consisting of SEQ ID NOS: 18, 19, 20, 21, or 22, or a reverse complement thereof.

In some embodiments, the method comprises deletion of the PsiM gene. In some embodiments, the PsiM gene is deleted using CRISPR/Cas9. In some embodiments, deleting the PsiM gene comprises using an sgRNA having at least 75%, at least 80%, at least 85%, at least 90%, at least 95%, or at least 99% sequence identity to a sequence selected from the group consisting of SEQ ID NO: 22, 23, 24, 25, or 26, or a reverse complement thereof.

In some embodiments, the method comprises knocking out one or more of the PsiD, PsiH, PsiK, and PsiM genes. In some embodiments, the method comprises knocking out two or more of the PsiD, PsiH, PsiK, and PsiM genes. In some embodiments, the method comprises knocking out three or more of the PsiD, PsiH, PsiK, and PsiM genes. In some embodiments, the method comprises knocking out all four of the PsiD, PsiH, PsiK, and PsiM genes.

In some embodiments, the method comprises knocking out one or more of the genes done at least in part using homologous recombination. In some embodiments, the method comprises knocking out one or more of the genes done at least in part using a zinc finger nuclease. In some embodiments, the method comprises knocking out one or more of the genes done at least in part using TALENs. In some embodiments, the method comprises knocking out one or more of the genes done at least in part using CRISPR/Cas9. In some embodiments, the method comprises knocking out one or more of the genes done at least in part using a small interfering RNA (siRNA). In some embodiments, the method comprises knocking out one or more of the genes done at least in part using a microRNA (miRNA). In some embodiments, the method does not comprise inserting exogenous genetic material.

In some embodiments, the production of psilocybin is reduced by an amount of greater than 90%, greater than 91%, greater than 92%, greater than 93%, greater than 94%, greater than 95%, greater than 96%, greater than 97%, greater than 98%, greater than 99%, greater than 99.5%, greater than 99.9%, greater than 99.95%, or greater than 99.99%, relative to a comparable wild-type fungus. In some embodiments, the fungus, when dried, comprises a weight/weight percent of psilocybin of less than 0.15, less than 0.10, less than 0.05, less than 0.001, or less than 0.005. In some embodiments, the fungus comprises no detectable psilocybin.

In some embodiments, the fungus further comprises a bioactive alkaloid other than psilocybin. In some embodiments, the bioactive alkaloid other than psilocybin is tryptamine, 4-hydroxytryptamine, norbaeocystin, or bacocystin. In some embodiments, the bioactive alkaloid other than psilocybin has a therapeutic or beneficial property. In some embodiments, the therapeutic or beneficial property is any of an antibacterial, antibiotic, antifungal, anticancer, immuno-suppressant, immune-boosting, anti-inflammatory, hypoglycemic, antioxidant, antiviral, anti-neurodegenerative, anti-epileptic, neuroprotective, antiangiogenic, antidiabetic, or hypocholesterolemic property. In some embodiments, the fungus comprises an increased amount of the bioactive alkaloid other than psilocybin, relative to a comparable wild-type fungus. In some embodiments, the increased amount is an increase of at least 5%, at least 10%, at least 15%, at least 20%, at least 25%, at least 30%, at least 40%, at least 50%, at least 75%, at least 100%, at least 200%, at least 300%, or at least 500%, relative to a comparable wild-type fungus.

The foregoing has outlined broadly and in summary certain pertinent features of the disclosure so that the detailed description of the invention that follows may be better understood, and so that the present contribution to the art can be more fully appreciated. Hence, this summary is to be considered as a brief and general synopsis of only some of the objects and embodiments disclosed herein, is provided solely for the benefit and convenience of the reader, and is not intended to limit in any manner the scope, or range of equivalents, to which the claims are lawfully entitled. Additional features of the invention are described hereinafter. It should be appreciated by those in the art that all disclosed specific compositions and methods are only exemplary, and may be readily utilized as a basis for modifying or designing other compositions and methods for carrying out the same purposes. Such equivalent compositions and methods will be appreciated to be also within the scope and spirit of the invention as set forth in the claims.

BRIEF DESCRIPTION OF THE FIGURES

To further clarify various aspects of the invention, a more particular description is rendered by reference to certain exemplary embodiments illustrated in the figures. It will be appreciated that these figures depict only illustrated embodiments of the invention and should not be considered limiting of its scope. They are merely provided as exemplary illustrations of certain concepts of some embodiments of the invention. These figures, and the elements depicted therein, are not necessarily drawn to consistent scale or to any scale. Unless context suggests otherwise, like elements are indicated by like numerals. Certain aspects of the invention are therefore further described and explained with additional specificity and detail, but still by way of example only, with reference to the accompanying figures in which:

FIG. 1 shows consensus sequence alignment of PsiD genes from *P. cubensis* and *P. cyanescens*. Exemplary regions of conserved stretches of nucleotides are indicated in gray. These regions can be targeted for knock out or silencing of PsiD genes using CRISPR or siRNA oligos across various species. Longer consensus regions (>9 bp) serve as preferable target regions for oligo binding.

FIG. 2 shows consensus sequence alignment of PsiK genes from *P. cubensis* and *P. cyanescens*. Exemplary regions of conserved stretches of nucleotides are indicated in gray. These regions can be targeted for knock out or silencing of PsiK genes using CRISPR or siRNA oligos across various species. Longer consensus regions (>9 bp) serve as preferable target regions for oligo binding.

FIG. 3. shows consensus sequence alignment of PsiM genes from *P. cubensis* and *P. cyanescens*. Exemplary regions of conserved stretches of nucleotides are indicated in gray. These regions can be targeted for knock out or silencing of PsiM genes using CRISPR or siRNA oligos across various species. Longer consensus regions (>9 bp) serve as preferable target regions for oligo binding.

FIG. 3. shows consensus sequence alignment of PsiHI genes from *P. cubensis* and *P. cyanescens*. Exemplary regions of conserved stretches of nucleotides are indicated in gray. These regions can be targeted for knock out or silencing of PsiH genes using CRISPR or siRNA oligos across various species. Longer consensus regions (>9 bp) serve as preferable target regions for oligo binding.

FIG. 4. shows consensus sequence alignment of PsiHI genes from *P. cubensis* and *P. cyanescens*. Exemplary regions of conserved stretches of nucleotides are indicated in gray. These regions can be targeted for knock out or silencing of PsiH genes using CRISPR or siRNA oligos across various species. Longer consensus regions (>9 bp) serve as preferable target regions for oligo binding.

FIG. 5. shows consensus sequence alignment of PsiD polypeptides from *P. cubensis* and *P. Cyanescens*. Exemplary regions of conserved stretches of amino acids are indicated in gray.

FIG. 6. shows consensus sequence alignment of PsiK polypeptides from *P. Cubensis* and *P. Cyanescens*. Exemplary regions of conserved stretches of amino acids are indicated in gray.

FIG. 7. shows consensus sequence alignment of PsiM polypeptides from *P. Cubensis* and *P. Cyanescens*. Exemplary regions of conserved stretches of amino acids are indicated in gray.

FIG. 8. shows consensus sequence alignment of PsiH polypeptides from *P. Cubensis* and *P. Cyanescens*. Exemplary regions of conserved stretches of amino acids are indicated in gray.

Figure 9:
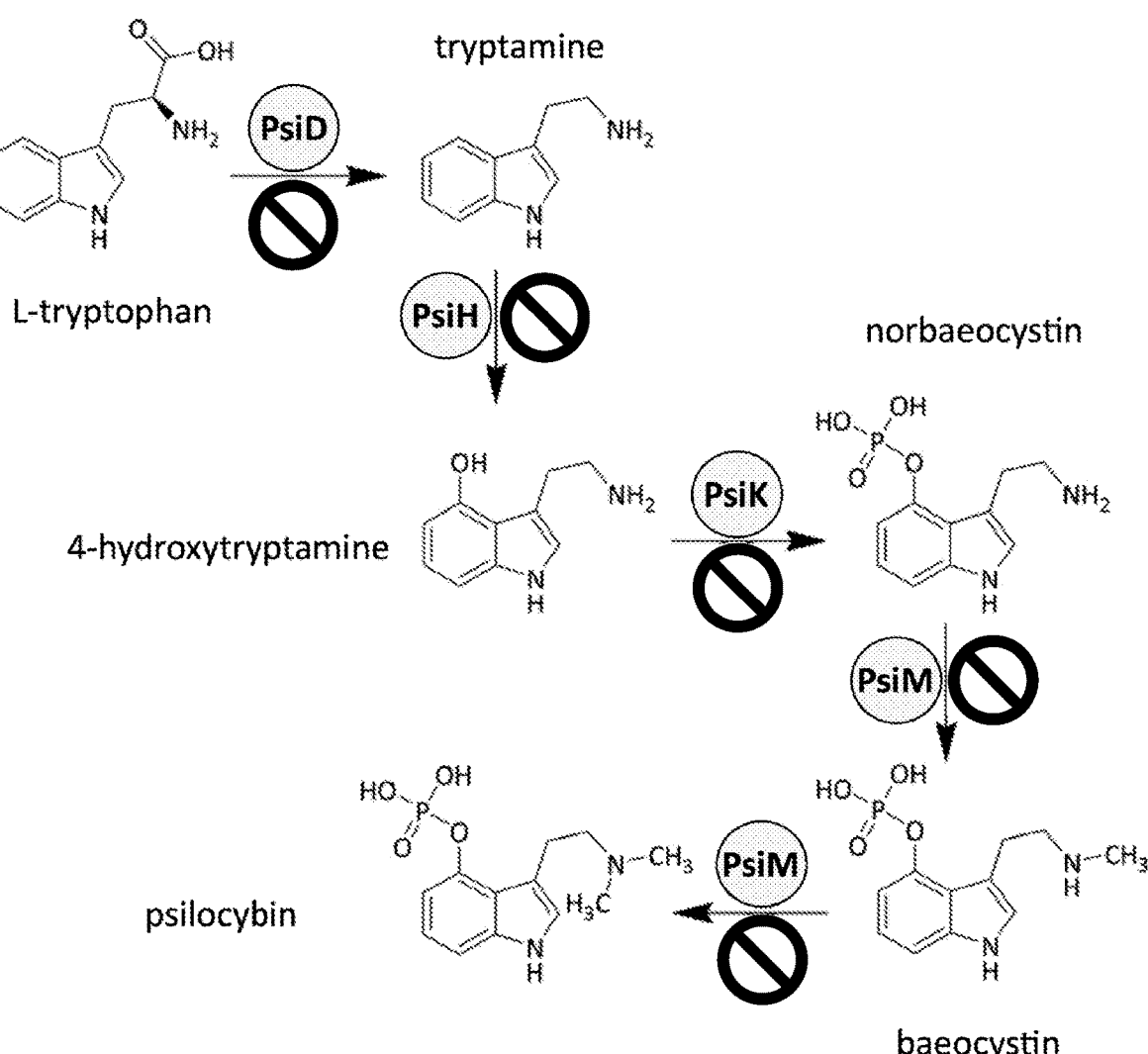
FIG. 9 shows a schematic of biosynthesis of psilocybin from L-tryptophan catalyzed by PsiD, PsiH, PsiK, and PsiM (adapted from Fricke, J., Blei, F., & Hoffmeister, D. (2017). Enzymatic Synthesis of Psilocybin. *Angewandte Chemie Int'l Ed.,* 56 (40), 12352-12355). The in vivo biosynthetic production of psilocybin in *P. cubensis* starting from L-tryptophan is depicted, with the PsiD, PsiH, PsiK, and PsiM enzymes depicted alongside the steps they catalyze, and with the accompanying circles with a diagonal line across demonstrating that, in different embodiments herein, one or more of such enzymes and the steps that they catalyze are disrupted.
Figure 10:
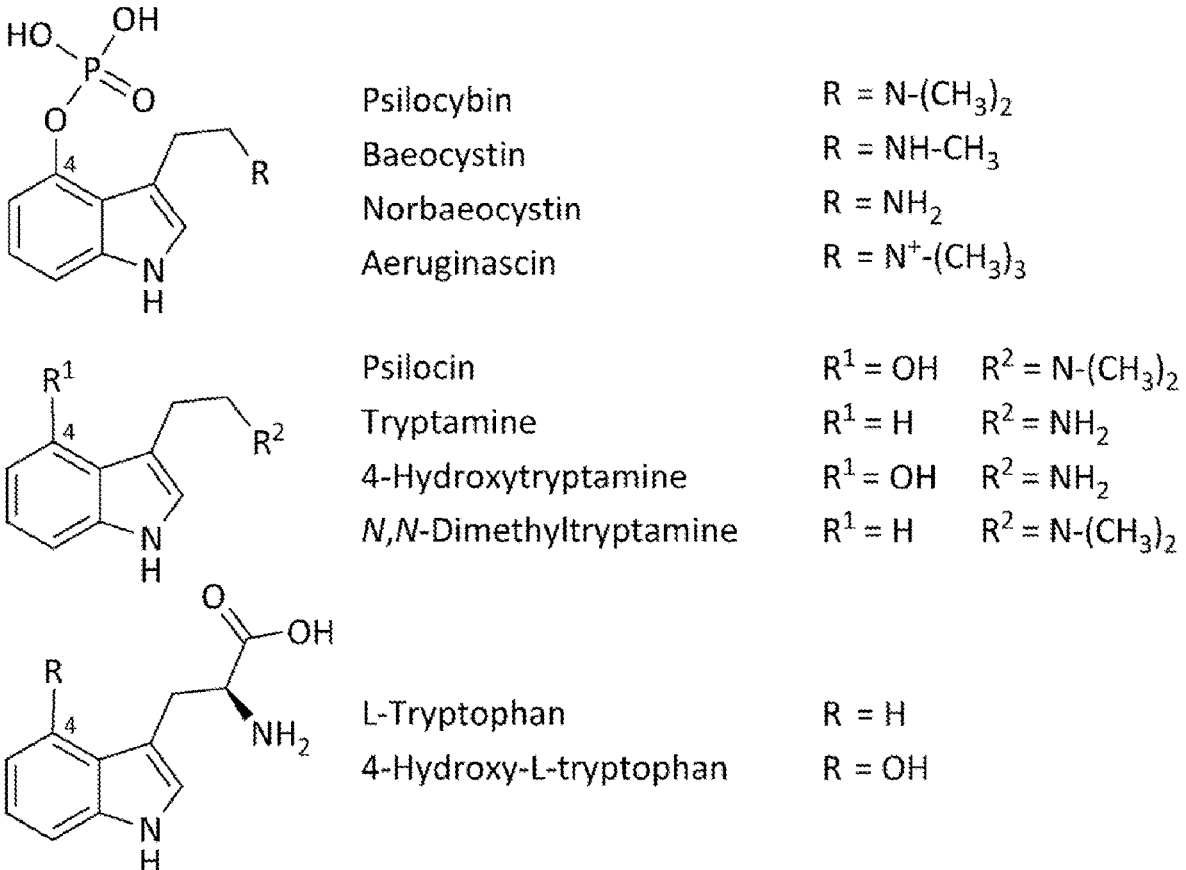
FIG. 10 shows chemical structures of psilocybe natural products and enzyme products (adapted from Fricke et al. 2017).

DETAILED DESCRIPTION OF THE
INVENTION

While various aspects and features of certain embodiments are summarized above, the following detailed description illustrates several exemplary embodiments in further detail to enable one having ordinary skill in the art to which the invention belongs ("one of skill") to practice such embodiments, and to make and use the full scope of the invention claimed.

It will be understood that many modifications, substitutions, changes, and variations in the described examples, embodiments, applications, and details of the invention illustrated herein can be made by those skilled in the art without departing from the spirit of the invention, or the scope of the invention as described in the appended claims, and the general principles defined herein may be applied to a wide range of aspects. Thus, the invention is not intended to be limited to the aspects presented, but is to be accorded the widest scope consistent with the principles and novel features disclosed. The description below is designed to make such embodiments apparent to a person of ordinary skill, in that the embodiments shall be both readily cognizable and readily creatable without undue experimentation, solely using the teachings herein together with general knowledge of the art.

While the methods described and illustrated herein may include particular steps, it should be apparent that other methods including fewer, more, or different steps than those described and shown are also within the spirit and scope of the invention. The described methods and uses of discussed and associated steps shown herein therefore should be understood as being provided for purposes of illustration, not limitation. It should be further understood that the specific order or hierarchy of steps in the methods and uses disclosed are only exemplary approaches.

As used in this specification and the appended claims, the singular forms "a," "an," and "the" include plural referents unless the context clearly dictates otherwise. While the term "one or more" may be used, its absence (or its replacement by the singular) does not signify the singular only. The terms "comprising," "including," "such as," and "having" are intended to be inclusive and not exclusive (i.e., there may be other elements in addition to the recited elements). Thus, the term "including" as used herein means, and is used interchangeably with, the phrase "including but not limited to." The term "or" is used herein to mean, and is used interchangeably with, the term "and/or," unless context clearly indicates otherwise.

All numbers expressing quantities, properties, reaction conditions, and so forth, used to describe and claim certain embodiments of the disclosure are to be understood as being modified by the term "about," even where they are not so expressly modified, and as not being modified by the term "about," even where they are so expressly modified. Accordingly, each such number should be understood as being both modified and not modified by the term "about."

In some embodiments, numerical parameters set forth in the description and claims are approximations that can vary depending upon the desired properties sought to be obtained by a particular embodiment. In some embodiments, "about" refers to plus or minus five percent (±5%) of the recited unit of measure. The term "substantially," where it is applied to modify a feature or limitation herein, and where not otherwise defined or described, will be read in the context of the disclosure and in light of the knowledge in the art to provide the appropriate certainty, e.g., by using a standard that is recognized in the art for measuring the meaning of "substantially" as a term of degree, or by ascertaining the scope as would one of skill.

The headings within this document are being utilized only to expedite its review by a reader. They should not be construed as limiting the invention in any manner.

Definitions

Unless defined otherwise, all technical and scientific terms herein have the meaning as commonly understood by one of skill. Further definitions that may assist the reader in understanding the disclosed embodiments are as follows; however, it will be appreciated that such definitions are not intended to limit the scope of the invention, which is properly interpreted and understood by reference to the full description (as well as any plain meaning known to one of skill) in view of the language used in the appended claims. The terminology used herein is for the purpose of describing particular embodiments only and is not intended to be limiting.

The terms "nucleic acid," "polynucleotide," and "oligonucleotide" are used interchangeably and refer to a deoxyribonucleotide or ribonucleotide polymer, in linear or circular conformation, and in either single- or double-stranded form. These terms are not to be construed as limiting with respect to the length of a polymer. These terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; e.g., an analogue of A will base-pair with T. "Oligo" is used interchangeably with and simply as shorthand for "oligonucleotide."

The terms "polypeptide," "peptide," and "protein" are used interchangeably to refer to a polymer of amino acid residues of any length. These terms also apply to amino acid polymers in which one or more amino acids are chemical analogues or modified derivatives of a corresponding naturally-occurring amino acid.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. In some embodiments, binding interactions are characterized by a dissociation constant ($K_d$) of $10^{-6}$ or lower.

"Affinity" refers to the strength of binding, with increased binding affinity being correlated, for example, with a lower $K_d$.

A "binding protein" refers to a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "sequence" refers to a nucleotide sequence of any length, which can be DNA or RNA, linear, circular or branched, and either single-stranded or double stranded.

A "donor sequence" refers to a nucleotide sequence that is inserted into a genome. A donor sequence can be of any length, for example, between 2 and 10,000 nucleotides in length (or any integer value there between or there above), between about 100 and 1,000 nucleotides in length (or any integer there between), or between about 200 and 500 nucleotides in length.

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In some embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kb (e.g., for insertion of a gene at a predetermined ectopic site in a chromosome). Two poly-nucleotides comprising the homologous non-identical sequences need not be the same length, e.g., an exogenous polynucleotide (i.e., a donor polynucleotide) of between about 20 and about 10,000 nucleotides or bp can be used.

Techniques for determining nucleic acid and amino acid sequence identity are known in the art. Typically, such techniques include determining the nucleotide sequence of the mRNA for a gene and/or determining the amino acid sequence encoded thereby and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively.

"Gene Cluster" refers to a group of genes that together comprise a biosynthetic pathway.

"Inactivating gene expression" refers to methods by which the expression of a gene is reduced or eliminated. The inactivation of gene expression can occur by targeting one or more of: functional DNA elements such as promoters, CpG islands, transcriptional start site (TSS), splice sites, transla-tion initiation sites, and exons (coding regions) using genome editing techniques, such as clustered regularly inter-spaced short palindromic repeats (CRISPR). (See Guide-lines for optimized gene knockout using CRISPR/Cas9, Van Campenhout et al., *Biotechniques*, Vol. 66, No. 6, 295-302, June 2019 & Jinek, M. et al. A Programmable Dual-RNA-Guided DNA Endonuclease in Adaptive Bacterial Immunity. *Science* (80) 337, 816-821 (2012)). The inactivation of gene expression can also occur at the transcriptional stage and at the translational stage through RNA-directed transcriptional gene silencing techniques such as small interfering RNAs (siRNAs) and microRNAs (miRNAs). siRNA methods involve the introduction of a synthetic siRNA into the target cells to elicit RNA interference (RNAi), thereby inhibiting the expression of a specific messenger RNA (mRNA) to produce a gene silencing effect. (See Transcriptional gene silencing in humans, Weinberg et al., *Nucleic Acids Research*, Volume 44, Issue 14, 19 Aug. 2016, Pages 6505-6517 & siRNA Versus miRNA as Therapeutics for Gene Silencing, Lam et al., *Molecular Therapy-Nucleic acids*, Volume 4, e252, Jan. 1, 2015). MicroRNAs repress the expression of mRNA targets by promoting translational repression and mRNA degradation. (See Gene silencing by microRNAs: contributions of translational repression and mRNA decay, Huntzinger et al., *Nature Reviews Genetics* vol. 12, 99-110 (2011); A guide to microRNA-mediated gene silencing, Huberdeau et al., *FEBS Journal* 286 (2019)

642-652). Although targeted gene engineering is used in preferred embodiments herein, conventional mutation tech-niques also can be used, such as TILLING (Targeting Induced Local Lesions IN Genomes). (See, e.g., Kurowska, Marzena et al. TILLING: a shortcut in functional genomics. *Journal of Applied Genetics* vol. 52, 4 (2011): 371-90).

"Disrupting," for example with respect to "disrupting the biosynthesis of psilocybin in a mushroom," refers to an alteration of structure and/or function compared to a refer-ence or control, such as a wild-type mushroom. For example, "disrupting the biosynthesis of psilocybin in a mushroom" may refer to introducing a genetic defect into one or more genes of the psilocybin biosynthetic pathway and/or into a genetic element involved in control of that pathway, and/or may refer to an alteration in the function of the psilocybin biosynthetic pathway, such as a disruption of psilocybin production; the meaning thus will be understood by context. In some embodiments, "disrupted" includes disruption of one of more of the psilocybin biosynthetic pathway enzymes. In some embodiments, "disruption" includes down-regulation, such as down-regulation of expression (of a gene) and/or down-regulation of activity (of an enzyme).

Terms such as "disrupt," "reduce," "diminish," "inhibit," "suppress," and the like will generally refer to a decrease in a specified parameter or a specified activity of at least about 5%, 10%, 25%, 35%, 40%, 50%, 60%, 75%, 80%, 90%, 95%, 97%, 98%, 99% or 100%. These terms are generally intended to be relative to a reference or control, such as disclosed herein. Similarly, terms of augmentation will generally refer to an increase in a specified parameter or a specified activity of at least about a 1.1-fold, 1.25-fold, 1.5-fold, 2-fold, 3-fold, 4-fold, 5-fold, 6-fold, 8-fold, 10-fold, 12-fold, 15-fold, 20-fold or more increase, also relative to a reference or control.

"Genetic modification" refers to the direct manipulation of an organism's genes and/or gene control regions using genetic engineering. Genetic modification can be manifested at the gene level, transcriptional level, and translational level. It encompasses engineered changes in nucleic acid sequence such as mutations in a promoter or another control region that disrupt the expression of the gene. It also encompasses disruptions in expression of genes by means of gene deletion using DNA editing carried by CRISPR, TAL-ENS, or zinc finger nucleases. It also encompasses disrup-tions in gene expression through RNAi using siRNA and miRNA.

In general, "CRISPR system" refers collectively to tran-scripts and other elements involved in the expression of or directing the activity of CRISPR-associated ("Cas") genes, including sequences encoding a Cas gene, a "tracr" (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus.

In some embodiments (equivalently, and simply as short-hand, "in embodiments"), one or more elements of a CRISPR system is derived from a type I, type II, or type III CRISPR system. In some embodiments, one or more ele-ments of a CRISPR system is derived from a particular organism comprising an endogenous CRISPR system, such as *Streptococcus pyogenes*. In general, a CRISPR system is characterized by elements that promote the formation of a CRISPR complex at the site of a target sequence (also referred to as a "protospacer" in the context of an endogenous CRISPR system).

In the context of formation of a CRISPR complex, "target sequence" refers to a sequence to which a guide sequence is designed to have complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence may comprise any polynucleotide, such as DNA or RNA polynucleotides. In some embodiments, a target sequence is located in the nucleus or cytoplasm of a cell. In some embodiments, the target sequence may be within an organelle of a eukaryotic cell, for example, mitochondrion or chloroplast. A sequence or template that may be used for recombination into the targeted locus comprising the target sequences is referred to as an "editing template" or "editing polynucleotide" or "editing sequence." In aspects of the invention, an exogenous template polynucleotide may be referred to as an editing template. In an aspect of the invention the recombination is homologous recombination.

Typically, in the context of an endogenous CRISPR system, formation of a CRISPR complex (comprising a guide sequence hybridized to a target sequence and complexed with one or more Cas proteins) results in cleavage of one or both strands in or near (e.g., within 1, 2, 3, 4, 5, 6, 7, 8, 9, 10, 20, 50, or more than 50 base pairs from) the target sequence. Without wishing to be bound by theory, the tracr sequence, which may comprise or consist of all or a portion of a wild-type tracr sequence (e.g., about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence. In some embodiments, the tracr sequence has sufficient complementarity to a tracr mate sequence to hybridize and participate in formation of a CRISPR complex. As with the target sequence, it is believed that complete complementarity is not needed, provided there is sufficient to be functional.

In some embodiments, the tracr sequence has at least 50%, 60%, 70%, 80%, 90%, 95%, or 99% of sequence complementarity along the length of the tracr mate sequence when optimally aligned. In some embodiments, one or more vectors driving expression of one or more elements of a CRISPR system are introduced into a host cell such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction.

A "complementary sequence" refers to the sequence of the lower (antisense) strand in the same direction as the upper strand. The "reverse complement" refers to the sequence of the upper strand in the direction from its 3'- to its 5'-end. (As DNA is antiparallel, the reverse complement sequence may be used to keep the 5' and 3' ends properly oriented, as known to those of skill.)

In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g., each in a different intron, two or more in at least one intron, or all in a single intron). In some embodiments, the CRISPR enzyme, guide sequence, tracr mate sequence, and tracr sequence are operably linked to and expressed from the same promoter.

The term "fungi" refers to a diverse group of eukaryotic single-celled or multinucleate organisms that live by decomposing and absorbing the organic material in which they grow, comprising the mushrooms, molds, mildews, smuts, rusts, and yeasts, and classified in the kingdom Fungi or, in some classification systems, in the division Fungi (Thallophyta) of the kingdom Plantae. Some fungi comprise a fruiting body and long, branching filamentous structure called hypha. The hyphae are the main mode of vegetative growth and are collectively called mycelium. In some aspects of the invention are disclosed genetically modifying fungi comprising a fruiting body and mycelium such that they no longer produce hallucinogenic compounds such as psilocybin. In some embodiments, such genetically modified fungi and compositions or other products thereof, such as extracts thereof, are devoid of hallucinogenic compounds. In some embodiments, such compositions, extracts, and other products are utilized as nutraceuticals, as therapeutics, and for other purposes, such as disclosed herein and appreciated by those in the art.

"Nutraceutical" may refer to a preparation that could be marketed as a dietary supplement (sometimes called a nutritional supplement), e.g., in the U.S. under the appropriate regulations of the Federal Food, Drug, and Cosmetic Act (FDCA) (22 U.S.C. §§ 301 et seq.) and Dietary Supplement Health and Education Act (DSHEA) of 1994. A dietary supplement is a product taken by mouth that contains a dietary ingredient intended to supplement the diet. Dietary supplements can also be extracts or concentrates, and may be found in many forms such as tablets, capsules, softgels, gelcaps, liquids or powders. Although "nutraceuticals" could be marketed as dietary supplements, products need not in fact meet any specific regulatory standards (such as under DSHEA or other FDA regulations), or be considered under any specific regulatory standards to be considered nutraceuticals for purposes of the definition herein. Thus, it will be appreciated that within the definition of nutraceuticals are also products that are sold as "natural products," or otherwise outside of any specific regulatory regime.

The term "fruiting body" refers to the generally fleshy fruiting body of a fungus (such as a basidiomycete), especially one that is edible, typically comprising a cap (or "pileus") and a stem (or "stipe"), and which may appear above ground (when naturally grown, e.g., as in nature).

The term "mycelium" refers to the mass of vegetative, thread-like, and typically branched network of filamentous hyphae, which is the primary growth form of most fungi and is often within the soil or organic matter or the tissues of a host, or otherwise below ground (when naturally grown).

The term "protoplast" refers to an isolated cell whose cell wall has been removed. The cell wall can be removed by tripping, weakening, creating gaps in, or otherwise removing the cell wall, from a plant, bacterial, or fungal cell by mechanical, chemical, or enzymatic means.

The term "spore" refers to the single-celled, haploid unit of sexual or asexual reproduction produced (and when naturally grown, dispersed) by a fungus.

The term "transformed into" refers to the transfer of exogenous nucleic acid sequences to the interior of a fungal protoplast or mycelium by electrical, mechanical, or chemical means other than natural genetic transfer. Generally, transformation is such that the genetic coding or regulatory capacity will be changed with respect to an untreated fungal protoplast or mycelium.

A "mushroom" refers to a plurality of fungal cells that are largely differentiated into a structure that is present at any stage of a mushroom's development, whether usually found above ground, underground, or contained within a biosynthetic production system. Such structures include, but are not limited to, fruiting bodies, sclerotia, protoplasts, spores, and mycelium.

A "magic mushroom" refers to a mushroom (such as from the genus *Psilocybe*) containing psychedelic (or "hallucinogenic") bioactive alkaloids (such as psilocybin).

A "mushroom extract" refers to a condensed and/or concentrated form of a mushroom in which the bioactive compounds of interest found in the mushroom are condensed and/or concentrated by treatment with an extractant, for example distilled water, 50-80% percent (v/v) ethanol, and a solvent such as diethyl ether. In some embodiments, preparing a mushroom extract comprises milling, chopping, blending, grinding, ultrasonic vibrating, and/or otherwise processing the mushroom such that the mushroom has lost its naturally-occurring physical form. In some embodiments, preparing a mushroom extract comprises treatment with enzymes, including fungal enzymes.

The "psilocybin biosynthetic pathway" refers generally to that comprising the four genes, and the four enzymes they each encode, known as PsiD, PsiM, PsiH, and PsiK. Following this pathway, psilocybin is synthesized enzymatically from L-tryptophan, as depicted in FIG. 9. The psilocybin biosynthetic pathway is further described in the section so-entitled below.

"PsiD" may refer both to an L-tryptophan decarboxylase enzyme (a "PsiD enzyme"), and to a gene that encodes it (a "PsiD gene"), as context indicates. A PsiD enzyme is a fungal L-tryptophan decarboxylase which is involved in the first step of biosynthesis of psilocybin. A PsiD enzyme catalyzes the decarboxylation of L-tryptophan to tryptamine.

"PsiM" may refer both to a methyltransferase enzyme catalyzing iterative N-methyl transfer (a "PsiM enzyme"), and to a gene that encodes it (a "PsiM gene"), as context indicates. Although stylistic conventions for genes and their proteins differ (capitalization and italicization conventions, for example), herein for purposes of convenience genes and enzymes may both be referred to similarly (e.g., a "PsiM" gene, a "PsiM" enzyme), and clarity is achieved by context. A PsiM enzyme is a methyltransferase which catalyzes iterative methyl transfer to the amino group of norbaeocystin to yield psilocybin via a monomethylated intermediate, baeocystin.

"PsiH" may refer both to a tryptamine 4-monooxygenase enzyme (a "PsiH enzyme"), and to a gene that encodes it (a "PsiH gene"), as context indicates. A PsiH enzyme is a P450 monooxygenase that converts tryptamine to 4-hydroxytryptamine.

"PsiK" may refer both to a phosphotransferase enzyme (a "PsiK enzyme"), and a gene that encodes it (a "PsiK gene"), as context indicates. A PsiK enzyme is a kinase that catalyzes the 4-O-phosphorylation step by converting 4-hydroxytryptamine into norbaeocystin.

"fsyl" refers to a *Psilocybe cubensis* (as shorthand, following convention, *P. cubensis*), gene or an orthologous fungal gene encoding cytosine deaminase EC 3.5.4.1.

"pyrG" refers to a *P. cubensis* gene or an orthologous fungal gene encoding orotate 5' phosphate decarboxylase EC 4.1.1.23.

"5-FC" refers to 5-fluorouracil (5-fluoro-1H-pyrimidine-2,4-dione, CAS #51-21-8).

"5-FOA" refers to 5-fluoroorotic acid (5-fluoro-2,4-dioxo-1H-pyrimidine-6-carboxylic acid, CAS #703-95-7).

Further definitions that may assist a reader in understanding the disclosed embodiments are provided in disclosure below; however, it will be appreciated that all definitions herein are not intended to limit the scope of the invention, which shall be properly interpreted and understood by reference to the full specification (as well as any plain meaning known to one of skill in the relevant art) in view of the language used in the claims. The terminology used herein is for the purpose of describing particular embodiments only and is not intended to be limiting.

Bioactive Alkaloids from Fungi

In some aspects are disclosed genetically modified fungi that do not produce one or more bioactive alkaloids, such as a bioactive tryptamine, such as a hallucinogenic tryptamine, such as psilocybin. In some further aspects are disclosed genetically modified fungi that do not produce a hallucinogenic tryptamine, such as psilocybin, but that produce one or more other bioactive alkaloids, such as a bioactive tryptamine, such as a "minor" tryptamine or "complex" tryptamine.

In some embodiments, a disclosed genetically modified fungus produces a reduced amount of a bioactive alkaloid, such as a hallucinogenic tryptamine, such as psilocybin. In some embodiments, a genetically modified fungus produces a substantially reduced amount of a hallucinogenic tryptamine, such as psilocybin. In some embodiments, a genetically modified fungus produces a negligible amount of a hallucinogenic tryptamine, such as psilocybin, including an amount below a threshold of measurement or detection. In some embodiments, a substantially reduced amount of a bioactive alkaloid, such as a hallucinogenic tryptamine, such as psilocybin, includes an amount representing a reduction of the bioactive alkaloid, such as psilocybin, of greater than 90%, greater than 91%, greater than 92%, greater than 93%, greater than 94%, greater than 95%, greater than 96%, greater than 97%, greater than 98%, greater than 99%, greater than 99.5%, greater than 99.9%, greater than 99.95%, and greater than 99.99%, including up to 100%, compared to a comparable wild-type fungus, such as a comparable wild-type fungus as disclosed herein or as will be appreciated as being comparable in the art.

In some embodiments, a disclosed genetically modified fungus produces an increased amount of one or more bioactive alkaloids, such as a bioactive tryptamine. In some embodiments, a genetically modified fungus produces an increased amount of a "minor" tryptamine (e.g., aeruginascin, baeocystin, norbaeocystin, norpsilocin, and the like). In some embodiments, a genetically modified fungus produces an increased amount of one or more tryptamines that are naturally produced by the psilocybin biosynthetic pathway, e.g., any one or more of tryptamine, 4-hydroxytryptamine, norbaeocystin, or baeocystin (see also, e.g., FIG. 9), or N-methyltryptamine (NMT) or N,N-dimethyltryptamine (DMT). In some embodiments, a genetically modified fungus produces an increased amount of a "complex" tryptamine, such as a beta-carboline (e.g., perlolyrine, harmaline, harmane, harmine, harmol, and the like). In some embodiments, an increased amount of a bioactive alkaloid is an increase of at least 5%, at least 10%, at least 15%, at least 20%, at least 25%, at least 30%, at least 40%, at least 50%, at least 75%, at least 100%, and numbers in between, as well as greater multiples, such as at least 3×, 4×, 5× and greater than 5×, compared to a comparable wild-type fungus, such as a comparable wild-type fungus as disclosed herein or as will be appreciated as being comparable in the art.

Exemplary non-limiting examples of bioactive alkaloids from fungi include:

"Tryptamine" refers to 2-(1H-indol-3-yl) ethanamine (CAS #61-54-1).

"Serotonin" refers to 3-(2-Aminoethyl)-1H-indol-5-ol (CAS #50-67-9).

"4-Hydroxytryptamine" refers to 3-(2-aminoethyl)-1H-indol-4-ol (CAS #570-14-9).

"N-acetyl-hydroxytryptamine" refers to N-hydroxy-N-[2-(1H-indol-3-yl)ethyl]acetamide.

4-hydroxy-L-tryptophan refers to (2S)-2-amino-3-(4-hydroxy-1H-indol-3-yl) propanoic acid.

5-hydroxy-L-tryptophan refers to (2S)-2-amino-3-(5-hydroxy-1H-indol-3-yl) propanoic acid.

7-hydroxy-L-tryptophan refers to (2S)-2-amino-3-(7-hydroxy-1H-indol-3-yl) propanoic acid.

"Aeruginascin" refers to N,N,N-trimethyl-4-phosphoryloxytryptamine (CAS #114264-95-8).

"4-hydroxy-N,N,N-trimethyltryptamine" refers to 2-(4-hydroxy-1H-indol-3-yl)ethyl-trimethylazanium, a metabolite of aeruginascin, (CHEBI: 193061)

"Baeocystin" refers to [3-[2-(methylamino)ethyl]-1H-indol-4-yl] dihydrogen phosphate (CAS #21420-58-6).

"Cordysinin C" refers to (1R)-1-(9H-beta-carbolin-1-yl) ethanol (CAS #1330197-18-6).

"Cordysinin D" refers to (1S)-1-(9H-beta-carbolin-1-yl) ethanol (CAS #110282-66-1).

"Harmaline" refers to 7-methoxy-1-methyl-4,9-dihydro-3H-pyrido[3,4-b]indole (CAS #304-21-2)

"Harmane" refers to 1-methyl-9H-pyrido[3,4-b]indole (CAS #486-84-0).

"Harmine" refers to 7-methoxy-1-methyl-9H-pyrido[3,4-b]indole (CAS #442-51-3).

"Perlolyrine" refers to [5-(9H-pyrido[3,4-b]indol-1-yl)furan-2-yl]methanol, (CAS #29700-20-7).

"Harmol" refers to 1-methyl-9H-pyrido[3,4-b]indol-7-ol (CAS #487-03-6).

"Norbaeocystin" refers to [3-(2-aminoethyl)-1H-indol-4-yl] dihydrogen phosphate (CAS #21420-59-7).

"Norharmane refers to 9H-pyrido[3,4-B]indole (CAS #244-63-3).

"Norpsilocin" refers to 3-[2-(methylamino)ethyl]-1H-indol-4-ol (CAS #28363-70-4).

"Psilocybin" refers to 4-phosphoryloxy-N,N-dimethyltryptamine (CAS #520-52-5).

"Psilocin" refers to 4-hydroxy-N,N-dimethyltryptamine (CAS #520-53-6).

"NMT" refers to N-methyltryptamine (CAS #61-49-4).

"DMT" refers to N,N-dimethyltryptamine (CAS #61-50-7).

"β-carboline" may refer either to 9H-Pyrido[3,4-b]indole (CAS #244-63-3) or to the class of compounds known collectively as "beta-carbolines," depending on context.

Other examples of bioactive alkaloids from fungi will be readily known or identifiable to those of skill. See, e.g., Zorrilla J G, Evidente A. Structures and Biological Activities of Alkaloids in Mushrooms, a Fungal Subgroup. *Biomol-*

*ecules.* 2022; 12 (8): 1025; Wieczorek, Piotr Paweł et al. Bioactive alkaloids of hallucinogenic mushrooms. *St. Nat Prods Chem.* 2015; 46:133-168.

Psilocybin-Producing Fungi and Other Bioactive Alkaloid-Producing Fungi

In some aspects are disclosed genetically modified fungi that do not produce psilocybin and/or another bioactive alkaloid. In some embodiments, such genetically modified fungi are made by selecting a bioactive alkaloid-producing fungus, such as a psilocybin-producing fungus, and performing the steps of the disclosed methods to obtain a genetically modified fungus. In embodiments, a non-hallucinogenic psychedelic fungus is produced by the disclosed methods.

In some embodiments, the bioactive alkaloid-producing fungus is a psilocybin-producing fungus. Psilocybin-producing fungi are known in the art, and include, as non-limiting examples, numerous species from the genera *Athelia, Conocybe, Copelandia, Fibularhizoctonia, Galerina, Gymnopilus, Inocybe, Mycena, Panaeolus, Pholiotina, Pluteus,* and *Psilocybe.* Different species of psilocybin-producing fungi will be readily known or readily identifiable to those in the art.

Herein, a "psilocybin-producing" fungus and a "psychedelic" fungus may be used interchangeably, and both terms may be used to refer to a fungus in which the natural wild-type fungus produces psilocybin (and hence, "hallucinogenic" or "psychedelic" effects upon ingestion), as well as to a genetically modified fungus of the disclosure (e.g., a gene knockout fungus which no longer produces psilocybin or hallucinogenic effects produced according to a disclosed method).

In some embodiments, a psilocybin-producing fungus is a *Psilocybe* spp. fungus.

In some embodiments, the Psilocybe spp. fungus is any of a *P. acutipilea, P. allenii, P. alutacea, P. angulospora, P. antioquiensis, P. araucariicola, P. atlantis, P. aquamarina, P. armandii (Mexicana), P. aucklandiae, P. aztecorum, P. azurescens, P. baeocystis, P. banderillensis, P. bispora, P. brasiliensis, P. brunneocystidiata, P. caeruleoannulata, P. caerulescens, P. caerulipes, P. callosa, P. carbonaria, P. caribaea, P. chuxiongensis, P. collybioides, P. columbiana, P. congolensis, P. cordispora, P. cubensis, P. cyanescens, P. cyanofibrillosa, P. dumontii, P. egonii, P. eximia, P. fagicola, P. farinacea, P. fimetaria, P. fuliginosa, P. furtadoana, P. galindoi, P. gallaeciae, P. graveolens, P. guatapensis, P. heimii, P. herrerae, P. hispanica, P. hoogshagenii, P. inconspicua, P. indica, P. isabelae, P. jacobsii, P. jaliscana, P. kumaenorum, P. laurae, P. lazoi, P. liniformans, P. mexicana, P. mairei, P. makarorae, P. mammillata, P. medullosa, P. meridensis, P. meridionalis, P. mescaleroensis, P. moseri, P. muliercula, P. naematoliformis, P. natalensis, P. natarajanii, P. neorhombispora, P. neoxalapensis, P. ovoideocystidiata, P. papuana, P. paulensis, P. pelliculosa, P. pintonii, P. pleurocystidiosa, P. plutonia, P. portoricensis, P. pseudoaztecorum, P. puberula, P. quebecensis, P. rickii, P. rostrate, P. rzedowskii, P. samuiensis, P. schultesii, P. semilanceata, P. septentrionalis, P. serbica, P. sierrae, P. sylvatica, P. singer, P. strictipes, P. stuntzii, P. subacutipilea, P. subaeruginascens, P. subaeruginosa, P. subcaerulipes, P. subcubensis, P. subpsilocybioides, P. subtropicalis, P. tampanensis, P. thaicordispora, P. thaiaerugine omaculans, P. thaiduplicatocystidiata, P. uruguayensis, P. uxpanapensis, P. venenata, P. villarrealiae, P. weilii, P. weldenii, P. weraroa, P. wrightii, P. yungensis, P. zapotecoantillarum, P. zapotecocaribaea,* or *P. zapotecorum* species, including strains thereof. Further description of each of the above *Psilocybe* species is provided in the priority application hereto, U.S. Prov. App. No.

63/371,121, filed Aug. 11, 2022, and incorporated by reference for all purposes as if fully set forth herein.

Other psilocybin-producing *Psilocybe* fungi will be known to those of skill in the art.

In some embodiments, the *Psilocybe* spp. fungus is a P. carpophores fungus or strain. In some embodiments, the *Psilocybe* spp. fungus is a member of the *P. cyanescens* species complex.

In some embodiments, the *Psilocybe* spp. fungus is a *Psilocybe cubensis* fungus or strain.

In some embodiments, the *P. cubensis* strain is any of Golden Teacher, B+, Mazapatec, Z Strain, Treasure Coast, or Koh Samui Super Strain. In some embodiments, the *P. cubensis* strain is any of A+ (A-Strain), AA+ (Albino A+), Acadian Coast, Alice, Alamo, Alacabenzi, Albino Chodewave (ACW), Albino Monkey Dick/Dong (AMD), Ajax, ALAC (Alacabenzi Supreme), Albino MVP, American Mystic, AMAK (Albino Melmac), AMPE, AMVP (Albino Most Valued Producer), APE (Albino Penis Envy), APE-R, ARC (Albino Rollercoaster), Argentina, Australian, Avery's Albino, Aztec God, B+, Ban Hua Thanon (BHT), Ban Nathon Dhupatamyia (BND), Ban Phang Ka (BPK), Ban Thurain (BT), BeePee, Blue Avians, Blue Jay, Blue *Magnolia* Classic (BMC), Blue *Magnolia* Rust (BMR), Blue Meanie (*cubensis*), Blue Moon, Brazilian, Burma, Burmese Smurf, Cambodian, Chitwan, Chocolate Krinkle, Chodewave (OG CW), Clockwork Orange, Colombian Rust Spore (CRS), Colorado, Coneheads TAT, Corumba, Creeper (Keeper's Creeper), Crooked Mystery, Daddy Long Legs, Dancing Dragons, Destiny, Divinity, Eclipse, Ecuador, El Choco, Elephant Dung, End Game, Enigma, E-Froot, Entheogen Explosion, Escondido, Eyelike, F+, Falbino, FillJilly, Fiji, Gandalf, Ghost, Golden E4K, Golden Hawk, Golden Halo, Golden Mammoth, Golden Teacher (GT), Great White Monster (GWM), Ground Zero, Guadalajara, Gumby, Hanoi, Hillbilly/Menace, Huautla, Hung, Iceberg (ATLY), Illusion Weaver, Jack Frost, Jedi Mind Fuck (JMF), John Allen (Allen Strain), Juke's Peak, KAPE, KSAT, Koh Samui Classic (KSC), Koh Samui Super Strain (KSSS), LAPE (Long APE), L.A.S.S. (Lang Albino Super Squats), Leng, Leucistic JMF (Jedi Mind Fuck), Leucistic Treasure Coast (LTC), Lex Luther (Cream Lex Luther), Lightwave, Lipa Yai, Lizard King (LK), Loaves, Mak 120, Mak/AA, Makilla Gorilla, Malabar, Malaysian, Mars, Mazapatec, Maza-Bensi, McKennai, *Mexicana Cubensis*, Melmac Revert, Melmac 118, Melmac, Melmac TP (Thick Penis), Menace, Mexican Albino, Mexican Dutch King, Mexicube, Moby Dick, Mr. Krinkle, MVP (Most Valued Producer), Namaste, Nezuko, New Zealand Chaw, Normak (Normac), Nutcracker, Omni, Orissa India, Palenque, PEA+ (YETI), Peakock/Peacock, PE6, Pearly Gates, PES Amazonian (PESA), PES Hawaiian (PESH), Penis Envy (PE), PE+, Penis Envy Hawk (P.E. Hawk), Penis Envy Uncut (PEU), PF Albino, PF Classic, PF Redspore, Phobos, Pink Buffalo (PB), Plantasia Mystery, Puerto Rico (PR), Purple Mystic (PM), Quinn's Cut, R44, Redboy, Riddler, Riptide, Roatan Honduras, Roger Rabbit (RR), Rollercoaster, Rudolph, Rusty Whyte (RW), Saint Nick, Scylla, Shamans Gift, Shakti, Shooting Star, South African Transkei (SAT), South American, Sporeworks PE (SW PE), Stargazer, Starry Night, Sunny Side Up (SSU), SV-10, SyZyGy, Taman Negara, Tasmania, TAT Smurf, Tidalwave (TW), Tooth Decay, Tosohatchee, Trinity, Tsunami, True Albino Teacher (TAT), TAT Black Cap (TBC), TePe, Texas Gulf Coast (TGC), Thai Elephant Dung, Thai Lipa Yi, Treasure Coast, Vader, White Teacher, Wollongong, Wombat TAT, Xilo, XXX, Yeti, Ymir, Zillacybin (Zilla), or Z Strain. Other

*Psilocybe cubensis* strains, as well as other psilocybin-producing strains of species in other psilocybin-producing genera, will be readily known or identifiable by those of skill in the art.

In some embodiments, the bioactive alkaloid-producing fungus is a fungus which does not produce psilocybin but does contain PsiD, PsiH, PsiK, or PsiD genes. In some embodiments, the bioactive alkaloid-producing fungus contains homologous, non-identical sequences to PsiD, PsiH, PsiK, or PsiD genes in a psilocybin-producing fungus. In some embodiments, the bioactive alkaloid-producing fungus contains a homologous, non-identical sequence to PsiD, PsiH, PsiK, or PsiD genes which were acquired through horizontal gene transfer In some embodiments, the bioactive alkaloid-producing fungus has homologous, non-identical sequences genes that do not form a cluster, but code for enzymes which may be active in producing similar metabolites to a psilocybin-producing fungus. In some embodiments, the bioactive alkaloid-producing fungus with homologous, non-identical sequences to PsiD, PsiH, PsiK, or PsiD genes are manipulated to reduce tryptamine production and levels. In some embodiments, the bioactive alkaloid-producing fungus with homologous, non-identical sequences to PsiD, PsiH, PsiK, or PsiD genes are of the genera *Pleurotus, Lentinula* or *Trametes.*

For disclosed and other known psilocybin-producing fungi, and for other fungi that can be genetically modified according to the methods of the disclosure, such as the various genera, species, and strains listed above, those of skill will appreciate that genomic data, including genomes, transcripts, protein sequences, annotations, and data reports, are available as National Library of Medicine National Center for Biotechnology Information (NCBI) Datasets, (ncbi.nlm.nih.gov/datasets, e.g., for *P. cubensis*, ncbi.nlm-.nih.gov/datasets/taxonomy/181762/, NCBI Taxonomy ID 181762), including NCBI RefSeq assemblies and GenBank assemblies, and on the NCBI Genome Data Viewer (GDV), as well as on other databases known to those of skill.

Available datasets for exemplary species include, for instance, *P. azurescens* (Genome scaffold GCA_019721835.1); *P. cubensis* (Chromosome level genome assembly GCA_017499595.2); *P. cyanescens* (Genome scaffold GCA_002938375.1); *P. galindoi* (Genome scaffold GCA_019721455.1); and *P. tampanensis* (Genome scaffolds of three isolates GCA_019904355.1, GCA_019908715.1, GCA_019908695.1).

Non-Hallucinogenic Psychedelic Fungi and Other Genetically Modified Fungi

In some aspects, provided are methods of genetically modifying a bioactive alkaloid-producing fungus so that the fungus no longer produces the bioactive alkaloid, or produces the bioactive alkaloid below a desired threshold, such as producing a reduced amount of the bioactive alkaloid, or producing a substantially reduced amount of the bioactive alkaloid.

In some embodiments, the bioactive alkaloid is psilocybin, norpsilocin, psilocin, tryptamine, 4-hydroxytryptamine, N,N-dimethyltryptamine, baeocystin, norbaeocystin, serotonin, N-acetyl-hydroxytryptamine, 4-hydroxy-L-tryptophan, 5-hydroxy-L-tryptophan, 7-hydroxy-L-tryptophan, aeruginascin, 4-hydroxy-N,N,N-trimethyltryptamine, harmane, norharmane, harmine, harmol, harmaline, cordysinin C, cordysinin D, perlolyrine, β-carboline, or a derivative or analogue thereof (Zorrilla J G, Evidente A. Structures and Biological Activities of Alkaloids Produced by Mushrooms, a Fungal Subgroup. *Biomolecules.* 2022; 12 (8): 1025 and Blei F. et al. Simultaneous Production of Psilocybin and a Cocktail of β-Carboline Monoamine Oxidase Inhibitors in 'Magic' Mushrooms. *Chemistry.* 2020; 26 (3): 729-34; Wieczorek, Piotr Paweł et al. Bioactive alkaloids of hallucinogenic mushrooms. *Studies Nat Prods Chem.* 2015; 46:133-168).

In some embodiments, the bioactive alkaloid is a hallucinogenic alkaloid. In some embodiments, the hallucinogenic alkaloid is a hallucinogenic tryptamine. In some embodiments, the hallucinogenic tryptamine is psilocybin.

In some embodiments, wherein a disclosed method comprises genetically modifying a psilocybin-producing fungus so that fungus no longer produces psilocybin (or produces a reduced or substantially reduced amount of psilocybin, e.g., below a desired threshold), one or more additional bioactive alkaloids may also consequently be reduced, substantially reduced, or absent in the fungus. For example, small amounts of psilocin are typically found in psilocybin-producing fungi (Stamets *P. Psilocybin Mushrooms of the World: An Identification Guide.* Ten Speed Press; 1996. and Tylš F, Páleníček T, Horáček J. Psilocybin: Summary of knowledge and new perspectives. *Eur Neuropsychopharm.* 2014; 24 (3): 342-356). It is however believed that psilocybin is the precursor for naturally occurring psilocin (Nichols DE. Psilocybin: From ancient magic to modern medicine. *J Antibiot.* 2020; 73 (10): 679-686). Hence, in some embodiments where a disclosed method comprises interfering with the biosynthesis of psilocybin in a fungus, the method also directly or indirectly interferes with or disrupts the biosynthesis of psilocin, and a resulting genetically modified fungus can have a reduced or substantially reduced amount of psilocin, or be entirely lacking in psilocin (e.g., no psilocin is present at a detectable level using analytical techniques described herein and otherwise known to one of skill).

Likewise, in embodiments wherein a disclosed method comprises interfering with the biosynthesis of psilocybin in a fungus by interfering with or disrupting the function of a catalytic enzyme involved in the biosynthesis of psilocybin (e.g., PsiD, PsiM, PsiH, PsiK), such a method may also interfere or disrupt the biosynthesis of another bioactive alkaloid involved in the psilocybin biosynthetic pathway. For example, as shown in FIG. 9, which depicts the in vivo biosynthetic production of psilocybin in *P. cubensis* starting from L-tryptophan, PsiM is responsible for the conversion of norbaeocystin to baeocystin, and the subsequent conversion of baeocystin to psilocybin. Hence, in embodiments wherein psilocybin biosynthesis is disrupted by interfering with the function of PsiM (e.g., by knocking out or reducing the PsiM expression, inactivating the catalytic function of PsiM, or another disclosed method), baeocystin levels in the resulting genetically modified fungus may also be reduced, substantially reduced, or absent. As another example and again with reference to FIG. 9, PsiK is responsible for the conversion of 4-hydroxytryptamine to norbaeocystin. Hence, in some embodiments wherein psilocybin biosynthesis is disrupted by interfering with the function of PsiK (e.g., by knocking out or reducing the PsiK expression, inactivating the catalytic function of PsiK, or another disclosed method), levels of norbaeocystin and baeocystin in the resulting genetically modified fungus may also be reduced, substantially reduced, or absent.

It will be appreciated that while in some embodiments, genetic modification is of a psychedelic fungi to eliminate or reduce the amount of a hallucinogenic tryptamine, for instance psilocybin, this disclosure also can be readily applied to eliminate or reduce the amount of one or more other compounds from a fungus, for example to knock out individual compounds so as to compare single knock out variations against each other to test the "entourage effect," or to knock out individual compounds that are otherwise undesired for any reason (illegality, allergenicity, individual sensitivity, achieving synergistic levels or ratios of compounds, etc.).

In some embodiments, a substantially reduced amount will be a reduction of 50%, 60%, 70%, 80%, 90% or greater than 90%, compared to an unmodified fungus, an average of unmodified fungi, or another amount known in the art. In some preferred embodiments, a substantially reduced amount is a reduction of greater than 90%, such as 92.5%, 95%, 97.5% or greater than 97.5%. In some further preferred embodiments, a substantially reduced amount is a reduction of greater than 97.5%, such as 98.0%, 98.5%, 99.0%, or greater than 99.0%, including 99.25%, 99.5%, 99.6%, 99.7%, 99.8%, 99.90%, 99.95%, and 99.99%, including greater than 99.99%, such as an amount below the limit of detection, as determined by area normalization of an HPLC profile or other similar detection method. In some yet further preferred embodiments, no measurable amount is present in a genetically modified mushroom of the disclosure.

In some embodiments, the substantially reduced amount is a substantially reduced amount of psilocybin. In some such embodiments, the substantially reduced amount of psilocybin is a reduction of 50%, 60%, 70%, 80%, 90% or greater than 90%, compared to an unmodified fungus (e.g., an unmodified mushroom from the same strain or species), an average of unmodified fungi (e.g., a representative sample of unmodified mushrooms from the same strain or species), or another amount known in the art (e.g., the average amount of psilocybin for that strain or species, as reported in the literature or otherwise known to ordinary artisans). In some preferred embodiments, the substantially reduced amount of psilocybin is a reduction of psilocybin of greater than 90%, such as 92.5%, 95%, 97.5% or greater than 97.5%. In some further preferred embodiments, a substantially reduced amount of psilocybin is a reduction of psilocybin of greater than 97.5%, such as 98.0%, 98.5%, 99.0%, or greater than 99.0%, including 99.25%, 99.5%, 99.6%, 99.7%, 99.8%, 99.90%, 99.95%, and 99.99%, including greater than 99.99%, such as an amount below the limit of detection, as determined by area normalization of an HPLC profile or other similar detection method. In some yet further preferred embodiments, no measurable psilocybin is present in a genetically modified mushroom of the disclosure.

The average amount of psilocybin present in a mushroom that is not modified according to the disclosure will be known in the art or readily ascertainable to those of skill. As examples, it has been reported that the following *Psilocybe* spp. have the following amounts of psilocybin by dry weight percent (% w/w): *P. azurescens* (1.78); *P. bohemica* (1.34); *P. semilanceata* (0.98); *P. baeocystis* (0.85); *P. cyanescens* (0.85); *P. tampanensis* (0.68); *P. cubensis* (0.63); *P. weilii* (0.61); *P. hoogshagenii* (0.60); *P. stuntzii* (0.36); *P. cyanofibrillosa* (0.21); *P. liniformans* (0.16). (See, e.g., Stamets, *Psilocybin Mushrooms of the World,* 1996.) It will be readily understood that such amounts may vary according to growth conditions and even within a single flush, and that taking an average from fungi within a comparable strain may provide greater accuracy; such measurements will be readily understood to those in the art. As a general rule of thumb, the amount of psilocybin in a *Psilocybe* spp. or other mushroom that is not genetically modified to reduce psilocybin biosynthesis will be understood to be in the range of 0.5 to 1.5% (inclusive) of the dry weight of the mushroom, to be about 1% w/w, or to be 1% w/w.

In some embodiments, psilocybin biosynthesis will be understood to be disrupted or prevented if a genetically modified mushroom of the disclosure contains less than 0.1% psilocybin as determined by dry weight, preferably less than 0.05% psilocybin as determined by dry weight, and more preferably less than 0.01% psilocybin as determined by dry weight. In some embodiments, a genetically modified mushroom of the disclosure will contain less than 0.10%, less than 0.09%, less than 0.08%, less than 0.07%, less than 0.06%, less than 0.05%, less than 0.04%, less than 0.03%, less than 0.02%, less than 0.01%, less than 0.005%, or less than 0.001% psilocybin as determined by dry weight. In some preferred embodiments, a genetically modified mushroom of the disclosure will contain no measurable psilocybin.

The Psilocybin Biosynthetic Pathway

In some aspects are disclosed methods of disrupting or preventing biosynthesis of a bioactive alkaloid in a bioactive alkaloid-producing fungus. In some embodiments, the disclosed methods disrupt or prevent the biosynthesis of psilocybin in a psilocybin-producing fungus.

In some embodiments, disrupting or preventing biosynthesis of psilocybin in a psilocybin-producing fungus comprises disrupting or preventing the function of one or more of the enzymes of the psilocybin biosynthetic pathway, or of the genes that encode them.

The psilocybin biosynthetic pathway from L-tryptophan involves the action of four different enzymes: PsiD (IUBMB Enzyme Nomenclature; Enzyme commission number; EC 4.1.1.105); PsiK (EC 2.7.1.222); PsiH (EC 1.14.99.59); and PsiM (EC 2.1.1.345). (See, e.g., Blei F, Baldeweg F, Fricke J, Hoffmeister D. Biocatalytic Production of Psilocybin and Derivatives in Tryptophan Synthase-Enhanced Reactions. *Chemistry.* 2018; 24 (40): 10028-10031; Fricke J, Blei F, Hoffmeister D. Enzymatic Synthesis of Psilocybin. *Angew Chem Int Ed Engl.* 2017; 56 (40): 12352-55, both of which are incorporated by reference, as if fully set forth herein. The synthetic steps, adapted from Fricke et al. 2017, are schematically illustrated in FIG. 9.

In some embodiments, PsiD has at least 60%, at least 80%, at least 85%, at least 90%, at least 91%, at least 92%, at least 93%, at least 94%, at least 95%, at least 96%, at least 97%, at least 98%, at least 99%, or 100% amino acid sequence identity with the protein sequence deposited in GenBank accession number ASU62239.1 (*Psilocybe cubensis*) or the GenBank accession number ASU62242.1 (*Psilo-*

*cybe cyanescens*), or with the amino acid sequence (SEQ ID NO: 1) encoded by polynucleotide SEQ ID NO: 2.

In some embodiments, PsiK has at least 60%, at least 80%, at least 85%, at least 90%, at least 91%, at least 92%, at least 93%, at least 94%, at least 95%, at least 96%, at least 97%, at least 98%, at least 99%, or 100% amino acid sequence identity with the protein sequence deposited in GenBank accession number ASU62237.1 (*Psilocybe cubensis*) or the GenBank accession number ASU62240.1 (*Psilocybe cyanescens*), or with the amino acid sequence (SEQ ID NO: 3) encoded by polynucleotide SEQ ID NO: 4.

In some embodiments, PsiH has at least 60%, at least 80%, at least 85%, at least 90%, at least 91%, at least 92%, at least 93%, at least 94%, at least 95%, at least 96%, at least 97%, at least 98%, at least 99%, or 100% amino acid sequence identity with the protein sequence deposited in GenBank accession number ASU62246.1 (*Psilocybe cubensis*) or the GenBank accession number ASU62250.1 (*Psilocybe cyanescens*), or with the amino acid sequence (SEQ ID NO: 5) encoded by polynucleotide SEQ ID NO: 6.

In some embodiments, PsiM has at least 60%, at least 80%, at least 85%, at least 90%, at least 91%, at least 92%, at least 93%, at least 94%, at least 95%, at least 96%, at least 97%, at least 98%, at least 99%, or 100% amino acid sequence identity with the protein sequence deposited in GenBank accession number ASU62238.1 (*Psilocybe cubensis*) or the GenBank accession number ASU62241.1 (*Psilocybe cyanescens*), or with the amino acid sequence (SEQ ID NO: 7) encoded by polynucleotide SEQ ID NO: 8.

PsiD, PsiK, PsiH, and PsiM Nucleotide and Amino Acid Sequences

In some aspects are disclosed methods of disrupting or preventing biosynthesis of psilocybin in a psilocybin-producing fungus. In some embodiments, disrupting or preventing such psilocybin biosynthesis comprises disrupting or preventing the function of one or more of the enzymes of the psilocybin biosynthetic pathway, and/or of the genes that encode them.

In some embodiments, disrupting or preventing biosynthesis of psilocybin in a psilocybin-producing fungus comprises disrupting or preventing the function of one or more of the PsiD, PsiK, PsiH, and PsiM enzymes and/or of the PsiD, PsiK, PsiH, and PsiM genes.

Nucleotide sequences of PsiD, PsiK, PsiH, and PsiM genes and encoded amino acid sequences of PsiD, PsiK, PsiH, and PsiM enzymes will be known to those in the art. Exemplary nucleotide sequences of PsiD, PsiK, PsiH, and PsiM genes and encoded amino acid sequences of PsiD, PsiK, PsiH, and PsiM enzymes are provided below from an exemplary *P. cubensis* psilocybin-producing fungus, as SEQ ID NOS: 1-8:

```
SEQ ID NO: 1-PsiD Amino acid sequence-L-tryptophan decarboxylase-P. cubensis:
          10         20         30         40         50
MQVIPACNSA AIRSLCPTPE SFRNMGWLSV SDAVYSEFIG ELATRASNRN
          60         70         80         90        100
YSNEFGLMQP IQEFKAFIES DPVVHQEFID MFEGIQDSPR NYQELCNMFN
         110        120        130        140        150
DIFRKAPVYG DLGPPVYMIM AKLMNTRAGF SAFTRQRLNL HFKKLFDTWG
         160        170        180        190        200
LFLSSKDSRN VLVADQFDDR HCGWLNERAL SAMVKHYNGR AFDEVFLCDK
         210        220        230        240        250
NAPYYGFNSY DDFFNRRFRN RDIDRPVVGG VNNTTLISAA CESLSYNVSY
         260        270        280        290        300
DVQSLDTLVF KGETYSLKHL LNNDPFTPQF EHGSILQGFL NVTAYHRWHA
         310        320        330        340        350
PVNGTIVKII NVPGTYFAQA PSTIGDPIPD NDYDPPPYLK SLVYFSNIAA
         360        370        380        390        400
```

```
RQIMFIEADN KEIGLIFLVF IGMTEISTCE ATVSEGQHVN RGDDLGMFHF
         410        420        430
GGSSFALGLR KDCRAEIVEK FTEPGTVIRI NEVVAALKA

SEQ ID NO: 2-PsiD Nucleotide sequence-P. cubensis:
    1     atgcaggtga tacccgcgtg caactcggca gcaataagat cactatgtcc tactcccgag
   61     tcttttagaa acatgggatg gctctctgtc agcgatgcgg tctacagcga gttcatagga
  121     gagttggcta cccgcgcttc caatcgaaat tactccaacg agttcggcct catgcaacct
  181     atccaggaat tcaaggcttt cattgaaagc gacccggtgg tgcaccaaga atttattgac
  241     atgttcgagg gcattcagga ctctccaagg aattatcagg aactatgtaa tatgttcaac
  301     gatatctttc gcaaagctcc cgtctacgga gaccttggcc ctcccgttta tatgattatg
  361     gccaaattaa tgaacacccg agcgggcttc tctgcattca cgagacaaag gttgaacctt
  421     cacttcaaaa aacttttcga tacctgggga ttgttcctgt cttcgaaaga ttctcgaaat
  481     gttcttgtgg ccgaccagtt cgacgacaga cattgcggct ggttgaacga gcgggccttg
  541     tctgctatgg ttaaacatta caatggacgc gcatttgatg aagtcttcct ctgcgataaa
  601     aatgccccat actacggctt caactcttac gacgacttct ttaatcgcag atttcgaaac
  661     cgagatatcg accgacctgt agtcggtgga gttaacaaca ccaccctcat ttctgctgct
  721     tgcgaatcac tttcctacaa cgtctcttat gacgtccagt ctctcgacac tttagttttc
  781     aaaggagaga cttattcgct taagcatttg ctgaataatg accctttcac cccacaattc
  841     gagcatggga gtattctaca aggattcttg aacgtcaccg cttaccaccg atggcacgca
  901     cccgtcaatg ggacaatcgt caaaatcatc aacgttccag gtacctactt gcgcaagcc
  961     ccgagcacga ttggcgaccc tatcccggat aacgattacg acccacctcc ttaccttaag
 1021     tctcttgtct acttctctaa tattgccgca aggcaaatta tgtttattga gccgacaac
 1081     aaggaaattg gctcatttt ccttgtgttc atcggcatga ccgaaatctc gacatgtgaa
 1141     gccacggtgt ccgaaggtca acacgtcaat cgtggcgatg acttgggaat gttccatttc
 1201     ggtggttctt cgttcgcgct tggtctgagg aaggattgca gggcagagat cgttgaaaag
 1261     ttcaccgaac ccgaacagt gatcagaatc aacgaagtcg tcgctgctct aaaggcttag SEQ ID NO: 3-PsiK Amino acid sequence-4-hydroxytryptamine kinase-P. cubensis:
         10        20        30        40        50
MAFDLKTEDG LITYLTKHLS LDVDTSGVKR LSGGFVNVTW RIKLNAPYQG
         60        70        80        90        100
HTSIILKHAQ PHMSTDEDFK IGVERSVYEY QAIKLMMANR EVLGGVDGIV
        110       120       130       140       150
SVPEGLNYDL ENNALIMQDV GKMKTLLDYV TAKPPLATDI ARLVGTEIGG
        160       170       180       190       200
FVARLHNIGR ERRDDPEFKF FSGNIVGRTT SDQLYQTIIP NAAKYGVDDP
        210       220       230       240       250
LLPTVVKDLV DDVMHSEETL VMADLWSGNI LLQLEEGNPS KLQKIYILDW
        260       270       280       290       300
ELCKYGPASL DLGYFLGDCY LISRFQDEQV GTTMRQAYLQ SYARTSKHSI
        310       320       330       340       350
NYAKVTAGIA AHIVMWTDfM QWGSEEERIN FVKKGVAAFH DARGNNDNGE
        360
ITSTLLKESS TA SEQ ID NO: 4-PsiK Nucleotide sequence-P. cubensis:
    1     atggcgttcg atctcaagac tgaagacggc ctcatcacat atctcactaa acatctttct
   61     ttggacgtcg acacgagcgg agtgaagcgc cttagcggag gctttgtcaa tgtaacctgg
  121     cgcattaagc tcaatgctcc ttatcaaggt catacgagca tcatcctgaa gcatgctcag
  181     ccgcacatgt ctacggatga ggattttaag ataggtgtag aacgttcggt ttacgaatac
  241     caggctatca agctcatgat ggccaatcgg gaggttctgg gaggcgtgga tggcatagtt
  301     tctgtgccag aaggcctgaa ctacgactta gagaataatg cattgatcat gcaagatgtc
  361     gggaagatga gaccctttt agattatgtc accgccaaac cgccacttgc gacggatata
  421     gcccgccttg ttgggacaga aattgggggg ttcgttgcca gactccataa cataggccgc
  481     gagaggcgag acgatcctga gttcaaattc ttctctggaa atattgtcgg aaggacgact
  541     tcagaccagc tgtatcaaac catcataccc aacgcagcga aatatggcgt cgatgacccc
  601     ttgctgccta ctgtggttaa ggaccttgtg gacgatgtca tgcacagcga agagaccctt
  661     gtcatggcgg acctgtggag tggaaatatt cttctccagt tggaggaggg aaacccatcg
  721     aagctgcaga agatatatat cctggattgg gaactttgca gtacggccc agcgtcgttg
  781     gacctgggct atttcttggg tgactgctat ttgtatcccc gctttcaaga cgagcaggtc
  841     ggtacgacga tgcggcaagc ctacttgcaa agctatgcgc gtacgagcaa gcattcgatc
  901     aactacgcca aagtcactgc aggtattgct gctcatattg tgatgtggac cgactttatg
  961     cagtggggga gcgaggaaga aaggataaat tttgtgaaaa aggggtagc tgcctttcac
 1021     gacgccaggg gcaacaacga caatgggaa attacgtcta ccttactgaa ggaatcatcc
 1081     actgcgtaa SEQ ID NO: 5-PsiH Amino acid sequence-Tryptamine 4-monooxygenase-P. cubensis:
         10        20        30        40        50
MIAVLESFVI AGCIYYIVSR RVRRSRLPPG PPGIPIPFIG NMFDMPEESP
         60        70        80        90        100
WLTFLQWGRD YNTDILYVDA GGTEMVILNT LETITDLLEK RGSIYSGRLE
        110       120       130       140       150
STMVNELMGW EFDLGFITYG DRWREERRMF AKEFSEKGIK QFRHAQVKAA
        160       170       180       190       200
HQLVQQLTKT PDRWAQHIRH QIAAMSLDIG YGIDLAEDDP WLEATHLANE
        210       220       230       240       250
GLAIASVPGK FWVDSFPSLK YLPAWFPGAV FKRKAKVWRE AADHMVDMPY
```

```
        260        270        280        290        300
ETMRKLAPQG LTRPSYASAR LQAMDLNGDL EHQEHVIKNT AAEVNVGGGD
        310        320        330        340        350
TTVSAMSAFI LAMVKYPEVQ RKVQAELDAL TNNGQIPDYD EEDDSLPYLT
        360        370        380        390        400
ACIKELFRWN QIAPLAIPHK LMKDDVYRGY LIPKNTLVFA NTWAVLNDPE
        410        420        430        440        450
VYPDPSVFRP ERYLGPDGKP DNTVRDPRKA AFGYGRRNCP GIHLAQSTVW
        460        470        480        490        500
IAGATLLSAF NIERPVDQNG KPIDIPADFT TGFFRHPVPF QCRFVPRTEQ
VSQSVSGP
```

SEQ ID NO: 6-PsiH Nucleotide sequence-*P. cubensis*:
```
    1        atgatcgctg tactattctc cttcgtcatt gcaggatgca tatactacat cgtttctcgt
   61        agagtgaggc ggtcgcgctt gccaccaggg ccgcctggca ttcctattcc cttcattggg
  121        aacatgtttg atatgcctga agaatctcca tggttaacat ttctacaatg gggacgggat
  181        tacagtctgt cttgccgcgt tgacttctaa tatatgaaca gctaatatat tgtcagacac
  241        cgatattctc tacgtggatg ctggagggac agaaatggtt attcttaaca cgttggagac
  301        cattaccgat ctattagaaa agcgagggtc catttattct ggccggtgag ctgatgttga
  361        gtttttgca attgaatttg tggtcacacg tttccagact tgagagtaca atggtcaacg
  421        aacttatggg gtgggagttt gacttagggt tcatcacata cggcgacagg tggcgcgaag
  481        aaaggcgcat gttcgccaag gagttcagtg agaagggcat caagcaattt cgccatgctc
  541        aagtgaaagc tgcccatcag cttgtccaac agcttaccaa aacgccagac cgctgggcac
  601        aacatattcg ccagtaagta ctacttgagg aaaatagcgt acgcttcgct gaccggtccg
  661        tacatcaaag tcagatagcg gcaatgtcac tggatattgg ttatggaatt gatcttgcag
  721        aagacgaccc ttggctggaa cgcacccatt tggctaatga aggcctcgcc atagcatcag
  781        tgccgggcaa attttgggtc gattcgttcc cttctcgtga gcatccttct tctatgtagg
  841        aagggaagga gtctaacaag tgttagtaaa ataccttcct gcttggttcc caggtgctgt
  901        cttcaagcgc aaagcgaagg tctggcgaga agccgccgac catatggttg acatgcctta
  961        tgaaactatg aggaaattga cagttagtca aatgcgttct ccccgtattt tttcaatact
 1021        ctaacttcag ctcacagcct caaggattga ctcgtccgtc gtatgcttca gctcgtctgc
 1081        aagccatgga tctcaacggt gaccttgagc atcaagaaca cgtaatcaag aacacagccg
 1141        cagaggttaa tgtcggtaag tcaaaagcgt ccgtcggcaa ttcaaaattc aggcgctaaa
 1201        gtgggtcttc tcaccaaggt ggaggcgata ctgtaaggat ttctcaatcg ttagagtata
 1261        agtgttctaa tgcagtacat actccaccaa ccagactgtc tctgctatgt ctgcgttcat
 1321        cttggccatg gtgaagtacc ctgaggtcca gcgaaaggtt caagcggagc ttgatgctct
 1381        gaccaataac ggccaaattc ctgactatga cgaagaagat gactccttgc catacctcac
 1441        cgcatgtatc aaggagcttt tccggtggaa tcaaatcgca cccctcgcta taccgcacaa
 1501        attaatgaag gacgacgtgt accgcgggta tctgattccc aagaacactc tagtcttcgc
 1561        aaacacctgg tgaggctgtc cattcattcc tagtacatcc gttgccccac taatagcatc
 1621        ttgataacag ggcagtatta aacgatccag aagtctatcc agatccctct gtgttccgcc
 1681        cagaaagata tcttggtcct gacgggaagc ctgataacac tgtacgcgac ccacgtaaag
 1741        cggcatttgg ctatggacga cgaaattgct aagtgcgctt cagaacccc cccttccgtt
 1801        gactagtgcc atgcgcgcat acaatatcgc tattgatctg atataacttc cctgcggcat
 1861        ttattttggc attcctttag tcccggaatt catctagcgc agtcgacggt ttggattgca
 1921        ggggcaaccc tcttatcagc gttcaatatc gagcgacctg tcgatcagaa tgggaagccc
 1981        attgacatac cggctgattt tactacagga ttcttcaggt agctaatttc cgtctttgtg
 2041        tgcataatac ccctaacgac gcacgtttac ctttttgtaa agacacccag tgcctttcca
 2101        gtgcaggttt gttcctcgaa cagagcaagt ctcacagtcg gtatccggac cctga
```

SEQ ID NO: 7-PsiM Amino acid sequence-Psilocybin synthase-*P. cubensis*:
```
         10         20         30         40         50
MHIRNPYRTP IDYQALSEAF PPLKPFVSVN ADGTSSVDLT IPEAQRAFTA
         60         70         80         90        100
ALLHRDFGLT MTIPEDRLCP TVPNRLNYVL WIEDIFNYTN KTLGLSDDRP
        110        120        130        140        150
IKGVDIGTGA SAIYPMLACA RFKAWSMVGT EVERKCIDTA RLNVVANNLQ
        160        170        180        190        200
DRLSILETSI DGPILVPIFE ATEEYEYEFT MCNPPFYDGA ADMQTSDAAK
        210        220        230        240        250
GFGFGVGAPH SGTVIEMSTE GGESAFVAQM VRESLKLRTR CRWYTSNLGK
        260        270        280        290        300
LKSLKEIVGL LKELEISNYA INEYVQGSTR RYAVAWSFTD IQLPEELSRP
SNPELSSLF
```

SEQ ID NO: 8-PsiM Nucleotide sequence-*P. cubensis*:
```
    1        atgcatatca gaaatcctta ccgtacacca attgactatc aagcactttc agaggccttc
   61        cctcccctca agccatttgt gtctgtcaat gcagatggta ccagttctgt tgacctcact
  121        atcccagaag cccagagggc gttcacggcc gctcttcttc atcgtgactt cgggttcacc
  181        atgaccatac cagaagaccg tctgtgccca acagtcccca ataggttgaa ctacgttctg
  241        tggattgaag atattttcaa ctacacgaac aaaaccctcg gcctgtcgga tgaccgtcct
  301        attaaaggcg ttgatattgg tacaggagcc tccgcaattt atcctatgct tgcctgtgct
  361        cggttcaagg catggtctat ggttggaaca gaggtcgaga ggaagtgcat tgacacggcc
  421        cgcctcaatg tcgtcgcgaa caatctccaa gaccgtctct cgatattgga gacatccatt
  481        gatggtccta ttctcgtccc catttttcag gcgactgaag aatacgaata cgagtttact
  541        atgtgtaacc ctccattcta cgacggtgct gccgatatgc agacttcgga tgctgccaaa
  601        ggatttggat ttggcgtggg cgctccccat tctggaacag tcatcgaaat gtcgactgag
  661        ggaggtgaat cggctttcgt cgctcagatg gtccgtgaga gcttgaagct tcgaacacga
  721        tgcagatggt acacgagtaa cttgggaaag ctgaaatcct tgaaagaaat agtggggctg
```

-continued

```
781      ctgaaagaac ttgagataag caactatgcc attaacgaat acgttcaggg gtccacacgt
841      cgttatgccg ttgcgtggtc tttcactgat attcaactgc ctgaggagct ttctcgtccc
901      tctaaccccg agctcagctc tottttctag
```

Additional sequences SEQ ID NOS: 9-12 follow, representing the coding regions of mRNA expressed from *P. cubensis* genes PsiD, PsiK, PsiH, and PsiM. In these sequences bold regions indicate where exemplar siRNA silencing oligos bind selected from SEQ ID NOS: 32-71 below, and bold underlined regions indicate where exemplar crRNA oligo sequences for CRISPR knockout bind selected from SEQ ID NOS: 13-31 below:

SEQ ID NO: 9-*P. cubensis* strain FSU 12409 tryptophan decarboxylase (psiD) mRNA
(GenBank: KY984101.1):
ATGCAGGTGATACCCGCGTGCAACTCGGCAGCAATAAGATCACTATGTCCTACTCCCGAGTCTTTTAGAA
ACATGGGATGGCTCTCTGTCAGCGATGCGGTCTACAGCGAGTTCATAGGAGAGTTGGCTACCCGCGCTTC
CAATCGAAATTACTCCAACGAGTTCGGCCTCATGCAACCTATCCAGGAATTCAAGGCTTTCATTGAAAGC
GACCCGGTGGTGCACCAAGAATTTATTGACATGTTCGAGGGCATTCAGGACTCTCCAAGGAATTATCAGG
AACTATGTAATATGTTCAACGATATCTTTCGCAAAGCTCCCGTCTACGGAGACCTTGGCCCTCCCGTTTA
TATGATTATGGCCAAATTAATGAACACCCGAGCGGGCTTCTCTGCATTCACGAGACAAAGGTTGAACCTT
CACTTCAAAAAACTTTTCGATACCTGGGGATTGTTCCTGTCTTCGAAAGATTCTCGAAATGTTCTTGTGG
CCGACCAGTTCGACGACAGGGCTGGTTGAACGAGCGGGCCACATTGCTTGTCTGCTATGGTTAAACATTA
CAATGGACGCGCATTTGATGAAGTCTTCCTCTGCGATAAAAATGCCCCATACTACGGCTTCAACTCTTAC
GACGACTTCTTTAATCGCAGATTTCGAAACCGAGATATCGACCGACCTGTAGTCGGTGGAGTTAACAACA
CCACCCTCATTTCTGCTGCTTGCGAATCACTTTCCTACAACGTCTCTTATGACGTCCAGTCTCTCGACAC
TTTAGTTTTCAAAGGAGAGACTTATTCGCTTAAGCATTTGCTGAATAATGACCCTTTCACCCCACAATTC
GAGCATGGGAGTATTCTACAAGGATTCTTGAACGTCACCGCTTACCACCGATGGCACGCACCCGTCAATG
GGACAATCGTCAAAATCATCAACGTTCCAGGTACCTACTTTGCGCAAGCCCCGAGCACGATTGGCGACCC
TATCCCGGATAACGATTACGACCCACCTCCTTACCTTAAGTCTCTTGTCTACTTCTCTAATATTGCCGCA
AGGCAAATTATGTTTATTGAAGCCGACAACAAGGAAATTGGCCTCATTTTCCTTGTGTTCATCGGCATGA
CCGAAATCTCGACATGTGAAGCCACGGTGTCCGAAGGTCAACACGTCAATCGTGGCGATGACTTGGGAAT
GTTCCATTTCGGTGGTTCTTCGTTCGCGCTTGGTCTGAGGAAGGATTGCAGGGCAGAGATCGTTGAAAAG
TTCACCGAACCCGGAACAGTGATCAGAATCAACGAAGTCGTCGCTGCTCTAAAGGCTTAG SEQ ID NO: 10-*P. cubensis* strain FSU 12409 4-hydroxytryptamine kinase (psiK) mRNA
(GenBank: KY984099.1):
ATGGCGTTCGATCTCAAGACTGAAGACGGCCTCATCACATATCTCACTAAACATCTTTCTTTGGACGTCG
ACACGAGCGGAGTGAAGCGCCTTAGCGGAGGCTTTGTCAATGTAACCTGGCGCATTA̲AGCTCAATGCTCC
TTATCAAGGTCATACGAGCATCATCCTGAAGCATGCTCAGCCGCACATGTCTACGATGAGGATTTTAAG
ATAGGTGTAGAACGTTCGGTTTACGAATACCAGGCTATCAAGCTCATGATGGCCAATCGGGAGGTTCTGG
GAGGCGTGGATGGCATAGTTTCTGTGCCAGAAGGCCTGAACTACGACTTAGAGAATAATGCATTGATCAT
GCAAGATGTCGGGAAGATGAAGACCCTTTTAGATTATGTCACCGCCAAACCGCCACTTGCGACGGATATA
GCCCGCCTTGTTGGGACAGAAATTGGGGGGTTCGTTGCCAGACTCCATAACATAGGCCGCGAGAGGCGAG
ACGATCCTGAGTTCAAATTCTTCTCTGGAAATATTGTCGGAAGGACGACTTCAGACCAGCTGTATCAAAC
CATCATACCCAACGCAGCGAAATATGGCGTCGATGACCCCTTGCTGCCTACTGTGGTTAAGGACCTTGTG
GACGATGTCATGCACAGCGAAGAGACCCTTGTCATGGCGGACCTGTGGAGTGGAAATATTCTTCTCCAGT
TGGAGGAGGGAAACCCATCGAAGCTGCAGAAGATATATATCCTGGATTGGGAACTTTGCAAGTACGGCCC
AGCGTCGTTGGACCTGGGCTATTTCTTGGGTGACTGCTATTTGATATCCCGCTTTCAAGACGAGCAGGTC
GGTACGACGATGCGGCAAGCCTACTTGCAAAGCTATGCGCGTACGAGCAAGCATTCGATCAACTACGCCA
AAGTCACTGCAGGTATTGCTGCTCATATTGTGATGTGGACCGACTTTATGCAGTGGGGGAGCGAGGAAGA
AAGGATAAATTTTGTGAAAAAGGGGGTAGCTGCCTTTCACGACGCCAGGGGCAACAACGACAATGGGGAA
ATTACGTCTACCTTACTGAAGGAATCATCCACTGCGTAA SEQ ID NO: 11-*P. cubensis* strain FSU 12409 norbaeocystin methyltransferase (psiM) mRNA
(GenBank: KY984100.1):
ATGCATATCAGAAATCCTTACCGTACACCAATTGACTATCAAGCACTTTCAGAGGCCTTCCCTCCCCTCA
AGCCATTTGTGTCTGTCAATGCAGATGGTACCAGTTCTGTTGACCCCACTATCCCAGAAGCCCAGAGGGC
GTTCACGGCCGCTCTTCTTCATCGTGACTTCGGGCTCACCATGACCATACCAGAAGACCGTCTGTGCCCA
ACAGTCCCCA̲ATAGGTTGAACTACGTTCTGTGGATTGAAGATATTTTCAACTACACGAACAAAACCCTCG
GCCTGTCGGATGACCGTCCTATTAAAGGCGTTGATATTGGTACAGGAGCCTCCGCAATTTATCCTATGCT
TGCCTGTGCTCGGTTCAAGGCATGGTCTATGGTTGGAACAGAGGTCGAGAGGAAGTGCATTGACACGGCC
CGCCTCAATGTCGTCGCGAACAATCTCCAAGACCGTCTCTCGATATTAGAGACATCCATTGATGGTCCTA
TTCTCGTCCCCATTTTCGAGGCGACTGAAGAATACGAATACGAGTTTACTATGTGTAACCCTCCATTCTA
CGACGGTGCTGCCGATATGCAGACTTCGGATGCTGCCAAAGGATTTGGATTTGGCGTGGGCGCTCCCCAT
TCTGGAACAGTCATCGAAATGTCGACTGAGGGAGGTGAATCGGCTTTCGTCGCTCAGATGGTCCGTGAGA
GCTTGAAGCTTCGAACACGATGCAGATGGTACACGAGTAACTTGGGAAAGCTGAAATCCTTGAAAGAAAT
AGTGGGGCTGCTGAAAGAACTTGAGATAAGCAACTATGCCATTAACGAATACGTTCAGGGGTCCACACGT
CGTTATGCCGTTGCGTGGTCTTTCACTGATATTCAACTGCCTGAGGAGCTTTCTCGTCCCTCTAACCCCG
AGCTCAGCTCTCTTTTCTAG SEQ ID NO: 12-P. cubensis strain FSU 12409 putative monooxygenase (psiH) gene,
(GenBank: MF000993.1):
ATGATCGCTGTACTATTCTCCTTCGTCATTGCAGGATGCATATACTACATCGTTTCTCGTAGAGTGAGGC
GGTCGCGCTTGCCACCAGGGCCGCCTGGCATTCCTATTCCCTTCATTGGGAACATGTTTGATATGCCTGA
AGAATCTCCATGGTTAACATTTCTACAATGGGGACGGGATTACAGTCTGTCTTGCCGCG̲TTGACTTCTAA̲
̲TATATGAACAGCTAATATATTGTCAGACACCGATATTCTCTACGTGGATGCTGGAGGGACAGAAATGGTT
ATTCTTAACACGTTGGAGACCATTACCGATCTATTAGAAAAGCGAGGGTCCATTTATTCTGGCCGGTGAG
CTGATGTTGAGTTTTTTGCAATTGA̲ATTTGTGGTCACACGTTTCCAGACTTGAGAGTACAATGGTCAACG
AACTTATGGGGTGGGAGTTTGACTTAGGGTTCATCACATACGGCGACAGGTGGCGCGAAGAAAGGCGCAT -continued

```
GTTCGCCAAGGAGTTCAGTGAGAAGGGCATCAAGCAATTTCGCCATGCTCAAGTGAAAGCTGCCCATCAG
CTTGTCCAACAGCTTACCAAAACGCCAGACCGCTGGGCACAACATATTCGCCAGTAAGTACTACTTGAGG
AAAATAGCGTACGCTTCGCTGACCGGTCCGTACATCAAAGTCAGATAGCGGCAATGTCACTGGATATTGG
TTATGGAATTGATCTTGCAGAAGACGACCCTTGGCTGGAAGCGACCCATTTGGCTAATGAAGGCCTCGCC
ATAGCATCAGTGCCGGGCAAATTTTGGGTCGATTCGTTCCCTTCTCGTGAGCATCCTTCTTCTTCTATGTAGG
AAGGGAAGGAGTCTAACAAGTGTTAGTAAAATACCTTCCTGCTTGGTTCCCAGGTGCTGTCTTCAAGCGC
AAAGCGAAGGTCTGGCGAGAAGCCGCCGACCATATGGTTGACATGCCTTATGAAACTATGAGGAAATTAG
CAGTTAGTCAAATGCGTTCTCCCCGTATTTTTTCAATACTCTAACTTCAGCTCACAGCCTCAAGGATTGA
CTCGTCCGTCGTATGCTTCAGCTCGTCTGCAAGCCATGGATCTCAACGGTGACCTTGAGCATCAAGAACA
CGTAATCAAGAACACAGCCGCAGAGGTTAATGTCGGTAAGTCAAAAGCGTCCGTCGGCAATTCAAAATTC
AGGCGCTAAAGTGGGTCTTCTCACCAAGGTGGAGGCGATACTGTAAGGATTTCTCAATCGTTAGAGTATA
AGTGTTCTAATGCAGTACATACTCCACCAACCAGACTGTCTCTGCTATGTCTGCGTTCATCTTGGCCATG
GTGAAGTACCCTGAGGTCCAGCGAAAGGTTCAAGCGGAGCTTGATGCTCTGACCAATAACGGCCAAATTC
CTGACTATGACGAAGAAGATGACTCCTTGCCATACCTCACCGCATGTATCAAGGAGCTTTTCCGGTGGAA
TCAAATCGCACCCCTCGCTATACCGCACAAATTAATGAAGGACGACGTGTACCGCGGGTATCTGATTCCC
AAGAACACTCTAGTCTTCGCAAACACCTGGTGAGGCTGTCCATTCATTCCTAGTACATCCGTTGCCCCAC
TAATAGCATCTTGATAACAGGGCAGTATTAAACGATCCAGAAGTCTATCCAGATCCCTCTGTGTTCCGCC
CAGAAAGATATCTTGGTCCTGACGGGAAGCCTGATAACACTGTACGCGACCCACGTAAAGCGGCATTTGG
CTATGGACGACGAAATTGGTAAGTGCGCTTTCAGAACCCCCCCTTCCGTTGACTAGTGCCATGCGCGCAT
ACAATATCGCTATTGATCTGATATAACTTCCCTGCGGCATTTATTTTGGCATTCCTTTAGTCCCGGAATT
CATCTAGCGCAGTCGACGGTTTGGATTGCAGGGGCAACCCTCTTATCAGCGTTCAATATCGAGCGACCTG
TCGATCAGAATGGGAAGCCCATTGACATACCGGCTGATTTTACTACAGGATTCTTCAGGTAGCTAATTTC
CGTCTTTGTGTGCATAATACCCCTAACGACGCACGTTTACCTTTTTGTAAAGACACCCAGTGCCTTTCCA
GTGCAGGTTTGTTCCTCGAACAGAGCAAGTCTCACAGTCGGTATCCGGACCCTGA
```

The following sequences (SEQ ID NOS: 13-31) are examples of single targeting crRNA sequences that can be used to create deletions in the PsiD gene (SEQ ID NOS: 13-17 have target match positions shown above in SEQ ID NO: 9), PsiK gene (SEQ ID NOS: 18-21 match SEQ ID NO: 10), PsiM gene (SEQ ID NOS: 23-26 match SEQ ID NO: 11), PsiH gene (SEQ ID NOS: 27-31 match SEQ ID NO: 12) respectively of *P. cubensis*. The single crRNA are suitable for use with high fidelity Cas9 derivative in plasmid transfections or introduced ribonucleoprotein (RNP) complexes as described in embodiments herein. The targeting oligonucleotides are illustrated as 5'→3' spacer DNA plus PAM (protospacer adjacent motif). Further SEQ ID NOS: 13-31 follow, representing CRISPR knockout oligonucleotides:

| SEQ ID NO: | CRISPR gene knockout | Oligonucleotide |
|---|---|---|
| SEQ ID NO: 13 | CRISPR PsiD knockout | 5' GGTGATACCCGCGTGCAACT CGG-3' |
| SEQ ID NO: 14 | CRISPR PsiD knockout | 5' GATGGCTCTCTGTCAGCGATG CGG-3' |
| SEQ ID NO: 15 | CRISPR PsiD knockout | 5' GCGAGTTCATAGGAGAGT TGG-3' |
| SEQ ID NO: 16 | CRISPR PsiD knockout | 5' GAAATTACTCCAACGAGTT CGG-3' |
| SEQ ID NO: 17 | CRISPR PsiD knockout | 5' GCAACCTATCCAGGAATTCA AGG-3' |
| SEQ ID NO: 18 | CRISPR PsiK knockout | 5' GTTCGATCTCAAGACTGAAGA CGG-3' |
| SEQ ID NO: 19 | CRISPR PsiK knockout | 5' TCTTTGGACGTCGACACGAG CGG-3' |
| SEQ ID NO: 20 | CRISPR PsiK knockout | 5' GAGGCTTTGTCAATGTAACC TGG-3' |
| SEQ ID NO: 21 | CRISPR PsiK knockout | 5' GCATGCTCAGCCGCACATGTCTA CGG-3' |
| SEQ ID NO: 22 | CRISPR PsiM knockout | 5' TGACTATCAAGCACTTTCAG AGG-3' |
| SEQ ID NO: 23 | CRISPR PsiM knockout | 5' TTTGTGTCTGTCAATGCAGA TGG-3' |
| SEQ ID NO: 24 | CRISPR PsiM knockout | 5' CACTATCCCAGAAGCCCAGA GGG-3' |
| SEQ ID NO: 25 | CRISPR PsiM knockout | 5' GCTCTTCTTCATCGTGACTTC GGG-3' |
| SEQ ID NO: 26 | CRISPR PsiM knockout | 5' GTCTGTGCCCAACAGTCCCCAAT AGG-3' |
| SEQ ID NO: 27 | CRISPR PsiH knockout | 5' GTACTATTCTCCTTCGTCATTGC AGG-3' |
| SEQ ID NO: 28 | CRISPR PsiH knockout | 5' GCGCTTGCCACCAGGGCCGCC TGG-3' |
| SEQ ID NO: 29 | CRISPR PsiH knockout | 5' GATATGCCTGAAGAATCTCCA TGG-3' |
| SEQ ID NO: 30 | CRISPR PsiH knockout | 5' GGATGCTGGAGGGACAGAAA TGG-3' |
| SEQ ID NO: 31 | CRISPR PsiH knockout | 5' CCGATCTATTAGAAAAGCGA GGG-3' |

The sequences SEQ ID NOS: 32-71 below represent alternative siRNA oligonucleotides that can be used to silence the corresponding Psi gene (e.g., SEQ ID NOS: 32-36, 52-56 for silencing PsiD, SEQ ID NOS: 37-41, 57-59, 61 for PsiK, SEQ ID NOS: 43-46, 62-66 for PsiM, SEQ ID NOS: 47-51, 67-71 for PsiH).

The positions of siRNA sequences SEQ ID NOS: 52-56 are shown targeting PsiD in bold in SEQ ID NO: 9. The positions of siRNA sequences SEQ ID NOS: 37-39, 41 are shown targeting PsiK in SEQ ID NO: 10. The positions of siRNA sequences SEQ ID NOS: 42-46 are shown targeting PsiM in SEQ ID NO: 11. The positions of siRNA sequences SEQ ID NOS: 47-51 are shown targeting PsiH in SEQ ID NO: 12.

Sequences from SEQ ID NOS: 32-71 have a 9 bp spacer loop sequence (GCTGGTGGA). Optionally, additional sequences can be created by using spacer lengths that are 3, 4, 5, 6, 7, 9, and 23 bases. Sequences denoted SEQ ID NOS: 32-71 also have AA or GG at the 5' end, which may provide stability. (See Functional anatomy of siRNAs for mediating efficient RNAi in *Drosophila melanogaster* embryo lysate; Martinez et al., *EMBO J.* 2001 Dec. 3; 20 (23): 6877-88); *Sui* G et al., A DNA vector-based RNAi technology to suppress gene expression in mammalian cells. *Proc Natl Acad Sci.* 2002 Apr. 16; 99 (8): 5515-20). The bases denoted at the end of sequence as (TTTT) or (UUUU) are optional and could be either longer (6 bases) or shorter (4 bases). (See Using siRNA for gene silencing is a rapidly evolving tool in molecular biology, siRNA Design Guidelines, Tech. Bulletin #506, ThermoFisher Scientific.)

SEQ ID NOS: 32-71 follow, representing gene siRNA oligos or their DNA templates:

```
SEQ ID NO: 32-PsiD siRNA oligonucleotide DNA sequence
5' AATAAGATCACTATGTCCTAC(GCTGGTGGA)GTAGGACATAGTGATCTTATT(TTTT)-3'

SEQ ID NO: 33-PsiD siRNA oligonucleotide DNA sequence
5' AATTTATTGACATGTTCGAGG(GCTGGTGGA)CCTCGAACATGTCAATAAATT(TTTT)-3'

SEQ ID NO: 34-PsiD siRNA oligonucleotide DNA sequence
5' GGAGAGTTGGCTACCCGCGCT(GCTGGTGGA)AGCGCGGGTAGCCAACTCTCC(TTTT)-3'

SEQ ID NO: 35-PsiD siRNA oligonucleotide DNA sequence
5' AAGCTCCCGTCTACGGAGACC(GCTGGTGGA)GGTCTCCGTAGACGGGACGTT(TTTT)-3'

SEQ ID NO: 36-PsiD siRNA oligonucleotide DNA sequence
5' GGGCTTCTCTGCATTCACGAG(GCTGGTGGA)CTCGTGAATGCAGAGAAGCCC(TTTT)-3'

SEQ ID NO: 37-PsiK siRNA oligonucleotide DNA sequence
5' AACGTTCGGTTTACGAATACC(GCTGGTGGA)GGTATTCGTAAACCGAACGTT(TTTT)-3'

SEQ ID NO: 38-PsiK siRNA oligonucleotide DNA sequence
5' AAGGCCTGAACTACGACTTAG(GCTGGTGGA)CTAAGTCGTAGTTCAGGCCTT(TTTT)-3'

SEQ ID NO: 39-PsiK siRNA oligonucleotide DNA sequence
5' AACATAGGCCGCGAGAGGCGAG(GCTGGTGGA)CTCGCCTCTCGCGGCCTATGTT(TTTT)-3'

SEQ ID NO: 40-PsiD siRNA oligonucleotide DNA sequence
5' GGCTGGTTGAACGAGCGGGCC(GCTGGTGGA)GGCCCGCTCGTTCAACCAGCC(TTTT)-3'

SEQ ID NO: 41-PsiK siRNA oligonucleotide DNA sequence
5' GGCGGACCTGTGGAGTGGAAA(GCTGGTGGA)TTTCCACTCCACAGGTCCGCC(TTTT)-3'

SEQ ID NO: 42-PsiM siRNA oligonucleotide DNA sequence
5' AATGTCGTCGCGAACAATCTC(GCTGGTGGA)GAGATTGTTCGCGACGACATT(TTTT)-3'

SEQ ID NO: 43-PsiM siRNA oligonucleotide DNA sequence
5' AACCCTCCATTCTACGACGGT(GCTGGTGGA)ACCGTCGTAGAATGGAGGGTT(TTTT)-3'

SEQ ID NO: 44-PsiM siRNA oligonucleotide DNA sequence
5' AACAGTCATCGAAATGTCGAC(GCTGGTGGA)GTCGACATTTCGATGACTGTT(TTTT)-3'

SEQ ID NO: 45-PsiM siRNA oligonucleotide DNA sequence
5' GGATGCTGCCAAAGGATTTGG(GCTGGTGGA)CCAAATCCTTTGGCAGCATCC(TTTT)-3'

SEQ ID NO: 46-PsiM siRNA oligonucleotide DNA sequence
5' GGTACACGAGTAACTTGGGAA(GCTGGTGGA)TTCCCAAGTTACTCGTGTACC(TTTT)-3'

SEQ ID NO: 47-PsiH siRNA oligonucleotide DNA sequence
5' AATGGGGACGGGATTACAGTC(GCTGGTGGA)GACTGTAATCCCGTCCCCATT(TTTT)-3'

SEQ ID NO: 48-PsiH siRNA oligonucleotide DNA sequence
5' AATATATTGTCAGACACCGAT(GCTGGTGGA)ATCGGTGTCTGACAATATATT(TTTT)-3'

SEQ ID NO: 49-PsiH siRNA oligonucleotide DNA sequence
5' AATGGTCAACGAACTTATGGG(GCTGGTGGA)CCCATAAGTTCGTTGACCATT(TTTT)-3'

SEQ ID NO: 50-PsiH siRNA oligonucleotide DNA sequence
5' GGAGTTCAGTGAGAAGGGCAT(GCTGGTGGA)ATGCCCTTCTCACTGAACTCC(TTTT)-3'

SEQ ID NO: 51-PsiH siRNA oligonucleotide DNA sequence
5' GGCAATGTCACTGGATATTGG(GCTGGTGGA)CCAATATCCAGTGACATTGCC(TTTT)-3'
```

-continued

```
SEQ ID NO: 52-PsiD siRNA oligonucleotide
5' AAUAAGAUCACUAUGUCCUAC(GCUGGUGGA)GUAGGACAUAGUGAUCUUAUU(UUUU)-3'

SEQ ID NO: 53-PsiD siRNA oligonucleotide
5' AAUUUAUUGACAUGUUCGAGG(GCUGGUGGA)CCUCGAACAUGUCAAUAAAUU(UUUU)-3'

SEQ ID NO: 54-PsiD siRNA oligonucleotide
5' GGAGAGUUGGCUACCCGCGCU(GCUGGUGGA)AGCGCGGGUAGCCAACUCUCC(UUUU)-3'

SEQ ID NO: 55-PsiD siRNA oligonucleotide
5' AAGCUCCCGUCUACGGAGACC(GCUGGUGGA)GGUCUCCGUAGACGGGACGUU(UUUU)-3'

SEQ ID NO: 56-PsiD siRNA oligonucleotide
5' GGGCUUCUCUGCAUUCACGAG(GCUGGUGGA)CUCGUGAAUGCAGAGAAGCCC(UUUU)-3'

SEQ ID NO: 57-PsiK siRNA oligonucleotide
5' AACGUUCGGUUUACGAAUACC(GCUGGUGGA)GGUAUUCGUAAACCGAACGUU(UUUU)-3'

SEQ ID NO: 58-PsiK siRNA oligonucleotide
5' AAGGCCUGAACUACGACUUAG(GCUGGUGGA)CUAAGUCGUAGUUCAGGCCUU(UUUU)-3'

SEQ ID NO: 59-PsiK siRNA oligonucleotide
5' AACAUAGGCCGCGAGAGGCGAG(GCUGGUGGA)CUCGCCUCUCGCGGCCUAUGUU(UUUU)-3'

SEQ ID NO: 60-PsiD siRNA oligonucleotide
5' GGCUGGUUGAACGAGCGGGCC(GCUGGUGGA)GGCCCGCUCGUUCAACCAGCC(UUUU)-3'

SEQ ID NO: 61-PsiK siRNA oligonucleotide
5' GGCGGACCUGUGGAGUGGAAA(GCUGGUGGA)UUUCCACUCCACAGGUCCGCC(UUUU)-3'

SEQ ID NO: 62-PsiM siRNA oligonucleotide
5' AAUGUCGUCGCGAACAAUCUC(GCUGGUGGA)GAGAUUGUUCGCGACGACAUU(UUUU)-3'

SEQ ID NO: 63-PsiM siRNA oligonucleotide
5' AACCCUCCAUUCUACGACGGU(GCUGGUGGA)ACCGUCGUAGAAUGGAGGGUU(UUUU)-3'

SEQ ID NO: 64-PsiM siRNA oligonucleotide
5' AACAGUCAUCGAAAUGUCGAC(GCUGGUGGA)GUCGACAUUUCGAUGACUGUU(UUUU)-3'

SEQ ID NO: 65-PsiM siRNA oligonucleotide
5' GGAUGCUGCCAAAGGAUUUGG(GCUGGUGGA)CCAAAUCCUUUGGCAGCAUCC(UUUU)-3'

SEQ ID NO: 66-PsiM siRNA oligonucleotide
5' GGUACACGAGUAACUUGGGAA(GCUGGUGGA)UUCCCAAGUUACUCGUGUACC(UUUU)-3'

SEQ ID NO: 67-PsiH siRNA oligonucleotide
5' AAUGGGGACGGGAUUACAGUC(GCUGGUGGA)GACUGUAAUCCCGUCCCCAUU(UUUU)-3'

SEQ ID NO: 68-PsiH siRNA oligonucleotide
5' AAUAUAUUGUCAGACACCGAU( GCUGGUGGA)AUCGGUGUCUGACAAUAUAUU(UUUU)-3'

SEQ ID NO: 69-PsiH siRNA oligonucleotide
5' AAUGGUCAACGAACUUAUGGG(GCUGGUGGA)CCCAUAAGUUCGUUGACCAUU(UUUU)-3'

SEQ ID NO: 70-PsiH siRNA oligonucleotide
5' GGAGUUCAGUGAGAAGGGCAU(GCUGGUGGA)AUGCCCUUCUCACUGAACUCC(UUUU)-3'

SEQ ID NO: 71-PsiH siRNA oligonucleotide
5' GGCAAUGUCACUGGAUAUUGG(GCUGGUGGA)CCAAUAUCCAGUGACAUUGCC(UUUU)-3'
```

Protein coding nucleotide sequences SEQ ID NOS: 72-75 of the Psi cluster core psilocybin synthetic genes from *P. cyanescens* were aligned with their orthologs from *P. cubensis* SEQ ID NOS: 2, 4, 6, 8 in FIGS. 1-4 in order to identify regions of extensive identity and potential target regions of conserved structure and function.

SEQ ID NOS: 72-75 follow, representing the consensus protein coding nucleotide sequence of mRNA of *P. cyanescens* PsiD, PsiK, PsiM, PsiH respectively.

```
SEQ ID NO: 72-PsiD Nucleotide sequence, P. cyanescens (GenBank: KY984104.1):
      1    ATGCAGGTAC TGCCCGCGTG CCAATCTTCC GCGCTTAAAA CATTGTGCCC ATCCCCGAG
     61    GCCTTTCGAA AGCTCGGTTG GCTCCCTACT AGCGACGAGG TTTACAACGA ATTCATCGAT
    121    GACTTGACCG GTCGCACGTG CAATGAAAAG TACTCCAGCC AGGTTACACT TTTGAAGCCT
    181    ATCCAAGATT TCAAGACATT CATCGAGAAT GATCCCATAG TGTATCAAGA ATTTATCTCT
    241    ATGTTTGAAG GAATCGAGCA GTCTCCCACC AACTACCACG AGCTATGTAA CATGTTCAAC
    301    GACATCTTTC GCAAAGCCCC ACTCTACGGC GATCTTGGTC CTCCGGTTTA CATGATCATG
    361    GCCAGAATAA TGAATACGCA GGCGGGGTTTC TCTGCGTTCA CAAAAGAGAG CTTGAACTTC
```

-continued

```
 421   CATTTCAAAA AGCTCTTCGA CACCTGGGGG CTATTCCTTT CCTCGAAAAA CTCTCGAAAC
 481   GTGCTTGTTG CAGACCAGTT TGACGATAAG CATTACGGGT GGTTCAGCGA GCGAGCCAAG
 541   ACTGCCATGA TGATTAATTA TCCAGGGCGT ACATTCGAGA AAGTCTTCAT CTGCGACGAG
 601   CACGTTCCAT ACCATGGCTT CACTTCCTAT GACGATTTCT TCAATCGCAG GTTCAGGGAC
 661   AAGGATACAG ATCGGCCCGT AGTCGGTGGG GTTACTGACA CCACTTTAAT CGGGGCTGCC
 721   TGTGAATCGT TGTCATATAA CGTCTCTCAC AACGTCCAGT CTCTTGACAC GCTAGTCATC
 781   AAGGGAGAGG CCTATTCACT TAAACATCTA CTTCATAACG ACCCCTTCAC ACCGCAATTC
 841   GAACATGGGA GCATCATTCA AGGATTCCTA AATGTCACCG CTTACCACCG CTGGCACTCC
 901   CCCGTCAATG GCACGATTGT GAAGATCGTC AACGTTCCAG GTACCTACTT CGCTCAAGCT
 961   CCATATACAA TTGGATCTCC TATCCCCGAT AACGACCGCG ACCCGCCTCC TTACCTCAAG
1021   TCACTCGTAT ACTTCTCCAA CATCGCTGCA CGGCAAATTA TGTTCATCGA GGCCGACAAC
1081   AAAGACATCG GCCTCATTTT CTTGGTCTTC ATTGGAATGA CTGAGATCTC GACTTGCGAG
1141   GCGACGGTGT GCGAAGGTCA GCATGTCAAC CGCGGTGACG ATTTGGGCAT GTTCCATTTC
1201   GGTGGTTCAT CTTTTGCCCT TGGCTTGCGG AAGGACTCGA AGGCGAAGAT TTTGGAAAAG
1261   TTCGCGAAAC CGGGGACCGT TATTAGGATC AACGAGCTAG TTGCATCTGT AAGGAAGTAG
```

SEQ ID NO: 73-PsiM Nucleotide sequence, *P. cyanescens* (GenBank: KY984103.1):

```
   1   ATGCATATCA GGAACCCATA CCGCGATGGT GTTGACTACC AAGCACTCGC TGAAGCATTT
  61   CCGGCTCTCA AACCACATGT CACAGTAAAT TCAGACAATA CGACCTCCAT CGACTTTGCT
 121   GTGCCAGAAG CCCAAAGACT GTATACAGCT GCCCTICTAC ACCGGGATTT CGGTCTTACG
 181   ATCACACTCC CGGAAGACCG TCTTTGTCCG ACAGTGCCTA ATCGGCTCAA CTATGTCCTT
 241   TGGGTTGAAG ATATCCTTAA AGTCACTTCA GATGCTCTCA GTCTTCCGGA TAATCGTCAA
 301   GTTAAGGGGA TCGATATCGG AACTGGCGCA TCAGCGATAT ATCCCATGCT CGCATGCTCT
 361   CGTTTTAAGA CATGGTCCAT GGTTGCAACA GAGGTAGACC AGAAGTGTAT TGACACTGCT
 421   CGTCTCAACG TCATTGCCAA CAACCTCCAA GAACGTCTCG CAATTATAGC CACCTCCGTC
 481   GATGGTCCTA TACTTGTCCC CCTCTTGCAG GCGAATTCTG ATTTTGAGTA CGATTTTACG
 541   ATGTGTAATC CGCCCTTCTA CGATGGGGCA TCCGACATGC AGACATCGGA TGCTGCGAAG
 601   GGGTTTGGAT TCGGTGTGAA CGCTCCGCAT ACCGGCACGG TGCTCGAGAT GGCCACCGAG
 661   GGAGGTGAAT CGGCCTTCGT AGCCCAAATG GTCCGCGAAA GTTTGAATCT TCAAACACGA
 721   TGCAGGTGGT TCACGAGTAA TTTGGGGAAA TTGAAGTCCT TGTACGAAAT TGTGGGGCTG
 781   CTGCGAGAAC ATCAGATAAG TAACTACGCA ATCAACGAAT ACGTCCAAGG AGCCACTCGT
 841   CGATATGCGA TTGCATGGTC GTTCATCGAT GTTCGACTGC CTGATCATTT GTCCCGTCCA
 901   TCTAACCCCG ACCTAAGCTC TCTTTTCTAG
```

SEQ ID NO: 74-PsiK Nucleotide sequence, *P. cyanescens* (GenBank: KY984102.1):

```
   1   ATGACTTTCG ATCTCAAGAC TGAAGAAGGC CTGCTCTCAT ACCTCACAAA GCACCTATCG
  61   CTGGACGTTG CTCCCAACGG GGTGAAACGT CTTAGTGGAG GCTTCGTCAA CGTTACCTGG
 121   CGGGTCGGGC TCAATGCCCC TTATCATGGT CACACGAACA TTATTCTGAA GCATGCTCAA
 181   CCGCACCTGT CTTCAGACAT AGATTTCAAG ATAGGTGTTG AACGATCGGC GTACGAGTAT
 241   CAAGCGCTCA AAATCGTGTC AGCCAATAGC TCCCTTCTAG GCAGCAGCGA TATTCGGGTC
 301   TCTGTACCAG AAGGTCTTCA CTACGACGTC GTTAATAACG CATTGATCAT GCAAGATGTC
 361   GGGACAATGA AGACCCTGTT GGACTATGTC ACTGCCAAAC CACCAATTTC TGCAGAGATC
 421   GCCAGTCTCG TAGGCAGTCA AATTGGTGCA TTTATCGCTA GGCTGCACAA CCTCGGCCGC
 481   GAGAATAAAG ACAAGGACGA CTTCAAGTTC TTCTCTGGAA ACATCGTCGG GAGAACAACC
 541   GCAGACCAGT TGTATCAAAC CATCATACCT AATGCCGCTA AATACGGTAT CGACGATCCA
 601   ATTCTCCCAA TTGTGGTAAA GGAGTTGGTG GAGGAGGTCA TGAATAGTGA AGAAACGCTT
 661   ATCATGGCGG ATTTATGGAG TGGCAATATT CTTCTCCAGT TTGATGAAAA CTCGACGGAA
 721   TTGACGAGGA TATGGCTGGT AGACTGGGAG TTGTGCAAAT ATGGTCCACC GTCTTTGGAC
 781   ATGGGGTACT TCTTAGGCGA CTGTTTCCTG GTCGCTCGAT TTCAAGATCA GCTCGTAGGG
 841   ACATCAATGC GACAGGCCTA CTTGAAGAGC TACGCAAGGA ATGTCAAGGA GCCAATCAAT
 901   TATGCAAAAG CCACCGCAGG CATCGGCGCG CATCTCGTCA TGTGGACTGA TTTCATGAAG
 961   TGGGGGAACG ATGAAGAGAG GGAAGAGTTT GTTAAGAAAG GCGTGGAAGC CTTCCATGAA
1021   GCAAATGAGG ACAATAGAAA CGGGGAGATT ACGTCTATAC TTGTGAAGGA AGCATCGCGC
1081   ACTTAG
```

SEQ ID NO: 75-PsiH Nucleotide sequence, *P. cyanescens* (GenBank: MF000997.1):

```
   1   ATGATTGTTC TATTGGTCTC GCTCGTCCTT GCAGGATGCA TATACTACGC CAACGCTCGT
  61   AGAGTAAGGC GCTCGCGCTT ACCACCGGGC CCGCCTGGCA TACCACTGCC CTTCATTGGG
 121   AATATGTTTG ATATGCCTTC AGAGTCACCG TGGTTAAGAT TTCTTCAATG GGGACGGGAC
 181   TATCGTACGT CAAACATTGT TTTGATTTGC GCATTTAATT GATATCTCTA GACACTGATA
 241   TCCTTTACTT GAATGCTGGC GGAACGGAAA TAATTATTCT GAACACACTG GATGCTATAA
 301   CCGACTTGTT GGAAAAGCGA GGGTCGATGT ATTCGGGTCG GTAAGTTGTT GCTATGTCTT
 361   TTATGGATAA GATATTAAAG AAGATGCGTC AGACTCGAGA GCACCATGGT GAACGAACTC
 421   ATGGGGTGGG AGTTCGACTT GGGATTCATA ACCTATGGTG AAAGATGGCG CGAAGAAAGA
 481   CGCATGTTCG CCAAGGAGTT CAGCGAAAAA AACATCAGGC AATTCCGCCA CGCCCAAATT
 541   AAAGCTGCCA ATCAGCTTGT TCGGCAGCTG ATCAAAACGC CAGATCGTTG GTCGCAGCAC
 601   ATCCGGCAGT AAGTTGTAAA AATATAGACA AGCATCGAGT CGAGGCTGAC CATTAATTAT
 661   GGTACAGTCA GATAGCAGCC ATGTCTCTAG ACATTGGTTA TGGAATTGAT CTCGCAGAGG
 721   ATGACCCCTG GATTGCAGCA ACCCAGCTAG CTAACGAAGG GCTCGCCGAA GCTTCAGTCG
 781   CGGGCAGTTT CTGGGTCGAC TCATTCCCCG CCCGTGAGTG CTTTTCTTCC TCCATTAGAC
 841   TACTAGTCAC GAATCATTTG ATTTCTACTC AGTCAAATAC CTTCCTTCAT GGCTTCCTGG
 901   TGCAGGATTC AAGCGCAAAG CAAAGGTATG GAAGGAAGGT GCTGACCATA TGGTGAACAT
 961   GCCGTATGAA ACGATGAAAA AATTGACTGT ATGTTATCTT CCGTGATGGC TCGTACGGAG
1021   AATTGCACTG ATTGCTACAC TACAGGTTCA AGGCTTGGCC CGACCTTCAT ATGCCTCAGC
1081   TCGTCTGCAG GCCATGGACC CCGATGGCGA TCTCGAGCAT CAGGAACACG TGATCAGAAA
1141   CACAGCGACT GAGGTCAATG TCGGTAAGTT ACTAGTAATG CCTCTTCGGC TATTAAAGAA
1201   TTGGGCGCTA ATTGATTTGC ATTGACCTAG GCGGAGGTGA TACGGTAAAT ATACCTCCTG
1261   CTACTACCCG ACTGCACGTT CTTACATGCT TTACATTTAA CATTCAGACT GTTTCTGCTG
1321   TGTCAGCCTT TATTTTGGCC ATGGTCAAAT ATCCAGAAGT TCAACGCCAA GTCCAAGCAG
```

-continued

```
1381    AACTGGATGC ACTCACCAGC AAAGGAGTTG TCCCAAACTA TGACGAAGAA GACGACTCCT
1441    TGCCATACCT TACGGCTTGC GTCAAGGAAA TCTTTCGATG GAACCAAATA GCACCCCTTG
1501    CTATCCCTCA TCGGCTGATC AAAGACGATG TTTATCGTGG GTATCTCATA CCAAAGAATG
1561    CTTTGGTCTA CGCCAACTCA TGGTATGGCG TTCTGTATTC CCTATATTCA TGCACATCCG
1621    CTCATTGTTT ACTCGTAGGG CTGTGTTGAA TGACCCAGAG GAGTACCCAA ATCCCTCTGA
1681    GTTCCGACCA GAACGATATT TGAGCTCTGA CGGAAAGCCC GACCCAACGG TCCGTGATCC
1741    CCGCAAAGCA GCATTTGGCT ATGGTCGACG CAACTGGTAA GCTTTTCAAT TCATATCTGA
1801    CTTCACAAGC CGCCGATCTG ATGCACTAAC CTGCGGCATT TTCTGTAGTC CCGGAATCCA
1861    CCTGGCACAA TCGACGGTAT GGATTGCTGG AGCCACTCTT CTCTCGGTAT TCAATATCGA
1921    ACGTCCTGTT GATGGGAATG GAAAACCCAT CGACATCCCG GCGACGTTCA CTACCGGATT
1981    CTTCAGGTAT TCAATTAAGC TCTTGCCCTA GGGCATGGAG TGATTGCATC TCATTAACGA
2041    TATGGAACTT TACAGACATC CCGAGCCTTT CCAGTGCAGA TTTGTCCCTC GCACTCAGGA
2101    GATTCTAAAA TCCGTTTCCG GT
```

Conceptual translations of coding sequences SEQ ID NOS: 76-79 of the Psi cluster core psilocybin synthetic enzymes from *P. cyanescens* were aligned with their orthologs from *P. cubensis* SEQ ID NOS: 1, 3, 5, and 7 in FIGS. 5-8 in order to identify regions of extensive identity and potential target regions of conserved structure and function.

SEQ ID NOS: 76-79 follow, representing the conceptual translations of coding sequences of mRNA of *P. cyanescens* PsiD, PsiM, PsiK, PsiH respectively.

enzymatic functions such as substrate binding, cofactor binding, allosteric modulator binding, substrate specificity and kinetics of catalysis, all of which properties can be measured following DNA sequence identification and in vitro expression of the edited variant gene.

SEQ ID NOS: 80-87 below are examples of extensive identical nucleotide sequences between the protein coding sequences of PsiK genes of *P. cubensis* and *P. cyanescens*:

```
SEQ ID NO: 76-PsiD Protein Sequence, P. cyanescens:
MQVLPACQSSALKTLCPSPEAFRKLGWLPTSDEVYNEFIDDLTGRTCNEKYSSQVTLLKPIQDFKTFIE
NDPIVYQEFISMFEGIEQSPTNYHELCNMFNDIFRKAPLYGDLGPPVYMIMARIMNTQAGFSAFTKESL
NFHFKKLFDTWGLFLSSKNSRNVLVADQFDDKHYGWFSERAKTAMMINYPGRTFEKVFICDEHVPYHGF
TSYDDFFNRRFRDKDTDRPVVGGVTDTTLIGAACESLSYNVSHNVQSLDTLVIKGEAYSLKHLLHNDPF
TPQFEHGSIIQGFLNVTAYHRWHSPVNGTIVKIVNVPGTYFAQAPYTIGSPIPDNDRDPPPYLKSLVYF
SNIAARQIMFIEADNKDIGLIFLVFIGMTEISTCEATVCEGQHVNRGDDLGMFHEGGSSFALGLRKDSK
AKILEKFAKPGTVIRINELVASVRK SEQ ID NO: 77-PsiM Protein Sequence, P. cyanescens:
MHIRNPYRDGVDYQALAEAFPALKPHVTVNSDNTTSIDFAVPEAQRLYTAALLHRDFGLTITLPEDRLC
PTVPNRLNYVLWVEDILKVTSDALGLPDNRQVKGIDIGTGASAIYPMLACSRFKTWSMVATEVDQKCID
TARLNVIANNLQERLAIIATSVDGPILVPLLQANSDFEYDFTMCNPPFYDGASDMQTSDAAKGFGFGVN
APHTGTVLEMATEGGESAFVAQMVRESLNLQTRCRWFTSNLGKLKSLYEIVGLLREHQISNYAINEYVQ
GATRRYAIAWSFIDVRLPDHLSRPSNPDLSSLF SEQ ID NO: 78-PsiK Protein Sequence, P. cyanescens:
MTFDLKTEEGLLSYLTKHLSLDVAPNGVKRLSGGFVNVTWRVGLNAPYHGHTSIILKHAQPHLSSDIDF
KIGVERSAYEYQALKIVSANSSLLGSSDIRVSVPEGLHYDVVNNALIMQDVGTMKTLLDYVTAKPPISA
EIASLVGSQIGAFIARLHNLGRENKDKDDFKFFSGNIVGRTTADQLYQTIIPNAAKYGIDDPILPIVVK
ELVEEVMNSEETLIMADLWSGNILLQFDENSTELTRIWLVDWELCKYGPPSLDMGYFLGDCFLVARFQD
QLVGTSMRQAYLKSYARNVKEPINYAKATAGIGAHLVMWTDFMKWGNDEEREEFVKKGVEAFHEANEDN
RNGEITSILVKEASRT SEQ ID NO: 79-PsiH Protein Sequence, P. cyanescens:
MIVLLVSLVLAGCIYYANARRVRRSRLPPGPPGIPLPFIGNMFDMPSESPWLRFLQWGRDYHTDILYLN
AGGTEIIILNTLDAITDLLEKRGSMYSGRLESTMVNELMGWEFDLGFITYGERWREERRMFAKEFSEKN
IRQFRHAQIKAANQLVRQLIKTPDRWSQHIRHQIAAMSLDIGYGIDLAEDDPWIAATQLANEGLAEASV
PGSFWVDSFPALKYLPSWLPGAGFKRKAKVWKEGADHMVNMPYETMKKLTVQGLARPSYASARLQAMDP
DGDLEHQEHVIRNTATEVNVGGGDTTVSAVSAFILAMVKYPEVQRQVQAELDALTSKGVVPNYDEEDDS
LPYLTACVKEIFRWNQIAPLAIPHRLIKDDVYRGYLIPKNALVYANSWAVLNDPEEYPNPSEFRPERYL
SSDGKPDPTVRDPRKAAFGYGRRNCPGIHLAQSTVWIAGATLLSVFNIERPVDGNGKPIDIPATFTTGF
FRHPEPFQCRFVPRTQEILKSVSG
```

Extensive identical nucleotide sequences SEQ ID NOS: 80-87 between the protein coding sequences of PsiK genes of *P. cubensis* and *P. cyanescens* are shown in FIG. 2 usually corresponding with extended regions of identical amino acid sequence in the conceptual translation FIG. 6. Such regions may be used for creating loss of function missense substitutions, for example by CRISPR-Cas gene editing with gap repair template oligonucleotides bearing novel sequence substitutions. Hence, in some embodiments, these sequences are targets for engineering loss and alteration of protein domains corresponding to structural folds and particular

| Extended identical sequences for PsiK genes of *P. cubensis* and *P. cyanescens* | |
| --- | --- |
| SEQ ID NO: 80 | 5'-TTCGATCTCAAGACTGAAGA-3' |
| SEQ ID NO: 81 | 5'-CTGAAGCATGCTCA-3' |
| SEQ ID NO: 82 | 5'-AAGATAGGTGT-3' |
| SEQ ID NO: 83 | 5'-GCATTGATCATGCAAGATGTCGGGA-3' |
| SEQ ID NO: 84 | 5'-ATGAAGACCCT-3' |

-continued

| Extended identical sequences for PsiK genes of P. cubensis and P. cyanescens | |
|---|---|
| SEQ ID NO: 85 | 5'-TTCTTCTCTGGAAA-3' |
| SEQ ID NO: 86 | 5'-TGTATCAAACCATCATACC-3' |
| SEQ ID NO: 87 | 5'-TATTCTTCTCCAGTT-3' |

Extensive identical nucleotide sequences SEQ ID NOS: 88-95 between the protein coding sequences of PsiM genes of *P. cubensis* and *P. cyanescens* are shown in FIG. 3 usually corresponding with extended regions of identical amino acid sequence in the conceptual translation FIG. 7. Such regions may be used for creating loss of function missense substitutions, for example by CRISPR-Cas gene editing with gap repair template oligonucleotides bearing novel sequence substitutions. Hence, in some embodiments, these sequences are targets for engineering loss and alteration of protein domains corresponding to structural folds and particular enzymatic functions such as substrate binding, cofactor binding, allosteric modulator binding, substrate specificity and kinetics of catalysis, all of which properties can be measured following DNA sequence identification and in vitro expression of the edited variant gene.

SEQ ID NOS: 88-95 below are examples of extensive identical nucleotide sequences between the protein coding sequences of PsiM genes of *P. cubensis* and *P. cyanescens*:

| Conserved sequences for PsiM genes of P. cubensis and P. cyanescens | |
|---|---|
| SEQ ID NO: 88 | 5'-CCAGAAGCCCA-3' |
| SEQ ID NO: 89 | 5'-GAAGACCGTCT-3' |
| SEQ ID NO: 90 | 5'-GAGGGAGGTGAATCGGC-3' |

-continued

| Conserved sequences for PsiM genes of P. cubensis and P. cyanescens | |
|---|---|
| SEQ ID NO: 91 | 5'-AACACGATGCAG-3' |
| SEQ ID NO: 92 | 5'-GTGGGGCTGCTG-3' |
| SEQ ID NO: 93 | 5'-AACGAATACGT-3' |
| SEQ ID NO: 94 | 5'-TCTAACCCCGA-3' |
| SEQ ID NO: 95 | 5'-AGCTCTCTTTTCTAG-3' |

Extensive identical nucleotide sequences SEQ ID NOS: 96-108 between the protein coding sequences of PsiH genes of *P. cubensis* and *P. cyanescens* are shown in FIG. 4 usually corresponding with extended regions of identical amino acid sequence in the conceptual translation FIG. 8. Such regions may be used for creating loss of function missense substitutions, for example by CRISPR-Cas gene editing with gap repair template oligonucleotides bearing novel sequence substitutions. Hence, in some embodiments, these sequences are targets for engineering loss and alteration of protein domains corresponding to structural folds and particular enzymatic functions such as substrate binding, cofactor binding, allosteric modulator binding, substrate specificity and kinetics of catalysis, all of which properties can be measured following DNA sequence identification and in vitro expression of the edited variant gene.

SEQ ID NOS: 96-108 below are examples of extensive identical nucleotide sequences between the protein coding sequences of PsiH genes of *P. cubensis* and *P. cyanescens*:

| Conserved sequences for Psill genes of P. cubensis and P. cyanescens | |
|---|---|
| SEQ ID NO: 96 | 5'-TTGCAGGATGCATATACTA-3' |
| SEQ ID NO: 97 | 5'-CCCTTCATTGGGAACATGTTTGATATGCCT-3' |
| SEQ ID NO: 98 | 5'-CAATGGGGACGGGA-3' |
| SEQ ID NO: 99 | 5'-GAAAAGCGAGGGTC-3' |
| SEQ ID NO: 100 | 5'-ATGGGGTGGGAGTT-3' |
| SEQ ID NO: 101 | 5'-CGCATGTTCGCCAAGGAGTTCAG-3' |
| SEQ ID NO: 102 | 5'-CAAAACGCCAGA-3' |
| SEQ ID NO: 103 | 5'-TTCAAGCGCAAAGC-3' |
| SEQ ID NO: 104 | 5'-CAGCTCGTCTGCA-3' |
| SEQ ID NO: 105 | 5'-AATGTCGGTAAGT-3' |
| SEQ ID NO: 106 | 5'-ACTATGACGAAGAAGATGACTCCTTGCCATACCT-3' |
| SEQ ID NO: 107 | 5'-GCATTTGGCTATGG-3' |
| SEQ ID NO: 108 | 5'-TTTCCAGTGCAG-3' |

Extensive identical nucleotide sequences SEQ ID NOS: 109-117 between the protein coding sequences of PsiD genes of *P. cubensis* and *P. cyanescens* are shown in FIG. 1 usually corresponding with extended regions of identical amino acid sequence in the conceptual translation FIG. 5. Such regions may be used for creating loss of function missense substitutions, for example by CRISPR-Cas gene editing with gap repair template oligonucleotides bearing novel sequence substitutions. Hence, in some embodiments, these sequences are targets for engineering loss and alteration of protein domains corresponding to structural folds and particular enzymatic functions such as substrate binding, cofactor binding, allosteric modulator binding, substrate specificity and kinetics of catalysis, all of which properties can be measured following DNA sequence identification and in vitro expression of the edited variant gene.

SEQ ID NOS: 109-117 below are examples of extensive identical nucleotide sequences between the protein coding sequences of PsiD genes of *P. cubensis* and *P. cyanescens*:

| Conserved sequences for PsiD genes of *P. cubensis* and *P. cyanescens* | |
| --- | --- |
| SEQ ID NO: 109 | 5'-CAAGAATTTAT-3' |
| SEQ ID NO: 110 | 5'-CTATGTAATATGTTCAAC-3' |
| SEQ ID NO: 111 | 5'-ATCTTTCGCAAAGC-3' |
| SEQ ID NO: 112 | 5'-GTAGTCGGTGG-3' |
| SEQ ID NO: 113 | 5'-ACGTCCAGTCTCT-3' |
| SEQ ID NO: 114 | 5'-GTCACCGCTTACCACCG-3' |
| SEQ ID NO: 115 | 5'-TCAACGTTCCAGGTACCTACTT-3' |
| SEQ ID NO: 116 | 5'-GCCGACAACAA-3' |
| SEQ ID NO: 117 | 5'-ATGTTCCATTTC-3' |

Non-Hallucinogenic Psychedelic Fungi and Other Genetically Modified Fungi

In some aspects are disclosed non-hallucinogenic psychedelic fungi and other genetically modified fungi. In some embodiments, the genetically modified fungi are knockout fungi.

A "knockout" refers to an organism (such as a "knockout" fungi) produced by genetic techniques in which one or more genes in the organism, or one or more enzymes or other proteins that they encode, are rendered inoperative.

"Inoperative" refers to having been intentionally modified through genetic or molecular techniques such as disclosed herein to have disrupted (e.g., impaired or abolished) catalytic activity, substrate binding, or another generally essential functional property that is characteristic of the active, functional state (e.g., in a wild-type organism).

In some aspects of the invention are disclosed knockouts of one or more of a PsiD, PsiK, PsiH, and PsiM gene, whereby any of the PsiD, PsiK, PsiH, and PsiM genes, and/or any of the PsiD, PsiK, PsiH, and PsiM enzymes they encode, are rendered inoperative. In some embodiments, the PsiD, PsiK, PsiH, and/or PsiM gene knockouts of the invention provide a knockout fungus, which is a non-hallucinogenic psychedelic fungus, such as disclosed herein.

A "knockout" (KO) (or "gene knockout") also refers to an organism having at least one inoperative gene. For example, a "single knockout" (SKO) (or equivalently, "single gene knockout") refers to an organism having one inoperative gene. Those of skill will appreciate that reference to "one" inoperative gene (as well as any other number, as below) refers to one inoperative gene of interest, and therefore other (not of interest) genes also may be inoperative.

A "double knockout" (DKO) refers to an organism having two inoperative genes (that is, two of interest), for example where two genes have been knocked out at the same time.

A "triple knockout" (TKO) and a "quadruple knockout" (QKO) refer to an organism having three or four inoperative genes (of interest), respectively.

A "heterozygous knockout" or a "heterozygous KO" refers to an organism having only one of two gene copies (alleles) knocked out. A "homozygous knockout" or a "homozygous KO" refers to an organism having both alleles knocked out.

A "monokaryotic knockout" refers to a monokaryotic spore, protoplasts or mycelium derived from a single nucleus or identical nuclei all containing the same introduced deletion or null allele at the relevant locus or gene.

A "dikaryotic knockout" would be where two fungal strains containing monokaryotic knockout inactivations of the same gene or locus are crossed such that the resulting dikaryotic mycelium, *sclerotium* or mushroom contains no nuclei with a functional copy of the relevant locus or gene.

Gene knockout technology, and its general applications, is well known to those in the art. In disclosed embodiments, gene knockouts can be accomplished through a variety of techniques, combining the teachings of the present invention with the general knowledge in the art. Non-limiting examples of gene knockout techniques include: (a) homologous recombination; (b) cleavage using zinc-finger nucleases; (c) transcription activator-like effector nucleases (TALENs); and (d) clustered regularly interspaced short palindromic repeats (CRISPR)/Cas9.

a. Gene Knockouts Using Homologous Recombination

In some embodiments, a disclosed method comprises knocking out a gene (e.g., PsiD, PsiM, PsiK and/or PsiH) using homologous recombination. Homologous recombination generally involves creating a DNA construct containing the desired mutation. For knockout purposes, this typically involves a drug resistance marker in place of the desired knockout gene (e.g., PsiD, PsiM, PsiK and/or PsiH).

In some embodiments, a construct containing, e.g., a drug resistance marker or a marker gene that encodes a selectable metabolic enzyme of a length 1 kb, 2 kb, 3 kb, 4 kb, 5 kb, or 6 kb can be inserted using 35-50 bp or 100 bp of identical sequence to the PsiD, PsiM, PsiK, or PsiH gene.

In some embodiments, the drug resistance marker can be a nourseothricin resistance gene.

In some embodiments, the drug resistance marker can be a phleomycin resistance gene In some embodiments, the marker gene encoding a selectable metabolic enzyme can be the *P. cubensis* fsyl gene. In other embodiments, the marker gene encoding a selectable metabolic enzyme can be the *P. cubensis* pyrG gene.

An alternative method of introducing the Cas/sgRNA complex into the fungal nucleus can be achieved by transforming in vitro pre-assembled RNP. The RNP-based CRISPR system is superior to DNA-based CRISPR systems as the RNP-based system avoids strain construction and can be used across different species/strains. A system using in vitro-assembled Cas9 RNP coupled with microhomology repair templates was established and showed a greater gene-targeting efficiency across different genetic backgrounds of the fungus *Aspergillus fumigatus* compared with classical-gene replacement systems. Single and tandem insertions of a 2,890-bpHygR cassette flanked by either 35 bp or 50 bp of microhomology regions targeted and replaced the pksP gene locus (Afu2g17600) Al Abdallah Q., Ge W., Fortwendel J.R. A Simple and Universal System for Gene Manipulation in *Aspergillus fumigatus*: In Vitro-Assembled Cas9-Guide RNA Ribonucleoproteins Coupled with Microhomology Repair Templates. mSphere. 2017; 2: e00446-17. doi: 10.1128/mSphere.00446-17.)

In some embodiments, the construct contains two flanking regions of at least 35 bp of identical sequence to the PsiD gene. In some embodiments, the construct contains two flanking regions of at least 35 bp of identical sequence to the PsiM gene. In some embodiments, the construct contains two flanking regions of at least 35 bp of identical sequence to the PsiK gene. In some embodiments, the construct contains two flanking regions of at least 35 bp of identical sequence to the PsiH gene. The construct is delivered to cells of the psilocybin-producing fungus either through microinjection or electroporation.

Without being bound by theory, the cell's own repair mechanisms then recombine DNA of the construct that is homologous to PsiD, PsiM, PsiK or PsiH DNA in the fungal genome. This can result in the sequence of the PsiD, PsiM, PsiK or PsiH gene being altered, wherein the mRNA transcribed from this construct sequence may be translated into a nonfunctional protein, thereby resulting in the inactivation the desired PsiD, PsiM, PsiK or PsiH gene.

Protocols for gene inactivation by homologous recombination can be found in, e.g., Bradford et al., Overview: Generation of Gene Knockout Mice. *Current Protocols in Cell Biology.* 44. Wiley-Blackwell. Unit 19.12 19.12.1-17, which is hereby incorporated by reference.

b. Gene Knockouts Using Zinc-Finger Nucleases

In some embodiments, a disclosed method comprises knocking out a gene (e.g., PsiD, PsiM, PsiK and/or PsiH) using a zinc-finger nuclease. Zinc-finger nucleases generally consist of DNA binding domains that can precisely target a DNA sequence. Without being bound by theory, each zinc finger can recognize specific codons of a desired DNA sequence, and therefore can be modularly assembled to bind to a particular sequence. These binding domains can be coupled with a restriction endonuclease that can cause a double stranded break (DSB) in the DNA. Repair processes may introduce mutations that destroy functionality of the gene.

In some embodiments, a zinc-finger DNA-binding domain is generated to target a three base pair sequence in the DNA sequence of PsiD, PsiM, PsiK, or PsiH, and then fused to a restriction endonuclease domain. The construct is delivered to cells of the psilocybin-producing fungus by means known to one of skill, for example, through microinjection or electroporation. Without being bound by theory, upon binding to the target sequence, the endonuclease can cause a double stranded break in the sequence. Then, the cell's DNA repair mechanisms may repair the break, which can introduce insertions or deletions that render the sequence inoperative.

Protocols for gene inactivation by zinc finger nucleases can be found in Santiago et al., Targeted gene knockout in mammalian cells by using engineered zinc-finger nucleases, Proc Nat'l Acad Sci. 105 (15): 5809-5814 Apr. 15, 2008; see also, e.g., Song et al., The Use of CRISPR/Cas9, ZFNs, and TALENs in Generating Site-Specific Genome Alterations, *Methods Enzymol.,* Vol. 546 (2014), both of which are hereby incorporated by reference.

c. Gene Knockouts Using TALENS

In some embodiments, a disclosed method comprises knocking out a gene (e.g., PsiD, PsiM, PsiK, and/or PsiH) using a transcription activator-like effector nuclease (TALEN). TALENs generally contain a DNA binding domain and a nuclease that can cleave DNA. Without being bound by theory, the DNA binding region consists of amino acid repeats that can each recognize a single bp of the desired targeted DNA sequence. If this cleavage is targeted to a gene coding region, and non-homologous end joining (NHEJ)-mediated repair introduces insertions and deletions, a frameshift mutation may result, thereby disrupting function of the targeted gene.

In some embodiments, a TALEN is generated to target a 3 bp sequence in a PsiD, PsiH, PsiK, or PsiM DNA sequence. The construct is delivered to cells of the psilocybin-producing fungus by means known to one of skill, for example, through microinjection or electroporation. Without being bound by theory, upon binding to the target sequence, the endonuclease causes a double stranded break in the sequence. Then, DNA repair mechanisms, for example non-homologous end joining NHEJ-mediated repair mechanisms, may attempt to repair the break, which can disrupt the reading frame and resulting function of the gene.

Protocols for gene inactivation by TALENS can be found in Keith et al., TALENs: a widely applicable technology for targeted genome editing, *Nature Reviews Molecular Cell Biol.* 14 (1): 49-55, January 2013; see also, e.g., Song et al., The Use of CRISPR/Cas9, ZFNs, and TALENs in Generating Site-Specific Genome Alterations, *Methods Enzymol.,* Vol. 546 (2014), which are hereby incorporated by reference.

d. Gene Knockouts Using CRISPR/Cas9

In some embodiments, a disclosed method comprises knocking out a gene (e.g., PsiD, PsiM, PsiK, and/or PsiH) using clustered regularly interspaced short palindromic repeats (CRISPR). CRISPR/Cas9 is a method for genome editing that contains a guide RNA complexed with a Cas9 protein. Without being bound by theory, the guide RNA can be engineered to match a desired DNA sequence through simple complementary base pairing. The coupled Cas9 can then cause a double stranded break in the DNA. Following the same principle as zinc-fingers and TALENs, attempts to repair these double stranded breaks may result in frameshift mutations that result in a nonfunctional target gene.

Protocols for gene inactivation by CRISPR can be found in Guidelines for optimized gene knockout using CRISPR/Cas9, Van Campenhout et al., *Biotechniques,* Vol. 66, No. 6, 295-302, June 2019 and Wei et al., Efficient Gene Knockout in Goats Using CRISPR/Cas9 System, *PLoS ONE.* 9 (9): e106718, September 2014; see also, e.g., Song et al., The Use of CRISPR/Cas9, ZFNs, and TALENs in Generating Site-Specific Genome Alterations, *Methods Enzymol.,* Vol. 546 (2014), which are hereby incorporated by reference.

CRISPR Associated Endonucleases: CRISPR (Clustered Regularly Interspaced Short Palindromic Repeats) is found in bacteria and is believed to protect the bacteria from phage infection. It has been used as a means to alter gene expression in eukaryotic DNA, and to introduce insertions and deletions as a way of increasing or decreasing transcription in the DNA of a targeted cell or population of cells. See, e.g., Horvath P, Barrangou R. CRISPR/Cas, the immune system of bacteria and archaea. Science. 2010. 8; 327 (5962): 167-70; Terns M P, Terns R M. CRISPR-based adaptive immune systems. Curr Opin Microbiol. 2011; 14 (3): 321-7 and Wang H, Yang H, Shivalila C S, Dawlaty M M, Cheng A W, Zhang F, Jaenisch R. One-step generation of mice carrying mutations in multiple genes by CRISPR/Cas-mediated genome engineering. Cell. 2013; 153 (4): 910-8, all of which are incorporated by reference fully herein.

CRISPR methodologies employ a nuclease, CRISPR-associated (Cas), that complexes with small RNAs as guides (gRNAs) to cleave DNA in a sequence-specific manner upstream of the protospacer adjacent motif (PAM) in any genomic location. CRISPR may use separate guide RNAs known as the crRNA and tracrRNA. These two separate RNAs have been combined into a single RNA to enable site-specific mammalian genome cutting through the design of a short guide RNA. Cas and guide RNA (gRNA) may be synthesized by known methods. Cas/guide-RNA (gRNA)

uses a non-specific DNA cleavage protein Cas, and an RNA oligonucleotide to hybridize to target and recruit the Cas/gRNA complex. See, e.g., Chang N, Sun C, Gao L, Zhu D, Xu X, Zhu X, Xiong J W, Xi J J. Genome editing with RNA-guided Cas9 nuclease in zebrafish embryos. Cell Res. 2013; 23 (4): 465-72. and Hwang W Y, Fu Y, Reyon D, Maeder M L, Tsai S Q, Sander J D, Peterson R T, Yeh J R, Joung J K. Efficient genome editing in zebrafish using a CRISPR-Cas system. Nat Biotechnol. 2013; 31 (3): 227-9., all of which are incorporated by reference fully herein.

In general, the CRISPR/Cas proteins comprise at least one RNA recognition and/or RNA binding domain. RNA recognition and/or RNA binding domains interact with guide RNAs. CRISPR/Cas proteins can also comprise nuclease domains (i.e., DNase or RNase domains), DNA binding domains, helicase domains, RNase domains, protein-protein interaction domains, dimerization domains, as well as other domains. The mechanism through which CRISPR/Cas9-induced mutations inactivate PsiD, PsiM, PsiH, and PsiK genes can vary. For example, the mutation can affect PsiD, PsiM, PsiH, and PsiK gene expression or excises the gene in-whole or in part. The mutation can comprise one or more deletions. The size of the deletion can vary from a single nucleotide base pair to about 10,000 base pairs. In some embodiments, the deletion can include all or substantially all of the PsiD, PsiM, PsiH, and PsiK sequences. The mutation can also comprise one or more insertions, that is, the addition of one or more nucleotide base pairs to the PsiD, PsiM, PsiH, and PsiK sequences. The size of the inserted sequence also may vary, for example from about one base pair to about 300 nucleotide base pairs. The mutation can comprise one or more point mutations, that is, the replacement of a single nucleotide with another nucleotide. Useful point mutations are those that have functional consequences, for example, mutations that result in the conversion of an amino acid codon into a termination codon, or that result in the production of a nonfunctional protein.

In embodiments, the CRISPR/Cas-like protein can be a wild type CRISPR/Cas protein, a modified CRISPR/Cas protein, or a fragment of a wild type or modified CRISPR/Cas protein. The CRISPR/Cas-like protein can be modified to increase nucleic acid binding affinity and/or specificity, alter an enzymatic activity, and/or change another property of the protein. For example, nuclease (i.e., DNase, RNase) domains of the CRISPR/Cas-like protein can be modified, deleted, or inactivated. Alternatively, the CRISPR/Cas-like protein can be truncated to remove domains that are not essential for the function of the fusion protein. The CRISPR/Cas-like protein can also be truncated or modified to optimize the activity of the effector domain of the fusion protein.

In some embodiments, a CRISPR/Cas-like protein is derived from a wild-type Cas9 protein or fragment thereof. In other embodiments, the CRISPR/Cas-like protein is derived from modified Cas9 protein. For example, the amino acid sequence of the Cas9 protein can be modified to alter one or more properties (e.g., nuclease activity, affinity, stability) of the protein. Alternatively, Cas9 protein domains not involved in RNA-guided cleavage can be eliminated from the protein such that the modified Cas9 protein is smaller than the wild-type Cas9 protein.

Three types (I-III) of CRISPR systems have been identified. CRISPR clusters contain spacers, the sequences complementary to antecedent mobile elements. CRISPR clusters are transcribed and processed into mature CRISPR RNA (crRNA). In embodiments, the CRISPR/Cas system can be a type I, a type II, or a type III system. Non-limiting examples of suitable CRISPR/Cas proteins include Cas3, Cas4, Cas5, Case (or CasD), Cas6, Cas6e, Casof, Cas7, Cas8a1, Cas8a2, Cas8b, Cas8c, Cas9, Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Cszl, Csx15, Csf1, Csf2, Csf3, Csf4, and Cu1966.

In one embodiment, the RNA-guided endonuclease is derived from a type II CRISPR/Cas system. The CRISPR-associated endonuclease, Cas9, belongs to the type II CRISPR/Cas system and has strong endonuclease activity to cut target DNA. Cas9 is guided by a mature crRNA that contains about 20 base pairs (bp) of unique target sequence (called spacer) and a trans-activated small RNA (tracrRNA) that serves as a guide for ribonuclease III-aided processing of pre-crRNA. The crRNA: tracrRNA duplex directs Cas9 to target DNA via complementary base pairing between the spacer on the crRNA and the complementary sequence (called protospacer) on the target DNA. Cas9 recognizes a trinucleotide (NGG) protospacer adjacent motif (PAM) to specify the cut site (the 3rd nucleotide from PAM). The crRNA and tracrRNA can be expressed separately or engineered into an artificial fusion small guide RNA (sgRNA) via a synthetic stem loop (AGAAAU) to mimic the natural crRNA/tracrRNA duplex. Such sgRNA, like shRNA, can be synthesized or in vitro transcribed for direct RNA transfection or expressed from U6 or H1-promoted RNA expression vector, although cleavage efficiencies of the artificial sgRNA are lower than those for systems with the crRNA and tracrRNA expressed separately.

The CRISPR-associated endonuclease Cas9 nuclease can have a nucleotide sequence identical to the wild type *Streptococcus pyogenes* sequence. The CRISPR-associated endonuclease may be a sequence from other species, for example other *Streptococcus* species, such as thermophiles. The Cas9 nuclease sequence can be derived from other species including, but not limited to: Nocardiopsis dassonvillei, *Streptomyces* pristinaespiralis, *Streptomyces viridochromogenes, Streptomyces roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina*, Burkholderiales *bacterium, Polaromonas naphthalenivorans, Polaromonas* sp., Crocosphaera *watsonii*, Cyanothece sp., *Microcystis aeruginosa, Synechococcus* sp., *Acetohalobium arabaticum, Ammonifex degensii, Caldicelulosiruptor becscii, Candidatus desulforudis, Clostridium botulinum, Clostridium difficle, Finegoldia magna, Natranaerobius thermophiles, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus,* or Acaryochloris *marina. Pseudomonas aeruginosa, Escherichia coli,* or other sequenced bacteria genomes and archaea, or other prokaryotic microorganisms may also be a source of the Cas9 sequence utilized in the embodiments disclosed herein.

The Cas9 nuclease sequence can be a mutated sequence. For example, the Cas9 nuclease can be mutated in the conserved HNH and RuvC domains, which are involved in strand specific cleavage. For example, an aspartate-to-alanine (D10A) mutation in the RuvC catalytic domain allows the Cas9 nickase mutant (Cas9n) to nick rather than cleave DNA to yield single-stranded breaks, and the subsequent preferential repair through HDR can potentially decrease the frequency of unwanted indel mutations from off-target double-stranded breaks.

The Cas9 can be orthologous. Six smaller Cas9 orthologs have been used and reports have shown that Cas9 from *Staphylococcus aureus* (SaCas9) can edit the genome with efficiencies similar to those of SpCas9, while being more than 1 kilobase shorter.

In addition to the wild type and variant Cas9 endonucleases described, embodiments of the disclosure also encompass CRISPR systems including newly developed "enhanced-specificity" *S. pyogenes* Cas9 variants (eSpCas9), which dramatically reduce off target cleavage. These variants are engineered with alanine substitutions to neutralize positively charged sites in a groove that interacts with the non-target strand of DNA. This modification can reduce interaction of Cas9 with the non-target strand, thereby encouraging re-hybridization between target and non-target strands. The effect of this modification is a requirement for more stringent Watson-Crick pairing between the gRNA and the target DNA strand, which limits off-target cleavage (Slaymaker I M, Gao L, Zetsche B, Scott D A, Yan W X, Zhang F. Rationally engineered Cas9 nucleases with improved specificity. Science. 2016 Jan. 1; 351 (6268): 84-8).

Herein, the term "Cas" refers to all Cas molecules comprising variants, mutants, orthologues, high-fidelity variants and the like, unless a specific context demands otherwise.

Guide Nucleic Acid Sequences: Guide RNA sequences according to the present disclosure can be sense or antisense sequences. The specific sequence of the gRNA may vary, but, regardless of the sequence, useful guide RNA sequences will be those that minimize off-target effects while achieving high efficiency and complete ablation of the THC gene. The guide RNA sequence generally includes a proto-spacer adjacent motif (PAM). The sequence of the PAM can vary depending upon the specificity requirements of the CRISPR endonuclease used. In the CRISPR-Cas system derived from *S. pyogenes*, the target DNA typically immediately precedes a 5'-NGG proto-spacer adjacent motif (PAM). Thus, for the *S. pyogenes* Cas9, the PAM sequence can be AGG, TGG, CGG or GGG. Other Cas9 orthologues may have different PAM specificities. For example, Cas9 from *S. thermophilus* requires 5'-NNAGAA for CRISPR 1 and 5'-NGGNG for CRISPR3 and *Neisseria meningitidis* requires 5'-NNNNGATT. The specific sequence of the guide RNA may vary, but, regardless of the sequence, useful guide RNA sequences will be those that minimize off-target effects while achieving high efficiency and complete ablation of the THC gene. The length of the guide RNA sequence can vary from about 20 to about 60 or more nucleotides, for example about 20, about 21, about 22, about 23, about 24, about 25, about 26, about 27, about 28, about 29, about 30, about 31, about 32, about 33, about 34, about 35, about 36, about 37, about 38, about 39, about 40, about 45, about 50, about 55, about 60 or more nucleotides.

The guide RNA sequence can be configured as a single sequence or as a combination of one or more different sequences, e.g., a multiplex configuration. Multiplex configurations can include combinations of two, three, four, five, six, seven, eight, nine, ten, or more different guide RNAs. In certain embodiments, the composition comprises multiple different gRNA molecules, each targeted to a different target sequence. In certain embodiments, this multiplexed strategy provides for increased efficacy. These multiplex gRNAs can be expressed separately in different vectors or expressed in one single vector.

Non-Hallucinogenic PsiD, PsiK, PsiM, and/or PsiH Knockout Psychedelic Fungi

In some aspects are disclosed genetically modified fungi having one or more gene knockouts. In some embodiments, a genetically modified fungus is a non-hallucinogenic psychedelic fungus. In some embodiments, a non-hallucinogenic psychedelic fungus is a psilocybin-producing fungus with one or more gene knockouts. In some embodiments, a non-hallucinogenic psychedelic fungus is a psilocybin-producing fungus that has introduced into its genome an alteration which results in the loss of psilocybin biosynthesis. Such a non-hallucinogenic psychedelic fungus may include a genetic defect introduced directly into the coding sequence of at least one gene of the psilocybin biosynthetic pathway, including one gene, two genes, three genes, or four genes of the psilocybin biosynthetic pathway. In some embodiments, a non-hallucinogenic psychedelic fungus has a genetic defect introduced directly into the coding sequence of one or more of the PsiD, PsiK, PsiM, and PsiH genes.

In some embodiments, a non-hallucinogenic psychedelic fungus is a psychedelic fungus in which only one of the PsiD, PsiK, PsiM, or PsiH genes is inactivated.

In some embodiments, a non-hallucinogenic psychedelic fungus is a psychedelic fungus in which a PsiD gene is inactivated, thereby disrupting psilocybin synthesis at catalytic steps of the psilocybin biosynthetic pathway in which PsiD is involved, but leaving intact steps that do not involve this enzyme. In *P. cubensis*, the PsiD enzyme is principally responsible for catalyzing the decarboxylation of L-tryptophan to produce tryptamine (see also FIG. 9, in which each of the the PsiD, PsiK, PsiM, or PsiH enzymes, and the effects of their potential disruption according to different disclosed embodiments, is represented). Hence, in some embodiments, wherein the PsiD gene is inactivated, or the catalytic function of the PsiD enzyme is otherwise disrupted or interfered with, the resulting genetically modified fungus may contain increased or substantially similar levels of L-tryptophan; and reduced levels of any of tryptamine, 4-hydroxytryptamine, norbaeocystin, baeocystin, psilocybin, and psilocin; said levels being compared to an unmodified fungus, an average of unmodified fungi, or another amount known in the art.

In some embodiments, a non-hallucinogenic psychedelic fungus is a psychedelic fungus in which a PsiH gene is inactivated, thereby disrupting psilocybin synthesis at catalytic steps of the psilocybin biosynthetic pathway in which PsiH is involved, but leaving intact steps that do not involve this enzyme. In *P. cubensis*, the PsiH enzyme is principally responsible for catalyzing the oxidation of tryptamine to produce 4-hydroxytryptamine (see also FIG. 9). Hence, in some embodiments, wherein the PsiH gene is inactivated, or the catalytic function of the PsiH enzyme is otherwise disrupted or interfered with, the resulting genetically modified fungus may contain increased or substantially similar levels of L-tryptophan and/or tryptamine; and reduced levels of any of 4-hydroxytryptamine, norbaeocystin, baeocystin, psilocybin, and psilocin; said levels being compared to an unmodified fungus, an average of unmodified fungi, or another amount known in the art.

In some embodiments, a non-hallucinogenic psychedelic fungus is a psychedelic fungus in which a PsiK gene is inactivated, thereby disrupting psilocybin synthesis at catalytic steps of the psilocybin biosynthetic pathway in which PsiK is involved, but leaving intact steps that do not involve this enzyme. In *P. cubensis*, the PsiK enzyme is principally responsible for catalyzing the phosphorylation of 4-hydroxytryptamine to produce norbaeocystin (see also FIG. 9). Hence, in some embodiments, wherein the PsiK gene is inactivated, or the catalytic function of the PsiK enzyme is otherwise disrupted or interfered with, the resulting genetically modified fungus may contain increased or substantially similar levels of any of L-tryptophan, tryptamine, and 4-hydroxytryptamine; and reduced levels of any of norbaeocystin, baeocystin, psilocybin, and psilocin; said levels being compared to an unmodified fungus, an average of unmodified fungi, or another amount known in the art.

In some embodiments, a non-hallucinogenic psychedelic fungus is a psychedelic fungus in which a PsiM gene is inactivated, thereby disrupting psilocybin synthesis at catalytic steps of the psilocybin biosynthetic pathway in which PsiM is involved, but leaving intact steps that do not involve this enzyme. In *P. cubensis*, the PsiM enzyme is principally responsible for catalyzing the methylation of norbaeocystin to produce baeocystin, and subsequently the methylation of baeocystin to produce psilocybin (see also FIG. 9). Hence, in some embodiments, wherein the PsiM gene is inactivated, or the catalytic function of the PsiM enzyme is otherwise disrupted or interfered with, the resulting genetically modified fungus may contain increased or substantially similar levels of any of L-tryptophan, tryptamine, 4-hydroxytryptamine, and norbaeocystin; and reduced levels of any of baeocystin, psilocybin, and psilocin; said levels being compared to an unmodified fungus, an average of unmodified fungi, or another amount known in the art.

In some embodiments, a non-hallucinogenic psychedelic fungus is a psychedelic fungus in which the PsiD and PsiH genes are inactivated, thereby disrupting psilocybin synthesis at the catalytic steps of the psilocybin biosynthetic pathway in which the PsiD and PsiH enzymes are involved, but leaving intact steps that do not involve these enzymes.

In some embodiments, a non-hallucinogenic psychedelic fungus is a psychedelic fungus in which the PsiD and PsiM genes are inactivated, thereby disrupting psilocybin synthesis at the catalytic steps of the psilocybin biosynthetic pathway in which PsiD and PsiM are involved, but leaving intact steps that do not involve these enzymes.

In some embodiments, a non-hallucinogenic psychedelic fungus is a psychedelic fungus in which the PsiD and PsiK genes are inactivated, thereby disrupting psilocybin synthesis at the catalytic steps of the psilocybin biosynthetic pathway in which PsiD and PsiK are involved, but leaving intact steps that do not involve these enzymes.

In some embodiments, a non-hallucinogenic psychedelic fungus is a psychedelic fungus in which the PsiH and PsiK genes are inactivated, thereby disrupting psilocybin synthesis at the catalytic steps of the psilocybin biosynthetic pathway in which PsiH and PsiK are involved, but leaving intact steps that do not involve these enzymes.

In some embodiments, a non-hallucinogenic psychedelic fungus is a psychedelic fungus in which the PsiH and PsiM genes are inactivated, thereby disrupting psilocybin synthesis at the catalytic steps of the psilocybin biosynthetic pathway in which PsiH and PsiM are involved, but leaving intact steps that do not involve these enzymes.

In some embodiments, a non-hallucinogenic psychedelic fungus is a psychedelic fungus in which the PsiK and PsiM genes are inactivated, thereby disrupting psilocybin synthesis at the catalytic steps of the psilocybin biosynthetic pathway in which PsiK and PsiM are involved, but leaving intact steps that do not involve these enzymes.

In some embodiments, a non-hallucinogenic psychedelic fungus is a psychedelic fungus in which the PsiD, PsiH, and PsiK genes are inactivated, thereby disrupting psilocybin synthesis at the catalytic steps of the psilocybin biosynthetic pathway in which PsiD, PsiH and PsiK are involved, but leaving intact steps that do not involve these enzymes.

In some embodiments, a non-hallucinogenic psychedelic fungus is a psychedelic fungus in which the PsiH, PsiK, and PsiM genes are inactivated, thereby disrupting psilocybin synthesis at the catalytic steps of the psilocybin biosynthetic pathway in which PsiH, PsiK and PsiM are involved, but leaving intact steps that do not involve these enzymes.

In some embodiments, a non-hallucinogenic psychedelic fungus is a psychedelic fungus in which the PsiK, PsiM, and PsiD genes are inactivated, thereby disrupting psilocybin synthesis at the catalytic steps of the psilocybin biosynthetic pathway in which PsiK, PsiM and PsiD are involved, but leaving intact steps that do not involve these enzymes.

In some embodiments, a non-hallucinogenic psychedelic fungus is a psychedelic fungus in which each of the PsiD, PsiH, PsiK, and PsiM genes are inactivated, thereby disrupting psilocybin synthesis at the catalytic steps of the psilocybin biosynthetic pathway in which PsiD, PsiH, PsiK, and PsiM are involved, but leaving intact steps that do not involve these enzymes.

CRISPR/Cas9-Edited Fungi

In some aspects of the invention are disclosed CRISPR/Cas9-edited fungi. In some embodiments, CRISPR/Cas9-edited fungi are prepared by introducing a deletion in one or more of the psilocybin biosynthesis genes, and/or a portion of one or more of the psilocybin biosynthesis genes, i.e., the PsiD, PsiK, PsiM, and PsiH genes.

In some preferred embodiments, the disclosed CRISPR/Cas9-edited fungi comprise no foreign (i.e., exogenous) DNA integrated into the fungal genome. It will be appreciated by those in the art that, at the time of this disclosure, transgene-free CRISPR/Cas9-edited fungi are not a regulated article according to the U.S. Department of Agriculture (USDA). See Apr. 13, 2016 Ltr. from Michael J. Firko, PhD, APHIS Deputy Admin., Biotech. Reg. Svc's, USDA, available at www.aphis.usda.gov/biotechnology/downloads/re-g_loi/15-321-01_air_response_signed.pdf, confirming CRISPR/Cas9-edited *Agaricus bisporus* fungi "having small deletions (1-14 bp) in a specific polyphenol oxidase gene but containing no foreign DNA integrated into the mushroom genome" is not a regulated article under 7 C.F.R. § 340 (regulating certain organisms modified or produced through genetic engineering). Thus, in embodiments, among the advantages of the invention are the provision of non-hallucinogenic psychedelic fungi which are not regulated as genetically engineered (GE) organisms or as genetically modified organisms (GMOs).

In some embodiments, CRISPR/Cas9-edited fungi of the disclosure can be prepared as described in, e.g., FIG. 1 of Schuster, M., & Kahmann, R. (2019). "CRISPR-Cas9 genome editing approaches in filamentous fungi and oomycetes" *Fungal Genetics and Biology,* 130, 43-53, the entirety of which is incorporated by reference.

In some embodiments, Cas9 and sgRNA genes are delivered as DNA fragments. In some such embodiments, the DNA fragments are integrated into the genome at specific sites. In other embodiments, the DNA fragments are incorporated into the genome at random sites.

In some embodiments, the Cas9 gene is integrated into the genome, and the sgRNA gene is delivered transiently as part of a plasmid. In some such embodiments, the Cas9 gene is integrated into the genome at specific sites, and the sgRNA gene is delivered transiently as part of a plasmid. In other embodiments, the Cas9 gene is incorporated into the genome at random sites, and the sgRNA gene is delivered transiently as part of a plasmid.

In some embodiments, the Cas9 gene is integrated into the genome either at a defined or random site, and sgRNA is provided as an RNA molecule. In some such embodiments, the Cas9 gene is integrated into the genome at specific sites, and sgRNA is provided as an RNA molecule. In other embodiments, the Cas9 gene is incorporated into the genome at random sites, and sgRNA is provided as an RNA molecule.

In some embodiments, the Cas9 and sgRNA genes may be delivered as part of a plasmid. In some embodiments, the Cas9 gene is delivered as part of a plasmid. In some embodiments, the sgRNA gene is delivered as part of a plasmid. In some embodiments, the Cas9 gene is provided as part of a plasmid, and the sgRNA is delivered as an RNA molecule. In some embodiments, the Cas9 and sgRNA are delivered as preassembled ribonucleoprotein (RNP) complexes. In some embodiments, the Cas9 is delivered as a preassembled RNP complex. In embodiments, the sgRNA is delivered as a preassembled RNP complex.

The edited strain may vary depending on the delivery strategy employed. For example, in embodiments wherein Cas9 and sgRNA genes are delivered as DNA fragments, the edited strain may harbor both Cas9 and sgRNA expression cassettes. In other embodiments, such as wherein the Cas9 gene is integrated into the genome and the sgRNA gene is delivered transiently as part of a plasmid or as an RNA molecule, the edited strain may harbor only the Cas9 expression cassette. In some embodiments, such as wherein one or both of the Cas9 and sgRNA genes are delivered as part of a plasmid, or as preassembled RNP complexes, the edited strain may differ from the progenitor strain only in the edited site.

Protocols for gene editing using CRISPR are described in, e.g., U.S. Pat. Nos. 6,603,061; 7,868,149; 9,822,372; and 10,934,554; U.S. Pub. Nos. 2009/0100536-A1, 2022/0002742-A1, and 2022/0356484-A1; and Morrell et al, Crop genomics: advances and applications. *Nat Rev Genet.* 2011 Dec. 29; 13 (2): 85-96; as well as the further references cytoplasm into a smaller dsRNA molecule. This short dsRNA molecule is known as the siRNA, which has 21-23 nucleotides with 3' two-nucleotide overhangs. The siRNA interacts with and activates the RNA-induced silencing complex (RISC). The endonuclease argonaute 2 (AGO2) component of the RISC cleaves the passenger strand (sense strand) of the siRNA while the guide strand (antisense strand) remains associated with the RISC. Subsequently, the guide strand guides the active RISC to its target mRNA for cleavage by AGO2. As the guide strand only binds to mRNA that is fully complementary to it, siRNA causes specific gene silencing. The psilocybin biosynthetic pathway can be blocked by utilizing siRNA which in turn can silence the genes that are essential to the production of psilocybin such as PsiD, PsiK, PsiM, and PsiH.

The first essential step for successful siRNA silencing is the design of a siRNA sequence that is potent and specific to the intended mRNA to minimize any off-target effect. A conventional siRNA consists of 19-21 nucleotides with two nucleotide overhangs at the 3' end, usually TT and UU, which are important for recognition by the RNAi machinery. There are several siRNA design algorithms that are commonly known in art which can be utilized to design a specific siRNA molecule that is specific to the genes (PsiD, PsiH, PsiM and PsiK) involved in the psilocybin biosynthetic pathway. (See Chaudhary et al., Development of a software tool and criteria evaluation for efficient design of small interfering RNA, *Biochem Biophys Res Commun,* 404 (2011), pp. 313-320; Zhong et al., Computational detection and suppression of sequence-specific off-target phenotypes from whole genome RNAi screens. *Nucleic Acids Res,* 42 (2014), pp. 8214-8222; Naito et al., siRNA design software for a target gene-specific RNA interference, *Front Genet.,* 11 Jun. 2012; all of which are incorporated by reference herein.)

A summary of commonly employed strategies to enhance the efficacy and specificity of siRNAs and to reduce off-target effects is provided below. (See Lam et al., siRNA Versus miRNA as Therapeutics for Gene Silencing, *Molecular Therapy: Nucleic Acids* (2015) 4, e252.)

| siRNA feature | Strategy | Description |
|---|---|---|
| Strand selection | Apply asymmetry rule | Strand with a relatively unstable 5' end is selected as guide strand |
| | Utilize 5' nucleotide preference | Strand with U or A at position one at the 5' end is preferentially selected as guide strand |
| Activity | Manipulate G/C content | G/C content is ideally between 30-64%; G/C stretches of >9 nucleotides should be avoided |
| Off-target | Reduce siRNA concentration | Lowest possible siRNA concentration to achieve a therapeutic effect is used |
| | Use multiple siRNAs | siRNAs with different sequences for targeting the same mRNA are pooled for therapeutic effect |
| miRNA-like effect | Avoid sequences similar to miRNA | Avoid seed sequences of miRNA that have already been identified |
| Immune stimulation | Avoid immune stimulatory motifs | Avoid U-rich sequences and motifs that contain GUCCUUCAA, UGUGU, UGU, UGGC, if intended for human or animal consumption | disclosed herein, all of the contents and disclosure of each of which are herein incorporated by reference in their entirety.

Silencing of the Psilocybin Biosynthesis Pathway Using siRNA and miRNA

Double stranded RNA (dsRNA) that is either transcribed from cellular genes or infecting pathogens, or artificially introduced into the cells is processed by a specialized ribonuclease (RNase) III-like enzyme named Dicer in the The in silico selected siRNA target candidates that target the psilocybin biosynthetic pathway are then synthesized using commercial vendors such as Dharmacon or Integrated DNA technologies. In some embodiments, the siRNA delivery strategy employed comprises a soaking approach using chemically synthesized siRNA. In some embodiments, the siRNA delivery strategy employed comprises inserting inverted repeat transgenes (IRT) into the desired plasmid using long-hairpin RNA (IhRNA).

In some embodiments, siRNA delivery is accomplished as described in, e.g., FIG. 12.2 of Jain, C. K., Wadhwa, G. (2018). Computational Tools: RNA Interference in Fungal Therapeutics. In: Wadhwa, G. et al. (eds) *Current Trends in Bioinformatics: An Insight*. Springer, Singapore, the entirety of which is incorporated by reference.

In some embodiments, siRNA is delivered according to a soaking method. In some embodiments, the soaking method involves the soaking of fungi with siRNA. In some embodiments, siRNA is delivered by inserting IRTs into the desired plasmid using lhRNA. In some embodiments, the IRT consists of the sense and antisense orientation of the gene separated by a spacer. In some embodiments, IRT is incorporated into the desired plasmid and transformed into fungi. In some embodiments, Endogenous Dicer cleaves the hairpin loop which is formed upon transcription of IRT and siRNA(s) is generated. In some embodiments, the passenger strand it cleaves and the guide strand of siRNA enters the RISC where it cleaves the target mRNA.

An IRT is constructed using a target gene sequence, which is incorporated in an organism-specific plasmid. The plasmid containing IRT is transformed into the organism that upon transcription forms a hairpin loop which is cleaved by endogenous Dicer to generate siRNA(s). (See Nakade et al., Gene silencing of the *Lentinula edodes* lcc1 gene by expression of a homologous inverted repeat sequence, Microbiological Research, vol. 166, Issue 6, 20 Sep. 2011, pp. 484-493). The generated small interfering RNAs (siRNAs) cleave the endogenous mRNA(s) with the help of RISC. Considering that there are several hairpin-expressing RNA systems available for robust RNA silencing using a tissue-specific RNA pol II promoter for tissue-specific expression of dsRNA and that hairpin RNA assures efficient formation of dsRNA. (See Paddison et al., 2008, RNA interference, *Current Topics in Microbiology and Immunology*, vol. 320. Springer-Verlag, Berlin).

In some embodiments, the IRT is a long-hairpin RNA (lhRNA) which generally consists of more than 300 bp open reading frame, a spacer of approximately 250-500 oligonucleotides and an inverted repeat of the gene sequence. The IRT construct is inserted into the plasmid specific for a particular fungus and is transformed into the respective fungi either by protoplast formation or electroporation. In some embodiments, the IRT is a short-hairpin RNA (shRNA) which consists of a 19 bp siRNA sense and antisense sequence separated by a spacer of 9 nucleotides where the siRNA sequence should be 100% homologous to the target mRNA.

The synthetic siRNA target candidates thus obtained are introduced into the protoplasts of *Psilocybe* mushrooms following the protocols disclosed herein and in the Examples. Initial experiments are conducted using Cy3-labeled-siRNA molecules to test the uptake of siRNA molecules targeting the gene of interest (PsiD, PsiM, PsiK, PsiH) by the protoplasts. Subsequent experiments are conducted using unlabeled siRNA. Controls are generated using protoplasts treated with unrelated-siRNA, as well as cultures with no siRNA addition. (See Calkins et al., Development of an RNA interference (RNAi) gene knockdown protocol in the anaerobic gut fungus *Pecoramyces ruminantium* strain CIA, *PeerJ*. 2018; 6: e4276. doi: 10.7717/peerj.4276.)

The supernatant of both siRNA-treated and control cultures are periodically sampled (0.5 ml) and tested for the presence of psilocybin by means of the Keller reagent (glacial acetic acid containing iron chloride and concentrated sulphuric acid). *Psilocybe* cultures in which psilocybin production has been silenced by the siRNA candidates would not show a clear blue or violet Keller reaction whereas cultures that are control cultures having unrelated siRNA or untreated cultures would show the presence of blue color indicating the presence of psilocybin. The cultures which do not show a clear blue Keller or violet reaction are collected and propagated to yield large quantities of knocked out mushrooms for preparation of extracts. (See Injury-Triggered Blueing Reactions of *Psilocybe* "Magic" Mushrooms, Lenz et al. *Angewandte Chemie*, Vol. 59, Issue 4 Jan. 20, 2020 pp. 1450-1454.)

Blotting techniques, fluorescence imaging, and biochemical assays are the further confirmatory tests which can be used to analyze silencing at the RNA and protein levels. A study was carried out by Kadotani et al. (see Kadotani N et al (2003) RNA silencing in the phytopathogenic fungus *Magnaporthe oryzae*. MPMI 16:769-776) in the blast fungus *M. oryzae* (Holen T (2006) Efficient prediction of siRNAs with siRNArules 1.0: an open-source JAVA approach to siRNA algorithms. RNA 12 (9): 1620-1625) in which they investigated RNA silencing using enhanced green fluorescent protein (eGFP). Sense-sense, antisense-antisense, and sense-antisense IRT constructs of eGFP separated by a partial sequence of β-glucuronidase gene as internal spacer were employed. Significant silencing was induced only by sense-antisense IRT construct as detected by the loss of GFP fluorescence using an image analyzer. Studies have employed Northern blot analysis for studying gene silencing in fungi (See Yamada O et al (2007) Gene silencing by RNA interference in the Koji Mold *Aspergillus oryzae. Biosci Biotechnol Biochem*. 71:138-144). In some embodiments, such techniques are used to test the efficacy of silencing produced by siRNA candidates, according to the teachings herein and skill in the art.

Inactivation of PsiD, PsiK, PsiM, and/or PsiH Catalytic Function

In some embodiments, disclosed methods of disrupting or preventing biosynthesis of a bioactive alkaloid in a bioactive alkaloid-producing fungus comprise inactivating the catalytic function of an enzyme involved in the biosynthesis of the bioactive alkaloid. In some embodiments, disclosed methods of disrupting or preventing the biosynthesis of psilocybin in a psilocybin-producing fungus comprise inactivating the catalytic function of any one or more of PsiD, PsiK, PsiM, and/or PsiH. In another aspect, provided are genetically modified fungi (e.g., psilocybin-producing fungi) wherein one or more enzymes (e.g., PsiD, PsiK, PsiM, and/or PsiH) involved in the biosynthesis of a bioactive alkaloid (e.g., psilocybin) have been modified, e.g., according to methods and techniques disclosed herein, such that the catalytic function of the one or more enzymes is inactivated.

In some embodiments, PsiD, PsiK, PsiM, and/or PsiH is inactivated by inactivating the enzyme active site. This may be accomplished according to various strategies using methods disclosed herein. For example, the enzyme active site may be inactivated by a small deletion of nucleotides that encode the amino acid sequence of the enzyme active site, thereby resulting in the production of an enzyme lacking a functional active site and thus lacking (or having substantially reduced) catalytic activity. In another exemplary embodiment, methods disclosed herein may be used to introduce an amino acid substitution in the sequence of the enzyme active site, thereby modifying the function of the active site and inactivating (or substantially reducing) the catalytic function of the active site. In another exemplary embodiment, methods disclosed herein may be used to alter the genetic sequence in a gene encoding any one or more of PsiD, PsiK, PsiM and/or PsiH such that the amino acid sequence of the resulting enzyme is altered. In some embodiments, a frameshift mutation is made, resulting in a completely altered amino acid sequence downstream. In some embodiments, the active site sequence is deleted, so that the resulting protein does not contain an active site. In some embodiments, a point mutation is made in the active site sequence. In some embodiments, the point mutation is a missense mutation wherein a single nucleotide is changed so that the resulting amino acid sequence downstream is disrupted, inactivated, or substantially reduced in activity. In some embodiments, the point mutation is a nonsense mutation wherein a stop codon is inserted into the active site sequence, leading to a truncated enzyme lacking functional activity. In some embodiments, a mutation is made in the nucleotide which leads to protein misfolding or nonfunctional interactions in the protein which render the active site inactive or substantially reduced in activity.

Exemplary Features and Uses of Disclosed Genetically Modified Fungi

In some embodiments, genetically modifying a bioactive alkaloid-producing fungus prevents production of a bioactive alkaloid so that the fungus can be used for the production of the other compounds, such as other therapeutic compounds, but without that bioactive alkaloid.

In one preferred embodiment, genetically modifying a psilocybin-producing fungus prevents production of psilocybin so that the fungus can be used for the production of other therapeutic compounds which lack the hallucinogenic properties of psilocybin. In some embodiments, the other therapeutic compounds are *Psilocybe* entourage metabolites. In some embodiments, a *Psilocybe* entourage metabolite includes a non-hallucinogenic bioactive alkaloid.

In some embodiments, a disclosed genetically modified fungus is used to produce a non-hallucinogenic bioactive alkaloid. In some embodiments, the non-hallucinogenic bioactive alkaloid is any of baeocystin, norbaeocystin, aeruginascin, tryptophan, tryptamine, serotonin, N-acetyl-hydroxytryptamine, 4-hydroxytryptamine, 4-hydroxy-L-tryptophan, 5-hydroxy-L-tryptophan, 2-(4-hydroxy-1H-indol-3-yl)ethyl-trimethylazanium, 7-hydroxy-L-tryptophan, harmane, norharmane, harmine, harmol, harmaline, cordysinin C, cordysinin D, perlolyrine, β-carboline, bisnoryangonin, hispidin, bufotenin, or derivatives or analogues thereof.

In some embodiments, a disclosed genetically modified fungus is used to produce a therapeutic compound. In some embodiments, the therapeutic compound is any of a phenolic compound, a flavonoid, an antioxidant, a metal chelator, a steroid, a neurosteroid, a polysaccharide, a terpene, a terpenoid, a non-hallucinogenic alkaloid, folate, tocopherol, a volatile oil, ascorbic acid, a protein, a fat, a mineral, an enzyme, a carotenoid, a glycoside, a lactone, a lectin, or an organic acid. (See, e.g., Chugh RM at al. Fungal mushrooms: a natural compound with therapeutic applications. *Front Pharmacol.* 2022; 13:925387.)

In some embodiments, a disclosed genetically modified fungus is used to produce a compound with a therapeutic or beneficial property. In some embodiments, the therapeutic or beneficial property is any of an antibacterial, antibiotic, antifungal, anticancer, immunosuppressant, immune-boosting, anti-inflammatory, hypoglycemic, antioxidant, antiviral, anti-neurodegenerative, anti-epileptic, neuroprotective, antiangiogenic, antidiabetic, or hypocholesterolemic property. (See, e.g., Elkhateeb W A, et al. Medicinal mushrooms as a new source of natural therapeutic bioactive compounds. *Egypt Pharm J.* 2019; 18 (2): 88-101.)

In some embodiments, a disclosed genetically modified fungus is consumed fresh. In some embodiments, a disclosed genetically modified fungus is consumed dried.

In some embodiments, a disclosed therapeutic compound is extracted from a specific mushroom tissue. In some embodiments, the mushroom tissue is any of mycelium, fruiting body, protoplasts, or spores. In some embodiments, a disclosed therapeutic compound is extracted from more than one type of mushroom tissue, or from any type of mushroom tissue.

In some embodiments, a disclosed fungus is used as a product, is used to produce a product, or is used in a product. In some embodiments, example products include a nootropic, a supplement, a nutraceutical, a therapeutic, a microdose, a functional food, or a topical cream.

In some embodiments, a disclosed genetically modified fungus is processed for use in a formulation. In some embodiments, the formulation is for use as a nootropic, a supplement, a nutraceutical, a microdose, a functional food, or a skin cream. In some embodiments, the formulation consists of any suitable dosage form, including ground fungal material, aqueous oral dispersions, aqueous oral suspensions, solid dosage forms including oral solid dosage forms, aerosols, controlled release formulations, fast melt formulations, effervescent formulations, self-emulsifying dispersions, solid solutions, liposomal dispersions, lyophilized formulations, tablets, capsules, pills, powders, delayed-release formulations, immediate-release formulations, modified release formulations, extended-release formulations, pulsatile release formulations, multi particulate formulations, and mixed immediate release and controlled release formulations.

A genetically modified fungus formulation prepared in accordance with embodiments herein have multiple applications for the improvement of human health, including to reduce pain and treat pain disorders, to reduce and treat inflammation and inflammatory disorders, to benefit immunity and reduce or treat symptoms of immune disorders, including autoimmune diseases and disorders, and for the general improvement of physical health and wellness including relaxation and improvement in sleep, as illustrative and non-limiting examples.

In some aspects are provided methods of modulating neurotransmission comprising administering the disclosed extract to a subject, thereby modulating neurotransmission in said subject. In some embodiments, the neurotransmission is serotonergic neurotransmission. In some embodiments the serotonergic neurotransmission does not comprise significant activity (e.g., agonism) at a serotonin 2A (5-HT2A) receptor.

In some aspects are provided methods of treating a health condition, comprising administering to a patient an effective amount of the disclosed extract, compound, or pharmaceutical composition. In some embodiments, the health condition is a mental health disorder. In some embodiments, the mental health disorder is selected from depression, dysthymia, an anxiety and phobia disorders, generalized anxiety disorder, social anxiety disorder, panic disorder, post-traumatic stress disorder, an adjustment disorders, a feeding and eating disorders, binge eating disorder, bulimia, and anorexia nervosa, other binge behaviors, body dysmorphic syndromes, alcoholism, tobacco abuse, drug abuse or dependence disorders, disruptive behavior disorders, impulse control disorders, gaming disorders, gambling disorders, memory loss, dementia of aging, attention deficit hyperactivity disorder, personality disorders, antisocial personality disorder, avoidant personality disorder, borderline personality disorder, histrionic personality disorder, narcissistic personality disorder, obsessive compulsive disorder, paranoid personality disorder, schizoid personality disorder, schizotypal personality disorders, attachment disorders, autism, and dissociative disorders. In some embodiments, the mental health disorder is an anxiety disorder. In some embodiments, the anxiety disorder is any of acute stress disorder, anxiety due to a medical condition, generalized anxiety disorder, panic disorder, panic attack, a phobia, post traumatic stress disorder (PTSD), separation anxiety disorder, social anxiety disorder, substance-induced anxiety disorder, and selective mutism. In some embodiments, the mental health disorder is a substance use disorder. In some embodiments, the substance use disorder is any of alcohol use disorder, *cannabis* use disorder, hallucinogen use disorder, inhalant use disorder, opioid use disorder, sedative use disorder, stimulant use disorder, tobacco use disorder, and nicotine use disorder. In some embodiments, the mental health disorder is a behavioral addiction. In some embodiments, the behavioral addiction is selected from gambling disorder, gaming disorder, sexual addiction, compulsive buying disorder, and technology addiction. In some embodiments, the health condition is a sleep disorder. In some embodiments, the sleep disorder is any of an insomnia, a hypersomnia, a parasomnia, and a disorder of sleep-wake schedule.

In some embodiments, the health disorder is a physical health disorder. In some embodiments, the physical health disorder is a pain disorder. In some embodiments, the pain disorder is any of arthritis, allodynia, atypical trigeminal neuralgia, trigeminal neuralgia, somatoform disorder, hypoesthesia, hyperalgesia, neuralgia, heuritis, neurogenic pain, analgesia, anesthesia dolorosa, causalgia, sciatic nerve pain disorder, degenerative joint disorder, fibromyalgia, visceral disease, chronic pain disorders, migraine/headache pain, chronic fatigue syndrome, complex regional pain syndrome, neurodystrophy, plantar fasciitis, or pain associated with cancer. In some embodiments, the physical health disorder is a disorder that causes acute inflammation, or that exhibits chronic inflammation as a symptom.

In some embodiments, the physical health disorder is an autoimmune disorder. In some embodiments, the autoimmune disorder is any of acute disseminated encephalomyelitis (ADEM), Addison disease, allergy or hypersensitivity, amyotrophic lateral sclerosis, antiphospholipid antibody syndrome (APS), arthritis, autoimmune hemolysis Anemia, autoimmune hepatitis, autoimmune inner ear disease, autoimmune pancreatitis, bullous pemphigoid, celiac disease, Chagas disease, chronic obstructive pulmonary disease (COPD), type 1 diabetes (TID), endometriosis, fibromyalgia, goodpasture's syndrome, Graves' disease, Guillain-Barre syndrome (GBS), Hashimoto's thyroiditis, suppurative spondylitis, idiopathic thrombocytopenia purpura, inflammatory bowel disease, interstitial cystitis, lupus, including discoid lupus erythematosus, drug-induced lupus lupus erythematosus, lupus nephritis, neonatal lupus, subacute cutaneous lupus erythematosus, and systemic lupus erythematosus; morphea, multiple hard Keratosis (MS), myasthenia gravis, myopathy, narcolepsy, neuromuscular angina, pemphigus vulgaris, pernicious anemia, primary biliary cirrhosis, recurrent diffuse encephalomyelitis, including polyphasic diffuse encephalomyelitis, rheumatic fever, schizophrenia, scleroderma, Sjogren's syndrome, tendonitis, vasculitis, and vitiligo. In some embodiments, the autoimmune disorder is a systemic autoimmune disorder, including systemic lupus erythematosus (SLE), scleroderma, rheumatoid arthritis, and polymyositis. In embodiments, the autoimmune disorder is a local autoimmune disorder, including those of the endocrine system, including type 1 diabetes, Hashimoto's thyroiditis, and Addison's disease; the cutaneous, including pemphigus vulgaris; the blood, including autoimmune hemolytic anemia; and the nervous system, including multiple sclerosis.

In some aspects are provided methods of using the disclosed extract to improve health and wellness, comprising administering an effective amount of the extract, compound, or composition to a subject. In some embodiments, the improvement in health and wellness is a reduction in stress. In some embodiments, the improvement in health and wellness is an easing of muscular tension. In some embodiments, the improvement to health and wellness is a promotion of restorative sleep. In some embodiments, the improvement to health and wellness is any of a soothing of the body, a calming of the mind, and a reduction in physical distress. In some embodiments, the improvement to health and wellness includes any one or more of a reduction in feelings of nervousness, "jitters," nervous tension, or anxiety; a reduction in feelings of malaise, unhappiness, existential angst, ennui, and general discontent; and an increase in feelings of wellbeing, wellness, relaxation, contentment, happiness, openness to experience, and life satisfaction. In some aspects are provided methods of using the disclosed extract, compound, or composition to induce euphoria, comprising administering an effective amount of the extract, compound, or composition to an individual.

In accordance with one embodiment of the invention, the genetically modified fungus may be prepared for ingestion in the form of a liquid solution, liquid suspension, tincture, beverage concentrate, or beverage, for example, for the purposes described above. In accordance with another embodiment of the invention, the genetically modified fungus extract may be prepared for ingestion in the form of a tablet, a capsule, a softgel, and a gelcap, for the purposes described above, In accordance with another embodiment of the invention, the genetically modified fungus extract may be prepared for topical administration in the form of a cream, an ointment, a gel, a foam, and a liquid composition for transdermal application to alleviate pain, itching, and inflammation, as well as to moisturize, rejuvenate, and provide an immune boost to skin and nearby tissue, for example.

In some embodiments, a disclosed genetically modified fungus is grown in an industrial mushroom grow house. In some embodiments, a disclosed genetically modified fungus is grown in a consumer-friendly kit. In some embodiments, a disclosed genetically modified fungus is grown in a bioreactor, which may be consumer, commercial, or industrial sized. In some embodiments, a disclosed genetically modified fungus is grown in culture, such as on a growth medium or a culture medium.

In some embodiments, a disclosed genetically modified fungus is supplemented with factors during a growth stage to increase the activity of a specific biosynthetic pathway. In some embodiments, a disclosed genetically modified fungus is supplemented with factors during a growth stage to increase the production of a specific compound.

In some embodiments, genetically modifying a bioactive alkaloid-producing fungus prevents production of a bioactive alkaloid from both the mycelium and the above ground fruiting body (the cap and stipe) of the fungus. For example, in some fungal species the fruiting body and the mycelium both naturally produce psilocybin. In the species *Psilocybe samuiensis*, for instance, the dried cap of the mushroom contains the most psilocybin at about 0.23%-0.90%, and the mycelium contains about 0.24%-0.32%. Both the mushroom cap and the mycelium contain phytoactive compounds along with psilocybin. According to embodiments of this disclosure, knocking out the production of psilocybin from *P. samuiensis* thus ensures that extracts from both caps and mycelium lack psilocybin, and thus lack hallucinogenic properties.

In some embodiments, genetically modifying a bioactive alkaloid-producing fungus prevents production of a bioactive alkaloid. The genetically modified fungus thus carries out biotransformation of added substrates to desired non-hallucinogenic pharmaceutical products. This can be carried out at any scale including experimental biosynthesis in mycelium or sporocarps or by mycelium in bioreactor production. For precedents in intact fungi without genetic modification, see, e.g., Gartz, J. 1989. Biotransformation of Tryptamine Derivatives in Mycelial Cultures of *Psilocybe*. *J Basic Microbiol.* 29 (6): 347-52. Wolfgang Hüttel, Dirk Hoffmeister. 2010. Fungal Transformations in Pharmaceutical Sciences. In Industrial Applications, edited by Martin Hofrichter, 293-317. The Mycota. Springer Berlin, Heidelberg.

EXAMPLES

The following exemplary prophetic embodiments are included solely for illustrative purposes and are not intended to limit the scope of the invention or of any embodiments thereof.

Example 1: Gene Inactivation of Psilocybin Biosynthetic Pathway Using CRISPR-Cas9

Targeted gene deletion in *Psilocybe* mushrooms can be achieved by using a CRISPR genome editing method based on the use of RNA-guided DNA endonucleases. There are several alternative approaches to implement a CRISPR genome editing method. Likewise, there are also several alternative RNA-guided DNA endonucleases (e.g., Cas9, Cpf1, and MAD7) which, in some embodiments, are used with a CRISPR genome editing method.

In some embodiments, a RNA-guided DNA endonuclease is delivered into a cell as a plasmid expressing the endonuclease. In some embodiments, a RNA-guided DNA endonuclease is delivered into a cell directly as a protein. Without being bound by theory, a RNA-guided DNA endonuclease needs a target specific guide RNA (gRNA) to generate a double stranded break into the genomic target or locus. In some embodiments, a gRNA is delivered as a plasmid expressing the gRNA. In some embodiments, a gRNA is delivered directly as a chemically synthesized gRNA. (See, e.g., Qin et al., CRISPR-Cas9 assisted gene disruption in the higher fungus *Ganoderma* species, *Process Biochemistry*, vol. 56, 2017, Pages 57-61).

In some embodiments, the CRISPR genome editing method is a type II CRISPR/Cas9 system. Two components are generally used in a type II CRISPR/Cas9 system: a functional Cas9 nuclease and a chimeric guide RNA (gRNA) consisted of two regions, a CRISPR RNA (crRNA) harboring 20-nucleotide target-recognizing sequence at the 5'-end and a trans-activating crRNA (tracrRNA) for Cas9 binding. The crRNA is user-defined to match the target genomic locus such as one or more of genes of the psilocybin biosynthetic pathway (PsiD, PsiH, PsiM, and PsiK). It guides the gRNA to form an RNA/DNA hybrid at the target genomic locus and recruits the Cas9 nuclease to generate DNA DSB (double stranded break).

There are several promoters that can be used to drive the gRNA transcription. Common examples known in art include RNA polymerase II of *A. niger* (Pol II) promoter, U6 promoter of *A.Oryzae*—an RNA polymerase III (Pol III) promoter, U3 promoter of *A. fumigatus*, and transfer RNA (tRNA) promoter. (See Song et al., Efficient genome editing using tRNA promoter-driven CRISPR/Cas9 gRNA in *Aspergillus niger*, 2018, *PLoS ONE* 13 (8): e0202868.)

An alternative to expressing the cas9 gene and the sgRNA is to use pre-assembled RNP complexes of Cas9 protein and in vitro transcribed sgRNAs30,31. In fungi this method has been applied to several yeasts and multicellular ascomycetes, including multiple *Aspergillus* species, *Penicillium chrysogenum* and *Cryptococcus neoformans* (See Woo, J. W. et al. DNA-free genome editing in plants with preassembled CRISPR-Cas9 ribonucleoproteins. *Nat. Biotechnol.* 33, 1162-1164 (2015); Grahl, et al., Use of RNA-Protein Complexes for Genome Editing in Non-*albicans Candida* Species. mSphere 2, e00218-17 (2017); Kiel, J. A. et al., CRISPR/Cas9 Based Genome Editing of *Penicillium chrysogenum*. ACS Synth. Biol. 5, 754-764 (2016) and Wang, Y. et al. A 'suicide' CRISPR-Cas9 system to promote gene deletion and restoration by electroporation in *Cryptococcus neoformans. Sci. Rep.* 6, 31145 (2016).)

Gene replacement also can be used to knockout one, two, three, or all four of the PsiD, PsiM, PsiK, and PsiH genes. This protocol can be performed as described in Lax et al., Stable and reproducible homologous recombination enables CRISPR-based engineering in the fungus *Rhizopus microspores*, Cell Reports Methods, vol. 1, Issue 8, 20 Dec. 2021, 100124. Lax et al., Transformation and CRISPR-Cas9-mediated homologous recombination in the fungus *Rhizopus* microspores, Cell Reports Methods, vol. 3, Issue 1, 18 Mar. 2022, 101237, describe a stable, targeted integration of DNA templates by homologous recombination (HR) based on the CRISPR-Cas9 technology.

Culture of *Psilocybe* Mushrooms

*Psilocybe* carpophores are grown from a small agar inoculum in minimal medium at 30° C. For solid culture, the medium is supplemented with 1.5% agar. For phenotypic characterization, strains are grown for 7 days at 25° C. in a 16/8 hours day/night cycle. Mycelium from the periphery of actively growing colonies on solid culture and from shake flask cultures are used for the isolation of protoplasts. The mycelial cells are then treated with two mycolytic enzymes, Novozym 234 or lywallzyme to generate protoplasts. (See Jyun-De Wu et al., 2019, Optimization of Protoplast Preparation and Regeneration of a Medicinal Fungus *Antrodia cinnamomea, Mycobiology,* 47:4, 483-493). The protoplasts thus prepared can be cryopreserved if desired, following protocols such as taught in Sugano S S et al. Genome editing in the mushroom-forming basidiomycete *Coprinopsis cinerea*, optimized by a high-throughput transformation system. *Sci Rep.* 2017 Apr. 28; 7 (1): 1260. doi: 10.1038/s41598-017-00883-5, which is incorporated fully herein by reference. The protoplasts thus prepared are used for transformation that allows the introduction of CRISPR-Cas9 gene editing components.

Design and Synthesis of Gene-Specific sgRNAs for Gene Disruption

Candidate protospacers (including PAM site) are identified in the coding region of genes involved in the psilocybin biosynthetic pathway (PsiD, PsiH, PsiK, and PsiM) using CCtop program (See Stemmer et al., CCTop: An Intuitive, Flexible and Reliable CRISPR/Cas9 Target Prediction Tool, *Plos One,* 24 Apr. 2015, 10 (4): e0124633). The candidates are then checked against the full genome of *Psilocybe* fungi to identify potential off-target regions. Two sgRNAs are selected per targeted gene based on fewest off-targets and the presence of one or more guanines at the start of the sgRNA as this promotes a high yield of in vitro T7 transcription. The selected sgRNAs are synthesized in vitro according to the specifications of the GeneArt Precision sgRNA Synthesis Kit (ThermoFisher Scientific, USA).

Design of the Repair Templates for Homologous Recombination

A psi deletion vector is used as a template for homologous recombination. (See Ohm et al., Transcription factor genes of *Schizophyllum commune* involved in regulation of mushroom formation. *Mol. Microbiol.* 81, 1433-1445 (2011). This plasmid contains a nourseothricin resistance cassette flanked by 1200 bp homology arms outside the desired target gene. Moreover, the plasmid harbors a phleomycin resistance cassette that is only integrated if the plasmid integrates through a single cross-over (i.e., ectopically). Linear templates with reduced homology arm lengths (approximately 1000 bp, 750 bp, 500 bp, 250 bp and 100 bp) are made by PCR on the full vector. The primers were designed to bind 1000 bp, 750 bp, 500 bp, 250 bp and 100 bp outside of the nourseothricin resistance cassette.

Transformation

Protoplasts are prepared as previously described and stored at –80° C. until use. 20 μg Cas9 is mixed with the two sgRNAs (2 μg of each sgRNA) targeting the gene of interest (Psi D or PsiH or PsiK or PsiM) resulting in a 2:1:1 molar ratio of Cas9, sgRNA 1 and sgRNA 2 in 1× Cas9 buffer (20 mM HEPES, 100 mM NaCl, 5 mM MgCl2, 0.1 mM EDTA, pH 6.5). 12.5 μg of repair template comprising the nourseothricin resistance cassette is added. (See Vonk et al., High-throughput targeted gene deletion in the model mushroom *Schizophyllum commune* using pre-assembled Cas9 ribonucleoproteins, *Scientific Reports* vol. 9, no. 7632 (2019)).

individual cultures in 50 μl TE buffer (10 mM Tris pH 8.0, 1 mM EDTA) for PCR verification using the primers. The size of the DNA band is used to determine whether the gene of interest (PsiD, PsiH, PsiK, and PsiM) is replaced with the nourseothricin resistance cassette.

The same process can be repeated in sequential manner using different antibiotic selection cassettes in the repair plasmid (Amphotericin B, Chloramphenicol, Leptomycin B, etc.) if additional genes are to be inactivated. The same process can be performed in multiplex fashion using different repair plasmids containing different antibiotic resistance markers one for each gene of interest that is to be inactivated. The resultant colonies can be screened by growing them in media supplemented with respective antibiotics and then verified by using PCR or sequencing.

Likewise, the same process can be expanded to multiple species of *Psilocybe* mushrooms by using sequence alignment of genes of interest (PsiD, PsiH, PsiK, and PsiM) across species to determine the consensus regions for targeting. Thus, guide sequences can be determined for each gene by targeting the portion of the gene that falls under the consensus sequences. For instance, the gene sequence of PsiD from several species of *Psilocybe* can be aligned using software programs such as Clustal (at www.clustal.org), e.g., ClustalW, to determine the consensus region; sgRNAs are designed in silico using like or known software to target the consensus sequence in order to knockout PsiD expression in several species of *Psilocybe* mushrooms.

a. Inactivation of PsiD Gene Using CRISPR-Cas9

Two sgRNAs specific for a PsiD gene are designed in silico using computational programs as above. sgRNA sequences are given below, any of which can be used for knockout.

Exemplary CRISPR Oligos for PsiD Knock Out:

| SEQ ID NO: 13 | CRISPR PsiD knockout | 5' GGTGATACCCGCGTGCAACT CGG-3' |
| SEQ ID NO: 14 | CRISPR PsiD knockout | 5' GATGGCTCTCTGTCAGCGATG CGG-3' |
| SEQ ID NO: 15 | CRISPR PsiD knockout | 5' GCGAGTTCATAGGAGAGT TGG-3' |
| SEQ ID NO: 16 | CRISPR PsiD knockout | 5' GAAATTACTCCAACGAGTT CGG-3' |
| SEQ ID NO: 17 | CRISPR PsiD knockout | 5' GCAACCTATCCAGGAATTCA AGG-3' |

In the negative controls, Cas9 is replaced with dialysis buffer and sgRNA with MilliQ water. Cas9 and sgRNAs are pre-assembled for 10 minutes at 37° C. The regenerated protoplasts are plated on agar medium supplemented with nourseothricin and grown for 3 days. (See Ohm et al., An efficient gene deletion procedure for the mushroom-forming basidiomycete *Schizophyllum commune*, *World J Microbiol & Biotechnol.* vol. 26, pp. 1919-1923 (2010).)

Colonies are randomly selected per transformation after three days, subcultured in a phleomycin selection medium and then plated onto agar plates supplemented with both nourseothricin and phleomycin. DNA is isolated from the Protoplasts of *Psilocybe* species are prepared as above. The two sgRNAs (2 μg of each sgRNA) are transformed into the protoplasts as described earlier. The transformed protoplasts are plated. Colonies are selected and screened for antibiotic resistance markers followed by PCR sequencing to verify the deletion of the PsiD gene.

b. Inactivation of PsiH Gene Using CRISPR-Cas9

Two sgRNAs specific for a PsiH gene are designed in silico using computational programs as above. sgRNA sequences are given below, any of which can be used for knockout.

Exemplary CRISPR Oligos for PsiH Knock Out:

| SEQ ID NO: 27 | CRISPR PsiH knockout | 5' GTACTATTCTCCTTCGTCATTGC AGG-3' |
| SEQ ID NO: 28 | CRISPR PsiH knockout | 5' GCGCTTGCCACCAGGGCCGCC TGG-3' |
| SEQ ID NO: 29 | CRISPR PsiH knockout | 5' GATATGCCTGAAGAATCTCCA TGG-3' |

-continued

| | | |
|---|---|---|
| SEQ ID NO: 30 | CRISPR PsiH knockout | 5' GGATGCTGGAGGGACAGAAA TGG-3' |
| SEQ ID NO: 31 | CRISPR PsiH knockout | 5' CCGATCTATTAGAAAAGCGA GGG-3' |

Protoplasts of *Psilocybe* species are prepared as above. The two sgRNAs (2 µg of each sgRNA) are transformed into the protoplasts as described earlier. The transformed proto-plasts are plated. Colonies are selected and screened for antibiotic resistance markers followed by PCR sequencing to verify the deletion of the PsiH gene.

c. Inactivation of PSiM Gene Using CRISPR-Cas9

Two sgRNAs specific for a PsiM gene are designed in silico using computational programs as above. sgRNA sequences are given below, any of which can be used for knockout.

Exemplary CRISPR Oligos for PsiM Knock Out:

| | | |
|---|---|---|
| SEQ ID NO: 22 | CRISPR PsiM knockout | 5' TGACTATCAAGCACTTTCAG AGG-3' |
| SEQ ID NO: 23 | CRISPR PsiM knockout | 5' TTTGTGTCTGTCAATGCAGA TGG-3' |
| SEQ ID NO: 24 | CRISPR PsiM knockout | 5' CACTATCCCAGAAGCCCAGA GGG-3' |
| SEQ ID NO: 25 | CRISPR PsiM knockout | 5' GCTCTTCTTCATCGTGACTTC GGG-3' |
| SEQ ID NO: 26 | CRISPR PsiM knockout | 5' GTCTGTGCCCAACAGTCCCCAAT AGG-3' |

Protoplasts of *Psilocybe* species are prepared as above. The two sgRNAs (2 µg of each sgRNA) are transformed into the protoplasts as described earlier. The transformed proto-plasts are plated. Colonies are selected and screened for antibiotic resistance markers followed by PCR sequencing to verify the deletion of the PsiM gene.

d. Inactivation of PsiK Gene Using CRISPR-Cas9

Two sgRNAs specific for a PsiK gene are designed in silico using computational programs as above. sgRNA sequences are given below, any of which can be used for knockout.

Exemplary CRISPR Oligos for PsiK Knock Out:

| | | |
|---|---|---|
| SEQ ID NO: 18 | CRISPR PsiK knockout | 5' GTTCGATCTCAAGACTGAAGA CGG-3' |
| SEQ ID NO: 19 | CRISPR PsiK knockout | 5' TCTTTGGACGTCGACACGAG CGG-3' |
| SEQ ID NO: 20 | CRISPR PsiK knockout | 5' GAGGCTTTGTCAATGTAACC TGG-3' |
| SEQ ID NO: 21 | CRISPR PsiK knockout | 5' GCATGCTCAGCCGCACATGTCTA CGG-3' |

Protoplasts of *Psilocybe* species are prepared as above. The two sgRNAs (2 µg of each sgRNA) are transformed into the protoplasts as described earlier. The transformed proto-plasts are plated. Colonies are selected and screened for antibiotic resistance markers followed by PCR sequencing to verify the deletion of the PsiK gene.

e. Inactivation of PsiD and PsiH Gene Using CRISPR-Cas9

Four sgRNAs are used, two sgRNAs specific for a PsiD gene and two specific for a PsiH gene, which are designed in silico using computational programs as above. The sequences of sgRNAs are given above. Any one of sequences denoted by SEQ ID NOS: 13-17 can be used for PsiD gene inactivation and any one of sequences denoted by SEQ ID NOS: 27-31 can be used for PsiH gene inactivation.

Protoplasts of *Psilocybe* species are prepared as above. The four sgRNAs (2 µg of each sgRNA) are transformed simultaneously into the protoplasts as described earlier. The transformed protoplasts are plated. Colonies are selected and screened for the presence of two antibiotic resistance mark-ers (one for each knocked out gene) followed by PCR sequencing to verify the deletion of the PsiH and PsiD genes.

f. Inactivation of PsiD and PsiM Genes Using CRISPR-Cas9

Four sgRNAs are used, two sgRNAs specific for a PsiD gene and two specific for a PsiM gene, which are designed in silico using computational programs described above. The sequences of sgRNA are given below. Any one of sequences denoted by SEQ ID NOS: 13-17 can be used for PsiD gene inactivation and any one of sequences denoted by SEQ ID NOS: 22-26 can be used for PsiM gene inactivation.

Protoplasts of *Psilocybe* species are prepared as above. The four sgRNAs (2 µg of each sgRNA) are transformed simultaneously into the protoplasts as described earlier. The transformed protoplasts are plated. Colonies are selected and screened for the presence of two antibiotic resistance mark-ers (one for each knocked out gene) followed by PCR sequencing to verify the deletion of the PsiD and PsiM genes.

g. Inactivation of PsiH and PsiK Genes Using CRISPR-Cas9

Four sgRNAs are used, two sgRNAs specific for a PsiH gene and two specific for a PsiK gene, which are designed in silico using computational programs described above. The sequences of sgRNAs are given above. Any one of sequences denoted by SEQ ID NOS: 18-21 can be used for PsiK gene inactivation and any one of sequences denoted by SEQ ID NOS: 27-31 can be used for PsiH gene inactivation.

Protoplasts of *Psilocybe* species are prepared as above. The four sgRNAs (2 µg of each sgRNA) are transformed simultaneously into the protoplasts as described earlier. The transformed protoplasts are plated. Colonies are selected and screened for the presence of two antibiotic resistance mark-ers (one for each knocked out gene) followed by PCR sequencing to verify the deletion of the PsiH and PsiK genes.

h. Inactivation of PsiH and PsiM Gene Using CRISPR-Cas9

Four sgRNAs are used, two sgRNAs specific for a PsiH gene and two specific for a PsiM gene, which are designed in silico using computational programs described above. The sequences of sgRNAs are given above. Any one of sequences denoted by SEQ ID NOS: 22-26 can be used for PsiM gene inactivation and any one of sequences denoted by SEQ ID NOS: 27-31 can be used for PsiH gene inactivation.

Protoplasts of *Psilocybe* species are prepared as above. The four sgRNAs (2 μg of each sgRNA) are transformed simultaneously into the protoplasts as described earlier. The transformed protoplasts are plated. Colonies are selected and screened for the presence of two antibiotic resistance markers (one for each knocked out gene) followed by PCR sequencing to verify the deletion of the PsiH and PsiM genes.

i. Inactivation of PsiK and PsiM Gene Using CRISPR-Cas9

Four sgRNAs are used, two sgRNAs specific for a PsiK gene and two specific for a PsiM gene, which are designed in silico using computational programs described above. The sequences of sgRNAs are given above. Any one of sequences denoted by SEQ ID NOS: 18-21 can be used for PsiK gene inactivation and any one of sequences denoted by SEQ ID NOS: 22-26 can be used for PsiM gene inactivation.

Protoplasts of *Psilocybe* species are prepared as above. The four sgRNAs (2 μg of each sgRNA) are transformed simultaneously into the protoplasts as described earlier. The transformed protoplasts are plated. Colonies are selected and screened for the presence of two antibiotic resistance markers (one for each knocked out gene) followed by PCR sequencing to verify the deletion of the PsiK and PsiM genes.

j. Inactivation of PsiD and PsiK Gene Using CRISPR-Cas9

Four sgRNAs are used, two sgRNAs specific for a PsiD gene and two specific for a PsiK gene, which are designed in silico using computational programs described above. The sequences of sgRNAs are given above. Any one of sequences denoted by SEQ ID NOS: 18-21 can be used for PsiK gene inactivation and any one of sequences denoted by SEQ ID NOS: 13-17 can be used for PsiD gene inactivation.

Protoplasts of *Psilocybe* species are prepared as above. The four sgRNAs (2 μg of each sgRNA) are transformed simultaneously into the protoplasts as described earlier. The transformed protoplasts are plated. Colonies are selected and screened for the presence of two antibiotic resistance markers (one for each knocked out gene) followed by PCR sequencing to verify the deletion of the PsiD and PsiK genes.

k. Inactivation of PsiD, PsiH, and PsiK Genes Using CRISPR-Cas9

Six sgRNAs are used, two sgRNAs specific for PsiD gene, two sgRNAs specific for a PsiH gene, and two specific for a PsiK gene, which are designed in silico using computational programs described above. The sequences of sgRNAs are given above. Any one of sequences denoted by SEQ ID NOS: 18-21 can be used for PsiK gene inactivation, anyone of sequences denoted by SEQ ID NOS: 27-31 can be used for PsiH gene inactivation and any one of sequences denoted by SEQ ID NOS: 13-17 can be used for PsiD gene inactivation.

Protoplasts of *Psilocybe* species are prepared as above. The six sgRNAs (2 μg of each sgRNA) are transformed simultaneously into the protoplasts as described earlier. The transformed protoplasts are plated. Colonies are selected and screened for the presence of three antibiotic resistance markers (one for each knocked out gene) followed by PCR sequencing to verify the deletion of the PsiD, PsiH and PsiK genes.

l. Inactivation of PsiH, PsiK, and PsiM Genes Using CRISPR-Cas9

Six sgRNAs are used, two sgRNAs specific for a PsiH gene, two sgRNAs specific for a PsiK gene, and two specific for a PsiM gene, which are designed in silico using computational programs described above. The sequences of sgRNAs are given above. Any one of sequences denoted by SEQ ID NOS: 18-21 can be used for PsiK gene inactivation, anyone of sequences denoted by SEQ ID NOS: 27-31 can be used for PsiH gene inactivation and any one of sequences denoted by SEQ ID NOS: 22-26 can be used for PsiM gene inactivation.

Protoplasts of *Psilocybe* species are prepared as above. The six sgRNAs (2 μg of each sgRNA) are transformed simultaneously into the protoplasts as described earlier. The transformed protoplasts are plated. Colonies are selected and screened for the presence of three antibiotic resistance markers (one for each knocked out gene) followed by PCR sequencing to verify the deletion of the PsiH, PsiK, and PsiM genes.

m. Inactivation of PsiK, PsiM, and PsiD Genes Using CRISPR-Cas9

Six sgRNAs are used, two sgRNAs specific for a PsiK gene, two sgRNAs specific for a PsiM gene, and two specific for a PsiD gene, which are designed in silico using computational programs described above. The sequences of sgRNAs are given above. Any one of sequences denoted by SEQ ID NOS: 18-21 can be used for PsiK gene inactivation, anyone of sequences denoted by SEQ ID NOS: 13-17 can be used for PsiD gene inactivation and any one of sequences denoted by SEQ ID NOS: 22-26 can be used for PsiM gene inactivation.

Protoplasts of *Psilocybe* species are prepared as above. The six sgRNAs (2 μg of each sgRNA) are transformed simultaneously into the protoplasts as described earlier. The transformed protoplasts are plated. Colonies are selected and screened for the presence of three antibiotic resistance markers (one for each knocked out gene) followed by PCR sequencing to verify the deletion of the PsiK, PsiD, and PsiM genes.

n. Inactivation of PsiD, PsiH, PsiK, and PsiM Genes Using CRISPR-Cas9

Eight sgRNA are used, two sgRNAs specific for a PsiD gene, two sgRNAs specific for a PsiH gene, two sgRNAs specific for a PsiK gene, and two specific for a PsiM gene, which are designed in silico using computational programs described above. Any one of sequences denoted by SEQ ID NOS: 18-21 can be used for PsiK gene inactivation, anyone of sequences denoted by SEQ ID NOS: 27-31 can be used for PsiH gene inactivation, any one of sequences denoted by SEQ ID NOS: 22-26 can be used for PsiM gene inactivation and anyone of sequences denoted by SEQ ID NOS: 13-17 can be used for PsiD gene inactivation.

Protoplasts of *Psilocybe* species are prepared as above. The eight sgRNAs (2 μg of each sgRNA) are transformed simultaneously into the protoplasts as described earlier. The transformed protoplasts are plated. Colonies are selected and screened for the presence of four antibiotic resistance markers (one for each knocked out gene) followed by PCR sequencing to verify the deletion of the PsiK, PsiH, PsiM, and PsiD genes.

Example 2: Gene Inactivation of Psilocybin Pathway in Mushrooms Using siRNA

Double stranded RNA (dsRNA) that is either transcribed from cellular genes or infecting pathogens, or artificially introduced into the cells is processed in the cytoplasm into a smaller dsRNA molecule by a specialized ribonuclease (RNase) III-like enzyme named Dicer. This short dsRNA molecule is known as the siRNA, which has 21-23 nucleotides with 3' two-nucleotide overhangs. The siRNA interacts with and activates the RNA-induced silencing complex (RISC). The endonuclease argonaute 2 (AGO2) component of the RISC cleaves the passenger strand (sense strand) of the siRNA while the guide strand (antisense strand) remains associated with the RISC. Subsequently, the guide strand guides the active RISC to its target mRNA for cleavage by AGO2. As the guide strand only binds to mRNA that is fully complementary to it, siRNA causes specific gene silencing. The psilocybin biosynthetic pathway can be blocked by utilizing siRNA which in turn can silence the genes that are essential to the production of psilocybin such as PsiD, PsiK, PSiM, and PsiH.

The synthetic siRNA target candidates designed using in silico methods described elsewhere (See Chaudhary et al., Development of a software tool and criteria evaluation for efficient design of small interfering RNA, *Biochem Biophys Res Commun,* 404 (2011), pp. 313-320; Zhong et al., Computational detection and suppression of sequence-specific off-target phenotypes from whole genome RNAi screens *Nucleic Acids Res,* 42 (2014), pp. 8214-8222; Naito et al., siRNA design software for a target gene-specific RNA interference, *Front. Genet.,* 11 Jun. 2012) are transformed into the protoplasts of *Psilocybe* mushrooms following the protocols disclosed in Example 1. Initial experiments are conducted using Cy3-labeled-siRNA molecules to test the uptake of siRNA molecules targeting the gene of interest (PsiD, PsiM, PsiK and PsiH) by the protoplasts. Subsequent experiments are then conducted using unlabeled siRNA. Controls are generated using protoplasts treated with unrelated-siRNA, as well as cultures with no siRNA addition. The supernatant fluid of both miRNA-treated and control cultures are periodically sampled (0.5 ml) and tested for the presence of psilocybin by means of the Keller reagent (glacial acetic acid containing iron chloride and concentrated sulphuric acid). *Psilocybe* cultures in which psilocybin production has been silenced by the miRNA candidates would not show a clear blue or violet Keller reaction whereas cultures that are control cultures having unrelated miRNA or untreated cultures would show the presence of blue color indicating the presence of psilocybin.

a. Inactivation of PsiD Gene Using siRNA siRNA specific for PsiD gene is designed in silico using computational programs as described above. The sequences of siRNA candidates are given below.

Exemplary siRNA Oligos for PsiD Inactivation:

```
SEQ ID NO: 52-PsiD siRNA oligonucleotide
5'AAUAAGAUCACUAUGUCCUAC(GCUGGUGGA)GUAGGACAUAGUGAUCUUAUU(UUUU)-3'

SEQ ID NO: 53-PsiD siRNA oligonucleotide
5'AAUUUAUUGACAUGUUCGAGG(GCUGGUGGA)CCUCGAACAUGUCAAUAAAUU(UUUU)-3'

SEQ ID NO: 54-PsiD siRNA oligonucleotide
5'GGAGAGUUGGCUACCCGCGCU(GCUGGUGGA)AGCGCGGGUAGCCAACUCUCC(UUUU)-3'

SEQ ID NO: 55-PsiD siRNA oligonucleotide
5'AAGCUCCCGUCUACGGAGACC(GCUGGUGGA)GGUCUCCGUAGACGGGACGUU(UUUU)-3'

SEQ ID NO: 56-PsiD siRNA oligonucleotide
5'GGGCUUCUCUGCAUUCACGAG(GCUGGUGGA)CUCGUGAAUGCAGAGAAGCCC(UUUU)-3'

SEQ ID NO: 60-PsiD siRNA oligonucleotide
5'GGCUGGUUGAACGAGCGGGCC(GCUGGUGGA)GGCCCGCUCGUUCAACCAGCC(UUUU)-3'
```

Protoplasts of *Psilocybe* species are prepared as above. The siRNAs are transformed into the protoplasts as described earlier. The transformed protoplasts are plated. Colonies are randomly selected and subcultured. The cultures are sampled at different time intervals to check for the presence of Psilocybin using Keller reaction. Cultures that don't exhibit a clear blue or violet reaction are identified as the cultures where the production of psilocybin is silenced.

b. Inactivation of PSiH Gene Using siRNA siRNA specific for PsiH gene is designed in silico using computational programs as described above. The sequences of siRNA candidates are given below.

Exemplary siRNA Oligos for PsiK Inactivation:

```
SEQ ID NO: 57-PsiK siRNA oligonucleotide
5'AACGUUCGGUUUACGAAUACC(GCUGGUGGA)GGUAUUCGUAAACCGAACGUU(UUUU)-3'

SEQ ID NO: 58-PsiK siRNA oligonucleotide
5'AAGGCCUGAACUACGACUUAG(GCUGGUGGA)CUAAGUCGUAGUUCAGGCCUU(UUUU)-3'

SEQ ID NO: 59-PsiK siRNA oligonucleotide
5'AACAUAGGCCGCGAGAGGCGAG(GCUGGUGGA)CUCGCCUCUCGCGGCCUAUGUU(UUUU)-3'

SEQ ID NO: 61-PsiK siRNA oligonucleotide
5'GGCGGACCUGUGGAGUGGAAA(GCUGGUGGA)UUUCCACUCCACAGGUCCGCC(UUUU)-3'
```

Protoplasts of *Psilocybe* species are prepared as above. The siRNAs are transformed into the protoplasts as described earlier. The transformed protoplasts are plated. Colonies are randomly selected and sub-cultured. The cultures are sampled at different time intervals to check for the presence of Psilocybin using Keller reaction. Cultures that don't exhibit a clear blue or violet reaction are identified as the cultures where the production of psilocybin is silenced.

c. Inactivation of PSiM Gene Using siRNA siRNA specific for PsiM gene is designed in silico using computational programs as described above. The sequences of siRNA candidates are given below.

Exemplary siRNA Oligos for PsiM:

```
SEQ ID NO: 62-PsiM siRNA oligonucleotide
5'AAUGUCGUCGCGAACAAUCUC(GCUGGUGGA)GAGAUUGUUCGCGACGACAUU(UUUU)-3'

SEQ ID NO: 63-PsiM siRNA oligonucleotide
5'AACCCUCCAUUCUACGACGGU(GCUGGUGGA)ACCGUCGUAGAAUGGAGGGUU(UUUU)-3'

SEQ ID NO: 64-PsiM siRNA oligonucleotide
5'AACAGUCAUCGAAAUGUCGAC(GCUGGUGGA)GUCGACAUUUCGAUGACUGUU(UUUU)-3'

SEQ ID NO: 65-PsiM siRNA oligonucleotide
5'GGAUGCUGCCAAAGGAUUUGG(GCUGGUGGA)CCAAAUCCUUUGGCAGCAUCC(UUUU)-3'

SEQ ID NO: 66-PsiM siRNA oligonucleotide
5'GGUACACGAGUAACUUGGGAA(GCUGGUGGA)UUCCCAAGUUACUCGUGUACC(UUUU)-3'
```

Protoplasts of *Psilocybe* species are prepared as above. The siRNAs are transformed into the protoplasts as described earlier. The transformed protoplasts are plated. Colonies are randomly selected and sub-cultured. The cultures are sampled at different time intervals to check for the presence of Psilocybin using Keller reaction. Cultures that don't exhibit a clear blue or violet reaction are identified as the cultures where the production of psilocybin is silenced.

d. Inactivation of PsiK Gene Using siRNA siRNA specific for PsiK gene is designed in silico using computational programs as described above. The sequences of siRNA candidates are given below.

Exemplary siRNA Oligos for PsiH:

```
SEQ ID NO: 67-PsiH siRNA oligonucleotide
5'AAUGGGGACGGGAUUACAGUC(GCUGGUGGA)GACUGUAAUCCCGUCCCCAUU(UUUU)-3'

SEQ ID NO: 68-PsiH siRNA oligonucleotide
5'AAUAUAUUGUCAGACACCGAU(GCUGGUGGA)AUCGGUGUCUGACAAUAUAUU(UUUU)-3'

SEQ ID NO: 69-PsiH siRNA oligonucleotide
5'AAUGGUCAACGAACUUAUGGG(GCUGGUGGA)CCCAUAAGUUCGUUGACCAUU(UUUU)-3'

SEQ ID NO: 70-PsiH siRNA oligonucleotide
5'GGAGUUCAGUGAGAAGGGCAU(GCUGGUGGA)AUGCCCUUCUCACUGAACUCC(UUUU)-3'

SEQ ID NO: 71-PsiH siRNA oligonucleotide
5'GGCAAUGUCACUGGAUAUUGG(GCUGGUGGA)CCAAUAUCCAGUGACAUUGCC(UUUU)-3'
```

Protoplasts of *Psilocybe* species are prepared as above. The siRNAs are transformed into the protoplasts as described earlier. The transformed protoplasts are plated. Colonies are randomly selected and sub-cultured. The cultures are sampled at different time intervals to check for the presence of Psilocybin using Keller reaction. Cultures that don't exhibit a clear blue or violet reaction are identified as the cultures where the production of psilocybin is silenced.

e. Inactivation of PsiD and PsiH Gene Using siRNA

Two different siRNAs are used, an siRNA specific for PsiD gene and an siRNA specific for PsiH are designed in silico using computational programs as described above. The sequences of siRNA candidates are given above. Any one of sequences denoted by SEQ ID NOS: 52-56 can be used for PsiD gene inactivation and any one of sequences denoted by SEQ ID NOS: 67-71 can be used for PsiH gene inactivation.

Protoplasts of *Psilocybe* species are prepared as above. The siRNAs are transformed into the protoplasts as described earlier. The transformed protoplasts are plated. Colonies are randomly selected and sub-cultured. The cultures are sampled at different time intervals to check for the presence of Psilocybin using Keller reaction. Cultures that don't exhibit a clear blue or violet reaction are identified as the cultures where the production of psilocybin is silenced.

f. Inactivation of PsiD and PsiM Gene Using siRNA

Two different siRNAs are used, an siRNA specific for PsiD gene and an siRNA specific for PsiM are designed in silico using computational programs as described above. The sequences of siRNA candidates are given above. Any one of sequences denoted by SEQ ID NOS: 52-56 can be used for PsiD gene inactivation and any one of sequences denoted by SEQ ID NOS: 62-66 can be used for PsiM gene inactivation.

Protoplasts of *Psilocybe* species are prepared as above. The siRNAs are transformed into the protoplasts as described earlier. The transformed protoplasts are plated. Colonies are randomly selected and sub-cultured. The cultures are sampled at different time intervals to check for the presence of Psilocybin using Keller reaction. Cultures that don't exhibit a clear blue or violet reaction are identified as the cultures where the production of psilocybin is silenced.

g. Inactivation of PsiH and PsiK Gene Using siRNA

Two different siRNAs are used, an siRNA specific for PsiH gene and an siRNA specific for PsiK are designed in silico using computational programs as described above. The sequences of siRNA candidates are given above. Any one of sequences denoted by SEQ ID NOS: 57-59, 61 can be used for PsiK gene inactivation and any one of sequences denoted by SEQ ID NOS: 67-71 can be used for PsiH gene inactivation.

Protoplasts of *Psilocybe* species are prepared as above. The siRNAs are transformed into the protoplasts as described earlier. The transformed protoplasts are plated. Colonies are randomly selected and sub-cultured. The cultures are sampled at different time intervals to check for the presence of Psilocybin using Keller reaction. Cultures that don't exhibit a clear blue or violet reaction are identified as the cultures where the production of psilocybin is silenced.

h. Inactivation of PsiH and PsiM Gene Using siRNA

Two different siRNAs are used, an siRNA specific for PsiH gene and an siRNA specific for PsiM are designed in silico using computational programs as described above. The sequences of siRNA candidates are given above. Any one of sequences denoted by SEQ ID NOS: 62-66 can be used for PsiM gene inactivation and any one of sequences denoted by SEQ ID NOS: 67-71 can be used for PsiH gene inactivation.

Protoplasts of *Psilocybe* species are prepared as above. The siRNAs are transformed into the protoplasts as described earlier. The transformed protoplasts are plated. Colonies are randomly selected and sub-cultured. The cultures are sampled at different time intervals to check for the presence of Psilocybin using Keller reaction. Cultures that don't exhibit a clear blue or violet reaction are identified as the cultures where the production of psilocybin is silenced.

i. Inactivation of PsiK and PsiM Gene Using siRNA

Two different siRNAs are used, an siRNA specific for PsiK gene and an siRNA specific for PsiM are designed in silico using computational programs as described above. The sequences of siRNA candidates are given above. Any one of sequences denoted by SEQ ID NOS: 62-66 can be used for PsiM gene inactivation and any one of sequences denoted by SEQ ID NOS: 57-59, 61 can be used for PsiK gene inactivation.

Protoplasts of *Psilocybe* species are prepared as above. The siRNAs are transformed into the protoplasts as described earlier. The transformed protoplasts are plated. Colonies are randomly selected and sub-cultured. The cultures are sampled at different time intervals to check for the presence of Psilocybin using Keller reaction. Cultures that don't exhibit a clear blue or violet reaction are identified as the cultures where the production of psilocybin is silenced.

j. Inactivation of PsiD and PsiK Gene Using siRNA

Two different siRNAs are used, an siRNA specific for PsiD gene and an siRNA specific for PsiK are designed in silico using computational programs as described above. The sequences of siRNA candidates are given above. Any one of sequences denoted by SEQ ID NOS: 52-56 can be used for PsiD gene inactivation and any one of sequences denoted by SEQ ID NOS: 57-59, 61 can be used for PsiK gene inactivation.

Protoplasts of *Psilocybe* species are prepared as above. The siRNAs are transformed into the protoplasts as described earlier. The transformed protoplasts are plated. Colonies are randomly selected and sub-cultured. The cultures are sampled at different time intervals to check for the presence of Psilocybin using Keller reaction. Cultures that don't exhibit a clear blue or violet reaction are identified as the cultures where the production of psilocybin is silenced.

k. Inactivation of PsiD, PsiH, and PsiK Genes Using siRNA

Three different siRNAs are used, an siRNA specific for PsiD gene, an siRNA specific for PsiH gene and an siRNA specific for PsiK are designed in silico using computational programs as described above. The sequences of siRNA candidates are given above. Any one of sequences denoted by SEQ ID NOS: 52-56 can be used for PsiD gene inactivation, any one of sequences denoted by SEQ ID NOS: 67-71 can be used for PsiH gene inactivation and any one of sequences denoted by SEQ ID NOS: 57-59, 61 can be used for PsiK gene inactivation.

Protoplasts of *Psilocybe* species are prepared as above. The siRNAs are transformed into the protoplasts as described earlier. The transformed protoplasts are plated. Colonies are randomly selected and sub-cultured. The cultures are sampled at different time intervals to check for the presence of Psilocybin using Keller reaction. Cultures that don't exhibit a clear blue or violet reaction are identified as the cultures where the production of psilocybin is silenced.

l. Inactivation of PsiH, PsiK, and PsiM Genes Using siRNA

Three different siRNAs are used, an siRNA specific for PsiH gene, an siRNA specific for PsiK gene and an siRNA specific for PsiM are designed in silico using computational programs as described above. The sequences of siRNA candidates are given above. Any one of sequences denoted by SEQ ID NOS: 62-66 can be used for PsiM gene inactivation, any one of sequences denoted by SEQ ID NOS: 67-71 can be used for PsiH gene inactivation and any one of sequences denoted by SEQ ID NOS: 57-59, 61 can be used for PsiK gene inactivation.

Protoplasts of *Psilocybe* species are prepared as above. The siRNAs are transformed into the protoplasts as described earlier. The transformed protoplasts are plated. Colonies are randomly selected and sub-cultured. The cultures are sampled at different time intervals to check for the presence of Psilocybin using Keller reaction. Cultures that don't exhibit a clear blue or violet reaction are identified as the cultures where the production of psilocybin is silenced.

m. Inactivation of PsiK, PsiM, and PsiD Genes Using siRNA

Three different siRNAs are used, an siRNA specific for PsiK gene, an siRNA specific for PsiM gene and an siRNA specific for PsiD are designed in silico using computational programs as described above. The sequences of siRNA candidates are given above. Any one of sequences denoted by SEQ ID NOS: 52-56 can be used for PsiD gene inactivation, any one of sequences denoted by SEQ ID NOS: 62-66 can be used for PsiM gene inactivation and any one of sequences denoted by SEQ ID NOS: 57-59, 61 can be used for PsiK gene inactivation.

Protoplasts of *Psilocybe* species are prepared as above. The siRNAs are transformed into the protoplasts as described earlier. The transformed protoplasts are plated. Colonies are randomly selected and sub-cultured. The cultures are sampled at different time intervals to check for the presence of Psilocybin using Keller reaction. Cultures that don't exhibit a clear blue or violet reaction are identified as the cultures where the production of psilocybin is silenced.

n. Inactivation of PsiD, PsiH, PsiK, and PsiM Genes Using siRNA

Four different siRNAs are used, an siRNA specific for PsiD gene, an siRNA specific for PsiH gene, an siRNA specific for PsiK gene and an siRNA specific for PsiM are designed in silico using computational programs as described above. The sequences of siRNA candidates are given above. Any one of sequences denoted by SEQ ID NOS: 52-56 can be used for PsiD gene inactivation, any one of sequences denoted by SEQ ID NOS: 62-66 can be used for PsiM gene inactivation, any one of sequences denoted by SEQ ID NOS: 67-71 can be used for PsiH gene inactivation and any one of sequences denoted by SEQ ID NOS: 57-59, 61 can be used for PsiK gene inactivation.

Protoplasts of *Psilocybe* species are prepared as above. The siRNAs are transformed into the protoplasts as described earlier. The transformed protoplasts are plated. Colonies are randomly selected and sub-cultured. The cultures are sampled at different time intervals to check for the presence of Psilocybin using Keller reaction. Cultures that don't exhibit a clear blue or violet reaction are identified as the cultures where the production of psilocybin is silenced.

Example 3: Gene Inactivation of Psilocybin Pathway in Mushrooms Using miRNA

MicroRNAs (miRNAs) are a conserved class of small non-coding RNAs that assemble with Argonaute proteins into miRNA-induced silencing complexes (miRISCs) to direct post-transcriptional silencing of complementary mRNA targets. Silencing is accomplished through a combination of translational repression and mRNA destabilization, with the latter contributing to most of the steady-state repression in cell cultures. (See Quévillon Huberdeau M, Simard MJ. 2019, A guide to microRNA-mediated gene silencing. *FEBS J.* 2019 February; 286 (4): 642-652.) Degradation of the mRNA target is initiated by deadenylation, which is followed by decapping and 5'-to-3' exonucleolytic decay. The degradation of miRNA targets is catalyzed by enzymes involved in the 5'-to-3' mRNA decay pathway. In this pathway, mRNAs are first deadenylated, then decapped and finally degraded from the 5' end. (See Jonas, S., Izaurralde, E. Towards a molecular understanding of microRNA-mediated gene silencing. *Nat Rev Genet.* 16, 421-433 (2015).)

In silico algorithms are applied to predict miRNA targets that bind and inhibit the genes (PsiD, PsiH, PsiM, and PsiK) involved in the psilocybin biosynthetic pathway. Algorithms typically use miRNA sequence annotations obtained from databases such as miRbase. Then, miRNA-target interactions are predicted based on seed-pairing and scored according to additional features such as free-energy of binding and site conservation. (See Witkos et al., (2011) Practical aspects of microRNA target prediction. *Curr Mol Med* 11, 93-109; Riffo-Campos et al., 2016, Tools for sequence-based miRNA target prediction: what to choose? *Int J Mol Sci.* 17, pii: E1987.)

The in silico selected miRNA target candidates that target the psilocybin biosynthetic pathway are then synthesized using commercial vendors such as Dharmacon or Integrated DNA technologies. The miRNA target candidates thus obtained transformed into the protoplasts of *Psilocybe* mushrooms following the protocols disclosed in Example 1. Initial experiments are conducted using Cy3-labeled-miRNA molecules to test the uptake of miRNA molecules targeting the gene of interest (PsiD, PsiM, PsiK, and PsiH) by the protoplasts. Subsequent experiments are then conducted using unlabeled miRNA. Controls are generated using protoplasts treated with unrelated-miRNA, as well as cultures with no miRNA addition.

The supernatant of both miRNA-treated and control cultures are periodically sampled (0.5 ml) and tested for the presence of psilocybin by means of the Keller reagent (glacial acetic acid containing iron chloride and concentrated sulphuric acid). *Psilocybe* cultures in which psilocybin production has been silenced by the miRNA candidates would not show a clear blue or violet Keller reaction whereas cultures that are control cultures having unrelated miRNA or untreated cultures would show the presence of blue color indicating the presence of psilocybin. The cultures which do not show a clear blue Keller or violet reaction are collected and propagated to yield large quantities of knocked out mushrooms for preparation of extracts.

Example 4: Genome Editing in *Psilocybe cubensis* with Selection for Gene Disruption In this example is produced a stable fertile and true breeding mushroom (sporocarp and monokaryon and dikaryon mycelia) of *Psilocybe cubensis* (Psicub) by genome editing without producing psilocybin or psilocin. The mushroom is produced using a strategy described herein of introducing gene editing enzymes targeted to disrupt the coding frame of first exons of nonessential PsiK or PsiM psilocybin synthesis genes. To create genetic markers, we simultaneously disrupt first exons of a genetically unlinked essential metabolic gene for uracil synthesis fsyl or pyrG that when deleted becomes a positively and negatively selectable. The mushroom is used to enable the genetic and biochemical analysis of specialized metabolism of unique natural drug-like molecules for example indoleamine derivatives including 4-hydroxytryptophan, 4-hydroxytryptamine, beta-carbolines such as harmane and their metabolic products. The safety and biological activity of key metabolites stably produced by the modified mushroom are also identified, along with means for their genetic and environmental control. All metabolites may be targeted by this approach starting with the indoleamine derivatives. Through the practice of the example, a sustainable and medically appropriate source of mushroom-derived compounds that can be tested for their safety and biological activity alone for cosmetic, nutraceutical or food supplement use is created. Standardized extracts are in some embodiments tested in clinical trials for safety and efficacy in carefully calibrated combinations with purified therapeutic psilocybin or psilocin. It is anticipated that demand for this approach is significant especially in cases where these molecules are sanctioned for therapeutic use and where therapists and consumers prefer to use whole mushroom products rather than isolated active compounds.

a. Modification of Psilocybin Biosynthesis Pathway Genes

CRISPR-Cas9 inactivation of PsiK and PsiM genes by single unique crRNAs with common tracrRNA delivered as active nuclear targeted high specificity Cas9 riboprotein (RNP) complex to protoplasts by polyethylene glycol treatment (PEG—with or without TritonX-100) or electroporation. RNAs will be synthesized by IDT (Integrated DNA Technologies, Coralville, IA, US) chemically modified and delivered with manufacturer recommended carrier DNA (the sequence of which carrier DNA we have verified to have no similarity to any of the sequences in any of the publicly available Psicub genomes: Fricke, Janis, et al. 2017. "Enzymatic Synthesis of Psilocybin." *Angewandte Chemie* 56 (40): 12352-55, McKernan, Kevin, et al. 2021. "A Whole Genome Atlas of 81 *Psilocybe* Genomes as a Resource for Psilocybin Production." f1000 Research, July. doi.org/10.12688/f1000research.55301.2). The resulting monokaryotic or dikaryotic homozygous and dikaryotic compound heterozygous loss of function strains will be subjected to whole genome sequencing by Oxford Nanopore or Illumina technology and compared to publicly available whole genome assemblies (Mycocosm and NCBI: Fricke, J., et al. 2017, "Enzymatic Synthesis of Psilocybin." *Angewandte Chemie* 56 (40): 12352-55; McKernan, Kevin, et al. 2021. "A Whole Genome Atlas of 81 *Psilocybe* Genomes as a Resource for Psilocybin Production." f1000 Research, July. doi.org/10.12688/f1000research.55301.2) to identify any off-target induced mutations, and the recovered genetic variants identified by polymerase chain reaction (PCR) amplification and Sanger chain termination DNA sequencing.

The following tables of variants in *P. cubensis*, were generated by aligning sequences from JGI Mycocosm (Fricke et al. 2017) and NCBI GenBank (Boyce G. and Kasson, M.T., Ohio State University, direct submissions MH483013.1, MH483014.1; McKernan, Kevin, et. al. 2021. "A Whole Genome Atlas of 81 *Psilocybe* Genomes as a Resource for Psilocybin Production." f1000 Research, July. doi.org/10.12688/f1000research.55301.2), and can, in some embodiments, be used to determine the success or failure of oligonucleotide-targeted gene editing and gene silencing, PCR analysis of gene modification and qRT-PCR analysis of mRNA suppression by those gene modifications, according to the teachings herein and the general knowledge in the art.

The first table immediately below shows intraspecies SNP and small sequence variants by strain in the *P. cubensis* PsiK gene; the second table that follows shows intraspecies variation by strain in the PsiM gene that are incorporated into target oligo design strain by strain.

The first table below shows intraspecies SNP and small sequence variants by strain in the *P. cubensis* PsiK gene that are incorporated into target oligonucleotide design strain by strain:

| Sequence PsiK | P.envy genome ch10 assembly | Pcu1_1 genome scaffolds | mRNA | genomic DNA | genomic DNA | genomic DNA |
|---|---|---|---|---|---|---|
| Strain ID Accession | MGC-MH-2018 CM039007.1 | FSU 12409 72830 | FSU 12409 KY984099 | PC2 MH483013 | 2633 MG548656 | 2687 MG548657 |
| g.665174T | 132C | | | | | |
| g.1665267T | 225C | | | | | |
| g.1665977A | 935G | | | | | |
| g.1666040_1666041delinsGT | 998_999AC | | | | | |
| g.1666115A | 1073A | c.73A | C | | | |
| g.1666143_1666144delinsGC | 1101_1102GC | c.101GC | AG | | | |
| g.1666309C | 1267C | intron | T | C | | T |
| g.1666315T | 1273T | intron | G | T | | G |
| g.1666319G | 1277G | intron | A | G | | A |
| g1666326_1666328TAA | 1284_1286TAA | intron | delTAA | TAA | | delTAA |
| g.1666342A | A | c.237A | G | A | | G |
| g.1666396T | T | c.291T | C | T | | C |
| g.1666406T | T | c.301T | G | T | | G |
| g.1666433T | T | c.328T | G | T | | T |
| g.1666494T | T | c.389T | T | T | | C |
| g.1666605A | A | c.500A | G | A | | A |
| g.1666622a | G | c.517G | G | G | | G |
| g.1666675C | C | c.570C | T | C | | C |
| g.1666723T | T | c.618T | C | T | | T |
| g.1666807G | G | c.702G | A | G | | G |
| g.1666834G | G | c.729G | A | G | | G |
| g.1666870C | C | c.765C | T | C | | C |
| g.1666888C | C | c.783C | T | C | | C |
| g.1666894C | C | c.789C | A | C | | C |
| g.1666941A | A | c.836A | T | A | | A |
| g.1667026A | A | c.921A | T | | | |
| Protein | | | ASU62237 | QDI06053 | AXQ88157 | AXQ88158 |
| missense | | | p.25T | P | ? | ? |
| | | | p34G | E | ? | ? |
| | | | p101s | A | S | A |
| | | | p110L | V | L | 1 |
| | | | p130V | V | V | A |
| | | | p.167E | E | G | E |
| | | | p.2790 | L | Q | Q |

The second table, that follows, shows intraspecies variation by strain in the *P. cubensis* PsiM gene that are incorporated into target oligonucleotide design strain by strain:

| Sequence: PsiM | P. envy genome ch10 assembly | Pcu1_1 genome scaffolds | mRNA | genomic DNA |
|---|---|---|---|---|
| Strain Accession Conceptual consequence | MGC-MH-2018 JR316_0010788 | FSU 12409 72833 | FSU 12409 KY984100 | PC2 MH483014 |
| CC | | g.1675957_1675958delinsTG | | |
| | | g.1675922G > T | | |
| | | g.1675846G > T | | |

-continued

| Sequence: PsiM | | | | |
|---|---|---|---|---|
| Strain | P. envy genome | Pcu1_1 | | genomic |
| Accession | ch10 assembly | genome scaffolds | mRNA | DNA |
| Conceptual | MGC-MH-2018 | FSU 12409 | FSU 12409 | PC2 |
| consequence | JR316_0010788 | 72833 | KY984100 | MH483014 |
| | TGGACAC | g.1675793_675799del | | |
| | | g.1675640C > G | | |
| | | g.1675608G > A | | |
| | | g.1675601G > A | | |
| | | g.1675599G > A | | |
| | | g.1675464G > A | | |
| | | g.1675391A > G | | |
| 5' intergenic | | g.1675205T > C | | |
| 5' intergenic | | g.1675184G > C | | |
| Exon3 synonymous | g.1674836T | g.1674836T > C | C | |
| intron | | g.1674735A > G | | |
| intron | A | g.1674659del | | |
| Exon5 synonymous | | g.1674653A > G | G | |
| Exon5 p.R > K | | g.1674573G > A | A | |
| intron | A | A | | g.1674526A > T |
| 3'splice AG | G | G | g.1674506G > T | G |
| Exon7 synonymous | C | g.1674319C > T | T | C |
| intron | | g.1674200A > T | | |
| Exon8 synonymous | A | g.1674131A > T | T | A |
| intron | T | g.1674015 > del | | T |
| 5' Splice GT | G | G | g.1673759G > A | G |
| intron | | g.1673567T > C | | |
| 3' intergenic | | g.1672653T > C | | |
| | | g.1672527C > G | | |
| | | g.1675079_1675081ATG | | |
| | | g.1674442_1674444ATG | | |
| | | g.1674128_1674130ATG | | |
| | | g.1673966_1673968ATG | | |
| | | g.1673927_1673929ATG | | | b. Selection of Strains where Gene Editing is Successful

Selection for successful introduction of active and targeted Cas9 is achieved by crRNA-Cas9 RNP cleavage disrupting coding exonic sequences of either or both of two genes of the uracil biosynthetic pathway fsyl encoding cytosine deaminase EC 3.5.4.1 and pyrG encoding orotate 5' phosphate decarboxylase EC 4.1.1.23. Monokaryotic mycelial colonies from edited protoplasts are selected and identified on 5-FC and 5-FOA media that selectively kill fungal mycelia with unedited wild type fsyl and pyrG genotype. Those with coding sequence disrupting deletions in the fsyl, pyrG, PsiK and PsiM genes are then identified in colony samples of washed, thermally lysed (85° C.) mycelium by PCR amplification and gel electrophoresis with the following PCR primer pairs.

SEQ ID NOS: 118-125 below are exemplary PCR primer pairs for detection of deletions in genomic DNA from mycelial colonies. Expected deletions make the product shorter than the indicated wild type sequence:

| SEQ ID NO: | Primer | Sequence (5'→3') | Template strand | Tm ° C. | Product bp |
|---|---|---|---|---|---|
| SEQ ID NO: 118 | fcyl F1 | CCAATCACGACTCGCGGTAT | plus | 60.25 | |
| SEQ ID NO: 119 | fcyl R1 | ATTAACGGGTCTTCGGCAGG | minus | 60.11 | 578 |
| SEQ ID NO: 120 | PsiK F1 | TGGCGTTCGATCTCAAGACT | plus | 59.11 | |
| SEQ ID NO: 121 | PsiK R1 | CTCCCAGAACCTCCCGATTG | minus | 59.82 | 345 |
| SEQ ID NO: 122 | PsiM F1 | AGCCCGAAGTCACGATGAAG | plus | 60.11 | |
| SEQ ID NO: 123 | PsiM R1 | GACCAGTAGCTCTCCCCTCA | minus | 60.03 | 316 |
| SEQ ID NO: 124 | pyrGF1 | GCTCAGGTGTTGGAGCTTCT | plus | 59.96 | |
| SEQ ID NO: 125 | pyrG R1 | GGTGGTTTAACCGTGCGATG | minus | 59.83 | 472 |

Sequences Seq ID NOs: 126-144 are exemplary single targeting crRNA sequences for use in single gene editing or marker gene (fsyl or pyrG) knockout plus psilocybin synthesis gene (PsiK or PsiM) knockout with high fidelity Cas9 derivative RNP complexes illustrated as 5'→3' spacer DNA plus PAM (protospacer adjacent motif). For purposes of the SEQ ID NOS below, it should be understood that the SEQ ID NO consists of the spacer sequence and PAM together.

| | | Spacer sequence | PAM |
|---|---|---|---|
| | | *fsy1* | |
| SEQ ID NO: 126 | fsy1 crRNA1 | ACTAGGATAGATGACCCAAT | CGG |
| SEQ ID NO: 127 | fsy 1 crRNA2 | TCTATCTTTTCCCACTGTGA | CGG |
| SEQ ID NO: 128 | fsy 1 crRNA3 | CTTTTCCCACTGTGACGGCA | TGG |
| | | *pyrG* | |
| SEQ ID NO: 129 | pyrG crRNA1 | TGTTTCCAAGATCAATTTGG | CGG |
| SEQ ID NO: 130 | pyrG crRNA2 | TCTGCATACAAGAAGACCTA | TGG |
| SEQ ID NO: 131 | pyrG crRNA3 | GTTAGATACCCTATTTCCAT | AGG |
| SEQ ID NO: 132 | pyrG crRNA4 | ACAAGAAGACCTATGGAAAT | AGG |
| SEQ ID NO: 133 | pyrG crRNA5 | CATTGTTTCCAAGATCAATT | TGG |
| SEQ ID NO: 134 | pyrG crRNA6 | CAAGAAGACCTATGGAAATA | GGG |
| | | *psiK* | |
| SEQ ID NO: 135 | PsiK crRNA1 | TAAGATAGGTGTAGAACGTT | CGG |
| SEQ ID NO: 136 | PsiK crRNA2 | GTTTAGTGAGATATGTGATG | AGG |
| SEQ ID NO: 137 | PsiK crRNA3 | ACGGATGAGGATTTTAAGAT | AGG |
| SEQ ID NO: 138 | PsiK crRNA4 | AAGCTCAATGCTCCTTATCA | AGG |
| SEQ ID NO: 139 | PsiK crRNA5 | TCTCACTAAACATCTTTCTT | TGG |
| SEQ ID NO: 140 | PsiK crRNA6 | ATGCTCGTATGACCTTGATA | AGG |
| | | *psiM* | |
| SEQ ID NO: 141 | PsiM crRNA1 | GAAAGTGCTTGATAGTCAAT | TGG |
| SEQ ID NO: 142 | PsiM crRNA2 | TGACTATCAAGCACTTTCAG | AGG |
| SEQ ID NO: 143 | PsiM crRNA3 | TAGTCAATTGGTGTACGGTA | AGG |
| SEQ ID NO: 144 | PsiM crRNA4 | GATAGTGAGGTCAACAGAAC | TGG |

In one example, SEQ ID NOS: 137 and 140 are paired PAM-out crRNA sequences (spacer DNA plus PAM) on opposite strands for use with modified Cas9 nickase RNP complex with 71 bp between the predicted DNA cleavage sites:

| SEQ ID NO: 137 | PsiK crRNA3 | ACGGATGAGGATTTTAAGAT | AGG |
|---|---|---|---|
| SEQ ID NO: 140 | PsiK crRNA6 | ATGCTCGTATGACCTTGATA | AGG |

Introduction of gene editing RNP: Protoplasting of mycelia grown from plates into (3-5 days) liquid culture at 25-30° C. is optimized for Psicub within the range that has been achieved for several other tetraspore table mushrooms including *Pleurotus* ostreatus (Plo oyster mushroom, Boontawon, Tatpong, et al. 2021. "Efficient Genome Editing with CRISPR/Cas9 in *Pleurotus ostreatus.*" *AMB Express* 11 (1): 30), and *Lentinula edodes* (Le, shiitake, Zhou, Chenli, et al. 2017. "Establishment of Uracil Auxotrophic Dikaryotic Strains of *Lentinula Edodes* by Crossbreeding." *Breeding Science* 67 (2): 135-39). 2-mercaptoethanol and chitinase and pectinase enzymes such as Snailase (Abbexa LLC, Sugar Land, TX, US) are used to produce protoplasts in 0.6M potassium chloride, mannitol or sorbitol or similar osmotic protectants solutions with citrate or phosphate buffers of an optimized within a range of pH 5-7. Recovery of ice chilled, PEG-treated, carrier DNA transfected, RNP transfected and similarly electroporated protoplasts is achieved in 0.6M potassium chloride, mannitol or sorbitol media or similar osmotic protectants solutions with citrate and phosphate buffers of an optimized within a range of pH 5-7.

Mushroom recovery: Growth of monokaryotic and dikaryotic mycelium and crosses between spore-derived strains of compatible mating types will take place on 2% agar plates with potato dextrose PDA and yeast malt extract dextrose (YMD) plates, corresponding liquid media and in steam cooked rye or oat grain jars. 0.18 mM uracil and 20 mM uridine are used to grow fsyl and pyrG auxotrophic mutants and 0.05-0.1% (w/v) 5-FC or 5-FOA respectively to select for these mutants and against undeleted wild type uracil prototrophic alleles of fsyl and pyrG.

The use of unlinked markers is deliberate, fsyl is on chromosome 11 and pyrG on chromosome 4, with the Psi psilocybin synthesis gene cluster on chromosome 10. When we combine two monokaryons bearing different deletions in the same psi gene we select the double psi knockout dikaryon by complementation of the two uracil synthesis mutations on minimal medium plates lacking uracil. This approach is generally useful for unlinked knockouts and allows future exploration of targeted mutations in all of the genes of the psi cluster including tryptophan decarboxylase PsiD, monooxygenase PsiH, basic HLH transcriptional regulator psiR, MFS transporters PsiT1 and PsiT2, and the closely linked Psicub gene for casein kinase type 1 epsilon probably a circadian regulator.

Similarly, after sporulation, the fsyl and pyrG deletions can be selected against on minimal medium without uracil to recover the individual psi deletions again in monokaryons.

The selective growth conditions used previously for Plo and Le (Boontawon, Tatpong, et al. 2021. "Efficient Genome Editing with CRISPR/Cas9 in *Pleurotus ostreatus.*" *AMB Express* 11 (1): 30, Zhou, Chenli, et al. 2017. "Establishment of Uracil Auxotrophic Dikaryotic Strains of *Lentinula Edodes* by Crossbreeding." *Breeding Science* 67 (2): 135-39) will be adapted for the mycelia we isolate. Positive control fsyl and pyrG auxotrophic mutants will be created without gene editing from UV irradiated protoplasts by selection on 5-FC or 5-FOA containing uracil and uridine supplemented medium and verified by colony PCR and Sanger sequencing. These strains will be used as growth controls on solid and 5-FC or 5-FOA selective media.

Dried monokaryon and dikaryon mycelium will be reactivated and frozen to establish backup storage in $N_2(1)$, 4° C. and −80° C.

Monokaryon and dikaryon colonies will be tested on plates, in liquid culture and in grain jars with Kovacs and DMACA indole reagents (Hardy Diagnostics, Santa Maria, CA, US) to ensure that these are grown under conditions producing no more detectable indole compounds than commercially available mushrooms.

A healthy transcriptome: Healthy growth will be assessed using quantitative reverse transcriptase polymerase chain reaction amplification (Q-RT-PCR or qRT-PCR) of abundant mRNA transcripts using primer sequences including these that detect the major *P. cubensis* act1, cis1 and tef1 mRNA transcripts (see also, e.g., www.ncbi.nlm.nih.gov/probe/docs/techqpcr/).

Primer sequences: SEQ ID NOS: 145-150 are exemplary primers for qRT-PCR detection of abundant mRNA transcripts to assess growth of gene edited fungi containing deletions:

Kovacs and DMACA indole reagents and if indole negative, grown to sporocarp (fruiting body production and sporulation) by sphagnum calcium overlay in illuminated trays. Fruiting bodies will be tested daily with indole reagents and extracts submitted for metabolite identification via liquid chromatography mass spectrometry (LC-MS) against standards for all relevant metabolic products including L-tryptophan, 5-hydroxytryptophan, 4-hydroxytryptophan, tryptamine, kynurenine pathway metabolites and beta-carbolines (such as harmane: Blei F, Dörner S, Fricke J, Baldeweg F, Trottmann F, Komor A, Meyer F, Hertweck C, Hoffmeister D. Simultaneous Production of Psilocybin and a Cocktail of β-Carboline Monoamine Oxidase Inhibitors in 'Magic' Mushrooms. *Chemistry.* 2020; 26 (3): 729-34). Any incidental strongly indole staining fungal material and media will be autoclaved and disposed of by incineration by an appropriate medical waste service without further investigation.

Media for auxotrophs: Potato Dextrose Agar (PDA): 200 g/L potatoes, 20 g/L glucose, 20 g/L agar; Potato Dextrose Agar containing uracil (PDAU): PDA containing 0.05 mmol/L uracil; Potato Dextrose (PD): 200 g/L potatoes, 20 g/L glucose; Minimal medium (MM): $KH_2PO_3$ 1.0 g/L, $(NH_4)_2HPO_3$ 1.5 g/L, $MgSO_4·7H_2O$ 0.3 g/L, Thiamine HCL 500 μg/L, agar15 g/L; Minimal medium containing uracil (MMU): MM containing 0.05 mmol/L uracil; Minimal medium containing uracil and 5-FOA (MMUF): MM containing 0.05 mmol/L uracil, 0.5 g/L S-FOA. All the media were sterilized for 15 mins at 121° C. Fifteen milliliters of each media is poured into individual plastic Petri dishes with a 9 cm diameter. The mycelia are kept in a dark room at 25° C. for 7-14d. (See Zhou, Chenli, et al. 2017. "Establishment of Uracil Auxotrophic Dikaryotic Strains of *Lentinula Edodes* by Crossbreeding." *Breeding Science* 67 (2): 135-39.)

Media will be prepared by autoclaving or 0.2 micron filtration in disposable sterile plastic units as appropriate. All plates and growth media will be autoclaved in a separate autoclave before disposal via an appropriate lab waste service.

Example 5: Gene Editing in Intergenic Regions

Exemplar sequences SEQ ID NOS: 151-158 are used, from the public *Psilocybe cubensis* genome Psicub1_1 of non-overlapping intergenic regions in which gene editing oligonucleotides can be used to target noncoding elements and thereby disrupt transcription of these example psilocy-

| SEQ ID NO: | Primer | Sequence (5'→3') | Template strand | Tm ° C. | Product bp |
|---|---|---|---|---|---|
| SEQ ID NO: 145 | act1F1 | CAGGGTGTCATGGTTGGCA | plus | 60.23 | |
| SEQ ID NO: 146 | act1R1 | GTAGATGGGAACGGTGTGGG | minus | 60.11 | 462 |
| SEQ ID NO: 147 | cis1F1 | CGACACGCAAACCTTTGTCA | plus | 59.62 | |
| SEQ ID NO: 148 | cis1R1 | GCTTAACCGTACGCGACAAC | minus | 59.91 | 214 |
| SEQ ID NO: 149 | tef1F1 | CGATGTCCTGGGGCATCAAT | plus | 60.18 | |
| SEQ ID NO: 150 | tef1R1 | CGATTCCGGAAAGTCCACCA | minus | 60.04 | 361 |

Metabolites produced in psilocybin-free mushrooms: Loss of function deleted monokaryons of opposite mating type and compound heterozygous deleted dikaryons will be propagated in grain jars, tested for indole production with bin synthesis genes PsiD, PsiH, PsiK, PsiM, their metabolite transporters PsiT1 and PsiT2, candidate transcriptional regulator PsiR and candidate circadian expression regulator CSNKIE. Oligonucleotide targeting via sequence identity in CRISPR-Cas gene editing, TALENs or zinc finger nuclease gene editing and siRNA or miRNA targeted to transcribed noncoding regions not limited to promoter and enhancer RNA, 5' noncoding elements, 3' noncoding regions and introns. Genome sequence is from Fricke et al. 2017 and annotated on the JGI Mycocosm platform, mycocosm.jgi-.doe.gov/Psicub1_1/Psicub1_1.home.html.

Below, potential transcription factor binding sites in predicted promoter or enhancer elements are bold underlined; predicted Transcriptional Start Sites (TSS) are highlighted gray and *italic double* *underlined*; canonical ATG translation initiation codons are bold italicized.

```
SEQ ID No: 151-Results for 1004 residue sequence "PsiR"
jgi|Psicub1_1|30566|e_gw1.755.12.1:
    1    CGATCAACTT AGACCTGCGG GTGGGCGAGT GATGTTGGCG AAGAGTTTGC AACCAGTAAA CATACTCGTA CCTATTCAAG
   81    TTTTCAACCG TTCTATCTGG ATGTAAATGT GGAATGCAGT AATTTGTCGC TTCGATTAGA TATAGGCACC CAGGGGAATC
  161    CATCGGACGT TGCAGGTATG GTAGTTGGTT TGACACCTAT TCAGTAGTAT TCTTCGTGTT GATATTTTAT TGTCGTATGG
  241    AGTATTTCTC TTAGTAATAG TTTATTCATT TCCTTTGTTA CCCTCCACTT GCAAGCATTA ATAGGAAGGT GGAATACTTA
  321    GAATTGATAA TGACTTTCCA ACTTAGTTAA CTGTCATTAC TAGTAGGAGT TGGAGCGTGA GTCGTCCAGA CCTGGAGGAC
  401    AAAACCATCT TCAGTGGAAT TGACGATTTG AAACCTTTTG AATAAATAAC AAGTAAATGG GGTTTTGCCC AAGAGTAATG
  481    TAATGAATAT CACACAAGAG TATGTACCCT TTATGTTTCT GCTCGGCGAG GAGAACAAAG GCAGACACAA TAGACCGGCA
  561    TTTCGGGCCG ATGTTTGTTC CAGATATTGC AGCCGGAACA ATGCCGTGGT GGCGTGGGAA CTCGTGATCT GTTGATAGTC
  641    TGACCGCCAG GTCACAGGGT TTCTGATCAC GACAGTCGTG ACTTTCACGC CCCCATTCCC CCCCAATATC CCCCCTGCCC
  721    CTGCCTCCAG AGCGTCCCCT CCGGATCTCT CTTCTAGGTC CCCATTCTGA AGGTGAATCC TCATAGCTGA CCCCAGTGCG
  801    AGCACGTTCC AACTTTCCGC TTTTTTCTAG CCCAAATATC AACCAAGCAA GACCCGGGGC ATCCTCCATA TCTCCCCCCA
  881    ACGGCGCCAA AGTCCAGTCT TCAGGCCTAA AGCCTCCCAA TAGTCGACAC CCTATCTGAC AACGGGCCCA TAACCCCCAG
  961    ATAAACTCTT ᴵATCAAGAA AGTCAACCCA TCTGCGCTCC AATG SEQ ID No: 152-Results for 1004 residue sequence "CSNK1E-like"
jgi|Psicub1_1|30521|e_gw1.755.3.1:
    1    AACAGTTTCT TTGCCGATGA TCCACCTCTC ATGTTTACTG AAGCTAGATC GGTAGCACCT TTGAAACTTG CAATGTAGGT
   81    GACTGTTATG GACTGTGCTG GTGCATTGAC AGAAAGGACA AGGAGCGGGT GCTTGTCTTT ACGTTGTTTT GATAAGCTTT
  161    GTGTTGTCAA GACGTCCTCG ACAATGAGAG GTCCGGGAGC TGCATAGATG ACCATTCCTG GAGTGATGTC TTCGACGTTG
  241    ACTTCTGAGC GGGACATTGT GCGGTTCTTA TTGACACTGA GTCGATTTTC ACCTTTGATT TTATACAGAG CGTAAGTCAG
  321    CCACGGTGAC AGGACTCAGG GCGCCTACAG TCGGAGGAAA ACATCGGAAC ACGCCAGCTG ATGTTTCAAA CATCCAAGTG
  401    GCAAGGAAAT CATTGTTGTG GCTGGTCAAG GGAATAAATA GTTTGACCAT GTTTTCTTCG GGATTAATCA TGTCCTGCTC
  481    TTCTGGCGAC CATTTTTGTA CCAGGAACGA TAGCATGACA GGATGCATGA GGTCGAACAC CGTGAGTAAA ACGGAAACAC
  561    AAAATCCAAA TCTTTGCTTA CGAGTTCGGA AAGGAGTTGT AGACCAGCAA CATGCTTTGA TGAAGGTGAA TTAGTATGAA
  641    TCACTGTTCA TTCATAAGTT GCACGAAGAT AACAAGTGTT CCTCGAGATA TTAAGGAGAT TTAAGCAATT TTGAATATCG
  721    TAAAACTACT GTGTTCATGC ATGCATGCAT CGTTGAGAGC AAAAGGAAGT TATGGTCATC AGGGGATTTC AACTTTCACA
  801    TGCTGTCACC GGAGTGCAAT TCCGCCGTGG TCATACACTA ACAAACAAAA CCGTGACGAG ACGTACCTTA CAATCCTACA
  881    GAACTATTCA TTCTGACTTA CCTTACCCCG CCCCAATCTT GCACCTAAAC TGACATTACA CCTAGGCTTᴵ ACACCATCTA
  961    TCAGCTGCGT ACAACATCAG TTCTCACAGG TTGTTTGCGT CATG SEQ ID No: 153-Results for 1004 residue sequence "PsiT1"
jgi|Psicub1_1|30574|e_gw1.755.30.1:
    1    GAGCATTTGA CCCTTCGATA AGACAGGTAC TATATAGTAT GGACGAACAG GTTTAGTCAC TATCAGGTCA TCGAAACCGT
   81    GACGACTCAG CCCATGGACA ATGTGGCAGA CGACAAGAAA GTTTGGTGAT AAACGGTGAC CAACCGTATA GATATTGTAA
  161    GTCGATATGT AAGCCAAGCA CTTAGTAGAG AGATTTAATT TGCCCTTGAA GAGCCTGTTA AAGTCAAACG TGCATATTCG
  241    ACGAGACTGA CAAGGATTTC CAGTGATCAA AGGAGTACCA TACTCTTCGA GTAGTCACCC CAAGGCAATA CAGGTAGATG
  321    CCCATATAGT TGTAGCGCCG ATGGTATGAA TGACGGAATG TATACAAGAG GCTTGCTTAG TGAAATAAGT CTGATAGGTT
  401    GTGGTCGCCT GAAATGGGTA TTTTGTGAGA TGCCTCAGCC CAACCTCAGC CTGGCAGTGT GCGCTTCAAG TCGAGTAAAG
  481    AGGTAGTACT TGTTGCCACC AGCACACCAA GCCACCACGA GAGGTAGGCT ATTTGAAGAG ATTTGAAGGC CCATAAAGAG
  561    TTGGGGGTAA TTTTACACAG TATTAAGCAA GCATGAAAGC AGTGCCATCA GAAAAAGGTT GTTGTTTGCT GATAACGTAA
  641    TCGTTACCTG TCATCACACT TCGTTGAATT TTAGCGAGAC CACATTTTTC TTTTAACAAC GACGGTCAAC ATTGACATTA
  721    GAAAACCATA AATTGTTCCT CATTTCACTT TCAAGCTTTT CTGAGATCAA ATAGTTCATT CAATCACAGC TTTTCATGCA
  801    TTGAAGGTTT TTGAGCACAA TCGACGTTTC AATGGGGTCG CTGCGCGTAT ACATGTGGTC ACTTTTGATG CGCATTCTAA
  881    TGGTCAGCAG GTTTTCCATA TGTTATGAAA AAGAATAAGC GAGGTATAGG TATGTTGATG CCTCTTATAT AACGTACGCT
  961    CACTTAGTAA AGTTGTCᴵTC GCTTTCCGAC AGTGCTCTTT AATG SEQ ID No: 154-Results for 499 residue sequence "PsiK"
jgi|Psicub1_1|72830|gm1.1231_g:
    1    TGGACAAAAC ATCATGCTAA AATGGATCTC ACACTGATTG GTTTTGGCAC CCTTCTCTTG CGTAATGCAT CGCCTGACAC
   81    AGGGATTGTA GTACGCGACC TGGCAGTTCC AAATTTTGGT TAGTCTTGAA CCTTGCCATG ATTTGCCTTA GCTACCTTCC
  161    GGGAAGTTAT CTGGCCGTAG CTTCTCCGCA GCGTGCCTTA AAGGCTTCCA ATTAAAGGAA TATTCCATCA TCCTGAGTAT
  241    CTAAAACTCG AAGATAAGGA AATGCTAAAT GGTTGACTTA GTTTAACAGT GTAGTATACT TGATTTATGT ACGGTATGTT
  321    TTTTGCTCGG CGATGTAATC GCACGGCGTT ACGTGCTACG TCGATGTTGA TGAGCTGCTT TTGCGCATCG TTCCAAAAAT
  401    AGACTTAATC TTAAGTACTT AGCCCAGCGA GTTCAAATTG AAAAGᴵGAGC GACTCTCCTC GGTTCCCCCT TCTTAAGAGC
  481    TTTAACTTCT CTTACTATG SEQ ID No: 155-Results for 319 residue sequence "PsiH"
jgi|Psicub1_1|30581|e_gw1.755.84.1:
    1    TGTAGCTGTT CATACATGTA TAATGCAAAT TTTGTAGAAG TGCTCGTGCT CGTCTATTAC TAGTACTACC TGACTCTAAA
   81    GTGGGGAGAT CAGAGGGTGG ACGAGAGCAT TTCCATCTGG ATAGTTAAAA GAACACCCAT ACGTCAGCTC GACCGAACAA
  161    GATCATTTCT AGATCTAATT TTGGAACGAA GAGTGGGGCT TAAAAGGGAC AAAGAAGATA ATGTTCGGCT TTGCACAATG
  241    CCTATTCGCC TCGAGGTTCG TCACGTTTAT TGGTTAAAAG AATCCGTCGC ᴵGAGGCTCAC TGᴵGCATCTC CCCATCATG SEQ ID No: 156-Results for 1004 residue sequence "PsiT2"
jgi|Psicub1_1|30509|e_gw1.755.57.1:
    1    GCAATTGAAG ATAGATTACC AGTTTCTGTA AATGAAGGCA ATATTGACCT TGAAGTCACC ATTGCATTTT TGTATCGCAT
   81    GCCCTTCATT GAAACGTCAT AATTGTTCCA GAACACCCTC GATGTGTGAA GATGATGGTT CCATTGCCGC CTATAGTCTC
  161    CTCCTTCGAC CTTATAATGG GCACAAGAAC CCCGGCACGA TAGGAGCCTT GTCTAAAGGT TGGTTAGTGA GGGAACCACG
```

```
241    TTCTAAATTT TCCCTTATAA TACCTTCTTT TCCTATCAGT TACTCGATTG CTTCTCTACG CCAACTGCTA ATTGGCAGTA
321    GCACGATTTA TCGTGTGCCG CAGATTGGTG AAATGTTCAC TTATATTGAC ACCTTTTCAC TGATATGAAA GCCATTTCCC
401    TCGGACGAAG TCGGGTTTGA TCTCACTTGT GACAGCTGAC CGGGCTGGGA GCGGAACCAT CCAAATGATA CAACGGTTCT
481    TGTGTCCAGA CTTCTTAGTG TGCGCAAGAA GCTATTACTG TAGTGTCGAT AGGACATGGT TGACCTTCGT TCGACGCGAC
561    GTACTGGCTA ATATTCATTA GCGCCGCCCG CTCCATGAGT AATGGAATCC GATTTGCTCG CACAAGTAAT GATGCATCTG
641    TCGTCATACT ACCCAAAATC CTTGTTCGGA GAAAACGGGA ACCGACGAAC TTCAAGATGG GCAAGGAAAA GGCAGTGACA
721    GCCGGATCGC AAGATACAAG TCCGATGGAG TTTTTAAACC GGAGTCGATG CCCAGCCAAT AATATTGCAT GATAGCCGAT
801    ATGCCGAGTG ATGCCATCAC CAATTTTGTC CTTTTCGGGT TAGATCTATA GGGGCAAACA GGGACAATTC AAAAGACCCA
881    CCCACGCCGA AAATGGCCCA GAGCTTCTTA ATGACAACTA ATTAAAGATT TGCATTTAGC CAGCGAGACT CTGACGAAAT
961    TCGGAGCTCT TTTCCCCTCT CTTGAACCAT CCCCTTACCC TATG
```

SEQ ID No: 157-Results for 1004 residue sequence "PsiM"
jgi|Psicub1_1|72833|gm1.1234_g:
```
  1    TGTTTATTTA ACACTTGTAC CCCAAAATAT TACGGCACCC AAAAATAAAT ACAGTTTGCT CGGCGCTAGT CAGTGAATGA
 81    CGCACCTAAA TAGATCATAT TGTTGCAACA TTACCCATGC CATGCCACTG TGGTGCCCCT ACTCTGACCG AACTTCGATA
161    TCCAACTCAC CCTAATAATT AAATATACCA CCGTAAAAAA GAAGGGAGAA AAGTCTTCCA AGTGCTACG TCCCCACTGT
241    TTTGGGGTTT CCAGAGCCCA AAAATCTCAA TCGGCCCCAG AGTGGACACG AACCAGGAAT CCTACTCGGT ACTGAAGAAG
321    GGATTATCTA TTGTTAGGGC GTACTGAGGC CCCAAAAATG AGTAGCTCTA TTCGGTGAAG CAAGATATAT TAACTATTAT
401    TAGAGCACGT TGGCAACTTG ACATCATTAC AGGTTCATCT TGAAGGTATG CATTATGCCT GTTTGGGTAT CGCATCTTGA
481    CGAACTCTCA AAGTCTTGAC CAAGCGATCC AAACTGAAGC GACGCCGGAC GCGAATGTAA TGCAAAGACT TTCTTCCTTT
561    GACCCAATTG GGCTTTTCCC TTTGTGTCTA ATCGGATACT TTAAAGTCAA TTATCTCATC ATGCCACTGC TCTTATCTAA
641    CATTAGTCCT TCACCTTCAA TTCAATGACG GCCTTTCCTT TGAGAAGATC GAATATACGG TGAATACATA CCTTCAGCAG
721    CGTGGCGATT CATAATAAGT GTACTCAAAG GGTCCTTCTA TTTAACAGGT ATTATTATGA CGGCGAATAT GAAAACGTAA
801    AACAATGTAA CCCCCTGCAT GAGATGATAT CATATCACGC ATGATCCTCA TGCCTGAAAA GATTGTGTAC ACGTTGCGAA
881    CAGATTAGAT TGTACCCCAC GATGGTCGAC TTCTATACTA ACTGATAGAT ACATAAGGCT AGTGTCCTGA AGGTCAAGAC
961    CAGTAGCTCT CCCCTCATCC TGTATCCAA AATACACCGC TATG
```

SEQ ID No: 158-Results for 1004 residue sequence "PsiD"
jgi|Psicub1_1|87665|fgenesh1_pm.NODE_755_#_10:
```
  1    AACACGATTT GTAGGGTACT TTATGTTATC TTTTAAATCA ATTAAATTTG CTCATTCTTG GCCGTATATA TAGGAGATTT
 81    ATGGAGGTTT TCATCTTGCT TTCACAGTCT CACCATAATA ATCGTGTGCA TTCATACAGT AATGGCGATT TCATCTAACC
161    GCACACAATA GAAATCGGAA GCAGGTCGGT TGCAACCAAG TTCCAACTGC CGCTTTGACT CCACCTCACC TTTCCCTCAG
241    CCGGACAGCC TGCTTTTCTT CTTAGTTGTT CGGTGCAACA CTGGAACGCT GGAAAGATTG TCGGCTGTTC TCCATTCTGA
321    GTATCTATAA TTTCTTTCTA TTCGGGGTGT GTTCGGTTCG AGCATGGCGC GTATTGGCTA GGTTCTCCAA TTTCATTCGT
401    CAGGTATGAC CTGGGTATGA CCGACCTGTT CAATTCTCGT AATTGATATT TCAACAATTC CTCTTAGATA TCCATCTCTG
481    AGATTGGTAA GGAGTATCAC GACAGGCCTA ACACTAGATC ACCTTTCCTA CCTTCCATGC ACGCTTACAT CTCATGCTTG
561    CTGTAGTAAA GAAGAGGTCG TGTGCCACAT TGCTCGAACA AAGCATGCAT TACGTCAATA CCACTGGATT AGGTTGAAGA
641    ACCGGCGATC TGGGCAGACG CGCCACGCTC TGAGTACCTA AGGGTGTACT TAAATTTATC ACAGCTTGAC GTTTGACCTG
721    GAAGCTTGAT TTACGCAAGG TTGGAACTTG CACCCCCCGG TCGAGCATCT CTCTCTAGTC ATAGTTTATC TTTGTATAAA
801    TGGGGGCCTC AACGCAAGGC CGCAAACTA CTCCCAACTT TTATAACTCA TTTCTGCTCC CAACACTTGA TCATGCAGGT
881    GATACCCGCG TGCAACTCGG CGTACGTCGT TTGTATTCGC TGACTTCACC CGCTAATTAC TATAACTTGA AAACACAGAG
961    CAATAAGATC ACTATGTCCT ACTCCCGAGT CTTTTAGAAA CATG
```

Annotation of noncoding sequences used several prediction methods to make use of nucleotide sequence databases [40] and eukaryotic and prokaryotic transcription start sites, promoter and enhancer elements, and consensus DNA binding sites of fungal transcription factor proteins:

(1) Promoter prediction in prokaryotic and eukaryotic promoter sequences from free energy of nucleic acid [45] sequence hybridization, using PromPredict nucleix.mbu.iisc.ac.in/prompredict/prompredict.html, see Kanhere A Bansal M 2005a Structural properties of promoters: similarities and differences between prokaryotes and eukaryotes; *Nucleic Acids Res.* [50] 33:3165-3175.

(2) TSSFinder sucest-fun.org/wsapp/tssfinder/, see Mauro de Medeiros Oliveira, 2021.TSSFinder—fast and accurate ab initio prediction of the core promoter in eukaryotic genomes. Briefings Bioinfor., vol. 22, Issue 6, November 2021, bbab198, doi.org/10.1093/bib/bbab198.

(3) Neural Net eukaryotic promoter prediction, using fruitfly.org/cgi-bin/seq_tools/promoter.pl, see Reese MG, 2001. Application of a time-delay neural network to promoter annotation in the *Drosophila melanogaster* genome, *Comput. Chem.* 26 (1), 51-6.

(4) Manual sequence inspection for transcription factor binding sites found in enhancer and promoter elements in fungi and other eukaryotes. See, e.g., Piscitelli 2011, *P. ostreatus* laccase genes doi: 10.2174/138920211795564331, and epd.epfl.ch/promoter_elements.php.

Some of the elements found in noncoding regions of the psilocybin synthetic cluster:

```
TATAA promoter element consensus sequence TATAWAWR 25-30 bp before TSS

BRE (G/A) TGGGGG

NIT2 TATCT

Hse (NGAAN) n stress transcription factor control seems to be a common element

CAAT GGCCAATCT 60-100 bp 5' from transcription start site (TSS)

GC Box GGGCGG 110 bp 5' from transcription start site (TSS)
```

CreA GCGGGG

STRE CCCCT

Clock bHLH binds to ACGTG or GCGTG

MyoD, Twist bind to CAGCTG or CACCTG

Example 6: Preparation of Mushroom Extracts

The psilocybin knockout mushrooms thus prepared based on previous examples are freeze dried (Scan Vac CoolSafe Pro, Labogene, Lynge, Denmark) and kept at 4'C in hermetically vacuum-sealed plastic bags.

Preparation of Mushroom Extracts

Dried mushroom samples are finely milled to produce mushroom powder using one or more of blenders, grinders, ultrasonic vibrators or food processors. The powder is extracted using one or more of three different extractants: distilled water, 50 percent (v/v) ethanol and a solvent such as diethylether.

For water extraction (WE), powdered samples (10 g) are boiled in water (500 mL) for 30 min and centrifuged at 12,000 revolutions per minute (rpm) for 15 min; then, supernatants are filtered through a Buchner funnel with Whatman No. 4 filter paper and the filtrate is collected. The obtained extract is concentrated under vacuum at 40° C. using a rotary evaporator (Rotavapor R-124; Bucchi Labortechnic; Flawil, Switzerland) and then adding 100 mL of distilled water, mixed well and transferred into a dark plastic bottle and stored at 20° C. until analysis.

For 50 percent (v/v) ethanol extraction (50% EE), each powdered sample (10 g) is mixed with 100 mL of 50 percent (v/v) ethanol and is shaken at 150 rpm at room temperature for 24 h then centrifuged a 12,000 rpm for 15 min. The supernatant is filtered through a Buchner funnel with Whatman No. 4 filter paper and the filtrate is collected. The residue was re-extracted under the same conditions. The obtained extract was concentrated under vacuum at 40° C. using the rotary evaporator and 50 percent EE (100 mL) is added, mixed well and transferred into a dark plastic bottle and stored at 20° C. until analysis.

For diethyl ether extraction (DE), each powdered sample (10 g) mixed with 100 mL of diethyl ether is shaken at 150 rpm at room temperature for 24 h and then centrifuged at 12,000 rpm for 15 min. The supernatant is filtered through a Buchner funnel with Whatman No. 4 filter paper and the filtrate is collected. The residue is re-extracted under the same conditions. The combined diethyl ether extract is transferred into a dark plastic bottle and concentrated by flushing with 99.995 percent nitrogen gas and stored at 20° C. until analysis. When using a dried diethyl ether extract for analysis, 100 mL of diethyl ether is added and mixed well before analysis. (See S. Boonsong et al., Antioxidant activities of extracts from five edible mushrooms using different extractants, *Agriculture & Natural Resources* 50 (2016) 89-97; U.S. Pat. No. 3,183,172-A)

In some preferred embodiments herein of disclosed non-hallucinogenic psychedelic fungi, mushroom extracts prepared from such fungi will have no or substantially no hallucinogenic effects when consumed, when compared to an extract from wild-type mushrooms, since the psilocybin biosynthetic pathway has been suppressed or otherwise disrupted. The extracts contain phytoactive compounds that have anti-inflammatory properties. The extracts contain compounds which cause oxidation reduction (reducing the amount of reactive oxygen species) and thus which serve as free radical scavengers. The extracts also have potent antibacterial activities. The extracts thus prepared can serve as nutraceuticals enabling in the reduction of inflammation, allergies, boost immunity, reduces fatigue and depression. The following assay illustrates ways to characterize the amount of phenolic, flavonoid contents and their therapeutic properties such as anti-inflammatory and antibacterial properties.

Quantitative Analysis of Psilocybin in Mushroom Extracts

The amount of psilocybin present in the mushroom extracts can be determined by using LC-MS/MS methods known in art. Analytical standards for both native and deuterated psilocybin and psilocin are purchased from Cerilliant (TX, USA). An initial sample weight of 100 mg fresh homogenized *Psilocybe* mushroom of the invention that has one or more genes of the psilocybin biosynthetic pathway (PsiD, PSiM, PsiH, and PsiK) knocked out or silenced is extracted in 10 mL of methanol and vortexed. The mushroom matrix is left to further extract at 4° C. overnight. Deuterated internal standards were added to each vial.

The mushroom extract is then diluted to a dilution factor of 1:40,000. An unmodified *Psilocybe* mushroom of the same species where the biosynthetic pathway of Psilocybin is intact is used as a control sample. Control mushroom extracts are prepared in the same process as described. (See Gambaro et al., 2015, Identification of Hallucinogenic Mushrooms Seized on the Illegal Market Using a DNA-Based Approach and LC-MS/MS Determination of Psilocybin and Psilocin. *J Anal BioAnal Tech.* 6 (6), 578-585.) An injection volume of 2 µL is separated on a Phenomenex Luna Omega Polar C18 (4.6 µm×150 mm) using mobile phases of formic acid, water, and acetonitrile at a flow rate of 1.2 mL/min. (Mobile Phase A: 0.1% formic acid in water; Mobile Phase B: 0.1% formic acid in acetonitrile).

The fractions thus separated using liquid chromatography are analyzed using SCIEX Triple Quad 3500 Mass Spec System in positive polarity with the MRM mode. The following source parameters are optimized for analysis:

| Source Parameter | Optimized Value |
|---|---|
| Curtain Gas | 40 |
| Ion Spray Voltage | 3500 |
| CAD Gas | 11 |
| Heater Temperature | 600 |
| Nebulizer Gas (GS1) | 50 |

A psilocybin calibration curve is generated following standard protocols known in art. The results of the mass spec and the calibration curve are used to determine the concentration of psilocybin. The control sample where the psilocybin biosynthetic pathway is unmodified is expected to show 1-2 mg/ml of Psilocybin which would correspond to about 1-2 weight percent of the mushroom extract. Likewise, the mushroom extracts of the invention are expected to show less than 0.1 mg/ml which would correspond to about 0.1 weight percent of the mushroom extract. Thus the mushroom extracts of the invention would have little or negligible amounts of psilocybin and cannot cause any hallucinogenic effects when consumed. (See Oetjen et al., Quantification of Psilocybin and Psilocin in Mushroom by LC-MS/MS, *SCIEX, USA,* 2020.)

Analysis for Phenolic Compounds in Mushroom Extracts

The total phenolic compounds of mushroom extract are determined according to Turkoglu et al. (Turkoglu, et al., 2007, Antioxidant and antimicrobial activities of *Laetiporus sulphureus* (Bull.) Murrill. *Food Chem.* 101, 267e273) with slight modifications. Briefly, the extract (1 mL) in a volumetric flask is diluted with distilled water (46 mL). Folin-Ciocalteu reagent (1 mL) is added and the contents of the flask are mixed thoroughly for 3 min; then, $Na_2CO_3$ (2% v/v, 3 mL) is added. The mixture is allowed to stand for 90 min with intermittent shaking at room temperature. The absorbance of each mixture is measured at 760 nm. The concentration of total phenolic compounds is measured by plotting the calibration curve of a gallic acid standard, determined as mg of gallic acid equivalents per gram of dried mushroom.

Analysis of Total Flavonoid Contents in Mushroom Extracts

The flavonoid contents of the mushroom extract are measured according to the method of Turkoglu et al. (2007). The extract (1 mL) is diluted with 4.3 mL of 80 percent (v/v) aqueous ethanol containing 0.1 mL of 10 percent (v/v) aluminum nitrate and 0.1 mL of 1 M aqueous potassium acetate and allowed to stand for 40 min at room temperature. The absorbance is determined spectrophotometrically at 415 nm. The total flavonoid contents are measured by plotting the calibration curve of a quercetin standard, determined as milligrams of quercetin equivalents per gram of dried mushroom.

Analysis of Antioxidant Activities in Mushroom Extracts a. 2,2-Diphenyl-1-Picrylhydrazyl Radical-Scavenging Activity Assay The free radical-scavenging activities of mushroom extract are assayed using the method of Devi et al. (Devi et al., 2008. Bioprotective properties of seaweeds: in vitro evaluation of antioxidant activity and antimicrobial activity against food borne bacteria in relation to polyphenolic content. *BMC. Complement. Altern. Med.* 8, 38). Briefly, 3 mL of each mushroom extract with different concentrations (50 mg/mL, 100 mg/mL, 150 mg/mL, 250 mg/mL, 500 mg/mL) are mixed with 1 mL of DPPH (0.1 mM) solution in methanol. The mixture is shaken vigorously and left to stand for 30 min in the dark at room temperature and the absorbance was then measured with a quartz glass cuvette (Hellma; Mullheim, Germany) at 517 nm against a blank using a UV-visible spectrophotometer (Pharma Spec UV-1700; Shimadzu; Kyoto, Japan). A low absorbance of the reaction mixture would indicate the presence of a high free-radical-scavenging activity. BHA and a-tocopherol are used as positive controls. The capability to scavenge the DPPH radical is calculated using Equation (1):

$$DPPH \text{ scavenging effect (\%)} = (A_{blank} A_{sample})/A_{blank} \times 100 \quad (1)$$

where $A_{blank}$ and $A_{sample}$ are the absorbance of the control reaction (containing all reagents except the test extract) and the absorbance of the test extract, respectively.

b. Reducing Power Assay

The reducing power of mushroom extract is determined according to the modified method of Barros et al. (Barros et al., I.C.F.R., 2008, Antioxidant activity of *Agaricus* sp. mushrooms by chemical, biochemical and electrochemical assays. *Food Chem.* 111, 61-66). Various concentrations (50 mg/mL, 100 mg/mL, 150 mg/mL, 250 mg/mL, 500 mg/mL) of mushroom extract (2.5 mL) are mixed with sodium phosphate buffer (2.5 mL, 0.2 M, pH 6.6) and 2.5 mL of 1 percent (v/v) potassium ferricyanide. The mixture is incubated at 50 C for 20 min and 2.5 mL of 10 percent (v/v) trichloroacetic acid was added to the mixture and centrifuged at 1000 rpm for 8 min. The upper layer of solution (5 mL) is mixed with distilled water (5 mL) and 1 mL of 0.1 percent (v/v) ferric chloride ($FeCl_3$). The absorbance of the test extract is measured at 700 nm; a higher absorbance would indicate the presence of a higher reductive capability. BHA and atocopherol are used as the positive controls.

c. Superoxide Anion Radical-Scavenging Activity Assay

Superoxide radicals of mushroom extract are determined according to Elmastasa et al. (Elmastasa et al., 2007. Determination of antioxidant activity and antioxidant compounds in wild edible mushrooms. *J. Food Compost. Anal.* 20, 337-345). Each extract (1 mL) with different concentrations (50 mg/mL, 100 mg/mL, 150 mg/mL, 250 mg/mL, 500 mg/mL) is mixed with 1 mL of phosphate buffer (0.05 M; pH 7.8), riboflavin (1 mL; 3 10 6 M), methionine (1 mL; 1 10 2 M) and nitroblue tetrazolium (NBT; 1 mL; 1 10 4 M). The photo-induced reactions are performed in an aluminum, foil lined box with two fluorescent lamps (20 W) and the distance between the reactant and the lamps is adjusted until the intensity of illumination reached 4000 lx and the reactant is illuminated at 25° C. for 25 min. The photochemically reduced riboflavins will generate $O_2$, which reduces NBT to form blue formazan. The absorbance of the reaction mixture is measured at 560 nm. BHA and a-tocopherol are used as positive controls. The degree of scavenging is calculated using Equation (2):

$$\% \text{ Scavenging} = (A_{control} A_{ssample})/A_{control} \times 100 \quad (2)$$

where $A_{control}$ and $A_{sample}$ are the absorbance of un-illuminated reaction mixture and the absorbance of mushroom extract added with reaction mixture, respectively.

d. Ferrous Activity Assay

The chelating effect on the ferrous ions of the mushroom extract is estimated using the method of Yaltirak et al. (Yaltirak, et al., 2009. Antimicrobial and antioxidant activities of *Russula delica* Fr. *Food Chem. Toxicol.* 47, 2052-2056). Each extract (1 mL) with different concentrations (50 mg/mL, 100 mg/mL, 150 mg/mL, 250 mg/mL, 500 mg/mL) is mixed with 3.7 mL of methanol and 0.1 mL of 2 mM ferrous chloride. The reaction is initiated by the addition of 0.2 mL of 5 mM ferrozine. The mixture is shaken vigorously and left to stand at room temperature for 10 min. The absorbance of the mixture is measured spectrophotometrically at 562 nm against a blank; ethylenediaminetetraacetic acid (EDTA) is used as the positive control. The results are expressed as the percentage of inhibition of the ferrozine-$Fe^{2+}$ complex formation which was calculated using Equation (3):

$$\% \text{ Inhibition} = (A_{control} - A_{sample})/A_{control} \times 100 \quad (3)$$

where $A_{control}$ and $A_{sample}$ are the absorbance of the ferrozine-Fe2bcomplex and the absorbance of test extract, respectively.

e. Antibacterial Activity

The antibacterial effect of methanolic extract of *Psilocybe* mushrooms is tested against Gram-positive and Gram-negative bacteria following the procedures detailed in Sanches et al. An evaluation of antibacterial activities of *Psidium guajava* (L.) *Braz Arch Biol Tech.* 2005; 48 (3): 429-436). Since many plant phenolics have been found to be responsible for several biological properties, including antimicrobial properties (Yathirak et al., Antimicrobial and antioxidant activities of *Russula delica Fr., Food Chem Toxicol.* 2009 August; 47 (8): 2052-6), it is expected that the antimicrobial activity of mushroom extracts would be related to its antioxidant compounds.

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, e.g., Sambrook et al. *Molecular Cloning: A Laboratory Manual,* 2d ed., Cold Spring Harbor Lab. Press, 1989; 3d ed., 2001; Ausubel et al., *Current Protocols In Molecular Biology,* John Wiley & Sons, New York, 1987 & periodic updates; The series *Methods In Enzymology,* Acad. Press, San Diego; Wolfe, *Chromatin Structure And Function,* 3rd ed., Academic Press, San Diego, 1998; *Methods In Enzymology,* Vol. 304, *"Chromatin"* (P. M. Wassarman & A. P. Wolffe, eds.), Academic Press, San Diego, 1999; and *Methods In Molecular Biology,* Vol. 119, "Chromatin Protocols" (P. B. Becker, ed.) Humana Press, Totowa, 1999.

Those skilled in the art will recognize, or be able to ascertain using no more than routine experimentation, many equivalents of the specific embodiments described herein. Such equivalents are intended to be encompassed by the following claims. Any combination of the embodiments disclosed in any plurality of the dependent claims or Examples is contemplated to be within the scope of the disclosure.

The invention may be embodied in other specific forms than those of the exemplary embodiments herein without departing from the true scope of the invention. Any references to the "invention" are intended to refer to the exemplary embodiments thereof and should not be construed to refer to all embodiments of the invention unless the context otherwise requires. The described embodiments are to be considered in all respects only as illustrative and not restrictive.

Recitation of a listing of elements in any definition of a variable herein includes definitions of that variable as any single element or combination (or sub combination) of listed elements. Recitation of an embodiment herein includes that embodiment as any single embodiment or in combination with any other embodiments or portions thereof.

Additional embodiments were originally disclosed in U.S. Prov. App. No. 63/371,121 as the originally filed claims. These claims, and each of the embodiments they represent, are also set forth again here, by being incorporated herein by reference, as if fully set forth herein.

The foregoing description, for purposes of explanation, uses specific nomenclature to provide a thorough understanding of the invention. However, it will be apparent to one of skill that specific details are not required in order to practice the invention. Thus, the foregoing description is presented for purposes of illustration and description, and is not intended to be exhaustive or to limit the invention to the precise forms disclosed; many modifications and variations are possible in view of these teachings. The embodiments were chosen and described in order to best explain the principles of the invention and its practical applications, through the elucidation of specific examples, and to thereby enable others skilled in the art to best utilize the invention and various embodiments with various modifications as are suited to the particular use contemplated, when such uses are beyond the specific examples disclosed. Other embodiments are within the following claims. Accordingly, the scope of the invention shall be defined solely by the following claims and their equivalents.

The invention claimed is:

1. A non-hallucinogenic psychedelic *Psilocybe* spp. fungus having reduced production of a bioactive alkaloid, wherein the fungus has disrupted activity of one or more of a PsiD, PsiH, PsiK, or PsiM enzyme, wherein the disrupted activity is a result of disrupted expression of one or more of a PsiD, PsiH, PsiK, or PsiM gene using an siRNA.

2. The non-hallucinogenic psychedelic fungus of claim 1, wherein the bioactive alkaloid is a hallucinogenic tryptamine.

3. The non-hallucinogenic psychedelic fungus of claim 2, wherein the hallucinogenic tryptamine is psilocybin.

4. The non-hallucinogenic psychedelic fungus of claim 1, wherein said fungus is a *Psilocybe cubensis* fungus.

5. The non-hallucinogenic psychedelic fungus of claim 1, wherein the fungus comprises no detectable transcript of one or more of a PsiD, PsiHI, PsiK, or PsiM gene, when measured by qRT-PCR.

6. The non-hallucinogenic psychedelic fungus of claim 1, having disrupted expression of a PsiD gene.

7. The non-hallucinogenic psychedelic fungus of claim 6, wherein the siRNA has at least 75%, at least 80%, at least 85%, at least 90%, at least 95%, or at least 99% sequence identity to a sequence selected from the group consisting of SEQ ID NOS: 52, 53, 54, 55, or 56, or a reverse complement thereof.

8. The non-hallucinogenic psychedelic fungus of claim 3, wherein the production of psilocybin is reduced by an amount of greater than 90%, greater than 91%, greater than 92%, greater than 93%, greater than 94%, greater than 95%, greater than 96%, greater than 97%, greater than 98%, greater than 99%, greater than 99.5%, greater than 99.9%, greater than 99.95%, or greater than 99.99%, relative to a comparable wild-type fungus.

9. The non-hallucinogenic psychedelic fungus of claim 3, wherein said fungus, when dried, comprises a weight/weight percent of psilocybin of less than 0.15, less than 0.10, less than 0.05, less than 0.001, or less than 0.005.

10. The non-hallucinogenic psychedelic fungus of claim 1, prepared as a ground mushroom powder.

11. The non-hallucinogenic psychedelic fungus of claim 1, prepared as a mushroom extract.

12. The non-hallucinogenic psychedelic fungus of claim 1, prepared as a nootropic, a supplement, a nutraceutical, a microdose, a functional food, a skin cream, a liquid solution, a liquid suspension, a tincture, a beverage concentrate, or a beverage.

* * * * *